(12) United States Patent
Blizzard et al.

(10) Patent No.: US 12,329,853 B2
(45) Date of Patent: Jun. 17, 2025

(54) COMPOSITIONS AND METHODS FOR TREATING OCULAR DISEASES

(71) Applicant: OCULAR THERAPEUTIX, INC., Bedford, MA (US)

(72) Inventors: Charles D. Blizzard, Nashua, NH (US); Ankita Desai, Reading, MA (US); Arthur Driscoll, Reading, MA (US); Michael Goldstein, Cambridge, MA (US)

(73) Assignee: Ocular Therapeutix, Inc., Bedford, MA (US)

( * ) Notice: Subject to any disclaimer, the term of this patent is extended or adjusted under 35 U.S.C. 154(b) by 321 days.

(21) Appl. No.: 18/081,229

(22) Filed: Dec. 14, 2022

(65) Prior Publication Data
US 2023/0285281 A1    Sep. 14, 2023

Related U.S. Application Data

(63) Continuation of application No. 17/673,265, filed on Feb. 16, 2022, now Pat. No. 11,622,935, which is a
(Continued)

(51) Int. Cl.
A61K 9/00    (2006.01)
A61K 9/14    (2006.01)
A61K 31/216    (2006.01)
A61K 31/5575    (2006.01)
A61K 47/10    (2017.01)
A61K 47/69    (2017.01)
(Continued)

(52) U.S. Cl.
CPC .......... *A61K 9/0051* (2013.01); *A61K 9/0048* (2013.01); *A61K 9/146* (2013.01); *A61K 31/216* (2013.01); *A61K 31/5575* (2013.01); *A61K 47/10* (2013.01); *A61K 47/6903* (2017.08); *A61K 47/6937* (2017.08); *A61P 27/06* (2018.01); *C08L 67/04* (2013.01); *C08L 2201/06* (2013.01); *C08L 2312/00* (2013.01)

(58) Field of Classification Search
CPC .................................................. A61K 9/0051
See application file for complete search history.

(56) References Cited

U.S. PATENT DOCUMENTS 3,949,750 A    4/1976    Freeman
3,993,071 A    11/1976    Higuchi et al.
(Continued)

FOREIGN PATENT DOCUMENTS

WO    2009/008946    1/2009
WO    2010/093873    8/2010
(Continued)

OTHER PUBLICATIONS

U.S. Appl. No. 17/169,020 (abandoned), filed Feb. 5, 2021.
(Continued)

*Primary Examiner* — Carlos A Azpuru
(74) *Attorney, Agent, or Firm* — LOWENSTEIN SANDLER LLP

(57) ABSTRACT

The present invention relates to the treatment of ocular diseases in a human subject. In particular, the invention relates to an intracameral administration of a sustained release biodegradable intracameral implant.

20 Claims, 13 Drawing Sheets

Related U.S. Application Data continuation of application No. PCT/US2021/016889, filed on Feb. 5, 2021, which is a continuation of application No. PCT/US2020/029830, filed on Apr. 24, 2020.

(60) Provisional application No. 63/139,123, filed on Jan. 19, 2021, provisional application No. 63/136,305, filed on Jan. 12, 2021, provisional application No. 62/970,828, filed on Feb. 6, 2020.

(51) Int. Cl.
*A61P 27/06* (2006.01)
*C08L 67/04* (2006.01)

(56) References Cited

U.S. PATENT DOCUMENTS

| | | |
|---|---|---|
| 4,915,684 A | 4/1990 | Mackeen et al. |
| 5,469,867 A | 11/1995 | Schmitt |
| 5,902,598 A | 5/1999 | Chen et al. |
| 6,027,470 A | 2/2000 | Mendius |
| 6,196,993 B1 | 3/2001 | Cohan et al. |
| 6,437,152 B1 | 8/2002 | Jackson et al. |
| 6,509,327 B1 | 1/2003 | Cagle et al. |
| 6,646,001 B2 | 11/2003 | Hellberg et al. |
| 6,982,090 B2 | 6/2006 | Gillespie |
| 7,109,371 B2 | 9/2006 | Clissold et al. |
| 7,166,730 B2 | 1/2007 | Nisnevich et al. |
| 7,799,336 B2 | 9/2010 | Hughes |
| 7,897,795 B2 | 3/2011 | Henschke et al. |
| 7,998,497 B2 | 8/2011 | de Juan, Jr. et al. |
| 8,178,582 B2 | 5/2012 | Kabra |
| 8,268,299 B2 | 9/2012 | Kabra et al. |
| 8,323,630 B2 | 12/2012 | Kabra et al. |
| 8,388,941 B2 | 3/2013 | Chowhan et al. |
| 8,409,606 B2 | 4/2013 | Sawhney et al. |
| 8,436,194 B2 | 5/2013 | Henschke et al. |
| 8,476,471 B2 | 7/2013 | Yiannikouros et al. |
| 8,512,738 B2 | 8/2013 | Hughes et al. |
| 8,512,749 B2 | 8/2013 | Edelman et al. |
| 8,519,178 B2 | 8/2013 | Hogan et al. |
| 8,535,705 B2 | 9/2013 | Edelman et al. |
| 8,563,027 B2 | 10/2013 | Jarrett et al. |
| 8,685,435 B2 | 4/2014 | Nivaggioli et al. |
| 8,691,265 B2 | 4/2014 | de Juan et al. |
| 8,715,712 B2 | 5/2014 | de Juan et al. |
| 8,722,735 B2 | 5/2014 | Kabra et al. |
| 8,742,143 B2 | 6/2014 | Henschke et al. |
| 8,747,884 B2 | 6/2014 | de Juan et al. |
| 8,754,123 B2 | 6/2014 | Kabra |
| 8,846,073 B2 | 9/2014 | Spada et al. |
| 8,900,622 B1 | 12/2014 | Hughes |
| 8,900,662 B2 | 12/2014 | Lee et al. |
| 8,901,319 B2 | 12/2014 | Chambournier et al. |
| 8,956,655 B2 | 2/2015 | Lyons et al. |
| 8,957,240 B2 | 2/2015 | Hogan et al. |
| 8,961,501 B2 | 2/2015 | Jarrett et al. |
| 9,061,065 B2 | 6/2015 | Robinson et al. |
| 9,115,109 B2 | 8/2015 | Wei et al. |
| 9,125,807 B2 | 9/2015 | Sawhney et al. |
| 9,126,898 B2 | 9/2015 | Oh et al. |
| 9,144,561 B2 | 9/2015 | Kabra |
| 9,149,428 B2 | 10/2015 | Spada et al. |
| 9,168,222 B2 | 10/2015 | Juan et al. |
| 9,187,593 B2 | 11/2015 | Dadey et al. |
| 9,205,150 B2 | 12/2015 | El-Hayek et al. |
| 9,212,125 B2 | 12/2015 | Kardos et al. |
| 9,254,267 B2 | 2/2016 | Sawhney |
| 9,278,139 B2 | 3/2016 | Rau et al. |
| 9,290,432 B2 | 3/2016 | Bischof et al. |
| 9,370,485 B2 | 6/2016 | Sawhney et al. |
| 9,393,223 B2 | 7/2016 | Hughes |
| 9,421,126 B2 | 8/2016 | Alster et al. |
| 9,445,944 B2 | 9/2016 | Rapacki et al. |
| 9,463,114 B2 | 10/2016 | Odrich et al. |
| 9,464,028 B2 | 10/2016 | Wei et al. |
| 9,492,316 B2 | 11/2016 | Ghebremeskel et al. |
| 9,504,653 B2 | 11/2016 | Liu et al. |
| 9,504,696 B2 | 11/2016 | Robinson et al. |
| 9,540,311 B2 | 1/2017 | Wei et al. |
| 9,549,852 B2 | 1/2017 | de Juan et al. |
| 9,555,045 B2 | 1/2017 | Garrigue et al. |
| 9,561,282 B2 | 2/2017 | Dadey et al. |
| 9,572,800 B2 | 2/2017 | Zarnitsyn et al. |
| 9,636,189 B2 | 5/2017 | Ahari et al. |
| 9,707,173 B2 | 7/2017 | Kabra |
| 9,707,238 B2 | 7/2017 | Chang et al. |
| 9,750,636 B2 | 9/2017 | Rubin et al. |
| 9,775,906 B2 | 10/2017 | Sawhney, II et al. |
| 9,828,356 B2 | 11/2017 | Wei et al. |
| 9,849,082 B2 | 12/2017 | de Juan et al. |
| 9,931,330 B2 | 4/2018 | Zarnitsyn et al. |
| 9,937,073 B2 | 4/2018 | de Juan et al. |
| 9,949,942 B2 | 4/2018 | Butuner |
| 10,004,636 B2 | 6/2018 | Alster et al. |
| 10,010,610 B2 | 7/2018 | Horn |
| 10,064,872 B2 | 9/2018 | Chang et al. |
| 10,100,028 B2 | 10/2018 | Yiannikouros et al. |
| 10,111,886 B2 | 10/2018 | Ng et al. |
| 10,300,014 B2 | 2/2019 | de Juan et al. |
| 10,226,417 B2 | 3/2019 | Jarrett et al. |
| 10,245,178 B1 | 4/2019 | Heitzmann et al. |
| 10,251,954 B2 | 4/2019 | Sawhney et al. |
| 10,278,919 B2 | 5/2019 | Robinson et al. |
| 10,383,817 B2 | 8/2019 | de Juan et al. |
| 10,420,724 B2 | 9/2019 | Jarrett et al. |
| 10,434,009 B2 | 10/2019 | Rapacki et al. |
| 10,441,543 B2 | 10/2019 | Spada et al. |
| 10,456,293 B2 | 10/2019 | Rubin et al. |
| 10,617,563 B2 | 4/2020 | Jarrett et al. |
| 10,736,774 B2 | 8/2020 | Alster et al. |
| 10,744,099 B2 | 8/2020 | Libin et al. |
| 10,786,462 B2 | 9/2020 | Jarrett et al. |
| 10,835,416 B2 | 11/2020 | de Juan et al. |
| 10,849,656 B2 | 12/2020 | Navratil et al. |
| 10,864,218 B2 | 12/2020 | Hughes |
| 10,874,605 B2 | 12/2020 | Nivaggioli et al. |
| 10,874,606 B2 | 12/2020 | de Juan, Jr. et al. |
| 10,905,765 B2 | 2/2021 | Jarrett et al. |
| 11,285,109 B2 | 3/2022 | Enomura et al. |
| 11,622,935 B2 | 4/2023 | Blizzard et al. |
| 2002/0169409 A1 | 11/2002 | Gillespie |
| 2003/0108511 A1 | 6/2003 | Sawhney |
| 2005/0197614 A1 | 9/2005 | Pritchard et al. |
| 2005/0232972 A1 | 10/2005 | Odrich |
| 2007/0298075 A1 | 12/2007 | Borgia et al. |
| 2008/0124400 A1 | 5/2008 | Liggins et al. |
| 2008/0140192 A1 | 6/2008 | Humayun et al. |
| 2008/0247984 A1 | 10/2008 | Messersmith et al. |
| 2010/0278898 A1 | 11/2010 | Hughes et al. |
| 2012/0059338 A1 | 3/2012 | Beeley et al. |
| 2012/0156259 A1 | 6/2012 | Rau et al. |
| 2014/0121612 A1 | 5/2014 | Rubin et al. |
| 2014/0128478 A1 | 5/2014 | Asgharian et al. |
| 2014/0371308 A1 | 12/2014 | Hughes |
| 2015/0272898 A1 | 10/2015 | Hughes et al. |
| 2015/0374633 A1 | 12/2015 | Fedorchak et al. |
| 2016/0296627 A1 | 10/2016 | Garcia et al. |
| 2016/0331738 A1 | 11/2016 | Jarrett et al. |
| 2016/0354309 A1 | 12/2016 | Heitzmann et al. |
| 2017/0037002 A1 | 2/2017 | Vajda et al. |
| 2017/0073323 A1 | 3/2017 | Wei et al. |
| 2017/0182173 A1 | 6/2017 | Ng et al. |
| 2018/0085307 A1 | 3/2018 | Sawhney et al. |
| 2018/0353431 A1 | 12/2018 | Guo et al. |
| 2019/0021991 A9 | 1/2019 | Heitzmann et al. |
| 2019/0038636 A1 | 2/2019 | Vrabec |
| 2019/0216727 A1 | 7/2019 | Odrich et al. |
| 2019/0224046 A1 | 7/2019 | Heitzmann et al. |
| 2019/0336441 A1 | 11/2019 | Whitcup et al. |
| 2020/0038326 A1 | 2/2020 | Spada et al. |
| 2020/0113836 A1 | 4/2020 | Bae et al. |
| 2020/0138701 A9 | 5/2020 | Odrich et al. |

(56) References Cited

U.S. PATENT DOCUMENTS

| | | | |
|---|---|---|---|
| 2020/0206137 A1 | 7/2020 | Gambino et al. | |
| 2020/0246222 A1 | 8/2020 | Malanga et al. | |
| 2020/0261878 A1 | 8/2020 | Kim | |
| 2020/0306182 A1 | 10/2020 | Das et al. | |
| 2020/0337990 A1 | 10/2020 | Goldstein et al. | |
| 2020/0345544 A1 | 11/2020 | Ketelson et al. | |
| 2020/0345750 A1 | 11/2020 | Chang et al. | |
| 2020/0383915 A1 | 12/2020 | Jablonski et al. | |
| 2021/0007973 A1 | 1/2021 | Patel et al. | |
| 2021/0196729 A1 | 7/2021 | Hughes | |
| 2021/0283057 A1 | 9/2021 | Morinaga et al. | |
| 2022/0168224 A1 | 6/2022 | Enomura et al. | |

FOREIGN PATENT DOCUMENTS

| | | | |
|---|---|---|---|
| WO | 2010111449 A1 | 9/2010 | |
| WO | 2013039706 A1 | 3/2013 | |
| WO | 2013/086015 | 6/2013 | |
| WO | 2016/094646 | 6/2016 | |
| WO | 2016/183296 | 11/2016 | |
| WO | 2017/015591 | 1/2017 | |
| WO | 2017015616 A1 | 1/2017 | |
| WO | 2017015675 A1 | 1/2017 | |
| WO | 2017019773 A1 | 2/2017 | |
| WO | 2017/091749 | 6/2017 | |
| WO | 2018/058048 | 3/2018 | |
| WO | 2018058048 A1 | 3/2018 | |
| WO | 2019094652 A1 | 5/2019 | |
| WO | 20190946252 * | 5/2019 | ........... A61F 9/0017 |
| WO | 2020/219892 | 10/2020 | |

OTHER PUBLICATIONS

U.S. Appl. No. 16/857,464, filed Apr. 24, 2020.
U.S. Appl. No. 18/384,564, filed Oct. 27, 2023.
DURYSTA Prescribing Information, 2020 Allergan, 10 pgs.
Goldstein, et al., "A Prospective Multicenter, Open-Label First-in-Human Study to Evaluate the Safety, Tolerability and Efficacy of OTX-TIC, a Travoprost Intracameral Implant in Subjects with Primary Open-Angel Glaucoma or Ocular Hypertension: Preliminary Findings," Presented at the Association for Research in Vision and Ophthalmology Annual Meeting: Vancover, Canada, Apr. 28 May 2, 2019, 1 pg.
Blizzard, et al.,, Preclinical Assessment of OTX-TIC (Travoprost) Biodegradable Hydrogel Intracameral Implant for the Treatment of Glaucoma, ASCRS 2018, Apr. 15, 2018, 8 pgs.
Walters, et al., Evaluating the Safety, Tolerability and Efficacy of OTX-TIC, a Travoprost Intracameral Implant, in Subjects with Glaucoma: Interim Review, ASCRS 2019, May 5, 2019, 13 pgs.
Hart, et al., Trasforming Glaucoma Care with Drug Delivery Leveraging a Novel Technology Platform, Glaucoma 360, Feb. 1, 2019, 11 pgs.
Goldstein, et al., "Evaluating Safety Tolerability and Efficacy of an Intracameral Hydrogel-Based Travoprost Implant in Subjects with Glaucoma or Ocular Hypertension Phase 1 Trail Interim Review," ARVO Annual Meeting, May 2020, 13 pgs.
Langh, et al., "Effect of Hydrogel Persistence on Pharmacodynamics and Tolerability of OTX-TIC, Travoprost Intracameral Implant in Beagles," ARVO Annual Meeting, May 2020, 8 pgs.

Walters, et al., "Evaluating Safety, Tolerability and Efficacy of an Intracameral Hydrogel-Based Travoprost Implant in Subjects with Glaucoma Phase 1 Trial Interim Review," ASCRS Annual Meeting, May 16, 2020, 12 pgs.
Goldstein, Michael, "Transforming Glaucoma Care with Drug Delivery Leveraging a Novel Technology Platform," Glaucoma 360, Feb. 7, 2020, 16 pgs.
Goldstein, Michael, "OTX-TIC, an Intracameral Hydrogel-Based Travoprost Implant to Treat Patients with Glaucoma & Ocular Hypertension Phase 1 Trail Update," Glaucoma 360, Jan. 2021, 17 pgs.
Blizzard, et al., "Efficacy and Pharmacokinetics of a Sustained Release Travoprost Intracameral Hydrogel Implant in Beagle Dogs," presented at the Association for Research in Vision and Ophthalmology 2018 Annual Meeting: Honolulu, HI, Apr. 29-May 3, 2018, 1 pg.
Driscoll, et al., "Safety Analysis of a Sustained Release Travoprost Intracameral Hydrogel Implant in Beagle Dogs," Presented at the Association for Research in Vision and Ophthalmology 2018 Annual Meeting: Hanolulu HI, Apr. 29-May 3, 2018, 1 pg.
Blizzard, et al., "Pharmacokinetics of OTX-TIC, a Sustained Release Travoprost Intracameral Implant in Rabbits," Presented at the Assciation for Research in Vision and Ophthalmology Annual Meeting: Vancover, Canada, Apr. 28 May 2, 2019, 1 pg.
Driscoll, et al., "Effect of OTX_TIC, a Sustained Release Travoprost Intracameral Implant on Central Corneal Thickness in Beagles," Presented at the Association for Research in Vision and Ophthalmology Annual Meeting: Vancover, Canada, Apr. 28 May 2, 2019, 1 pg.
International Search Report and Written Opinion for PCT/US2021/016889 mailed May 28, 2021, 14 pages.
Declaration under 37 C.F.R. 1.132 dated Aug. 5, 2021 filed in U.S. Appl. No. 15/714,633.
"Error in Measurement", ([online] retrieved on Sep. 7, 2021 from https://mathbitsnotebook.com/Algebra1/Units/UNError.html; 3 pages). Year: 2021.
Encyclopeida.com "intracameral" [online] retrieved from: https://www.encyclopedia.com/caregiving/dictionaries-thesauruses-pictures-and-press-releases/intracameral; on May 26, 2021; 1 page). Year: 2021.
International Search Report for PCT/US2020/0029830 mailed Aug. 5, 2020, 4 pages.
Written Opinion of the International Searching Authority for PCT/US2020/029830 mailed Aug. 5, 2020, 6 pages.
Mattessich, et al., "Transforming Drug Delivery Leveraging a Novel Technology Platform," Sep. 2020.
Ocular Therapeutix™ Reports Second Quarter 2020 Financial Results and Business Update, Newly Published Physician Fee Schedules for 0356T for the Administration of Intracanalicular Inserts to Support Ongoing DEXTENZA® Launch, Firefox, 9 pgs.
Mattessich, et al. "Transforming Drug Delivery Leveraging a Novel Technology Platform," Oct. 10, 2020.
Bacharach et al., "Phase 3, Randomized, 20-Month Study of the Efficacy and Safety of Bimatoprost Implant in Patients with Open-Angle Glaucoma and Ocular Hypertension (ARTEMIS 2)". Drugs, vol. 81 No. 17, pp. 2017-2033, published by Adis.
Rahic et al., "Novel Drug Delivery Systems Fighting Glaucoma: Formulation Obstacles and Solutions", Pharmaceutics, vol. 13, No. 28, pp. 1-58, published by MDPI.
Ocular Therapeutix™ Provides 2022 Year End Corporate Update and Reviews Expected 2023 Milestones, Jan. 6, 2023, 3 pgs.

* cited by examiner

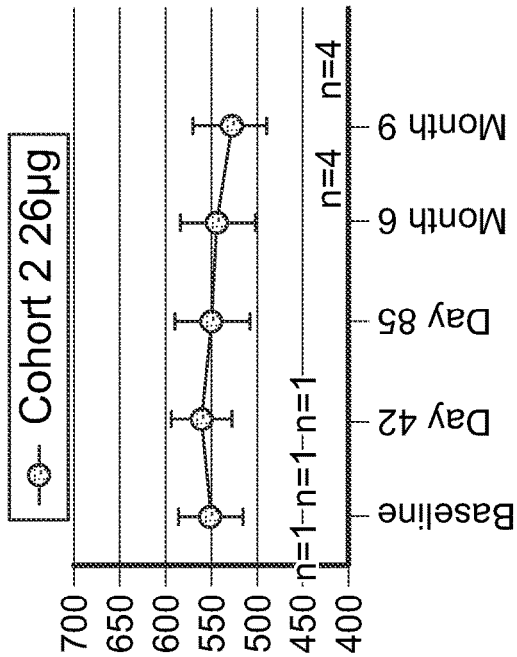
Fig. 3b
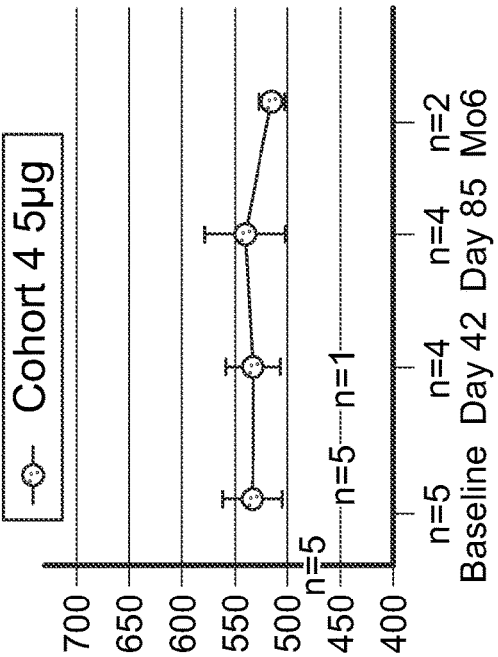
Fig. 3d
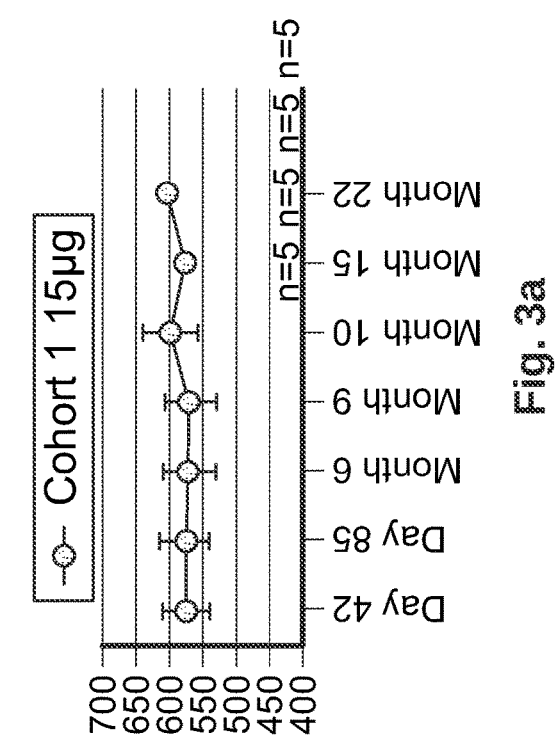
Fig. 3a
Fig. 3c

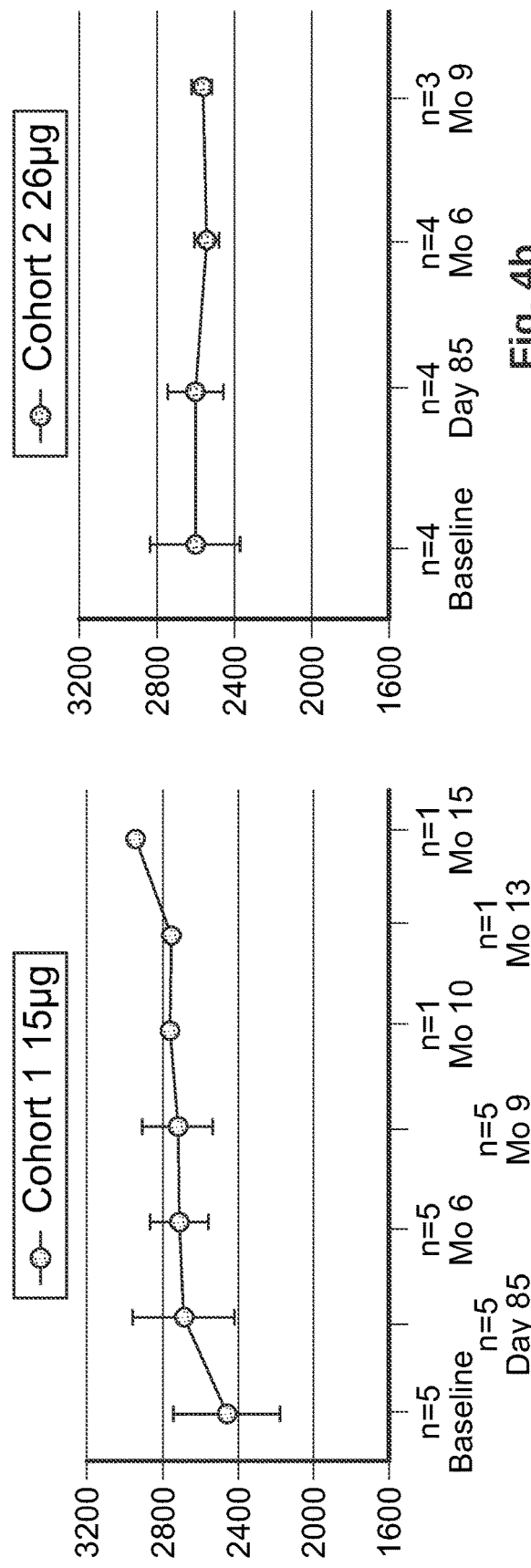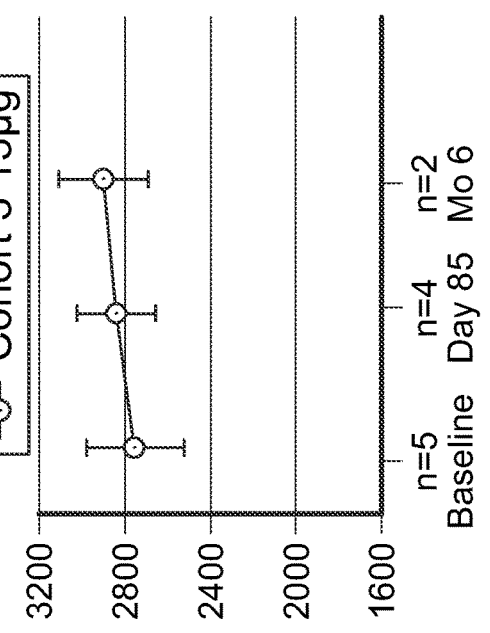
Fig. 4a
Fig. 4b
Fig. 4c

COMPOSITIONS AND METHODS FOR TREATING OCULAR DISEASES

TECHNICAL FIELD

The present invention relates to methods of treatment in human subjects with ocular diseases and corresponding intracameral implants. The present invention also relates to the treatment of the intraocular pressure in human subjects and corresponding intracameral implants. The present invention also relates to the treatment of the intraocular pressure in human subjects with ocular hypertension or glaucoma, e.g. open angle glaucoma. In certain embodiments the invention relates to an intracameral administration of a travoprost sustained release biodegradable intracameral implant.

BACKGROUND

Glaucoma is typically a progressive, chronic disease affecting millions of people (Simmons, S., T., Ophthalmic Formulations. Glaucoma Today Supplement to Advanced Ocular Care, 2010; The Eye Disease Prevalence Group., Prevalence of open-angle glaucoma among adults in the United States. Arch Ophthalmol, 2004. 122: p. 532-538). In fact, glaucoma has been reported to be one of the leading causes of irreversible blindness, and worldwide it is the second leading cause of blindness (Quigley, H. A. and A. T. Broman, The number of people with glaucoma worldwide in 2010 and 2020. Br J Ophthalmol, 2006. 90(3): p. 262-7). Some have projected that by the year 2040 more than 110 million people would be diagnosed with glaucoma (Tham, Y.-C., et al., Global Prevalence of Glaucoma and Projections of Glaucoma Burden through 2040. 8 Ophthalmology, 2014. 121(11): p. 2081-2090).

Glaucoma is defined as optic neuropathy leading to the loss of retinal ganglion cells and their axons and progressing in later stages to loss of visual field and, in very advanced cases, central visual acuity. Open-angle glaucoma is the most common form of the disease and primary open angle glaucoma (POAG) refers to eyes with open anterior drainage angles and elevated IOP.

Elevated fluid pressure within the eye (i.e., elevated intraocular pressure (IOP)), defined as pressures above the normal range of 10 to 21 mmHg, is the main risk factor for glaucoma. People with elevated IOP levels without any current optic-nerve damage are diagnosed with ocular hypertension, as opposed to glaucoma. However, people with ocular hypertension may be at risk of progressive damage to the optic nerve (glaucoma).

For both glaucoma and ocular hypertension (OHT), the most critical factor for effective therapy is to lower the IOP, and in doing so, the disease progression may be slowed along with the rate of visual field loss. Drugs that are classified as prostaglandins have been shown to effectively lower IOP (AAO, Glaucoma Preferred Practice Pattern. 2015). The Preferred Practice Patterns of the AAO recommend prostaglandins as the first line of therapy for POAG and OHT. The most commonly prescribed topical medications for the treatment of glaucoma in the United States are the prostaglandin analogues.

Travoprost is for example a suitable synthetic prostaglandin F 2α analogue. Its chemical name is (isopropyl (Z)-7-[(1R,2R,3R,5S)-3,5-dihydroxy-2-[(1E,3R)-3-hydroxy-4-[(α,α,α-trifluoro-m-isopropyl-tolyl)oxy]-1-butenyl]-cyclopentyl]-5-heptenoate. This prodrug is a synthetic prostaglandin analogue that is enzymatically converted to a free acid form in human cornea (Al-Jazzaf, A. M., L. DeSantis, and P. A. Netland, Travoprost: a potent ocular hypotensive agent. Drugs Today (Barc), 2003. 39(1): p. 61-74). Travoprost free acid like all prostaglandins is a selective FP prostanoid receptor agonist which is believed to reduce intraocular pressure by increasing trabecular meshwork and uveoscleral outflow (Lim, K. S., et al., Mechanism of action of bimatoprost, latanoprost, and travoprost in healthy subjects. A crossover study. Ophthalmology, 2008. 115(5): p. 790-795 e4 and Toris, C. B., B. A. T. Gabelt, and P. L. Kaufman, Update on the Mechanism of Action of Topical Prostaglandins for Intraocular Pressure Reduction. Survey of Ophthalmology, 2008. 53(6, Supplement): p. S107-S120). Travoprost is the active ingredient in Travatan®, Travatan Z® (Appendix A: package insert), and Izba™ (all Alcon Laboratories, Inc., Ft Worth, TX), which are all topical ophthalmic solutions intended to reduce elevated IOP. The dosage is typically one drop daily of a 0.004% or 0.003% solution applied daily to the affected eye(s).

Successful treatment for glaucoma requires daily self-administered treatment with topical eye drops. While topical antihypertensive medication may be effective in treating glaucoma, any one of the available therapies will only be as effective as the adherence to administration by individual patients. Known limitations associated with the application of topical eye drops include: (1) difficulty in administering drops, (2) limited accuracy of drops getting into the eye, (3) potential washout of drops by lacrimation or subsequent administration of other drops, (4) the need for a caregiver to administer drops and (5) poor subject compliance (Toris, C. B., B. A. T. Gabelt, and P. L. Kaufman, Update on the Mechanism of Action of Topical Prostaglandins for Intraocular Pressure Reduction. Survey of Ophthalmology, 2008. 53(6, Supplement): p. S107-S120). Kholdebarin, et al (Kholdebarin, R., et al., Multicenter study of compliance and drop administration in glaucoma. Can J Ophthalmol, 2008. 43(4): p. 454-61) reported that 34b of patients used improper administration technique. For some patients there is the need to administer multiple drops and this may compound the situation due to washout effects. In one study, nearly 9% of the patients who required more than one medication in the same eye failed to wait at least three minutes between administrations. Importantly, regardless of the number of medications, patients are expected to remain on treatment indefinitely and motivation to do so plays an important role. Accordingly, there is a need to provide an alternative to the daily administration of single or multiple eye drops for the treatment of glaucoma, especially in an aging population with the disease.

The risk of potential blindness as a long-term effect increases in cases of poorly managed glaucoma, and patient compliance becomes an important issue. Studies have shown that less than 50% of glaucoma patients continue therapy and refill prescriptions as required (Friedman, D. S., et al., Using Pharmacy Claims Data to Study Adherence to Glaucoma Medications: Methodology and Findings of the Glaucoma Adherence and Persistency Study (GAPS). Investigative Ophthalmology & Visual Science, 2007. 48(11): p. 5052-5057), and most patients are likely to discontinue use of a topical therapy within 1.2 years after filling their first prescription according to health insurance claims (Nordstrom, B. L., et al., Persistence and Adherence With Topical Glaucoma Therapy. American Journal of Ophthalmology, 2005. 140(4): p. 598.e1-598.e11). Thus, a delivery system that would provide long-term, 24 hour control of IOP could address a multitude of issues and potentially delay or prevent loss of vision resulting from glaucoma for a patient.

Drug delivery to the anterior segment continues to be a challenge with the ultimate goal of improving patient compliance, achieving an excellent safety profile and providing for sustained delivery over an extended period of time (Yellepeddi, V. K. and S. Palakurthi, Recent Advances in Topical Ocular Drug Delivery. Journal of Ocular Pharmacology and Therapeutics, 2015. 32(2): p. 67-82).

DURYSTA®, a bimatoprost intracameral implant approved by the FDA, is indicated for the reduction of intraocular pressure in patients with open angle glaucoma or ocular hypertension. The implant is limited to a single implant per eye without retreatment due to possible corneal endothelial cell loss and corneal adverse reactions and should be used with caution in patients with narrow angles or anatomical angle obstructions. Efficacy was evaluated in two multicenter, randomized, parallel-group, controlled 20-month (including 8-month extended follow-up) studies of DURYSTA compared to twice daily topical timolol 0.5% drops, in patients with open angel glaucoma or ocular hypertension. DURYSTA demonstrated an intraocular pressure reduction of approximately 5-8 mmHg in patients with a mean baseline intraocular pressure of 24.5 mmHg. The data show a raise in intraocular pressure for the DURYSTA group above the timolol group after week 12. DURYSTA® is an intracameral implant containing 10 μg of bimatoprost, in a solid polymer sustained-release drug delivery system. The drug delivery system consists of poly (D,Llactide), poly (D,L-lactide-co-glycolide), poly (D,L-lactide) acid end, and polyethylene glycol 3350. (Prescribing information revised November 2020).

OBJECTS AND SUMMARY OF THE INVENTION

It is an object of certain embodiments of the present invention to provide an implant suitable for being inserted into the anterior chamber of the eye (intracameral implant) with dimensions small enough to fit into the iridocorneal angle of the eye when inserted. In particular the implant should have a size small enough to fit a wide range of iridocorneal angle sizes including narrow angels.

It is an object of certain embodiments of the present invention to provide an implant suitable for being inserted into the anterior chamber of the eye (intracameral implant) with dimensions small enough to fit into the iridocorneal angle of the eye and gets fixated in the iridocorneal angle during the period of treatment and/or until it is biodegraded.

It is an object of certain embodiments of the present invention to provide an implant suitable for being inserted into the anterior chamber of the eye (intracameral implant) which after insertion swells due to the uptake of aqueous humor and becomes increasingly soft before it dissolves and fully degrades.

Another object of certain embodiments of the present invention is to provide a travoprost sustained release biodegradable intracameral implant and corresponding method of treatment with limited movement of the implant.

Another object of certain embodiments of the present invention is to provide a travoprost sustained release biodegradable intracameral implant which is gentle to the endothelium.

It is an object of certain embodiments of the present invention to provide a method and corresponding use of treating ocular diseases in human subjects for an extended period of time, e.g. ranging from about 1 to about 24 months.

It is an object of certain embodiments of the present invention to provide a method and corresponding use of treating ocular diseases in human subjects for an unlimited period of time.

It is an object of certain embodiments of the present invention to provide a method and corresponding use for safely and effectively treating the intraocular pressure in human subjects for an extended period of time, e.g. ranging from about 2 to about 12 months or 3 to about 9 months, e.g. for about 3 to about 4 months or for about 3 to about 6 months or for about 6 to about 9 months.

It is an object of certain embodiments of the present invention to provide a method and corresponding use for safely and effectively treating the intraocular pressure in human subjects for an unlimited period of time.

It is an object of certain embodiments of the present invention to provide a method and corresponding use for safely and effectively treating the intraocular pressure in human subjects with ocular hypertension or glaucoma, e.g. open angle glaucoma, for an extended period of time, e.g. ranging from about 2 to about 12 months or from about 3 to about 9 months, e.g. for about 3 to about 4 months or about 3 to about 9 months for about 6 to about 9 months.

It is an object of certain embodiments of the present invention to provide a method and corresponding use for safely and effectively treating the intraocular pressure in human subjects with ocular hypertension or glaucoma, e.g. open angle glaucoma, for an unlimited period of time.

Another object of certain embodiments of the present invention to provide a prostaglandin antagonist (e.g., travoprost) sustained release biodegradable intracameral implant which provides a constant or substantially constant prostaglandin antagonist release with limited burst at the beginning for safely and effectively treating the intraocular pressure in human subjects with ocular hypertension or glaucoma, e.g. open angle glaucoma.

Another object of certain embodiments of the present invention is to provide a prostaglandin antagonist (e.g., travoprost) sustained release biodegradable intracameral implant and corresponding method of treatment which do not cause inconvenience or discomfort once implanted into the anterior chamber of the human subject's eye, such as a sensation of having a foreign object in the eye or eye pain.

Another object of certain embodiments of the present invention is to provide a method for preservative free treating the intraocular pressure in human subjects.

Another object of certain embodiments of the present invention is to provide a travoprost sustained release biodegradable intracameral implant and corresponding method of treatment and wherein the implant is cosmetically invisible.

Another object of certain embodiments of the present invention is to provide a travoprost sustained release biodegradable intracameral implant and corresponding method of treatment wherein the implant can be monitored in the eye.

Another object of certain embodiments of the invention is to provide a prostaglandin antagonist (e.g., travoprost) release biodegradable intracameral implant which is easily insertable into the human subject's eye, such as the anterior chamber or the posterior chamber of the human subject's eye.

Another object of certain embodiments of the present invention is to provide a prostaglandin antagonist (e.g., travoprost) sustained release biodegradable intracameral implant which is sufficiently small to be inserted into the human subject's eye, such as the anterior chamber or the posterior chamber of the human subject's eye.

Another object of certain embodiments of the present invention is to provide a travoprost sustained release biodegradable intracameral implant and corresponding method of treatment which is biodegradable in a residual-free manner once inserted into the anterior chamber of the human subject's eye and does not need to be removed by a surgery, i.e. the implant is fully biodegradable.

Another object of certain embodiments of the present invention is to provide a travoprost sustained release biodegradable intracameral implant and corresponding method of treatment which can be used for a continuous treatment of the intraocular pressure associated with open angle glaucoma and/or ocular hypertension in a human subject.

Another object of certain embodiments of the present invention is to provide a travoprost sustained release biodegradable intracameral implant and corresponding method of treatment, wherein said implant provides a long-term treatment effect.

Another object of certain embodiments of the present invention is to provide a travoprost sustained release biodegradable intracameral implant and corresponding method of treatment, wherein said implant provides a long-term treatment effect and causes no change of pachymetry and endothelial cell count. One or more of these objects of the present invention and others are solved by one or more embodiments as disclosed and claimed herein.

The individual aspects of the present invention are disclosed in the specification and claimed in the independent claims, while the dependent claims claim particular embodiments and variations of these aspects of the invention. Details of the various aspects of the present invention are provided in the detailed description below.

BRIEF DESCRIPTION OF THE DRAWINGS

FIG. 3a Average pachymetry for cohort 1 of the clinical phase 1 study from baseline to month 22.

FIG. 3b Average pachymetry for cohort 2 of the clinical phase 1 study from baseline to month 9.

FIG. 3c Average pachymetry for cohort 3 of the clinical phase 1 study from baseline to month 9.

FIG. 3d Average pachymetry for cohort 4 of the clinical phase 1 study from baseline to month 6.

FIG. 4a Average ECC for cohort 1 of the clinical phase 1 study from baseline to month 9.

FIG. 4b Average ECC for cohort 2 of the clinical phase 1 study from baseline to month 9.

FIG. 4c Average ECC for cohort 3 of the clinical phase 1 study from baseline to month 6.

DEFINITIONS

Figure 1A:
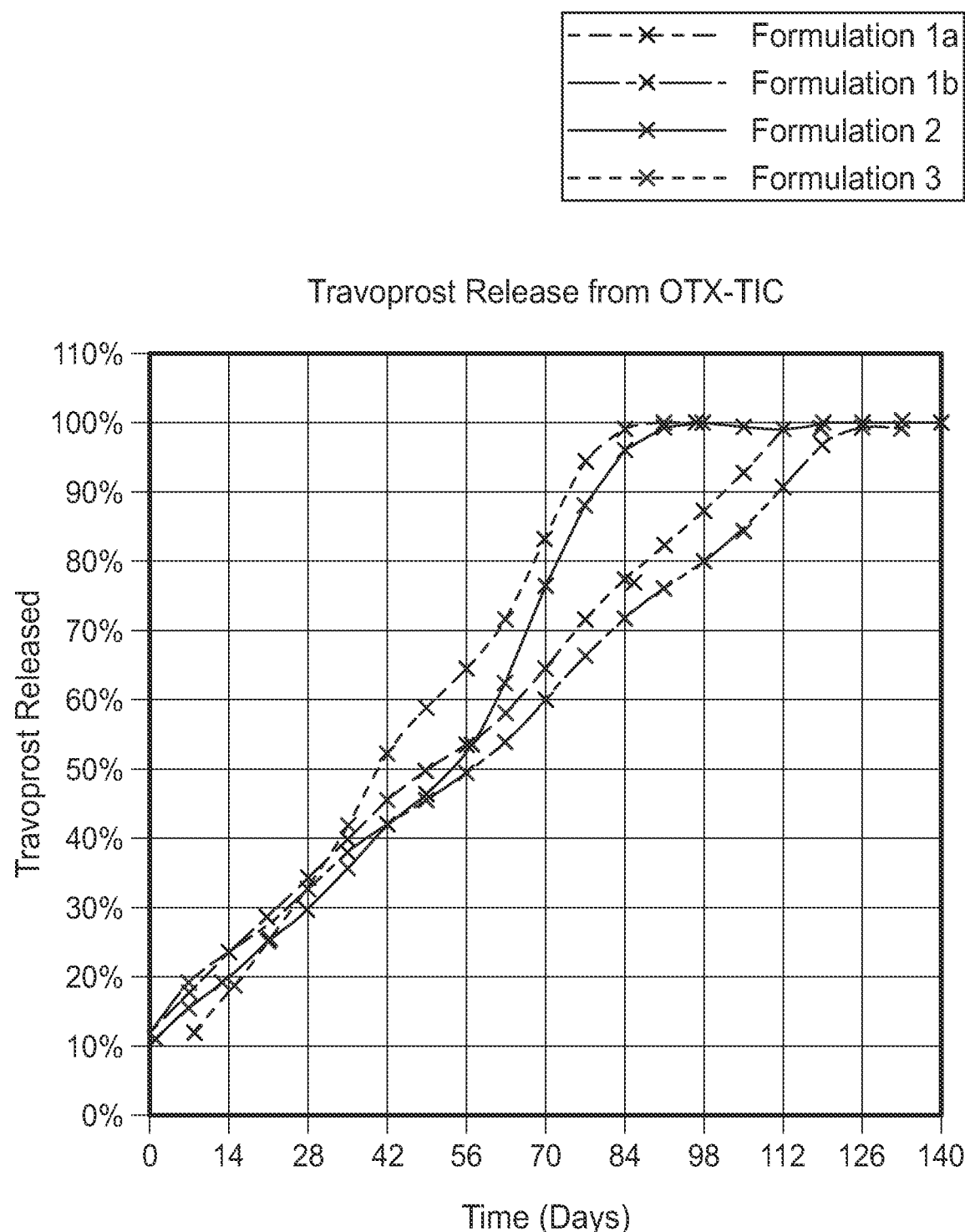
FIG. 1a An illustration of in vitro releases of formulations 1a, 1b, 2 and 3 measured at 37° C.

The term "intracameral implant" as used herein is interchangeably used with the term "intracameral insert" and refers to an object that contains an API, such as a prostaglandin antagonist (e.g., travoprost) and that is suitable to be administered, i.e. inserted to the anterior segment of the eye where it remains for a certain period of time while it releases the active agent into the surrounding environment e.g. the aqueous humor. The implant could likewise be inserted into the posterior segment. An implant is in the form of a fiber before being inserted, which shape may be maintained to a certain degree upon placing the implant into the desired location, although dimensions of the implant (e.g. length and/or diameter) may change after administration due to hydration as further disclosed herein. In other words, what is inserted into the eye is not a solution or suspension, but an already shaped, defined object. The implant is completely formed, e.g., according to the methods disclosed herein, prior to being administered. An intracameral implant can be designed to be biodegradable over the course of time (as disclosed below), and thus may thereby soften, change its shape and/or decrease in size, and ultimately might be eliminated/biodegraded either by complete dissolution or disintegration. In the present invention the term "implant" is used to refer both to an implant in a hydrated (also called "swollen") state when it contains water (e.g. after the implant has been (re-)hydrated once administered to the eye or otherwise immersed into an aqueous environment) and to an implant in its dry (dried/dehydrated) state, e.g., when it has been dried to a low water content of e.g. not more than 1% by weight or when the preparation results in a low water content insert without the necessity of a drying step. The water content of the implant is measured using a Karl Fischer coulometric method, such as shown in Example 2c.

The term "inserted" is interchangeably used with the terms "placed" or "injected" or "administered" or "implanted". Each term describes the intracameral implantation of the OTX-TIC implant into the anterior chamber of the eye where it then resides in the iridocorneal angle.

The term "ocular" as used in the present invention refers to the eye in general, or any part or portion of the eye (as an "ocular implant" can in principle be administered to any part or portion of the eye). The present invention in certain embodiments is directed to intracameral injection of an ocular implant, and to the lowering of the intraocular pressure in subjects with glaucoma and/or ocular hypertension, as further disclosed below.

The term "biodegradable" refers to a material or object (such as the intracameral implant according to the present invention) which becomes degraded in vivo, i.e., when placed in the human body. In the context of certain embodiments of the present invention, as disclosed in detail herein below, the implant comprising the hydrogel within which the active ingredient is contained, slowly biodegrades over time once administered into the anterior segment of the eye, and which resides within the iridocorneal angle of the eye. In certain embodiments, biodegradation takes place at least in part via ester hydrolysis in the aqueous environment of the anterior segment of the eye. The implant slowly softens and disintegrates, resulting in clearance through the liquefying and clearing through aqueous humor outflow pathways.

A "hydrogel" is a three-dimensional network of one or more hydrophilic natural or synthetic polymers (as disclosed herein) that can swell in water and hold an amount of water while maintaining or substantially maintaining its structure, e.g., due to chemical or physical cross-linking of individual polymer chains. Due to their high-water content, hydrogels are soft and flexible, which make them similar to natural tissue. In the present invention the term "hydrogel" is used to refer both to a hydrogel in the hydrated state when it contains water (e.g. after the hydrogel has been formed in an aqueous solution, or after the hydrogel has been hydrated or (re-)hydrated once inserted into the eye or otherwise immersed into an aqueous environment) and to a hydrogel in its dry (dried/dehydrated) state, e.g., when it has been dried to a low water content of e.g. not more than 1% by weight or when the preparation results in a low water content insert without the necessity of a drying step. In the present invention, wherein an active principle is contained (e.g. dispersed) in a hydrogel, the hydrogel may also be referred to as a "matrix".

The term "polymer network" describes a structure formed of polymer chains (of the same or different molecular structure and of the same or different molecular weight) that are cross-linked with each other. The types of polymers suitable for the purposes of the present invention are disclosed herein below. The polymer network may be obtained by reacting an electrophilic group-containing multi-arm-polymer precursor with a nucleophilic group-containing cross-linking agent.

The term "fiber" as disclosed herein refers to a shape that is essentially cylindrical and characterized by a diameter and a length.

The term "amorphous" refers to a polymer or polymer network, which does not exhibit crystalline structures in X-ray or electron scattering experiments.

The term "semi-crystalline" refers to a polymer or polymer network, which possesses some crystalline character, i.e., exhibits some crystalline properties in X-ray or electron scattering experiments.

As used herein, "homogenously dispersed" means the component, such as the travoprost or travoprost particles, are uniformly dispersed throughout the hydrogel or polymer network The term "precursor" herein refers to those molecules or compounds that are reacted with each other and that are thus connected via crosslinks to form a polymer network and thus a hydrogel matrix. While other materials might be present in the hydrogel, such as APIs or buffers, they are not referred to as "precursors".

The parts of the precursor molecules that are still present in a final polymer network are also called "units" herein. The "units" are thus the building blocks or constituents of a polymer network forming the hydrogel. For example, a polymer network suitable for use in the present invention may contain identical or different polyethylene glycol units as further disclosed herein.

The term "sustained release" for the purposes of the present invention is meant to characterize products which are formulated to make the API available over an extended period of time, thereby allowing a reduction in dosing frequency compared to an immediate release dosage form, such as a solution of API that is topically applied onto the eye (such as travoprost-comprising eye drops). Other terms that may be used herein interchangeably with "sustained release" are "extended release" or "controlled release". Within the meaning of the invention, the term "sustained release" comprises constant API release in vitro.

The term "blend of particles" defines a mixture of particles, wherein each component of the mixture has an individual composition.

The term "repeated dose", "repeated application" or "repeated use" as used herein, refers to a further treatment by intracamerally inserting the API-containing intracameral implant of the present invention into the anterior chamber of the eye, after the same eye has been treated before using an equal or similar intracameral implant according to the present invention, after the intracameral implant used before has been biodegraded within the eye. This includes continued treatment such as treatment for an unlimited period of time by repeated application.

The term "polylactide" as used herein usually refers to homopolymers obtained by polycondensation of lactic acid. In other words, a polylactide consists of lactic acid monomer units. Such polylactide can have an acid or an ester end group but is not constituted of other monomer units in the polymer backbone such as poly(lactic-co-glycolic acid). Polylactide can be formed by polymerization of D-Lactic acid, L-Lactic acid, or any mixture of D-lactic acid and L-lactic acid. The final polylactide may be called D,L-polylactide in the latter case.

The term "inherent viscosity" is used to denote a physical parameter of the polylactides (PLAs) used herein. The different molecular weight polymers are described as 4A, 7A, 9A and 5.5E PLA where the numerical value designates the target inherent viscosity (IV) of the polymer in chloroform which correlates to the PLA molecular weight and the letter suffix designates acid (A) or ester (E) end group. When measured in 0.5% w/v chloroform at 30° C., 4A PLA has an inherent viscosity of 0.35 to 0.45 dl/g; 7A PLA has an inherent viscosity of 0.60 to 0.80 dl/g and 9A PLA has an inherent viscosity of 0.80 to 1.0 dl/g. When measured in 0.1% w/v chloroform at 25° C., 5.5E PLA has an inherent viscosity of 0.55 to 0.75 dl/g.

The term "travoprost burst" as used herein denotes a rapid initial release of travoprost from the implant within a relatively short interval after insertion, e.g. for the first day following insertion. A travoprost burst may have an amount of a travoprost release between 10 and 20%, such as about 10 to about 15% or less than 15% (based on the total weight of travoprost in the intracameral implant) within one day, e.g. day 1, measured in vitro under physiological conditions as described herein, e.g. simulated physiological sink conditions in 50 mL of 1×PBS, 0.5% castor oil, 0.01% sodium fluoride buffer at pH 7.2-7.4 at 37° C. The term "burst" may also be used with respect to other active agents disclosed herein. According to the invention the burst is minimized.

The term "extended period of time" as used herein refers to any period of time that would be considered by those of ordinary skill in the art as being extended with respect to treating a disease, and in particular refers to periods such as at least about 1 week, or at least about 1 month or longer, such as up to about 24 months, or any intermediate periods such as specifically mentioned herein such as about 2 to 12 months or 3 to about 9 months, about 4 to about 7 months, about 3 to about 6 months.

The term "visualization agent" as used herein refers to a molecule or composition that is contained within the hydrogel of an implant providing the possibility to easily visualize the implant when inserted into the anterior segment of the eye. The visualization agent may be a fluorophore such as fluorescein, rhodamine, coumarin, and cyanine. In certain embodiments the visualization agent is fluorescein or includes a fluorescein moiety.

As used herein, the terms "aqueous humor" or "AH" refer to the liquid within the anterior chamber.

As used herein, the term "bilaterally" or "bilateral" refers—in the context of administration of the implants of the present invention- to an administration of the implants into both eyes of a patient. Independent for each eye.

The term "intracameral implant" refers to an implant that can be administered into the anterior segment of the eye, and which resides within the iridocorneal angle.

The terms "API", "active (pharmaceutical) ingredient", "active (pharmaceutical) agent", "active (pharmaceutical) principle", "(active) therapeutic agent", "active", and "drug" are used interchangeably herein and refer to the substance used in a finished pharmaceutical product (FPP) as well as the substance used in the preparation of such a finished pharmaceutical product, intended to furnish pharmacological activity or to otherwise have direct effect in the diagnosis, cure, mitigation, treatment or prevention of a disease, or to have direct effect in restoring, correcting or modifying physiological functions in a patient. In embodiments where the API is a prostaglandin antagonist, the agent may be, e.g., travoprost, bimatoprost or latanoprost.

The term "treat", "treating", or "treatment" are used interchangeably and refer to reversing, alleviating, delaying the onset of, or inhibiting the progress of a disclosed condition (e.g., ocular hypertension or glaucoma), or one or more symptoms thereof, as described herein. In other aspects, treatment may be administered in the absence of symptoms. For example, treatment may be administered to a susceptible individual prior to the onset of symptoms (e.g., in light of a history of symptoms and/or in light of exposure to a particular organism, or other susceptibility factors), i.e., prophylactic treatment. Treatment may also be continued after symptoms have resolved, for example to delay their recurrence.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Preferably, the subject is a human in need of treatment.

According to certain embodiments of the invention the API is travoprost. Travoprost, a prostaglandin F2a analogue, is a highly selective full agonist which has a high affinity for the prostaglandin FP receptor, and reduces the intraocular pressure by increasing the outflow of aqueous humor via trabecular meshwork and uveoscleral pathways. Travoprost is the isopropyl ester of a single enantiomer of the selective FP prostaglandin agonist, fluprostenol. Travoprost belongs to a class of prostaglandin F2a analogue prodrug esters (including latanoprost, bimatoprost, tafluprost) that facilitates corneal penetration and affords delivery of the active carboxylic acid (travoprost acid) to the aqueous humor. The prodrug esters are believed to be hydrolyzed by esterases in the cornea to the biologically active free acid in which carbons 17-20 have been substituted with a meta trifluoromethylphenoxy group. Compared to latanoprost, the free acid of travoprost was observed to have higher potency and greater selectivity for the FP prostanoid receptor based on results from in vitro binding affinity studies.

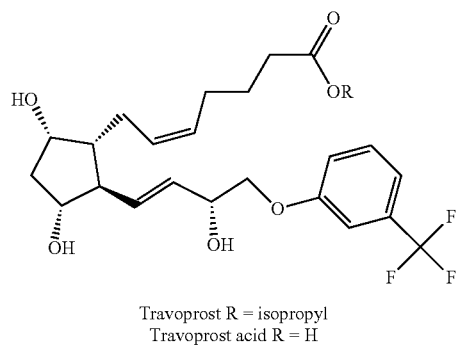

Travoprost R = isopropyl
Travoprost acid R = H

As used herein, the term "therapeutically effective" refers to the amount of API e.g. travoprost needed to produce a desired therapeutic result after administration. For example, in the context of the present invention, one desired therapeutic result would be the reduction of the IOP, e.g., as measured by in vivo tests known to the person of ordinary skill in the art. Amounts and doses of travoprost as provided herein refer to the isopropyl ester.

As used herein, the term "intraocular pressure" (IOP) is the fluid pressure inside the eye. Tonometry, such as Goldmann tonometry such as set forth in detail in Example 3 below, is the method eye care professionals use to determine IOP.

As used herein "pachymetry" is the method used to measure the central corneal thickness of a subject. Central corneal thickness measurements are carried out using an ultrasonic pachymeter such as defined in detail in Example 3 below.

As used herein, "endothelial cell count" or "ECC" is determined by specular microscopy as defined in Example 3 below.

As used herein, the term "glaucoma" may encompass the forms of open-angle glaucoma and angle-closure glaucoma. Subtypes of open-angle glaucoma disclosed herein may encompass normal-tension glaucoma, congenital glaucoma, secondary glaucoma, pigmentary glaucoma, pseudoexfoliative glaucoma, traumatic glaucoma, neovascular glaucoma, irido corneal endothelial syndrome (ICE), and/or uveitic glaucoma.

As used herein "no change of endothelial cell count occurring in the treated eye during the treatment period and/or entire treatment" means that the value of the endothelial cell count does not clinically meaningfully decrease. A single decrease of up to 20% from baseline in a subject during the treatment period and/or a continued decrease of up to 10% from baseline in a subject during the treatment period is clinically acceptable.

As used herein "no change of the thickness of the cornea or pachymetry occurs in the treated eye or during the treatment period and/or entire treatment" means that the value of the pachymetry does not clinically meaningfully decrease. A single decrease of up to 20% from baseline in a subject during the treatment period and/or a continued decrease of up to 10% from baseline in a subject during the treatment period is clinically acceptable.

As used herein, the term "open-angle glaucoma" is classified by ICD-10 Code H40. Open-angle glaucoma may be roughly classified into mild, moderate or severe open angle glaucoma.

As used herein, "ocular hypertension" usually refers to any situation in which the pressure inside the eye, i.e. IOP, is higher than normal. Eye pressure is measured in millimeters of mercury (mm Hg). Normal eye pressure is 21 mm Hg and lower, with an average of 16 mm Hg. Ocular hypertension is usually an eye pressure of above 21 mm Hg. The eye pressure is connected to the corneal thickness of an individual subject. Individuals with a thin cornea may have ocular hypertension despite of an intraocular eye pressure of below 21 mm Hg and individuals with a thick cornea may have normal eye pressure despite of an intraocular eye pressure of above 21 mm Hg. Therefore, it is also usual to apply a correction factor for the variation of the corneal thickness.

As used herein, the term "about" in connection with a measured quantity, refers to the normal variations in that measured quantity, as expected by one of ordinary skill in the art in making the measurement and exercising a level of care commensurate with the objective of measurement and the precision of the measuring equipment.

The term "at least about" in connection with a measured quantity refers to the normal variations in the measured quantity, as expected by one of ordinary skill in the art in making the measurement and exercising a level of care commensurate with the objective of measurement and precisions of the measuring equipment and any quantities higher than that.

As used herein, the singular forms "a," "an," and "the" include plural references unless the context clearly indicates otherwise.

The term "and/or" as used in a phrase such as "A and/or B" herein is intended to include both "A and B" and "A or B".

Open terms such as "include," "including," "contain," "containing" and the like mean "comprising." These open-ended transitional phrases are used to introduce an open ended list of elements, method steps, or the like that does not exclude additional, unrecited elements or method steps.

DETAILED DESCRIPTION

Prostaglandin Antagonist Particles

Prostaglandin antagonist (e.g., travoprost) particles according to the present invention are being in the form of prostaglandin antagonist (e.g., travoprost) intermixed with a biodegradable polymer. For example, the particles are microparticles. Such particles can be prepared by microencapsulation.

In specific embodiments, the prostaglandin antagonist (e.g., travoprost) particles have a diameter ranging from about 1 to about 150 μm determined by sieving or have an average diameter ranging from 1 to 150 μm determined by laser diffraction. In a more specific embodiment, the particles have a diameter ranging from about 1 to about 100 μm, about 20 to about 75 μm, about 20 to about 106 μm, or about 20 to about 55 μm determined by sieving or have an average diameter ranging from about 1 to about 100 μm, about 20 to about 75 μm, about 20 to about 106 μm, or about 20 to about 55 μm determined by laser diffraction. In a particular embodiment, the average particle diameter is 36 μm determined by laser diffraction.

In a specific embodiment, the biodegradable polymer comprises a polylactide. More specifically, the polylactide has an acid end group or an ester end group.

In one embodiment, the prostaglandin antagonist (e.g., travoprost) particles are a blend of different types of particles, such as particles in the form of prostaglandin antagonist (e.g., travoprost) intermixed with a first polylactide and particles in the form of prostaglandin antagonist (e.g., travoprost) intermixed with a second polylactide. More specifically, the first and the second polylactide each have an acid end group. In a more specific embodiment, the first polylactide has an inherent viscosity specification ranging from about 0.05 to about less than 0.5 dl/g, or ranging from about 0.35 to about 0.45 dl/g. Additionally or alternatively, the second polylactide has an inherent viscosity specification ranging from about 0.5 to less than about 0.80 dl/g, or ranging from about 0.6 to less than about 0.8 dl/g.

In a certain embodiment, the prostaglandin antagonist (e.g., travoprost) particles consist of a blend of two types of particles, the first type of particle being in the form of prostaglandin antagonist (e.g., travoprost) intermixed with the biodegradable polymer consisting of the first polylactide and the second type of particle being in the form of prostaglandin antagonist (e.g., travoprost) intermixed with the biodegradable polymer consisting of the second polylactide.

In one embodiment, the first and the second polylactide have a mass ratio in the particle blend of about 1.5:1 to about 1:1.5, or about 1:1.

In one embodiment, the prostaglandin antagonist (e.g., travoprost) particles are a blend of different types of particles including particles in the form of prostaglandin antagonist (e.g., travoprost) intermixed with a first polylactide, particles in the form of prostaglandin antagonist (e.g., travoprost) intermixed a second polylactide and particles in the form of prostaglandin antagonist (e.g., travoprost) intermixed with a third polylactide, wherein each of the polylactides have an acid end group. Specifically, the first polylactide has an inherent viscosity specification ranging from about 0.05 to less than about 0.5 dl/g, or ranging from about 0.35 to about 0.45 dl/g, the second polylactide has an inherent viscosity specification ranging from about 0.5 to less than about 0.80 dl/g, or ranging from about 0.6 to less than about 0.8 dl/g, and the third polylactide has an inherent viscosity specification ranging from about 0.8 to about 1.7 dl/g, or ranging from about 0.8 to about 1.0 dl/g.

More specifically, the biodegradable polymer comprises, such as consists of, a blend of three types of particles, the first type of particle being in the form of prostaglandin antagonist (e.g., travoprost) intermixed with the biodegradable polymer consisting of the first polylactide, and the second type of particles being in the form of prostaglandin antagonist (e.g., travoprost) intermixed with the biodegradable polymer consisting of the second polylactide and the third type of particles in the form of prostaglandin antagonist (e.g., travoprost) intermixed with the biodegradable polymer consisting of the third polylactide.

In further embodiments, a mass ratio of the first and the second polylactide in the particle blend is about 2:1 to about 1:2 or about 1:1.6.

In another embodiment, a mass ratio of the first and the third polylactide in the particle blend is about 2:1 to about 1:2, or about 1:1.4.

In another embodiment, the prostaglandin antagonist (e.g., travoprost) particles are a blend of different types of particles including particles in the form of prostaglandin antagonist (e.g., travoprost) intermixed with a first polylactide, particles in the form of prostaglandin antagonist (e.g., travoprost) intermixed with a second polylactide, particles in the form of prostaglandin antagonist (e.g., travoprost) intermixed with a third polylactide and particles in the form of prostaglandin antagonist (e.g., travoprost) intermixed with a fourth polylactide.

More specifically, the first polylactide has an inherent viscosity specification ranging from about 0.05 to less than about 0.5 dl/g, or ranging from about 0.35 to about 0.45 dl/g and has an acid end group, the second polylactide has an inherent viscosity specification ranging from about 0.5 to less than about 0.80 dl/g, or ranging from about 0.6 to less than about 0.8 dl/g and has an acid end group, the third polylactide has an inherent viscosity specification ranging from about 0.8 to about 1.7 dl/g, or ranging from about 0.8 to about 1.0 dl/g and has an acid end group, and the fourth polylactide has an inherent viscosity ranging from about 0.05 to about 1.7 dl/g, such as ranging from about 0.55 to about 0.75 dl/g, and has an ester end group.

Even more specifically, the prostaglandin antagonist (e.g., travoprost) particles may comprise, such as consist of, a blend of four type of particles, the first type of particle being in the form of prostaglandin antagonist (e.g., travoprost) intermixed with the biodegradable polymer consisting of the first polylactide, the second type of particles being in the form of prostaglandin antagonist (e.g., travoprost) intermixed with the biodegradable polymer consisting of the second polylactide, the third type of particles being in the form of prostaglandin antagonist (e.g., travoprost) intermixed with the biodegradable polymer consisting of the third polylactide and the fourth type of particles being in the form of prostaglandin antagonist (e.g., travoprost) intermixed with the biodegradable polymer consisting of the fourth polylactide.

In another embodiment, a mass ratio of the first and the second polylactide in the particle blend is about 1.25:1 to about 1:1.25 or about 1:1.

In a further embodiment, a mass ratio of the first and the third polylactide in the particle blend is about 3:1 to about 1:1, or about 2:1.

In a further embodiment, a mass ratio of the first and the fourth polylactide in the particle blend is about 1:1 to about 1:3, or about 1:2.5, or about 1:2.6.

In certain embodiments, the mass ratio between prostaglandin antagonist (e.g., travoprost) and the total amount of the biodegradable polymer in the prostaglandin antagonist (e.g., travoprost) particles is about 2:1 to 1:2 or about 0.77:1.

In a certain embodiment, the prostaglandin antagonist (e.g., travoprost) particles comprise, consist or consist essentially of prostaglandin antagonist (e.g., travoprost) and the biodegradable polymer and other pharmaceutically acceptable residual amounts of manufacturing components.

In a certain embodiment, the travoprost particles are a blend of at least two types of travoprost particles selected from the group consisting of
1) a first type of travoprost particles made of a mixture of:
   travoprost and
   a biodegradable polymer consisting of a polylactide or polylactides having an acid end group and an inherent viscosity specification ranging from about 0.05 to less than about 0.5 dl/g, such as from about 0.35 to about 0.45 dl/g,
   such as wherein the first type of particles contains from about 40 wt.-% to about 50 wt.-%, such as from about 43 wt.-% to about 45 wt.-% travoprost, based on the total mass of the first type of particles;
2) a second type of travoprost particles made of a mixture of:
   travoprost and
   a biodegradable polymer consisting of a polylactide or polylactides having an acid end group and an inherent viscosity specification ranging from about 0.5 to less than about 0.80 dl/g, such as ranging from about 0.6 to less than about 0.80 dl/g,
   such as wherein the second type of particles contains from about 40 wt.-% to about 50 wt.-%, such as from more than about 45 wt.-% to about 47 wt.-% travoprost, based on the total mass of the second type of particles;
3) a third type of travoprost particles made of a mixture of:
   travoprost and
   a biodegradable polymer consisting of a polylactide or polylactides having an acid end group and an inherent viscosity specification ranging from about 0.8 to about 1.7 dl/g, such as ranging from about 0.8 to about 1.0 dl/g,
   such as wherein the third type of particles contains from about 40 wt.-% to about 50 wt.-%, such as from about 41 wt.-% to about 43 wt.-% travoprost based on the total mass of third type of particles;
4) a fourth type of travoprost particles made of a mixture of:
   travoprost and
   a biodegradable polymer consisting of a polylactide or polylactides having an ester end group and an inherent viscosity specification ranging from about 0.05 to about 1.7 dl/g, such as ranging from about 0.55 to about 0.75 dl/g,
   such as wherein the fourth type of particles contains from about 40 wt.-% to about 50 wt.-%, such as from about 41 wt.-% to about 43 wt.-% travoprost based on the total mass of the fourth type of particles.

In a certain embodiment, the travoprost particles are a blend of at least two types of travoprost particles selected from
1) a first type of travoprost particles comprising:
   travoprost and
   biodegradable polymer comprising a polylactide or polylactides having an acid end group and an inherent viscosity specification ranging from about 0.05 to less than about 0.5 di/g,
   wherein the first type of particles comprises from about 40 wt.-% to about 50 wt.-% travoprost, based on the total mass of the first type of particles;
2) a second type of travoprost particles comprising:
   travoprost and
   biodegradable polymer comprising a polylactide or polylactides having an acid end group and an inherent viscosity specification ranging from about 0.5 to less than about 0.80 dl/g,
   wherein the second type of particles comprises from about 40 wt.-% to about 50 wt.-% travoprost, based on the total mass of the second type of particles;
3) a third type of travoprost particles comprising:
   travoprost and
   biodegradable polymer comprising a polylactide or polylactides having an acid end group and an inherent viscosity specification ranging from about 0.8 to about 1.7 dl/g,
   wherein the third type of particles comprises from about 40 wt.-% to about 50 wt.-% travoprost based on the total mass of third type of particles;
4) a fourth type of travoprost particles comprising:
   travoprost and
   biodegradable polymer comprising a polylactide or polylactides having an ester end group and an inherent viscosity specification ranging from about 0.05 to about 1.7 dl/g, wherein the fourth type of particles comprises from about 40 wt.-% to about 50 wt.-% travoprost based on the total mass of the fourth type of particles.

In a certain embodiment, the travoprost particles a blend of particles made of
1) a first type of travoprost particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles; and
2) a second type of travoprost particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particles contains from about 40 wt.-% to about 50 wt.-%, such as more than from about 45 wt.-% to about 47 wt.-% travoprost, based on the total mass of the second type of particles,
such as wherein the blend contains, based on the total amount of the blend, about 35 wt.-% to about 55 wt.-% particles of the first type of particles and about 35 wt.-% to about 55 wt.-% particles of the second type of particles; or
such as wherein about 35 wt.-% to about 55 wt.-% of the total amount of travoprost in the implant is present in the form of particles of the first type of particles and about 35 wt.-% to about 55 wt.-% of the total amount of travoprost in the implant is present in the form of particles of the second type of particles,
wherein optionally the polymer network is formed by reacting an electrophilic group-containing multi-arm-polymer precursor with a nucleophilic group-containing cross-linking agent, the electrophilic group is a succinimidylglutarate (SG) group and the multi-arm polymer precursor an 8-arm-15K-SG polyethylene glycol; and the nucleophilic group-containing cross-linking agent is a trilysine, or the polymer network comprises 8-arm-polyethylene glycols being cross-linked including a group represented by the following formula

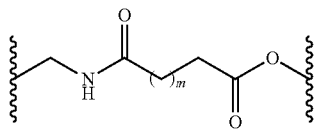

wherein m is 2.

In a certain embodiment, he travoprost particles are a blend of particles made of
1) a first type of particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles, 2) a second type of travoprost particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particle contains from about 40 wt.-% to about 50 wt.-%, such as more than from about 45 wt.-% to about 47 wt.-% travoprost, based on the total mass of the second type of particles, and
3) a third type of travoprost particles made of a mixture of travoprost and the biodegradable polymer consisting of a polylactide or polylactides having an acid end group and an inherent viscosity specification ranging from about 0.8 to about 1.7 dl/g, such as ranging from about 0.8 to about 1.0 dl/g, wherein the third type of particles contains from about 40 wt.-% to about 50 wt.-%, such as from about 41 wt.-% to about 43 wt.-% travoprost, based on the total mass of the third type of particles,
such as wherein the blend contains, based on the total amount of blend, about 20 wt.-% to about 35 wt.-% particles of the first type of particles and about 30 wt.-% to about 50 wt.-% particles of the second type of particles and about 25 wt.-% to about 45 wt.-% of particles of the third type of particles; or
such as wherein about 20 wt.-% to about 35 wt.-% of the total amount of travoprost in the implant is present in the form of particles of the first type of particles and about 30 wt.-% to about 50 wt.-% of the total amount of travoprost in the implant is present in the form of particles of the second type of particles, and about 25 wt.-% to about 45 wt.-% of the total amount of travoprost in the implant is present in the form of particles of the third type of particles,
wherein optionally the polymer network is formed by reacting an electrophilic group-containing multi-arm-polymer precursor with a nucleophilic group-containing cross-linking agent, the electrophilic group is a succinimidylglutarate (SG) group and the multi-arm polymer precursor an 8-arm-15K-SG polyethylene glycol; and the nucleophilic group-containing cross-linking agent is a trilysine or the polymer network comprises 8-arm-polyethylene glycols being cross-linked including a group represented by the following formula

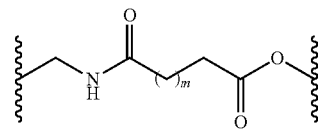

wherein m is 2.

In certain embodiments, the travoprost particles are a blend of particles made of
1) a first type of particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles, 2) a second type of particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particles contains from about 40 wt.-% to about 50 wt.-%, such as more than from about 45 wt.-% to about 47 wt.-% travoprost, based on the total mass of the second type of particles,
3) a third type of particles made of travoprost and the biodegradable polymer consisting of a polylactide or polylactides having an acid end group and an inherent viscosity specification ranging from about 0.8 to about 1.7 dl/g, such as ranging from about 0.8 to about 1.0 dl/g, wherein the third type of particles contain from about 40 wt.-% to about 50 wt.-%, such as from about 41 wt.-% to about 43 wt.-% travoprost, based on the total mass of the third type of particles, and
4) a fourth type of particles made of travoprost and the biodegradable polymer consisting of a polylactide or polylactides having an ester end group and an inherent viscosity specification ranging from about 0.05 to about 1.7 dl/g, such as ranging from about 0.55 to about 0.75 dl/g, wherein the fourth type of particles contains from about 40 wt.-% to about 50 wt.-%,
such as wherein the blend contains, based on the total amount of blend, about 15 wt.-% to about 25 wt.-% particles of the first type of particles and about 15 wt.-% to about 25 wt.-% particles of the second type of particles and about 5 wt.-% to about 15% of particles of the third type of particles and about 40 wt.-% to about 60 wt.-% of particles of the fourth type of particles; or
such as wherein about 15 wt.-% to about 25 wt.-% of the total amount of travoprost in the implant is present in the form of particles of the first type of particles and about 15 wt.-% to about 25 wt.-% of the total amount of travoprost in the implant is present in the form of particles of the second type of particles and about 5 wt.-% to about 15 wt.-% of the total amount of travoprost in the implant is present in the form of particles of the third type of particles and about 40 wt.-% to about 60 wt.-% of the total amount of travoprost in the implant is present in the form of particles of the fourth type of particles,
wherein optionally the polymer network is formed by reacting an electrophilic group-containing multi-arm-polymer precursor with a nucleophilic group-containing cross-linking agent, the electrophilic group is a succinimidylazelate (SAZ) group, and the multi-arm polymer precursor is a 8-arm-15K-SAZ polyethylene glycol; and the nucleophilic group-containing cross-linking agent is a trilysine, or the polymer network comprises 8-arm-polyethylene glycols being cross-linked including a group represented by the following formula

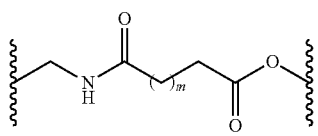

wherein m is 6.

In certain embodiments, the travoprost particles comprise a blend of particles comprising
1) a first type of travoprost particles comprising a mixture of travoprost and the biodegradable polymer comprises a polylactide or polylactides having an acid end group and an inherent viscosity specification ranging from about 0.05 to less than about 0.5 dl/g, wherein the first type of particles contains from about 40 wt.-% to about 50 wt.-%, travoprost, based on the total mass of the first type of particles; and
2) a second type of travoprost particles comprising a mixture of travoprost and the biodegradable polymer comprising a polylactide or polylactides having an acid end group and an inherent viscosity specification ranging from about 0.5 to less than about 0.80 dl/g, wherein the second type of particles contains from about 40 wt.-% to about 50 wt.-% travoprost, based on the total mass of the second type of particles,
wherein the blend comprises based on the total amount of the blend, about 35 wt.-% to about 55 wt.-% particles of the first type of particles and about 35 wt.-% to about 55 wt.-% particles of the second type of particles.
In a certain embodiment, the travoprost particles comprise a blend of particles comprising
1) a first type of particles comprising a mixture of travoprost and the biodegradable polymer comprising a polylactide or polylactides having an acid end group and an inherent viscosity specification ranging from about 0.05 to less than about 0.5 dl/g wherein the first type of particles contains from about 40 wt.-% to about 50 wt.-% travoprost, based on the total mass of the first type of particles,
2) a second type of travoprost particles comprising a mixture of travoprost and the biodegradable polymer comprising a polylactide or polylactides having an acid end group and an inherent viscosity specification ranging from about 0.5 to less than about 0.80 dl/g wherein the second type of particle contains from about 40 wt.-% to about 50 wt.-% travoprost, based on the total mass of the second type of particles, and
3) a third type of travoprost particles comprising a mixture of travoprost and the biodegradable polymer comprising a polylactide or polylactides having an acid end group and an inherent viscosity specification ranging from about 0.8 to about 1.7 dl/g wherein the third type of particles contains from about 40 wt.-% to about 50 wt.-% travoprost, based on the total mass of the third type of particles,
wherein the blend comprises, based on the total amount of blend, about 20 wt.-% to about 35 wt.-% particles of the first type of particles and about 30 wt.-% to about 50 wt.-% particles of the second type of particles and about 25 wt.-% to about 45 wt.-% of particles of the third type of particles.
In certain embodiments, the travoprost particles comprise a blend of particles comprising
1) a first type of particles comprising a mixture of travoprost and the biodegradable polymer comprising a polylactide or polylactides having an acid end group and an inherent viscosity specification ranging from about 0.05 to less than about 0.5 dl/g wherein the first type of particles contains from about 40 wt.-% to about 50 wt travoprost, based on the total mass of the first type of particles,
2) a second type of particles comprising a mixture of travoprost and the biodegradable polymer comprising a polylactide or polylactides having an acid end group and an inherent viscosity specification ranging from about 0.5 to less than about 0.80 dl/g wherein the second type of particles contains from about 40 wt.-% to about 50 wt.-% travoprost, based on the total mass of the second type of particles, 3) a third type of particles comprising travoprost and the biodegradable polymer comprising a polylactide or polylactides having an acid end group and an inherent viscosity specification ranging from about 0.8 to about 1.7 dl/g wherein the third type of particles contain from about 40 wt.-% to about 50 wt.-% travoprost, based on the total mass of the third type of particles, and 4) a fourth type of particles comprising travoprost and the biodegradable polymer comprising a polylactide or polylactides having an ester end group and an inherent viscosity specification ranging from about 0.05 to about 1.7 dl/g wherein the fourth type of particles contains from about 40 wt.-% to about 50 wt.-%, wherein the blend contains, based on the total amount of blend, about 15 wt.-% to about 25 wt.-% particles of the first type of particles and about 15 wt.-% to about 25 wt.-% particles of the second type of particles and about 5 wt.-% to about 15% of particles of the third type of particles and about 40 wt.-% to about 60 wt.-% of particles of the fourth type of particles.

In another embodiment, the particles are spherical particles.

According to a first specific aspect, the present invention is directed to prostaglandin antagonist (e.g., travoprost) particles made of a mixture composed of:

prostaglandin antagonist (e.g., travoprost) and a biodegradable polymer consisting of a polylactides having an acid end group and an inherent viscosity specification ranging from about 0.05 to less than about 0.5 dl/g, such as from about 0.35 to about 0.45 dl/g, wherein the mixture contains from about 40 wt.-% to about 50 wt.-%, such as from about 43 wt.-% to about 45 wt.-% prostaglandin antagonist (e.g., travoprost) based on the total mass of the mixture.

According to a second specific aspect, the present invention is directed to prostaglandin antagonist (e.g., travoprost) particles made of a mixture composed of:

prostaglandin antagonist (e.g., travoprost) and a biodegradable polymer consisting of a polylactides having an acid end group and an inherent viscosity specification ranging from about 0.5 to less than about 0.80 dl/g, such as ranging from about 0.6 to less than about 0.80 dl/g, wherein the mixture contains from about 40 wt.-% to about 50 wt.-%, such as more than from about 45 wt.-% to about 47 wt.-% prostaglandin antagonist (e.g., travoprost) based on the total mass of the mixture.

According to a third specific aspect, the present invention is directed to prostaglandin antagonist (e.g., travoprost) particles a mixture of:

prostaglandin antagonist (e.g., travoprost) and a biodegradable polymer consisting of a polylactides having an acid end group and an inherent viscosity specification ranging from about 0.8 to about 1.7 dl/g, such as ranging from about 0.8 to about 1.0 dl/g, wherein the mixture contains from about 40 wt.-% to about 50 wt.-%, such as from about 41 wt.-% to about 43 wt.-% prostaglandin antagonist (e.g., travoprost) based on the total mass of the mixture.

According to a fourth aspect, the present invention is directed to prostaglandin antagonist (e.g., travoprost) particles made of a mixture composed of:

prostaglandin antagonist (e.g., travoprost) and a biodegradable polymer consisting of a polylactides having an ester end group and an inherent viscosity specification ranging from about 0.05 to about 1.7 dl/g, such as ranging from about 0.55 to about 0.75 dl/g, wherein the mixture contains from about 40 wt.-% to about 50 wt.-%, such as from about 41 wt.-% to about 43 wt.-% prostaglandin antagonist (e.g., travoprost) based on the total mass of the mixture.

According to aspect (a), the present invention is directed to travoprost particles made of a mixture of:

Travoprost and a biodegradable polymer consisting of a polylactides having an acid end group and an inherent viscosity specification ranging from about 0.05 to less than about 0.5 dl/g, such as from about 0.35 to about 0.45 dl/g, wherein the mixture contains from about 40 wt.-% to about 50 wt.-%, such as from about 43 wt.-% to about 45 wt.-% travoprost based on the total mass of the mixture.

According to aspect (b), the present invention is directed to Travoprost particles made of a mixture of:

Travoprost and a biodegradable polymer consisting of a polylactides having an acid end group and an inherent viscosity specification ranging from about 0.5 to less than about 0.80 dl/g, such as ranging from about 0.6 to less than about 0.80 dl/g, wherein the mixture contains from about 40 wt.-% to about 50 wt.-%, such as more than from about 45 wt.-% to about 47 wt.-% travoprost based on the total mass of the mixture.

According to aspect (c), the present invention is directed to Travoprost particles made of a mixture of:

Travoprost and a biodegradable polymer consisting of a polylactides having an acid end group and an inherent viscosity specification ranging from about 0.8 to about 1.7 dl/g, such as ranging from about 0.8 to about 1.0 dl/g, wherein the mixture contains from about 40 wt.-% to about 50 wt.-%, such as from about 41 wt.-% to about 43 wt.-% travoprost based on the total mass of the mixture.

According to aspect (c), the present invention is directed to travoprost particles made of a mixture of:

Travoprost and a biodegradable polymer consisting of a polylactides having an ester end group and an inherent viscosity specification ranging from about 0.05 to about 1.7 dl/g, such as ranging from about 0.55 to about 0.75 dl/g, wherein the mixture contains from about 40 wt.-% to about 50 wt.-%, such as from about 41 wt.-% to about 43 wt.-% travoprost based on the total mass of the mixture.

As part of an embodiment, travoprost in the disclosed implants is microencapsulated, wherein the remaining features of the implants are described herein. Alternatively, travoprost in the disclosed implants is microencapsulated with poly(lactic-co-glycolic acid) (PLGA) or poly(lactic acid) (PLA), or a combination thereof, wherein the remaining features of the implants are described herein. In another alternative, travoprost in the disclosed implants is microencapsulated with PLA, wherein the remaining features of the implants are described herein.

Biodegradable Hydrogel

In certain embodiments of the present invention, the prostaglandin antagonist (e.g., travoprost) particles, as defined above, are dispersed in a biodegradable hydrogel. In other words, the prostaglandin antagonist (e.g., travoprost) particles are distributed within a matrix composed of said hydrogel in such certain embodiments. In a specific embodiment the prostaglandin antagonist (e.g., travoprost) particles are uniformly dispersed in said biodegradable polymer. PEG Hydrogel In certain embodiments, the hydrogel comprises a polymer network comprising one or more units of polyethylene glycol.

In a certain embodiments of the present invention, the polymer network forming the hydrogel contains polyethylene glycol (PEG) units. PEGs are known in the art to form hydrogels when cross-linked, and these PEG hydrogels are suitable for pharmaceutical applications e.g. as matrix for drugs intended to be administered to all parts of the human or animal body.

The polymer network of the hydrogel implants of the present invention may comprise one or more multi-arm PEG units having from 2 to 10 arms, or 4 to 8 arms, or 4, 5, 6, 7 or 8 arms. In certain embodiments, the PEG units used in the hydrogel of the present invention have 8 arms. In certain particular embodiments, an 8-armed PEG is utilized.

In certain embodiments, the polyethylene glycol units are 4- to 10-arm polyethylene glycol units, or 8-arm polyethylene glycol units.

The molecular weight of the polyethylene glycol refers to an average molecular weight, which may be selected from various average values known to the person of ordinary skill in the art, including number average molecular weight (Mn), weight average molecular weight (Mw), and peak average molecular weight. Any of such average values, and in particular the three aforementioned average molecular weights can be used in the context of the present invention. In certain embodiments, the average molecular weight of the polyethylene glycol units and precursors as disclosed herein is given as number average molecular weight.

Multi-arm PEG units with a specified molecular weight as used herein may be abbreviated in the form of e.g. 8a15 kPEG, referring to an 8-arm PEG with a molecular weight of 15,000 Daltons.

In a 4-arm PEG, each of the arms may have an average arm length (or molecular weight) of the total molecular weight of the PEG divided by 4. A 4a20 kPEG precursor, which is a particularly suitably precursor for use in the present invention thus has 4 arms with an average molecular weight of about 5,000 Daltons each. An 8a20k PEG precursor, which could also be used in combination with or alternatively to the 4a20 kPEG precursor in the present invention, thus has 8 arms each having an average molecular weight of 2,500 Daltons. Longer arms may provide increased flexibility as compared to shorter arms. PEGs with longer arms may swell more as compared to PEGs with shorter arms. A PEG with a lower number of arms also may swell more and may be more flexible than a PEG with a higher number of arms. In certain particular embodiments, only a 4-arm PEG precursor is utilized in the present invention. In certain particular embodiments, two different 4-arm PEG precursors are utilized in the present invention. In certain other embodiments, a combination of a 4-arm PEG precursor and an 8-arm precursor is utilized in the present invention. In addition, longer PEG arms have higher melting temperatures when dry, which may provide more dimensional stability during storage.

In certain embodiments, the polymer network is formed by reacting an electrophilic group-containing multi-arm-polymer precursor with a nucleophilic group-containing cross-linking agent. In particular certain embodiments wherein the multi-arm-polymer precursor is a 4- to 10-arm polyethylene glycol precursor, or an 8-arm polyethylene glycol precursor.

In certain embodiments, electrophilic end groups for use with PEG precursors for preparing the hydrogels of the present invention are N-hydroxysuccinimidyl (NHS) esters, including but not limited to NHS dicarboxylic acid esters such as the succinimidylmalonate group, succinimidylmaleate group, succinimidylfumarate group, "SAZ" referring to a succinimidylazelate end group, "SAP" referring to a succinimidyladipate end group, "SG" referring to a succinimidylglutarate end group, and "SS" referring to a succinimidylsuccinate end group.

In certain embodiments, the multi-arm polymer precursor is selected from the group consisting of 8-arm-15K-SG polyethylene glycol or 8-arm-15K-SAZ polyethylene glycol.

In certain embodiments, the electrophilic group is selected from the group consisting of a succinimidylglutarate (SG) group and a succinimidylazelate (SAZ) group.

In certain embodiments of the present invention, the polymer network is formed by reacting an electrophilic group-containing multi-arm-polymer precursor with a nucleophilic group-containing cross-linking agent, the electrophilic group is selected from the group consisting of a succinimidylglutarate (SG) group and a succinimidylazelate (SAZ) group, and the multi-arm polymer precursor is selected from the group consisting of 8-arm-15K-SG polyethylene glycol or 8-arm-15K-SAZ polyethylene glycol; and the nucleophilic group-containing cross-linking agent is a trilysine, or 8-arm-15K-SAZ polyethylene glycol; and the nucleophilic group-containing cross-linking agent is a trilysine, or the polymer network comprises 8-arm-polyethylene glycols being cross-linked including a group represented by the following formula

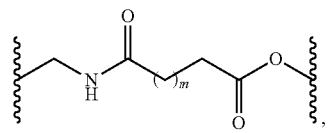

wherein m is 2 or 6.

Thus, in certain embodiments, the PEG-precursor is an NHS dicarboxylic acid ester-terminated multi-arm PEG precursor that can be represented by the formula:

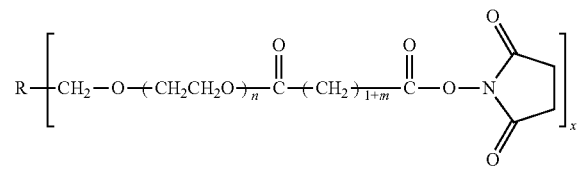

wherein n is determined by the molecular weight of the respective PEG-arm, m is an integer from 0 to 10, and specifically is 1, 2, 3, 4, 5, 6, 7, 8, 9, or 10, and x is the number of arms (and thus can e.g. 2, 4, 8, etc., see above).

Where m is 1, each arm is terminated with a succinimidylsuccinate (SS) end group, where m is 2, each arm is terminated with a succinimidylglutarate (SG) group, where m is 3, each arm is terminated with a succinimidyladipate (SAP) group, and where m is 6, each arm is terminated with a succinimidylazelate (SAZ) group. With these specific electrophilic end groups, multi-arm PEG units may be abbreviated in the form of e.g. 4a20 kPEG-SAP, referring to a 4-arm PEG with a succinimidyladipate end group and a molecular weight of 20,000. In the above formula, R is a core structure appropriate to provide the desired number of arms. For 4-arm PEG units and precursors, R can be a pentaerythritol structure, whereas for 8-arm PEG units and precursors, R can be a hexaglycerol structure.

In certain embodiments, the multi-arm-polymer precursor has a mass average molecular weight in the range from about 10,000 to about 20,000 Daltons. In a more specific certain embodiment, the multi-arm-polymer precursor has a mass average molecular weight of 15,000±10% Daltons.

The molecular weight of polyethylene glycol and polyethylene glycol derivatives can be determined by several methods, including gel electrophoresis such as SDS-PAGE (sodium dodecyl sulphate-polyacrylamide gel electrophoresis), gel permeation chromatography (GPC), GPC with dynamic light scattering (DLS) as well as Matrix-assisted laser desorption/ionization-time of flight (MALDI-TOF) spectrometry. The molecular weight of polyethylene glycol precursors as disclosed herein can be determined by any method known to the person of ordinary skill in the art, including SDS-PAGE, GPC and MALDI-TOF, and in particular is determined by GPC using a PEG standard of known molecular weight (determined e.g. by MALDI-TOF) and polydispersity (determined e.g. by GPC). In case a high accuracy is needed, MALDI-TOF can be used.

In certain embodiments, reactions of e.g. nucleophilic group-containing crosslinkers and electrophilic group-containing PEG units, such as a reaction of amine group-containing crosslinkers with activated ester-group containing PEG units, result in a plurality of PEG units being crosslinked by the crosslinker via an amide group.

In the case of PEGs with NHS-ester end groups such as succinimidylazelate (SAZ)-, succinimidyladipate (SAP)- or succinimidylgluatarate-(SG)-terminated PEG units (see above), the reaction with amine group-containing crosslinkers result in a plurality of PEG units being crosslinked by the crosslinker via a hydrolyzable linker having the formula:

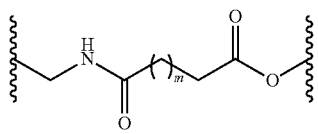

wherein m is an integer from 0 to 10, and specifically is 1, 2, 3, 4, 5, 6, 7, 8, 9, or 10. For a SAZ-end group, m would be 6. For a SAP-end group, m would be 3, for a SG-end group, m would be 2 and for an SS-end group, m would be 1.

In a certain embodiment, the nucleophilic group-containing crosslinking agent is an amine.

In another embodiment, the nucleophilic group-containing crosslinking agent is a small molecule amine with a molecular weight below 1,000 Da, comprising two or more primary aliphatic amine groups.

In a certain embodiment, the nucleophilic group-containing crosslinking agent is a small molecule amine selected from the group consisting of dilysine, trilysine, tetralysine, ethylenediamine, 1,3-diaminopropane, 1,3-diaminopropane, diethylenetriamine, and trimethylhexamethylenediamine.

In one embodiment, the nucleophilic group-containing crosslinking agent is a trilysine. In one specific embodiment, the nucleophilic group-containing crosslinking agent is trilysine acetate.

In another embodiment, the trilysine is labeled with a visualization agent selected from the group consisting of a fluorophore such as fluorescein, rhodamine, coumarin, and cyanine. Specifically, the nucleophilic group-containing crosslinking agent is fluorescein-conjugated trilysine. More specifically, the fluorescein-conjugated trilysine is obtained by reacting trilysine acetate with N-hydroxysuccinimide (NHS)-fluorescein. Even more specifically, wherein the trilysine is labeled by partial conjugation with the visualization agent.

In certain embodiments, the implant does not comprise a visualization agent e.g. the trilysine is not labeled with a visualization agent.

As part of an embodiment, provided herein is a sustained release biodegradable intracameral hydrogel implant comprising travoprost and a polymer network.

As part of a further embodiment, the polymer network of the disclosed hydrogel implant (e.g., as in the first embodiment) comprises a plurality of polyethylene glycol (PEG) units.

As part of a further embodiment, the plurality of polyethylene glycol (PEG) units included in the disclosed implants are cross-linked to form a polymer network comprising a plurality of multi-arm PEG units having at least 2 arms, wherein the remaining features of the implants are described herein e.g., as in the first or second embodiment. Alternatively, as part of a third embodiment, the polymer network of the disclosed implants comprise a plurality of multi-arm PEG units having from 2 to 10 arms, wherein the remaining features of the implants are described herein e.g., as in the above embodiments. In another alternative, the polymer network of the disclosed implants comprise a plurality of multi-arm PEG units having from 4 to 8 arms, wherein the remaining features of the implants are described herein e.g., as above. In another alternative, the polymer network of the disclosed implants comprise a plurality of 4-arm PEG units, wherein the remaining features of the implants are described herein e.g., as above. In another alternative, the polymer network of the disclosed implants comprise a plurality of 8-arm PEG units, wherein the remaining features of the implants are described above.

As part of a further embodiment, the polymer network of the disclosed implants comprises a plurality of PEG units having a number average molecular weight (Mn) ranging from about 5 KDa to about 50 KDa, wherein the remaining features of the implants are described herein. Alternatively, the polymer network of the disclosed implants comprise a plurality of PEG units having a number average molecular weight (Mn) ranging from about 5 KDa to about 40 KDa, wherein the remaining features of the implants are described. In another alternative, the polymer network of the disclosed implants comprise a plurality of PEG units having a number average molecular weight (Mn) ranging from about 5 KDa to about 30 KDa, wherein the remaining features of the implants are described herein. In another alternative, the polymer network of the disclosed implants comprise a plurality of PEG units having a number average molecular weight (Mn) ranging from about 10 KDa to about 50 KDa, wherein the remaining features of the implants are described herein. In another alternative, the polymer network of the disclosed implants comprise a plurality of PEG units having a number average molecular weight (Mn) ranging from about 10 KDa to about 40 KDa, wherein the remaining features of the implants are described herein. In another alternative, the polymer network of the disclosed implants comprise a plurality of PEG units having a number average molecular weight (Mn) ranging from about 10 KDa to about 30 KDa, wherein the remaining features of the implants are described herein. In another alternative, the polymer network of the disclosed implants comprise a plurality of PEG units having a number average molecular weight (Mn) ranging from about 10 KDa to about 20 KDa, wherein the remaining features of the implants are described herein. In another alternative, the polymer network of the disclosed implants comprise a plurality of PEG units having a number average molecular weight (Mn) ranging from about 30 KDa to about 50 KDa, wherein the remaining features of the implants are described herein e. In another alternative, the polymer network of the disclosed implants comprise a plurality of PEG units having a number average molecular weight (Mn) ranging from about 35 KDa to about 45 KDa, wherein the remaining features of the implants are described herein. In another alternative, the polymer network of the disclosed implants comprise a plurality of PEG units having a number average molecular weight (Mn) ranging from about 15 KDa to about 30 KDa, wherein the remaining features of the implants are described herein e. In another alternative, the polymer network of the disclosed implants comprise a plurality of PEG units having a number average molecular weight (Mn) ranging from about 15 KDa to about 25 KDa, wherein the remaining features of the implants are described herein e. In another alternative, the polymer network of the disclosed implants comprise a plurality of PEG units having a number average molecular weight (Mn) of at least about 5 KDa, wherein the remaining features of the implants are described herein e. In another alternative, the polymer network of the disclosed implants comprise a plurality of PEG units having a number average molecular weight (Mn) of at least about 10 KDa, wherein the remaining features of the implants are described herein. In another alternative, the polymer network of the disclosed implants comprise a plurality of PEG units having a number average molecular weight (Mn) of at least 15 about KDa, wherein the remaining features of the implants are described herein. In another alternative, the polymer network of the disclosed implants comprise a plurality of PEG units having a number average molecular weight (Mn) of at least 20 about KDa, wherein the remaining features of the implants are described herein. In another alternative, the polymer network of the disclosed implants comprise a plurality of PEG units having a number average molecular weight (Mn) of at least 30 about KDa, wherein the remaining features of the implants are described herein. In another alternative, the polymer network of the disclosed implants comprise a plurality of PEG units having a number average molecular weight (Mn) of at least 40 about KDa, wherein the remaining features of the implants are described herein. In another alternative, the polymer network of the disclosed implants comprise a plurality of PEG units having a number average molecular weight (Mn) of about 10 KDa, wherein the remaining features of the implants are described herein. In another alternative, the polymer network of the disclosed implants comprise a plurality of PEG units having a number average molecular weight (Mn) of about 15 KDa, wherein the remaining features of the implants are described herein. In another alternative, the polymer network of the disclosed implants comprise a plurality of PEG units having a number average molecular weight (Mn) of about 20 KDa, wherein the remaining features of the implants are described herein. In another alternative, the polymer network of the disclosed implants comprise a plurality of PEG units having a number average molecular weight (Mn) of about 40 KDa, wherein the remaining features of the implants are described herein.

In a further embodiment, the polymer network of the disclosed implants comprise a plurality of PEG units crosslinked by a hydrolyzable linker, wherein the remaining features of the disclosed implants are described herein. Alternatively, the polymer network of the disclosed implants comprise a plurality of PEG units crosslinked by a hydrolyzable linker having the formula:

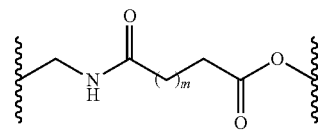

wherein m is an integer from 1 to 9 and wherein the remaining features of the implants are described herein. In another alternative, the polymer network of the disclosed implants comprise a plurality of PEG units crosslinked by a hydrolyzable linker having the

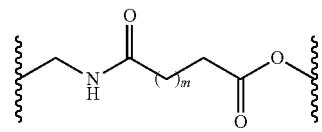

wherein m is an integer from 2 to 6 and wherein the remaining features of the implants are described herein. In another alternative the polymer network of the disclosed implants comprise a plurality of PEG units having the formula:

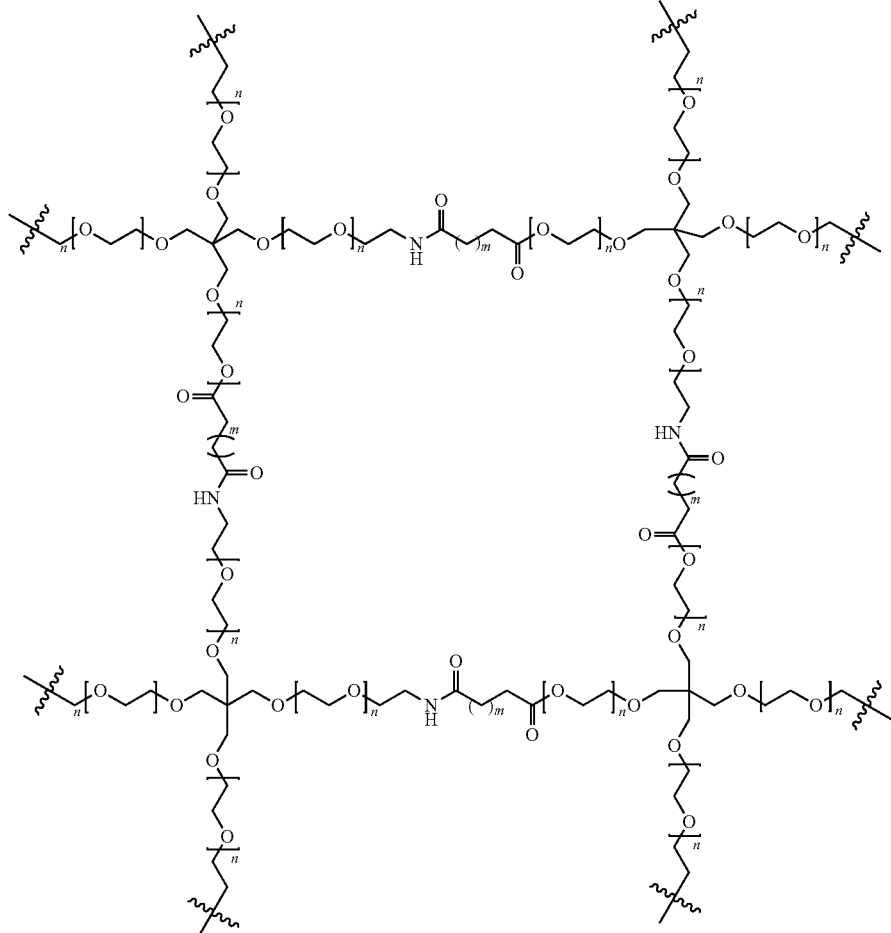

wherein n represents an ethylene oxide repeating unit and the wavy lines represent the points of repeating units of the polymer network, wherein the remaining features of the implants are described herein. In another alternative, the polymer network of the disclosed implants comprise a plurality of PEG units having the formula set forth above, but with an 8-arm PEG scaffold, wherein the remaining features of the implants are described herein.

In a further embodiment, the polymer network of the disclosed hydrogel implant is formed by reacting a plurality of polyethylene glycol (PEG) units comprising groups which are susceptible to nucleophilic attack with one or more nucleophilic groups to form the polymer network, wherein the remaining features of the hydrogel are described herein. Examples of suitable groups which are susceptible to nucleophilic attack include, but art not limited to activated esters (e.g., thioesters succinimidyl esters, benzotriazolyl esters, esters of acrylic acids, and the like). Examples of suitable nucleophilic groups include, but art not limited to, amines and thiols.

In a further embodiment, the polymer network of the disclosed hydrogel implant is formed by reacting a plurality of polyethylene glycol (PEG) units, each having a molecule weight as described above in the fourth embodiment and which comprise groups which are susceptible to nucleophilic attack, with one or more nucleophilic groups to form the polymer network, wherein the remaining features of the hydrogel are described herein e.g., as in the first through sixth embodiments. Alternatively, as part of a seventh embodiment, the polymer network of the disclosed hydrogel implant is formed by reacting a plurality of polyethylene glycol (PEG) units, each having a molecule weight as described above in the fourth embodiment and which comprise a succinimidyl ester group, with one or more nucleophilic groups to form the polymer network, wherein the remaining features of the hydrogel are described herein e.g., as in the first through sixth embodiments. In another alternative, as part of a seventh embodiment, the polymer network of the disclosed hydrogel implant is formed by reacting a plurality of polyethylene glycol (PEG) units selected from 4a20K PEG SAZ, 4a20K PEG SAP, 4a20K PEG SG, 4a20K PEG SS, 8a20K PEG SAZ, 8a20K PEG SAP, 8a20K PEG SG, 8a20K PEG SS, wherein the remaining features of the hydrogel are described herein e.g., as in the first through sixth embodiments.

In a further embodiment, the polymer network of the disclosed hydrogel implant is formed by reacting a plurality of polyethylene glycol (PEG) units comprising groups which are susceptible to nucleophilic attack with one or more amine groups to form the polymer network, wherein the remaining features of the hydrogel are described herein. Alternatively, the polymer network of the disclosed hydrogel implant is formed by reacting a plurality of polyethylene glycol (PEG) units comprising groups which are susceptible to nucleophilic attack with one or more PEG or Lysine based-amine groups to form the polymer network, wherein the remaining features of the hydrogel are described herein. In another alternative, the polymer network of the disclosed hydrogel implant is formed by reacting a plurality of polyethylene glycol (PEG) units comprising groups which are susceptible to nucleophilic attack with one or more PEG or Lysine based-amine groups selected from 4a20K PEG NH2, 8a20K PEG NH2, and trilysine, or salts thereof, wherein the remaining features of the hydrogel are described herein.

As part of a further embodiment, the polymer network of the disclosed implants are amorphous (e.g., under aqueous conditions such as in vivo), wherein the remaining features of the implants are described herein.

Alternatively, as part of a further embodiment, the polymer network of the disclosed implants are semi-crystalline (e.g., in the absence of water), wherein the remaining features of the compositions are described herein.

As part of a further embodiment, the travoprost of the disclosed implants is homogenously dispersed within the polymer network, wherein the remaining features of the implants are described herein.

Multiplicity of Prostaglandin Antagonist (e.g. Travoprost) Particles

In one aspect, the present invention is directed to a multiplicity of prostaglandin antagonist (e.g., travoprost) particles being formed from a blend of particles, the particles comprising, such as consisting of, a mixture of:
  prostaglandin antagonist (e.g., travoprost);
  a biodegradable polymer consisting of polylactides, as defined in the embodiments above, having an acid end group, and
  optionally other pharmaceutically acceptable residual amounts of manufacturing components.

In certain embodiments, the blend of particles is composed of three types of particles, wherein the three types of particles distinguish from each other by including polylactide components having different inherent viscosities.

More specifically, the three polylactides have an inherent viscosity specification ranging from about 0.05 to less than about 0.5 dl/g, such as about 0.35 to about 0.45 dl/g; ranging from about 0.5 to less than about 0.80 dl/g, such as about 0.6 to less than about 0.8 dl/g; and ranging from about 0.8 to about 1.7, such as about 0.8 to about 1.0 dl/g, respectively.

In another embodiment, the blend of particles is composed of two types of particles, wherein the two types of particles distinguish from each other by including polylactide components having different inherent viscosities. More specifically, the two polylactides have an inherent viscosity specification ranging from about 0.05 to less than about 0.5 dl/g, such as about 0.35 to about 0.45 dl/g; and ranging from about 0.5 dl/g to about 1.7 dl/g, such as about 0.6 to about 0.8 dl/g, respectively.

In certain embodiments, the travoprost particles have a diameter ranging from 1 to 100 μm, 20 to 75 μm, 20 to 106 μm, or 20 to 55 μm determined by sieving or have an average diameter ranging from 1 to 100 μm, 20 to 75 μm, 20 to 106 μm, or 20 to 55 μm determined by laser diffraction.

In one specific aspect, the present invention is directed to multiplicity of prostaglandin antagonist (e.g., travoprost) particles being formed from a blend of particles according to the first to fourth specific aspects of section "prostaglandin antagonist (e.g., travoprost) particles", such as based on the total amount of particles about 15 to about 25 wt.-% particles according to the first specific aspect of the section "prostaglandin antagonist (e.g., travoprost) particles" and about 15 to about 25 wt.-% particles according to the second specific aspect of the section "prostaglandin antagonist (e.g., travoprost) particles" and about 5 to about 15% of particles according to the third aspect of the section "prostaglandin antagonist (e.g., travoprost) particles" and about 40 to about 60 wt.-% of particles according to the fourth aspect in the section "prostaglandin antagonist (e.g., travoprost) particles"; or wherein about 15 wt.-% to about 25 wt.-% of the total amount of prostaglandin antagonist (e.g., travoprost) is present in the form of particles according to the first specific aspect of the section "prostaglandin antagonist (e.g., travoprost) particles" and about 15 wt.-% to about 25 wt.-% of the total amount of prostaglandin antagonist (e.g., travoprost) is present in the form of particles according to the second specific aspect of the section "prostaglandin antagonist (e.g., travoprost) particles" and about 5 wt.-% to about 15 wt.-% of the total amount of prostaglandin antagonist (e.g., travoprost) is present in the form of particles according to the third specific aspect of the section "prostaglandin antagonist (e.g., travoprost) microparticles" and about 40 wt.-% to about 60 wt.-% of the total amount of prostaglandin antagonist (e.g., travoprost) is present in the form of particles according to the fourth specific aspect of the section "prostaglandin antagonist (e.g., travoprost) particles".

In another specific aspect, the present invention is directed to a multiplicity of prostaglandin antagonist (e.g., travoprost) particles being formed from a blend of particles according to the first to third specific aspects of the section "prostaglandin antagonist (e.g., travoprost) particles", such as based on the total amount of particles about 20 to about 35 wt.-% particles according to the first specific aspect of the section "prostaglandin antagonist (e.g., travoprost) particles" and about 30 to about 50 wt.-% particles according to the second specific aspect of the section "prostaglandin antagonist (e.g., travoprost) particles" and about 25 to about 45 wt.-% of particles according to the third specific aspect of the section "prostaglandin antagonist (e.g., travoprost) particles"; or wherein about 20 wt.-% to about 35 wt.-% of the total amount of prostaglandin antagonist (e.g., travoprost) is present in the form of particles according to the first specific aspect of the section "prostaglandin antagonist (e.g., travoprost) particles" and about 30 wt.-% to about 50 wt.-% of the total amount of prostaglandin antagonist (e.g., travoprost) is present in the form of particles according to the second specific aspect of the section "prostaglandin antagonist (e.g., travoprost) particles", and about 25 wt.-% to about 45 wt.-% of the total amount of prostaglandin antagonist (e.g., travoprost) is present in the form of particles according to the third specific aspect of the section "prostaglandin antagonist (e.g., travoprost) particles".

In a further specific aspect, the present invention is directed to a multiplicity of prostaglandin antagonist (e.g., travoprost) particles being formed from a blend of particles according to the first and the second specific aspects of the section "prostaglandin antagonist (e.g., travoprost) particles" such as based on the total amount of particles about 35 to about 55 wt.-% particles according to the first specific aspect of the section "prostaglandin antagonist (e.g., travoprost) particles" and about 35 to about 55 wt.-% particles according to the second specific aspect of the section "prostaglandin antagonist (e.g., travoprost) particles"; or wherein about 35 wt.-% to about 55 wt.-% of the total amount of prostaglandin antagonist (e.g., travoprost) is present in the form of particles according to the first specific aspect of the section "prostaglandin antagonist (e.g., travoprost) particles" and about 35 wt.-% to about 55 wt.-% of the total amount of prostaglandin antagonist (e.g., travoprost) is present in the form of particles according to the second specific aspect of the section "prostaglandin antagonist (e.g., travoprost) particles According to one aspect, the present invention is directed to multiplicity of travoprost particles being formed from a blend of particles of aspects (a) to (d) disclosed herein, such as based on the total amount of particles about 15 to about 25 wt.-% particles of aspect (a) disclosed herein and about 15 to about 25 wt.-% particles of aspect (b) disclosed herein and about 5 to about 15/o of particles of aspect (c) disclosed herein and about 40 to about 60 wt.-% of particles of aspect (d) disclosed herein; or wherein about 15 wt.-% to about 25 wt.-% of the total amount of travoprost is present in the form of particles of aspect (a) disclosed herein and about 15 wt.-% to about 25 wt.-% of the total amount of travoprost is present in the form of particles of aspect (b) disclosed herein and about 5 wt.-% to about 15 wt.-% of the total amount of travoprost is present in the form of particles of aspect (c) disclosed herein and about 40 wt.-% to about 60 wt.-% of the total amount of travoprost is present in the form of particles of aspect (d) disclosed herein.

According to one aspect, the present invention is directed to a multiplicity of travoprost particles being formed from a blend of particles of aspects (a) to (c) disclosed herein, such based on the total amount of particles as about 20 to about 35 wt.-% particles of aspect (a) disclosed herein and about 30 to about 50 wt.-% particles of aspect (b) disclosed herein and about 25 to about 45 wt.-% of particles of aspect (c) disclosed herein; or wherein about 20 wt.-% to about 35 wt.-% of the total amount of travoprost is present in the form of particles of aspect (a) disclosed herein and about 30 wt.-% to about 50 wt.-% of the total amount of travoprost is present in the form of particles of aspect (b) disclosed herein, and about 25 wt.-% to about 45 wt.-% of the total amount of travoprost is present in the form of particles of aspect (c) disclosed herein.

According to one aspect, the present invention is directed to a multiplicity of travoprost particles being formed from a blend of particles of aspects (a) and (b) such as based on the total amount of particles about 35 to about 55 wt.-% particles of aspect (a) and about 35 to about 55 wt.-% particles of aspect (b); or wherein about 35 wt.-% to about 55 wt.-% of the total amount of travoprost is present in the form of particles of aspect (a) and about 35 wt.-% to about 55 wt.-% of the total amount of travoprost is present in the form of particles of aspect (b).

In another aspect, the present invention is directed to multiplicity of travoprost particles being formed from a blend of particles, the particles consisting of a mixture of:
  travoprost;
  a biodegradable polymer consisting of polylactides having an acid end group, and
  optionally other pharmaceutically acceptable residual amounts of manufacturing components.

Prostaglandin Antagonist (e.g. Travoprost)
Sustained Release Biodegradable Intracameral
Implant According to one aspect, the present invention is directed to prostaglandin antagonist (e.g., travoprost) sustained release sustained release biodegradable intracameral implant comprising, such as consisting of
  a multiplicity of prostaglandin antagonist (e.g., travoprost) particles as defined in the preceding section and/or the section "prostaglandin antagonist (e.g., travoprost) particles" above; and
  a biodegradable hydrogel as defined in the section "biodegradable hydrogel" above, wherein the multiplicity of prostaglandin antagonist (e.g., travoprost) particles are dispersed within the hydrogel.

According to another aspect, the present invention is directed to prostaglandin antagonist (e.g., travoprost) sustained release sustained release biodegradable intracameral implant comprising, such as consisting of,
  a biodegradable hydrogel as defined in the section "biodegradable hydrogel" above and prostaglandin antagonist (e.g., travoprost) particles as defined in the section "prostaglandin antagonist (e.g., travoprost) particles" above,
  the prostaglandin antagonist (e.g., travoprost) particles being in the form of prostaglandin antagonist (e.g., travoprost) intermixed with a polylactide.
  the prostaglandin antagonist (e.g., travoprost) particles being dispersed within the hydrogel, wherein the hydrogel comprises a polymer network being formed by reacting a 8-arm-15K-SG or 8-arm-15K-SAZ polyethylene glycol each having a mass average molecular weight of 15,000±10% Daltons with trilysine acetate.

According to another aspect, the present invention is directed to an intracameral implant comprising:
  a biodegradable hydrogel, wherein the hydrogel comprises a polymer network comprising one or more units of polyalkylene glycol, and travoprost particles,
  the travoprost particles being in the form of travoprost intermixed with a biodegradable polymer, and
  the travoprost particles being dispersed within the hydrogel.

According to another aspect, the present invention is directed to a travoprost sustained release biodegradable intracameral implant comprising:
  a biodegradable hydrogel, wherein the hydrogel comprises a polymer network comprising one or more units of polyalkylene glycol, and travoprost particles,
  the travoprost particles being in the form of travoprost intermixed with a biodegradable polymer, and
  the travoprost particles being dispersed within the hydrogel,
  wherein the implant has a length of about 1.00 mm to about 2.50 mm and a diameter of not more than 0.30 mm in its dried state.

According to another aspect, the invention is directed to an intracameral implant comprising:
  biodegradable hydrogel comprising (i) a polymer network comprising one or more units of polyalkylene glycol, and (ii) sustained release travoprost particles,
  the sustained release travoprost particles comprising travoprost and at least one biodegradable polymer, and
  the sustained release travoprost particles dispersed within the hydrogel.

In certain embodiments, the implant has a length of about 1 mm to about 2.5 mm in its dry state, a diameter of not more than 0.3 mm in its dried state and a total weight of about 20 μg to about 110 μg in its dry state.

In certain embodiments, the implant has a diameter of less than 0.5 mm after 24 hours of hydration in vitro in phosphate-buffered saline at a pH of 7.4 at 37° C.

In certain embodiments, the implant has a diameter ranging from about 0.3 mm to 0.49 mm after 24 hours of hydration in vitro in phosphate-buffered saline at a pH of 7.4 at 37° C.

In certain embodiments, the implant is adapted to be an intracameral implant.

In certain embodiments, the hydrogel dissolves within 2 to 4 months when implanted into the eye.

In certain embodiments, the hydrogel dissolves within 6 to 8 months when implanted into the eye.

Without wishing to be bound to any theory, it is believed that the hydrogel implant is small enough to sink into the iridocorneal angle (e.g. below Schwalbe's line) when inserted into the anterior chamber of the eye then swells sufficiently by taking up the aqueous humor and thereby gets fixated in the iridocorneal angle and will therefore not move during its entire period of being placed there. During the period of treatment, the implant gets increasingly soft and, therefore, can adapt further to the anatomical conditions thereby further prohibiting any movement before the hydrogel fully degrades. The prohibition of movement and its soft tissue-like texture provides for its gentleness to the endothelium and overall safety of the implant and, therefore, allows repeated administration. It is further believed that due to the possibility of size decrease such implants are suitable for a wide range of anatomical conditions including narrow iridocorneal angles.

The following embodiments relate to each of the aspects described in the preceding paragraphs.

In one embodiment, the prostaglandin antagonist (e.g., travoprost) particles comprise, such as consist of, a blend of two types of particles, the first type of particle being in the form of prostaglandin antagonist (e.g., travoprost) intermixed with the biodegradable polymer consisting of the first polylactide as defined above and the second type of particle being in the form of prostaglandin antagonist (e.g., travoprost) intermixed with the biodegradable polymer consisting of the second polylactide as defined above, and optionally the intracameral implant does not include a further polylactide.

In another embodiment, wherein the prostaglandin antagonist (e.g., travoprost) particles or comprise a blend of different types of particles, such as particles in the form of prostaglandin antagonist (e.g., travoprost) intermixed with a first polylactide as defined above and particles in the form of prostaglandin antagonist (e.g., travoprost) intermixed with a second polylactide as defined above, and optionally the intracameral implant does not include a further polylactide.

In a certain embodiment, the travoprost particles, as described herein, are a blend of at least two types of travoprost particles the blend being selected from the group consisting of:

1) a blend of particles made of
   a first type of travoprost particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles; and
   a second type of travoprost particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particles contains from about 40 wt.-% to about 50 wt.-%, such as more than from about 45 wt.-% to about 47 wt.-% travoprost, based on the total mass of the second type of particles,
   such as wherein the blend contains, based on the total amount of the blend, about 35 wt.-% to about 55 wt.-% particles of the first type of particles and about 35 wt.-% to about 55 wt.-% particles of the second type of particles; or
   such as wherein about 35 wt.-% to about 55 wt.-% of the total amount of travoprost in the implant is present in the form of particles of the first type of particles and about 35 wt.-% to about 55 wt.-% of the total amount of travoprost in the implant is present in the form of particles of the second type of particles, wherein optionally the polymer network is formed by reacting an electrophilic group-containing multi-arm-polymer precursor with a nucleophilic group-containing cross-linking agent, the electrophilic group is a succinimidyl-glutarate (SG) group and the multi-arm polymer precursor an 8-arm-15K-SG polyethylene glycol; and the nucleophilic group-containing cross-linking agent is a trilysine;

2) a blend of particles made of
   a first type of particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles,
   a second type of travoprost particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particle contains from about 40 wt.-% to about 50 wt.-%, such as more than from about 45 wt.-% to about 47 wt.-% travoprost, based on the total mass of the second type of particles, and
   a third type of travoprost particles made of a mixture of travoprost and the biodegradable polymer consisting of a polylactide or polylactides having an acid end group and an inherent viscosity specification ranging from about 0.8 to about 1.7 dl/g, such as ranging from about 0.8 to about 1.0 dl/g, wherein the third type of particles contains from about 40 wt.-% to about 50 wt.-%, such as from about 41 wt.-% to about 43 wt.-% travoprost, based on the total mass of the third type of particles,
   such as wherein the blend contains, based on the total amount of blend, about 20 wt.-% to about 35 wt.-% particles of the first type of particles and about 30 wt.-% to about 50 wt.-% particles of the second type of particles and about 25 wt.-% to about 45 wt.-% of particles of the third type of particles; or
   such as wherein about 20 wt.-% to about 35 wt.-% of the total amount of travoprost in the implant is present in the form of particles of the first type of particles and about 30 wt.-% to about 50 wt.-% of the total amount of travoprost in the implant is present in the form of particles of the second type of particles, and about 25 wt.-% to about 45 wt.-% of the total amount of travoprost in the implant is present in the form of particles of the third type of particles, wherein optionally the polymer network is formed by reacting an electrophilic group-containing multi-arm-polymer precursor with a nucleophilic group-containing cross-linking agent, the electrophilic group is a succinimidylglutarate (SG) group and the multi-arm polymer precursor an 8-arm-15K-SG polyethylene glycol; and the nucleophilic group-containing cross-linking agent is a trilysine; and 3) a blend of particles made of
   a first type of particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles,
   a second type of particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particles contains from about 40 wt.-% to about 50 wt.-%, such as more than from about 45 wt.-% to about 47 wt.-% travoprost, based on the total mass of the second type of particles,
   a third type of particles made of travoprost and the biodegradable polymer consisting of a polylactide or polylactides having an acid end group and an inherent viscosity specification ranging from about 0.8 to about 1.7 dl/g, such as ranging from about 0.8 to about 1.0 dl/g, wherein the third type of particles contain from about 40 wt.-% to about 50 wt.-%, such as from about 41 wt.-% to about 43 wt.-% travoprost, based on the total mass of the third type of particles, and
   a fourth type of particles made of travoprost and the biodegradable polymer consisting of a polylactide or polylactides having an ester end group and an inherent viscosity specification ranging from about 0.05 to about 1.7 dl/g, such as ranging from about 0.55 to about 0.75 dl/g, wherein the fourth type of particles contains from about 40 wt.-% to about 50 wt.-%,
such as wherein the blend contains, based on the total amount of blend, about 15 wt.-% to about 25 wt.-% particles of the first type of particles and about 15 wt.-% to about 25 wt.-% particles of the second type of particles and about 5 wt.-% to about 15% of particles of the third type of particles and about 40 wt.-% to about 60 wt.-% of particles of the fourth type of particles; or
such as wherein about 15 wt.-% to about 25 wt.-% of the total amount of travoprost in the implant is present in the form of particles of the first type of particles and about 15 wt.-% to about 25 wt.-% of the total amount of travoprost in the implant is present in the form of particles of the second type of particles and about 5 wt.-% to about 15 wt.-% of the total amount of travoprost in the implant is present in the form of particles of the third type of particles and about 40 wt.-% to about 60 wt.-% of the total amount of travoprost in the implant is present in the form of particles of the fourth type of particles, wherein optionally the polymer network is formed by reacting an electrophilic group-containing multi-arm-polymer precursor with a nucleophilic group-containing cross-linking agent, the electrophilic group is a succinimidylazelate (SAZ) group, and the multi-arm polymer precursor is a 8-arm-15K-SAZ polyethylene glycol; and the nucleophilic group-containing cross-linking agent is a trilysine.

In a further embodiment, the intracameral implant has an in vitro release with an average prostaglandin antagonist (e.g., travoprost) release ranging from of about 65% to about 85% with a mean absolute deviation of at most 5%, based on the % amount released per 70 days from day 1 to day 84, when measured at 37° C. in PBS at a pH of 7.2 to 7.4 under sink-conditions.

In certain embodiments, the implant shows a burst of less than 15%, based on the total weight of travoprost in the intracameral implant, on day 1 measured in vitro under simulated physiological sink conditions in 50 mL of 1×PBS, 0.5% castor oil, 0.01% sodium fluoride buffer at pH 7.2-7.4 at 37° C.

In a further embodiment, the implant has an in vitro release with an average prostaglandin antagonist (e.g., travoprost) release ranging from about 800 to about 1100 ng/week with a standard deviation ranging from 450 to 550 ng/week, wherein the average is based on the weekly prostaglandin antagonist (e.g., travoprost) release values between days 7 to 98 excluding post dose day 1 burst when measured at 37° C. in PBS at a pH of 7.2 to 7.4 under sink-conditions; or wherein the weekly prostaglandin antagonist (e.g., travoprost) release ranges from about 100 to about 2300 ng, when measured in a time interval between days 7 to 98 excluding post dose day 1 burst when measured at 37° C. in PBS at a pH of 7.2 to 7.4 under sink-conditions.

In another embodiment, the prostaglandin antagonist (e.g., travoprost) particles comprise or are a blend of different types of particles including particles in the form of prostaglandin antagonist (e.g., travoprost) intermixed with a first polylactide as defined above, particles in the form of prostaglandin antagonist (e.g., travoprost) intermixed a second polylactide as defined above and particles in the form of prostaglandin antagonist (e.g., travoprost) intermixed with a third polylactide as defined above, wherein each of the polylactides have an acid end group, and optionally the intracameral implant does not include a further polylactide.

In one embodiment, the prostaglandin antagonist (e.g., travoprost) particles comprise or consist of a blend of three types of particles, the first type of particle being in the form of prostaglandin antagonist (e.g., travoprost) intermixed with the biodegradable polymer consisting of the first polylactide as defined above, and the second type of particles being in the form of prostaglandin antagonist (e.g., travoprost) intermixed with the biodegradable polymer consisting of the second polylactide as defined above and the third type of particles in the form of prostaglandin antagonist (e.g., travoprost) travoprost intermixed with the biodegradable polymer as defined above consisting of the third polylactide as defined above, wherein optionally the intracameral implant does not include a further polylactide.

In a further embodiment, the intracameral implant has an in vitro release with an average prostaglandin antagonist (e.g., travoprost) release ranging from of about 60% to about 80% with a mean absolute deviation of at most 5%, or a prostaglandin antagonist (e.g., travoprost) release ranging from 60% to 80%, based on the %-amount released per 70 days from day 1 to day 98, when measured at 37° C. in PBS at a pH of 7.2 to 7.4 under sink-conditions.

In certain embodiments, the implant has an in vitro release with an average prostaglandin antagonist (e.g., travoprost) release ranging from about 800 to about 1100 ng/week with a standard deviation ranging from 450 to 550 ng/week, wherein the average is based on the weekly prostaglandin antagonist (e.g., travoprost) release values between days 7 to 98 excluding post dose day 1 bur when measured at 37° C. in PBS at a pH of 7.2 to 7.4 under sink-conditions st; or wherein the weekly prostaglandin antagonist (e.g., travoprost) release ranges from about 100 to about 2300 ng, when measured in a time interval between days 7 to 98 excluding post dose day 1 burst when measured at 37° C. in PBS at a pH of 7.2 to 7.4 under sink-conditions.

In certain embodiments, the prostaglandin antagonist (e.g., travoprost) particles comprise or are a blend of different types of particles including particles in the form of prostaglandin antagonist (e.g., travoprost) intermixed with a first polylactide as defined above, particles in the form of prostaglandin antagonist (e.g., travoprost) intermixed a second polylactide as defined above, particles in the form of prostaglandin antagonist (e.g., travoprost) intermixed with a third polylactide as defined above and particles in the form of prostaglandin antagonist (e.g., travoprost) intermixed with a fourth polylactide as defined above, and optionally, the intracameral implant does not include a further polylactide.

In further embodiments, the prostaglandin antagonist (e.g., travoprost) particles comprise or consist of a blend of four type of particles, the first type of particle being in the form of prostaglandin antagonist (e.g., travoprost) intermixed with the biodegradable polymer consisting of the first polylactide as defined above, the second type of particles being in the form of prostaglandin antagonist (e.g., travoprost) intermixed with the biodegradable polymer consisting of the second polylactide as defined above, the third type of particles being in the form of prostaglandin antagonist (e.g., travoprost) intermixed with the biodegradable polymer consisting of the third polylactide as defined above and the fourth type of particles being in the form of prostaglandin antagonist (e.g., travoprost) intermixed with the biodegradable polymer consisting of the fourth polylactide as defined above, and optionally the intracameral implant does not include a further polylactide.

In a certain embodiment, the intracameral implant has an in vitro release with an average prostaglandin antagonist (e.g., travoprost) release ranging from of about 5% to about 15% with a mean absolute deviation of at most 3%, based on the % amount released per 14 days from day 1 to day 112, when measured at 37° C. in PBS at a pH of 7.2 to 7.4 under sink-conditions.

In a further embodiment, the content of the biodegradable polymer with respect to the total weight of the travoprost sustained release biodegradable intracameral implant is about 10 wt.-% to about 35 wt.-%, or about 23 to about 27 wt.-%, or about 12 to about 17 wt.-%, or about 30 to about 35 wt.-%, or about 25 wt.-%, or about 15 wt.-%, or about 34 wt.-%.

In another embodiment, the content of the biodegradable hydrogel with respect to the total weight of the one sustained release biodegradable intracameral implant is about 30 to about 70 wt.-%, or about 32 to about 37 wt.-%, or about 45 to about 55 wt.-%, or about 60 to about 70 wt.-%, or about 49.3 wt.-% or about 37.5 wt.-% or about 50.1 wt.-% or about 66.8 wt.-%.

According to a further embodiment, the content of the nucleophilic group-containing crosslinking agent with respect to the total weight of the one sustained release biodegradable intracameral implant is about 1 to about 5 wt.-% or 1 to about 3 wt.-%, or 2 to about 4 wt.-% or 4 to about 5 wt.-%, or about 3.2 wt.-%, or about 2.3 wt.-%, or about 4.3 wt.-%.

In a certain embodiment, the content of the visualization agent with respect to the total weight of the one sustained release biodegradable intracameral implant is about 0.1 to about 0.5 wt.-%, or 0.2 wt.-%, or 0.3 wt.-%.

In a further embodiment, the implant contains a dose of about 2 µg to about 30 µg, or about 21 µg to about 30 µg, or about 11 µg to about 20 µg, or about 2 µg to about 10 µg of travoprost. In a specific embodiment, the implant contains a dose of about 5 µg of travoprost. In another specific embodiment, the implant contains a dose of about 15 µg of travoprost. In an alternative specific embodiment, the implant contains a dose of about 26 µg of travoprost.

In a certain embodiment, the total mass of the biodegradable polymer in the implant is less than 34 µg, less than 30 µg, less than 20 µg, or less than 10 µg.

In a certain embodiment, the travoprost in the implant is less than 25 µg, or less than 20 µg, or less than 10 µg.

In a certain embodiment, the total mass of the implant in its dried state is less than 103 µg, less than 80 µg or less than 50 µg.

In certain embodiments, the implant contains a dose of about 5 µg of travoprost and the multi-arm polymer precursor is an 8-arm-15K-SG polyethylene glycol and the nucleophilic group-containing cross-linking agent is a trilysine.

In certain embodiments, the implant contains a dose of about 15 µg of travoprost and the multi-arm polymer precursor is an 8-arm-15K-SG polyethylene glycol and the nucleophilic group-containing cross-linking agent is a trilysine.

In certain embodiments, the implant contains a dose of about 15 µg of travoprost and the multi-arm polymer precursor is an 8-arm-15K-SAZ polyethylene glycol and the nucleophilic group-containing cross-linking agent is a trilysine.

In certain embodiments, the implant contains a dose of about 26 µg of travoprost and the multi-arm polymer precursor is an 8-arm-15K-SAZ polyethylene glycol and the nucleophilic group-containing cross-linking agent is a trilysine.

In certain embodiments, the implant has a diameter of less than 0.50 mm after 24 hours of hydration in vitro in phosphate-buffered saline (PBS) at a pH of 7.4 at 37° C. In particular, the volume of PBS used for such hydration is 5 ml added to a sample tube. Said sample tube is in particular equilibrated at 37° C. before adding the 5 ml of PBS. More specifically the implant has a diameter ranging from about 0.30 mm to 0.49 mm, or from about 0.40 mm to about 0.49 mm, after 24 hours of hydration in vitro in phosphate-buffered saline at a pH of 7.4 at 37° C.

In certain embodiments, a ratio of a diameter of the implant after 24 hours of hydration in vitro in phosphate-buffered saline at a pH of 7.4 at 37° C. to the diameter of the implant in its dried state is less than 2.5. In particular, the volume of PBS used for such hydration is 5 ml added to a sample tube. Said sample tube is in particular equilibrated at 37° C. before adding the 5 ml of PBS.

In a particular embodiment, the implant is in the form of a fiber. In particular, the implant is in the form of a fiber that has a length of less than about 2.5 mm or about 1.0 mm to about 2.5 mm and a diameter of not more than 0.3 mm or 0.14 mm to about 0.29 mm in its dried state. Alternatively, the implant is in the form of a fiber that has a diameter of 0.6 mm or less and a length of 3.0 mm or less in equilibrium state after 24 hours of hydration in vitro in phosphate-buffered saline at a pH of 7.4 at 37° C.

In certain embodiments, the implant has a length of about 1.00 mm to about 2.50 mm and a diameter of not more than 0.30 mm in its dried state.

In certain embodiments, the implant is a fiber that has a length of about 1.5 mm to about 2.5 mm, or about 1.8 mm to about 2.2 mm; and a diameter of about 0.14 mm to about 0.29 mm, or about 0.20 mm to about 0.24 mm, or about 0.20 mm to about 0.28 mm, or about 0.19 mm to about 0.23 mm, or about 0.15 mm to about 0.19 mm in its dried state.

In certain embodiments, the implant in its dry from has a total weight of about 20 to about 150 µg, or about 70 µg to about 80 µg, or about 40 µg to about 50 µg, or about 90 µg to 110 µg. In a further embodiment, the implant in its dry form has a total weight of about 20 µg to about 110 µg, or of about 30 µg to about 105 µg.

In certain embodiments, the travoprost in the implant is less than 25 µg, or less than 20 µg, or less than 10 µg.

According to certain embodiments, the implant has an in vitro release with an average prostaglandin antagonist (e.g., travoprost) travoprost release ranging from about 500 to about 900 ng/week with a standard deviation ranging from 150 to 250 ng/week, wherein the average is based on the weekly prostaglandin antagonist (e.g., travoprost) travoprost release values between days 7 to 119 excluding post dose day 1 burst when measured at 37° C. in PBS at a pH of 7.2 to 7.4 under sink conditions; or wherein the weekly prostaglandin antagonist (e.g., travoprost) travoprost release ranges from about 100 to about 1500 ng, when measured in a time interval between days 7 to 119 excluding post dose day 1 burst; when measured at 37° C. in PBS at a pH of 7.2 to 7.2 under sink conditions.

According to another aspect, the present invention is directed to an intracameral implant including
  a multiplicity of travoprost particles according to any one of aspects (a) to (d) disclosed herein; and
  a biodegradable hydrogel,
wherein the multiplicity of travoprost particles are dispersed within the hydrogel.

According to another aspect, the present invention is directed to an intracameral implant including
  a biodegradable hydrogel and travoprost particles,
  the travoprost particles being in the form of travoprost intermixed with a polylactide,
  the travoprost particles being dispersed within the hydrogel, wherein the hydrogel comprises a polymer network being formed by reacting a 8-arm-15K-SG or 8-arm-15K-SAZ polyethylene glycol each having a mass average molecular weight of 15,000±10% Daltons with trilysine acetate; or the polymer network comprises 8-arm-polyethylene glycols being cross-linked including a group represented by the following formula

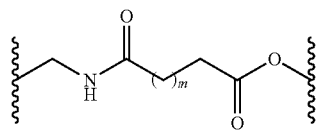

wherein m is 2 or 6.

Method of Manufacturing the Prostaglandin Antagonist (e.g. Travoprost) Sustained Release Biodegradable Intracameral Implant In a further aspect, the present invention is directed to method of manufacturing a prostaglandin antagonist (e.g., travoprost) sustained release sustained release biodegradable intracameral implant, the method comprising the steps of:
  a) preparing travoprost particles being in the form of prostaglandin antagonist (e.g., travoprost) intermixed with a biodegradable polymer,
  b) preparing a precursor mixture containing hydrogel precursors and the prostaglandin antagonist (e.g., travoprost) particles,
  c) cross-linking the precursor mixture using a cross-linker to form a polymer network and to obtain a hydrogel mixture comprising the polymer network, and
  d) drying the hydrogel mixture to provide the implant.

The types of components, the contents of the components and the mass ratios of the mass ratios described in the preceding sections "prostaglandin antagonist (e.g., travoprost) particles", "biodegradable hydrogel", "multiplicity of prostaglandin antagonist (e.g., travoprost) particles", and "prostaglandin antagonist (e.g., travoprost) sustained release biodegradable intracameral implant" also apply correspondingly for the method of manufacturing of the present invention.

In another aspect, the present invention is directed to a sustained release biodegradable intracameral implant obtainable by the method as described in the section "method of manufacturing the prostaglandin antagonist (e.g., travoprost) sustained release biodegradable implant".

In another aspect, the present invention is directed to a method of manufacturing an intracameral implant, the method comprising the steps of:
  a) preparing travoprost particles being in the form of travoprost intermixed with a biodegradable polymer,
  b) preparing a precursor mixture containing hydrogel precursors and the travoprost particles,
  c) cross-linking the precursor mixture using a cross-linker to form a polymer network and to obtain a hydrogel mixture comprising the polymer network, and
  d) drying the hydrogel mixture to provide the implant.

In another aspect, the present invention is directed to an intracameral implant obtainable by the method of the preceding paragraph.

Syringe for Intracameral Injection

According to one aspect, the present invention is directed to a syringe for intracameral injection including the prostaglandin antagonist (e.g., travoprost) sustained release biodegradable intracameral implant as defined above.

According to one aspect, the present invention is directed to a syringe for intracameral injection including an implant as disclosed herein.

A particular embodiment of said syringe is shown in Example 4.

Method of Treating Intraocular Pressure in a Human Subject

One aspect of the present invention is directed to method of treating intraocular pressure in a human subject with ocular hypertension or with glaucoma such as open angle glaucoma for a period ranging from about 2 to about 12 months or from about 3 to about 9 months with one single prostaglandin antagonist (e.g., travoprost) sustained release biodegradable intracameral implant, as defined in the sections above, per eye in need of treating, the method comprising per said eye:

Step 1: providing one prostaglandin antagonist (e.g., travoprost) sustained release biodegradable intracameral implant, as defined in the sections above, providing treatment for a period ranging from about 2 to about 12 months or from about 3 to about 9 months comprising:
a biodegradable hydrogel as defined in the sections above and prostaglandin antagonist (e.g., travoprost) particles as defined in the sections above,
the prostaglandin antagonist (e.g., travoprost) particles being in the form of prostaglandin antagonist (e.g., travoprost) intermixed with a biodegradable polymer, and
the prostaglandin antagonist (e.g., travoprost) particles being dispersed within the hydrogel; and Step 2: inserting the one sustained release biodegradable intracameral implant of step 1 into the anterior segment of said eye to place it within the iridocorneal angle of said eye.

One aspect of the present invention is directed to method of treating intraocular pressure in a human subject with ocular hypertension or with glaucoma such as open angle glaucoma for a period ranging from about 2 to about 12 months or from about 3 to about 9 months with one single prostaglandin antagonist (e.g., travoprost) sustained release biodegradable intracameral implant, as defined in the sections above, per eye in need of treating, the method comprising per said eye inserting the one sustained release biodegradable intracameral implant into the anterior segment of said eye to place it within the iridocorneal angle of said eye, wherein the implant is as defined in the sections above, providing treatment for a period ranging from about 2 to about 12 months or from about 3 to about 9 months comprising:
a biodegradable hydrogel as defined in the sections above and prostaglandin antagonist (e.g., travoprost) particles as defined in the sections above,
the prostaglandin antagonist (e.g., travoprost) particles being in the form of prostaglandin antagonist (e.g., travoprost) intermixed with a biodegradable polymer, and
the prostaglandin antagonist (e.g., travoprost) particles being dispersed within the hydrogel.

Another aspect of the present invention is directed to a travoprost sustained release biodegradable intracameral implant as described herein for use in a method of treating intraocular pressure in a human subject with ocular hypertension and/or glaucoma for a period ranging from about 1 to about 24 months such as from about 3 to about 9 months with one single travoprost sustained release biodegradable implant per eye in need of treating.

Another aspect of the present invention is directed to a method of treating intraocular pressure in a human subject with ocular hypertension and/or glaucoma for a period ranging from about 1 to about 24 months such as from about 3 to about 9 months with one single intracameral implant according to any one of claims 1 to 20 per eye in need of treating.

According to certain embodiments of the present invention, the implant is in a dried state prior to insertion and becomes hydrated once inserted into the eye. In certain embodiments the hydration occurs in less than 2 minutes.

In certain embodiments of the present invention, the treatment period is about 6 to about 9 months and the prostaglandin antagonist (e.g., travoprost) sustained release biodegradable intracameral implant provides treatment for about 6 to about 9 months. In another embodiment, the treatment period is about 4 to about 7 months and the prostaglandin antagonist (e.g., travoprost) sustained release biodegradable intracameral implant provides treatment for about 4 to about 7 months. In an alternative embodiment, the treatment period is about 3 to about 6 months and the prostaglandin antagonist (e.g., travoprost) sustained release biodegradable intracameral implant provides treatment for about 3 to about 6 months. In an alternative embodiment, the treatment period is about 3 to about 4 months and the prostaglandin antagonist (e.g., travoprost) sustained release biodegradable intracameral implant provides treatment for about 3 to about 4 months. In further embodiments, wherein the treatment period is about 7 to about 8 months, or about 7 to about 9 months, or about 4 months, or about 5 months, or about 6 months, or about 7 months, or about 8 months, or about 9 months and the prostaglandin antagonist (e.g., travoprost) sustained release biodegradable intracameral implant provides treatment for about 7 to about 8 months, or about 7 to about 9 months, or about 4 months, or about 5 months, or about 6 months, or about 7 months, or about 8 months, or about 9 months, respectively.

In certain embodiments,
the intracameral implant has an in vitro release with an average travoprost release ranging from of about 65% to about 85% with a mean absolute deviation of at most 5%, based on the % amount released per 70 days, from day 1 to day 84, when measured at 37° C. in PBS at a pH of 7.2 to 7.4 under sink-conditions wherein the treatment period is about 3 to about 6 months or is about 3 to 4 months; or
wherein the intracameral implant has an in vitro release with an average travoprost release ranging from of about 60% to about 80% with a mean absolute deviation of at most 5%, based on the %-amount released per 70 days, from day 1 to day 98, when measured at 37° C. in PBS at a pH of 7.2 to 7.4 under sink-conditions wherein the treatment period is about 3 to about 7 months or is about 4 to 7 months; or
wherein the intracameral implant has an in vitro release with an average travoprost release ranging from of about 5% to about 15% with a mean absolute deviation of at most 3%, based on the % amount released per 14 days, from day 1 to day 112, when measured at 37° C. in PBS at a pH of 7.2 to 7.4 under sink-conditions, wherein the treatment period is about 6 to about 9 months or about 6 to about 12 months.

In certain embodiments of the present invention, the treatment period is about 3 to about 7 months or is about 4 to 7 months or is about 3 to about 6 months or is about 3 to 4 months and the travoprost sustained release biodegradable intracameral implant provides treatment for about 3 to about 7 months or for about 4 to 7 months or for about 3 to about 6 months or for 3 to 4 months, wherein the polymer network is formed by reacting an electrophilic group-containing multi-arm-polymer precursor with a nucleophilic group-containing cross-linking agent, the electrophilic group is a succinimidylglutarate (SG) group and the multi-arm polymer precursor an 8-arm-15K-SG polyethylene glycol; and the nucleophilic group-containing cross-linking agent is a trilysine and the hydrogel dissolves within 2 to 4 months.

In certain embodiments, the treatment period is about 6 to about 9 months or about 6 to about 12 months and the travoprost sustained release biodegradable intracameral implant provides treatment for about 6 to 9 months or for about 6 to about 12 months, wherein the polymer network is formed by reacting an electrophilic group-containing multi-arm-polymer precursor with a nucleophilic group-containing cross-linking agent, the electrophilic group is a succinimidylazelate (SAZ) group, and the multi-arm polymer precursor is a 8-arm-15K-SAZ polyethylene glycol; and the nucleophilic group-containing cross-linking agent is a trilysine and the hydrogel dissolves within 6 to 8 months.

In certain embodiments, the treatment is continued after said treatment period is ranging from about 2 to about 12 months is ranging from about 3 to about 9 months by repeating step 1 and step 2. More specifically, the treatment is continued by repeating steps 1 and 2 until no further treatment is required. Even more specifically, he treatment includes a repetition of steps 1 and 2 once a year, two times a year, 3 times a year or four times a year in about equal time distances with a prostaglandin antagonist (e.g., travoprost) sustained release biodegradable intracameral implant providing treatment for about 12 months for once a year providing treatment for 6 to 9 months for 2 times a year and with a prostaglandin antagonist (e.g., travoprost) sustained release biodegradable intracameral implant providing treatment for 3 to 4 months for 3 times a year or 4 times a year.

In another embodiment, the first treatment period is 3 to 4 months and the prostaglandin antagonist (e.g., travoprost) sustained release biodegradable intracameral implant providing treatment for 3 to 4 months, and the treatment continues with a treatment period of 6 to 9 months with a prostaglandin antagonist (e.g., travoprost) sustained release biodegradable intracameral implant providing treatment for 6 to 9 months.

In certain embodiments the travoprost sustained release biodegradable intracameral implant or the hydrogel dissolves/fully biodegrades within 5 to 7 months or within 3 to 5 months.

In certain embodiments the treatment period ranges from 6 t 9 months or from 6 to 12 months and the travoprost sustained release biodegradable intracameral implant or the hydrogel dissolves/fully biodegrades within 5 to 7 months. In certain embodiments the treatment period ranges from 3 to 6 months and the travoprost sustained release biodegradable intracameral implant or the hydrogel dissolves/fully biodegrades within 3 to 5 months.

In certain embodiments, "glaucoma" may encompass the forms of open-angle glaucoma and angle-closure glaucoma. Subtypes of open-angle glaucoma disclosed herein may encompass normal-tension glaucoma, congenital glaucoma, secondary glaucoma, pigmentary glaucoma, pseudoexfoliative glaucoma, traumatic glaucoma, neovascular glaucoma, irido corneal endothelial syndrome (ICE), and/or uveitic glaucoma.

In certain embodiments, the treatment of the present invention is against mild, moderate or severe open angle glaucoma.

In certain embodiments, in the treatment of the present invention the intraocular pressure is decreased by at least 4 mmHg, or at least 5 mmHg from base line intraocular pressure during the treatment period such as described herein or such as about 1 to about 12 months or about 2 to about 12 months or about 3 to about 9 months, such as about 6 months to about 12 months or such as about 6 months to about 9 months or during continued treatment with repeated administration. According the certain embodiments the intraocular pressure is decreased up to 7 to 11 mmHg. Alternatively, in the treatment of the present invention the intraocular pressure is decreased by at least 20%, or at least 25%, or at least about 30%, or from about 20% to about 35%, or from about 20% to about 30% with respect to the base line intraocular pressure during the treatment period such as described herein or such as about 1 to about 12 months or about 2 to about 12 months or about 3 to about 9 months, such as about 6 months to about 12 months or such as about 6 months to about 9 months or during continued treatment with repeated administration. The decrease is measured at 2 weeks, 6 weeks, 12 weeks, 4 months, 6 months, 9 months and 12 months, which ever time points are applicable for the respective period of treatment. The measurement is conducted at 8 am, 10 am and 4 pm on each relevant time point. Alternatively the treatment is for the respective period of treatment at the respective time points noninferior with a different intraocular pressure medicament, such as travoprost eye drops, wherein the noninferiority margin is 1.5 mm Hg.

In certain embodiments the treatment prevents vision loss, such as periphery vision loss.

In certain embodiments the treatment prevents optic nerve fiber loss.

In certain embodiments the treatment prevents retina ganglion cell death

In certain embodiments the treatment prevents optic nerve damage.

In certain embodiments, in the treatment of the present invention the intraocular pressure is already significantly decreased at least five days or at least three days or at least two days following the administration.

In certain embodiments, in the treatment of the present invention the intraocular pressure is decreases comparable to topical travoprost therapy.

In certain embodiments, no change of endothelial cell count occurs in the treated eye during the treatment period and/or entire treatment.

In certain embodiments, no change of the thickness of the cornea occurs in the treated eye or during the treatment period and/or entire treatment.

In certain embodiments the implant does substantially not move as e.g. monitored by gonioscopy and slit lamp exam.

In certain embodiments the implant the implant is cosmetically invisible.

In certain embodiments, the treatment period is about 3 to about 6 months or is about 3 to 4 months and the travoprost sustained release biodegradable intracameral implant provides treatment about 3 to about 6 months or for 3 to 4 months, wherein the travoprost particles are a blend of particles made of
  a first type of travoprost particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles; and
  a second type of travoprost particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particles contains from about 40 wt.-% to about 50 wt.-%, such as more than from about 45 wt.-% to about 47 wt.-% travoprost, based on the total mass of the second type of particles, wherein the blend contains, based on the total amount of particles, about 35 wt.-% to about 55 wt.-% particles of the first type of particles and about 35 wt.-% to about 55 wt.-% particles of the second type of particles; or wherein about 35 wt.-% to about 55 wt.-% of the total amount of travoprost in the implant is present in the form of particles of the first type of particles and about 35 wt.-% to about 55 wt.-% of the total amount of travoprost in the implant is present in the form of particles of the second type of particles.

In certain embodiments, the treatment period is 4 to 7 months and the travoprost sustained release biodegradable intracameral implant provides treatment for about 4 to about 7 months, wherein the travoprost particles are a blend of particles made of
- a first type of particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles,
- a second type of particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particle contains from about 40 wt.-% to about 50 wt.-%, such as more than from about 45 wt.-% to about 47 wt.-% travoprost, based on the total mass of the second type of particles, and
- a third type of particles made of a mixture of travoprost and the biodegradable polymer consisting of a polylactide or polylactides having an acid end group and an inherent viscosity specification ranging from about 0.8 to about 1.7 dl/g, such as ranging from about 0.8 to about 1.0 dl/g, wherein the third type of particles contains from about 40 wt.-% to about 50 wt.-%, such as from about 41 wt.-% to about 43 wt.-% travoprost based on the total mass of the third type of particles, wherein the blend contains, based on the total amount of particles, about 20 wt.-% to about 35 wt.-% particles of the first type of particles and about 30 wt.-% to about 50 wt.-% particles of the second type of particles and about 25 wt.-% to about 45 wt.-% of particles of the third type of particles; or wherein about 20 wt.-% to about 35 wt.-% of the total amount of travoprost in the implant is present in the form of particles of the first type of particles and about 30 wt.-% to about 50 wt.-% of the total amount of travoprost in the implant is present in the form of particles of the second type of particles, and about 25 wt.-% to about 45 wt.-% of the total amount of travoprost in the implant is present in the form of particles of the third type of particles.

In certain embodiments, the treatment period is about 6 to about 12 months about 6 to about 9 months and the travoprost sustained release biodegradable intracameral implant provides treatment for about 6 to 12 months or for about 6 to 9 months, wherein the travoprost particles are a blend of particles made of
- a first type of particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles,
- a second type of particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particles contains from about 40 wt.-% to about 50 wt.-%, such as more than from about 45 wt.-% to about 47 wt.-% travoprost, based on the total mass of the second type of particles,
- a third type of particles made of travoprost and the biodegradable polymer consisting of a polylactide or polylactides having an acid end group and an inherent viscosity specification ranging from about 0.8 to about 1.7 dl/g, such as ranging from about 0.8 to about 1.0 dl/g, wherein the third type of particles contain from about 40 wt.-% to about 50 wt.-%, such as from about 41 wt.-% to about 43 wt.-% travoprost, based on the total mass of the third type of particles, and
- a fourth type of particles made of travoprost and the biodegradable polymer consisting of a polylactide or polylactides having an ester end group and an inherent viscosity specification ranging from about 0.05 to about 1.7 dl/g, such as ranging from about 0.55 to about 0.75 dl/g, wherein the fourth type of particles contains from about 40 wt.-% to about 50 wt.-%, such as from about 41 wt.-% to about 43 wt.-% travoprost, based on the total mass of the fourth type of particles, wherein the blend contains, based on the total amount of particles, about 15 wt.-% to about 25 wt.-% particles of the first type of particles and about 15 wt.-% to about 25 wt.-% particles of the second type of particles and about 5 wt.-% to about 15% of particles of the third type of particles and about 40 wt.-% to about 60 wt.-% of particles of the fourth type of particles; or wherein about 15 wt.-% to about 25 wt.-% of the total amount of travoprost in the implant is present in the form of particles of the first type of particles and about 15 wt.-% to about 25 wt.-% of the total amount of travoprost in the implant is present in the form of particles of the second type of particles and about 5 wt.-% to about 15 wt.-% of the total amount of travoprost in the implant is present in the form of particles of the third type of particles and about 40 wt.-% to about 60 wt.-% of the total amount of travoprost in the implant is present in the form of particles of the fourth type of particles.

In certain embodiments, the treatment period is about 3 to about 6 months or is about 3 to 4 months, the implant contains a dose of about 5 μg of travoprost, and wherein the implant has an in vitro release with an average travoprost release ranging from about 300 to about 500 ng/week with a standard deviation ranging from 100 to 200 ng/week, wherein the average travoprost release is based on the weekly travoprost release values between days 7 to 84 excluding post dose day 1 burst when measured at 37° C. in PBS at a pH of 7.2 to 7.4 under sink-conditions; or wherein the weekly travoprost release ranges from about 10 to about 700 ng, when measured in a time interval between days 7 to 84 excluding post dose day 1 burst when measured at 37° C. in PBS at a pH of 7.2 to 7.4 under sink-conditions.

In certain embodiments, the treatment period is about 3 to about 7 months or is about 4 to 7 months, the implant contains a dose of about 15 µg of travoprost, and the implant has an in vitro release with an average travoprost release ranging from about 800 to about 1100 ng/week with a standard deviation ranging from 450 to 550 ng/week, wherein the average is based on the weekly travoprost release values between days 7 to 98 excluding post dose day 1 burst when measured at 37° C. in PBS at a pH of 7.2 to 7.4 under sink-conditions st; or wherein the weekly travoprost release ranges from about 100 to about 2300 ng, when measured in a time interval between days 7 to 98 excluding post dose day 1 burst when measured at 37° C. in PBS at a pH of 7.2 to 7.4 under sink-conditions.

In certain embodiments, the treatment period is about 6 to about 9 months or about 6 to about 12 months, the implant contains a dose of about 15 µg of travoprost, and wherein the implant has an in vitro release with an average travoprost release ranging from about 500 to about 900 ng/week with a standard deviation ranging from 150 to 250 ng/week, wherein the average is based on the weekly travoprost release values between days 7 to 119 excluding post dose day 1 burst when measured at 37° C. in PBS at a pH of 7.2 to 7.4 under sink conditions; or wherein the weekly travoprost release ranges from about 100 to about 1500 ng, when measured in a time interval between days 7 to 119 excluding post dose day 1 burst; when measured at 37° C. in PBS at a pH of 7.2 to 7.2 under sink conditions.

In certain embodiments, the treatment period is about 6 to about 9 months or about 6 to about 12 months, the implant contains a dose of about 26 µg of travoprost, and wherein the implant has an in vitro release with an average travoprost release ranging from about 1000 to about 1500 ng/week with a standard deviation ranging from 100 to 400 ng/week, wherein the average is based on the weekly travoprost release values between days 7 to 119 excluding post dose day 1 burst when measured at 37° C. in PBS at a pH of 7.2 to 7.4 under sink-conditions; or wherein the weekly travoprost release ranges from about 100 to about 2000 ng, when measured in a time interval between days 7 to 119 excluding post dose day 1 burst when measured at 37° C. in PBS at a pH of 7.2 to 7.4 under sink-conditions.

In certain embodiments of the implant can be monitored in the eye, e.g. by gonioscopy and slit lamp exam.

In one specific aspect, the present invention is directed to a method of treating intraocular pressure in a human subject with ocular hypertension or glaucoma such as open angle glaucoma for a period of about 2 to about 12 months or about 6 to about 9 months with one single prostaglandin antagonist (e.g., travoprost) sustained release biodegradable intracameral implant per eye in need of such treatment, the method comprising per said eye:

Step 1: providing one prostaglandin antagonist (e.g., travoprost) sustained release biodegradable intracameral implant, as defined above, containing 21 to 30 µg prostaglandin antagonist (e.g., travoprost), wherein the implant is in the form of a fiber that has a length of about 1.0 mm to about 2.5 mm and a diameter of not more than 0.3 mm in its dried state, comprising:

a biodegradable hydrogel, as defined above, and prostaglandin antagonist (e.g., travoprost) particles, as defined above, the prostaglandin antagonist (e.g., travoprost) particles being in the form of prostaglandin antagonist (e.g., travoprost) intermixed with a biodegradable polymer, wherein the prostaglandin antagonist (e.g., travoprost) particles contain a blend of four types of particles, the first type of particles being in the form of prostaglandin antagonist (e.g., travoprost) intermixed with the biodegradable polymer consisting of a first polylactide having an inherent viscosity specification ranging from about 0.05 to less than 5 dl/g, such as about 0.35 to about 0.45 dl/g, and having an acid end group; and the second type of particles being in the form of prostaglandin antagonist (e.g., travoprost) intermixed with the biodegradable polymer consisting of a second polylactide having an inherent viscosity specification ranging from about 0.5 to less than about 0.8 dl/g, such as about 0.6 to less than 0.8 dl/g and having an acid end group; and the third type of particles being in the form of prostaglandin antagonist (e.g., travoprost) intermixed with the biodegradable polymer consisting of a third polylactide having an inherent viscosity specification ranging from about 0.8 to about 1.7 dl/g, such as 0.8 to about 1.0 dl/g and having an acid end group; and the fourth type of particles being in the form of prostaglandin antagonist (e.g., travoprost) intermixed with the biodegradable polymer consisting of a fourth polylactide having an inherent viscosity specification ranging from about 0.05 to about 1.7 dl/g, such as about 0.55 to 0.75 dl/g and having an ester end group; and the prostaglandin antagonist (e.g., travoprost) particles being dispersed within the hydrogel, wherein the hydrogel comprises a polymer network being formed by reacting a 8-arm-15K-SAZ polyethylene glycol with a mass average molecular weight of 15,000±10% Daltons with trilysine acetate; and Step 2: inserting the one sustained release biodegradable intracameral implant of step 1 into the anterior segment of said eye to place it within the iridocorneal angle of said eye.

In one specific aspect, the present invention is directed to a method of treating intraocular pressure in a human subject with ocular hypertension or glaucoma such as open angle glaucoma for a period of about 2 to about 12 months or about 6 to about 9 months with one single prostaglandin antagonist (e.g., travoprost) sustained release biodegradable intracameral implant per eye in need of such treatment, the method comprising per said eye, wherein the implant is as defined above, containing 21 to 30 µg prostaglandin antagonist (e.g., travoprost), wherein the implant is in the form of a fiber that has a length of about 1.0 mm to about 2.5 mm and a diameter of not more than 0.3 mm in its dried state, comprising:

a biodegradable hydrogel, as defined above, and prostaglandin antagonist (e.g., travoprost) particles, as defined above, the prostaglandin antagonist (e.g., travoprost) particles being in the form of prostaglandin antagonist (e.g., travoprost) intermixed with a biodegradable polymer, wherein the prostaglandin antagonist (e.g., travoprost) particles contain a blend of four types of particles, the first type of particles being in the form of prostaglandin antagonist (e.g., travoprost) intermixed with the biodegradable polymer consisting of a first polylactide having an inherent viscosity specification ranging from about 0.05 to less than 5 dl/g, such as about 0.35 to about 0.45 dl/g, and having an acid end group; and the second type of particles being in the form of prostaglandin antagonist (e.g., travoprost) intermixed with the biodegradable polymer consisting of a second polylactide having an inherent viscosity specification ranging from about 0.5 to less than about 0.8 dl/g, such as about 0.6 to less than 0.8 dl/g and having an acid end group; and the third type of particles being in the form of prostaglandin antagonist (e.g., travoprost) intermixed with the biodegradable polymer consisting of a third polylactide having an inherent viscosity specification ranging from about 0.8 to about 1.7 dl/g, such as 0.8 to about 1.0 dl/g and having an acid end group; and the fourth type of particles being in the form of prostaglandin antagonist (e.g., travoprost) intermixed with the biodegradable polymer consisting of a fourth polylactide having an inherent viscosity specification ranging from about 0.05 to about 1.7 dl/g, such as about 0.55 to 0.75 dl/g and having an ester end group; and the prostaglandin antagonist (e.g., travoprost) particles being dispersed within the hydrogel, wherein the hydrogel comprises a polymer network being formed by reacting a 8-arm-15K-SAZ polyethylene glycol with a mass average molecular weight of 15,000±10% Daltons with trilysine acetate.

In another specific aspect, the present invention is directed to method of intraocular pressure in a human subject with ocular hypertension or glaucoma such as open angle glaucoma for a period of about 2 to about 12 months or about 6 to about 9 months with one single prostaglandin antagonist (e.g., travoprost) sustained release biodegradable intracameral implant per eye in need of such treatment, the method comprising per said eye:

Step 1: providing one prostaglandin antagonist (e.g., travoprost) sustained release biodegradable intracameral implant, as defined above, containing 11 to 20 µg prostaglandin antagonist (e.g., travoprost), wherein the implant is in the form of a fiber that has a length of about 1.0 mm to about 2.5 mm and a diameter of not more than 0.3 mm in its dried state, comprising:

a biodegradable hydrogel, as defined above, and prostaglandin antagonist (e.g., travoprost) particles, as defined above, the prostaglandin antagonist (e.g., travoprost) particles being in the form of prostaglandin antagonist (e.g., travoprost) intermixed with a biodegradable polymer, wherein the prostaglandin antagonist (e.g., travoprost) particle contain a blend of four types of particles, the first type of particles being in the form of prostaglandin antagonist (e.g., travoprost) intermixed with the biodegradable polymer consisting of a first polylactide having an inherent viscosity specification ranging from about 0.05 to less than about 0.5 dl/g, such as about 0.35 to about 0.45 dl/g, and having an acid end group; and the second type of particles being in the form of prostaglandin antagonist (e.g., travoprost) intermixed with the biodegradable polymer consisting of a second polylactide having an inherent viscosity specification ranging from about 0.5 to less than about 0.8 dl/g, such as about 0.6 to less than about 0.8 dl/g, and having an acid end group; and the third type of particles being in the form of prostaglandin antagonist (e.g., travoprost) intermixed with the biodegradable polymer consisting of a third polylactide having an inherent viscosity specification ranging from about 0.8 to about 1.7 dl/g, such as about 0.8 to about 1.0 dl/g and having an acid end group; and the fourth type of particles being in the form of prostaglandin antagonist (e.g., travoprost) intermixed with the biodegradable polymer consisting of a fourth polylactide having an inherent viscosity specification of about 0.55 to 0.75 dl/g and having an ester end group, and the prostaglandin antagonist (e.g., travoprost) particles being dispersed within the hydrogel, wherein the hydrogel comprises a polymer network being formed by reacting a 8-arm-15K-SAZ polyethylene glycol with a mass average molecular weight of 15,000±10% Daltons with trilysine acetate; and Step 2: inserting the one sustained release biodegradable intracameral implant of step 1 into the anterior segment of said eye to place it within the iridocorneal angle of said eye.

In another specific aspect, the present invention is directed to method of intraocular pressure in a human subject with ocular hypertension or glaucoma such as open angle glaucoma for a period of about 2 to about 12 months or about 6 to about 9 months with one single prostaglandin antagonist (e.g., travoprost) sustained release biodegradable intracameral implant per eye in need of such treatment, the method comprising per said eye inserting the one sustained release biodegradable intracameral implant into the anterior segment of said eye to place it within the iridocorneal angle of said eye, wherein the implant is as defined above, containing 11 to 20 µg prostaglandin antagonist (e.g., travoprost), wherein the implant is in the form of a fiber that has a length of about 1.0 mm to about 2.5 mm and a diameter of not more than 0.3 mm in its dried state, comprising:

a biodegradable hydrogel, as defined above, and prostaglandin antagonist (e.g., travoprost) particles, as defined above, the prostaglandin antagonist (e.g., travoprost) particles being in the form of prostaglandin antagonist (e.g., travoprost) intermixed with a biodegradable polymer, wherein the prostaglandin antagonist (e.g., travoprost) particle contain a blend of four types of particles, the first type of particles being in the form of prostaglandin antagonist (e.g., travoprost) intermixed with the biodegradable polymer consisting of a first polylactide having an inherent viscosity specification ranging from about 0.05 to less than about 0.5 dl/g, such as about 0.35 to about 0.45 dl/g, and having an acid end group; and the second type of particles being in the form of prostaglandin antagonist (e.g., travoprost) intermixed with the biodegradable polymer consisting of a second polylactide having an inherent viscosity specification ranging from about 0.5 to less than about 0.8 dl/g, such as about 0.6 to less than about 0.8 dl/g, and having an acid end group; and the third type of particles being in the form of prostaglandin antagonist (e.g., travoprost) intermixed with the biodegradable polymer consisting of a third polylactide having an inherent viscosity specification ranging from about 0.8 to about 1.7 dl/g, such as about 0.8 to about 1.0 dl/g and having an acid end group; and the fourth type of particles being in the form of prostaglandin antagonist (e.g., travoprost) intermixed with the biodegradable polymer consisting of a fourth polylactide having an inherent viscosity specification of about 0.55 to 0.75 dl/g and having an ester end group, and the prostaglandin antagonist (e.g., travoprost) particles being dispersed within the hydrogel, wherein the hydrogel comprises a polymer network being formed by reacting a 8-arm-15K-SAZ polyethylene glycol with a mass average molecular weight of 15,000±10% Daltons with trilysine acetate.

In another specific aspect, the present invention is directed to a method treating intraocular pressure in a human subject with ocular hypertension or glaucoma such as open angle glaucoma for a period of about 3 to about 6 months or about 3 to about 4 months with one single prostaglandin antagonist (e.g., travoprost) sustained release biodegradable intracameral implant per eye in need of such treatment, the method comprising per said eye:

Step 1: providing one prostaglandin antagonist (e.g., travoprost) sustained release biodegradable intracameral implant, as defined above, containing 11 to 20 µg prostaglandin antagonist (e.g., travoprost), wherein the implant is in the form of a fiber that has a length of about 1.0 mm to about 2.5 mm and a diameter of not more than 0.3 mm in its dried state, comprising:

a biodegradable hydrogel, as defined above, and prostaglandin antagonist (e.g., travoprost) particles, as defined above, the prostaglandin antagonist (e.g., travoprost) particles being in the form of prostaglandin antagonist (e.g., travoprost) intermixed with a biodegradable polymer, wherein the prostaglandin antagonist (e.g., travoprost) particles contain a blend of three types of particles, the first type of particles being in the form of prostaglandin antagonist (e.g., travoprost) intermixed with the biodegradable polymer consisting of a first polylactide having an inherent viscosity specification ranging from about 0.05 to less than about 0.5 dl/g, such as about 0.35 to about 0.45 dl/g and having an acid end group; and the second type of particles being in the form of prostaglandin antagonist (e.g., travoprost) intermixed with the biodegradable polymer consisting of a second polylactide having an inherent viscosity specification ranging from about 0.5 to about 1.7 dl/g, such as about 0.6 to less than about 0.8 dl/g and having an acid end group; and the third type of particles being in the form of prostaglandin antagonist (e.g., travoprost) intermixed with the biodegradable polymer consisting of a third polylactide having an inherent viscosity specification ranging from about 0.8 to about 1.7 d/g, such as 0.8 to about 1.0 dl/g and having an acid end group; and the prostaglandin antagonist (e.g., travoprost) particles being dispersed within the hydrogel, wherein the hydrogel comprises a polymer network being formed by reacting a 8-arm-15K-SG polyethylene glycol with a mass average molecular weight of 15,000±10% Daltons with trilysine acetate; and Step 2: inserting the one sustained release biodegradable intracameral implant of step 1 into the anterior segment of said eye to place it within the iridocorneal angle of said eye.

In another specific aspect, the present invention is directed to a method treating intraocular pressure in a human subject with ocular hypertension or glaucoma such as open angle glaucoma for a period of about 3 to about 6 months or about 3 to about 4 months with one single prostaglandin antagonist (e.g., travoprost) sustained release biodegradable intracameral implant per eye in need of such treatment, the method comprising per said eye inserting the one sustained release biodegradable intracameral implant into the anterior segment of said eye to place it within the iridocorneal angle of said eye, wherein the implant is as defined above, containing 11 to 20 µg prostaglandin antagonist (e.g., travoprost), wherein the implant is in the form of a fiber that has a length of about 1.0 mm to about 2.5 mm and a diameter of not more than 0.3 mm in its dried state, comprising:

a biodegradable hydrogel, as defined above, and prostaglandin antagonist (e.g., travoprost) particles, as defined above, the prostaglandin antagonist (e.g., travoprost) particles being in the form of prostaglandin antagonist (e.g., travoprost) intermixed with a biodegradable polymer, wherein the prostaglandin antagonist (e.g., travoprost) particles contain a blend of three types of particles, the first type of particles being in the form of prostaglandin antagonist (e.g., travoprost) intermixed with the biodegradable polymer consisting of a first polylactide having an inherent viscosity specification ranging from about 0.05 to less than about 0.5 dl/g, such as about 0.35 to about 0.45 dl/g and having an acid end group; and the second type of particles being in the form of prostaglandin antagonist (e.g., travoprost) intermixed with the biodegradable polymer consisting of a second polylactide having an inherent viscosity specification ranging from about 0.5 to about 1.7 dl/g, such as about 0.6 to less than about 0.8 dl/g and having an acid end group; and the third type of particles being in the form of prostaglandin antagonist (e.g., travoprost) intermixed with the biodegradable polymer consisting of a third polylactide having an inherent viscosity specification ranging from about 0.8 to about 1.7 d/g, such as 0.8 to about 1.0 dl/g and having an acid end group; and the prostaglandin antagonist (e.g., travoprost) particles being dispersed within the hydrogel, wherein the hydrogel comprises a polymer network being formed by reacting a 8-arm-15K-SG polyethylene glycol with a mass average molecular weight of 15,000±10% Daltons with trilysine acetate.

In a further specific aspect, the present invention is directed to a method of treating intraocular pressure in a human subject with ocular hypertension or glaucoma such as open angle glaucoma for a period of about 3 to about 6 months or about 3 to about 4 months with one single prostaglandin antagonist (e.g., travoprost) sustained release biodegradable intracameral implant per eye in need of such treatment, the method comprising per said eye:

Step 1: providing one prostaglandin antagonist (e.g., travoprost) sustained release biodegradable intracameral implant, as defined above, containing 2 to 10 µg prostaglandin antagonist (e.g., travoprost), wherein the implant is in the form of a fiber that has a length of about 1.0 mm to about 2.5 mm and a diameter of not more than 0.3 mm in its dried state, comprising: a biodegradable hydrogel, as defined above, and prostaglandin antagonist (e.g., travoprost) particles, as defined above, the prostaglandin antagonist (e.g., travoprost) particles being in the form of prostaglandin antagonist (e.g., travoprost) intermixed with a biodegradable polymer, wherein the prostaglandin antagonist (e.g., travoprost) particles contain a blend of two types of particles, the first type of particle being in the form of prostaglandin antagonist (e.g., travoprost) intermixed with the biodegradable polymer consisting of a first polylactide having an inherent viscosity specification ranging from 0.05 to less than about 0.5 dl/g, such as about 0.35 to about 0.45 dl/g, and having an acid end group; and the second type of particles being in the form of prostaglandin antagonist (e.g., travoprost) intermixed with the biodegradable polymer consisting of a second polylactide having an inherent viscosity specification ranging from about 0.5 to about 1.7 dl/g, such as about 0.6 to about 0.8 dl/g and having an acid end group; and the prostaglandin antagonist (e.g., travoprost) particles being dispersed within the hydrogel, wherein the hydrogel comprises a polymer network being formed by reacting a 8arm-15K-SG polyethylene glycol with a mass average molecular weight of 15,000±10% Daltons with trilysine acetate; and Step 2: inserting the one sustained release biodegradable intracameral implant of step 1 into the anterior segment of said eye to place it within the iridocorneal angle of said eye.

In a further specific aspect, the present invention is directed to a method of treating intraocular pressure in a human subject with ocular hypertension or glaucoma such as open angle glaucoma for a period of about 3 to about 6 months or about 3 to about 4 months with one single prostaglandin antagonist (e.g., travoprost) sustained release biodegradable intracameral implant per eye in need of such treatment, the method comprising per said eye inserting the one sustained release biodegradable intracameral implant into the anterior segment of said eye to place it within the iridocorneal angle of said eye, wherein the implant is as defined above, containing 2 to 10 µg prostaglandin antagonist (e.g., travoprost), wherein the implant is in the form of a fiber that has a length of about 1.0 mm to about 2.5 mm and a diameter of not more than 0.3 mm in its dried state, comprising: a biodegradable hydrogel, as defined above, and prostaglandin antagonist (e.g., travoprost) particles, as defined above, the prostaglandin antagonist (e.g., travoprost) particles being in the form of prostaglandin antagonist (e.g., travoprost) intermixed with a biodegradable polymer, wherein the prostaglandin antagonist (e.g., travoprost) particles contain a blend of two types of particles, the first type of particle being in the form of prostaglandin antagonist (e.g., travoprost) intermixed with the biodegradable polymer consisting of a first polylactide having an inherent viscosity specification ranging from 0.05 to less than about 0.5 dl/g, such as about 0.35 to about 0.45 dl/g, and having an acid end group; and the second type of particles being in the form of prostaglandin antagonist (e.g., travoprost) intermixed with the biodegradable polymer consisting of a second polylactide having an inherent viscosity specification ranging from about 0.5 to about 1.7 dl/g, such as about 0.6 to about 0.8 dl/g and having an acid end group; and the prostaglandin antagonist (e.g., travoprost) particles being dispersed within the hydrogel, wherein the hydrogel comprises a polymer network being formed by reacting a 8arm-15K-SG polyethylene glycol with a mass average molecular weight of 15,000±10% Daltons with trilysine acetate.

In one further specific aspect, the present invention is directed to a method of treating intraocular pressure in a human subject with ocular hypertension or glaucoma such as open angle glaucoma for a period of about 2 to about 12 months or about 6 to about 9 months with one single prostaglandin antagonist (e.g., travoprost) sustained release biodegradable intracameral implant per eye in need of such treatment, the method comprising per said eye:

Step 1: providing one prostaglandin antagonist (e.g., travoprost) sustained release biodegradable intracameral implant, as defined above, containing 21 to 30 µg prostaglandin antagonist (e.g., travoprost), wherein the implant is in the form of a fiber that has a length of about 1.0 mm to about 2.5 mm and a diameter of not more than 0.3 mm in its dried state, comprising a biodegradable hydrogel, as defined above, and prostaglandin antagonist (e.g., travoprost) particles, as defined above, dispersed therein, wherein the intracameral implant has an in vitro release with an average prostaglandin antagonist (e.g., travoprost) release ranging from of about 5% to about 15% with a mean absolute deviation of at most 3%, or a prostaglandin antagonist (e.g., travoprost) release ranging from 5% to 15%, based on the % amount released per 14 days from day 1 to day 112, when measured at 37° C. in PBS at a pH of 7.2 to 7.4 under sink-conditions and the hydrogel dissolves/fully biodegrades within 6 to 8 months or with 5 to 7 months; and Step 2: inserting the one sustained release biodegradable intracameral implant of step 1 into the anterior segment of said eye to place it within the iridocorneal angle of said eye.

In one further specific aspect, the present invention is directed to a method of treating intraocular pressure in a human subject with ocular hypertension or glaucoma such as open angle glaucoma for a period of about 2 to about 12 months or about 6 to about 9 months with one single prostaglandin antagonist (e.g., travoprost) sustained release biodegradable intracameral implant per eye in need of such treatment, the method comprising per said eye inserting the one sustained release biodegradable intracameral implant into the anterior segment of said eye to place it within the iridocorneal angle of said eye, wherein the implant is as defined above, containing 21 to 30 µg prostaglandin antagonist (e.g., travoprost), wherein the implant is in the form of a fiber that has a length of about 1.0 mm to about 2.5 mm and a diameter of not more than 0.3 mm in its dried state, comprising a biodegradable hydrogel, as defined above, and prostaglandin antagonist (e.g., travoprost) particles, as defined above, dispersed therein, wherein the intracameral implant has an in vitro release with an average prostaglandin antagonist (e.g., travoprost) release ranging from of about 5% to about 15% with a mean absolute deviation of at most 3%, or a prostaglandin antagonist (e.g., travoprost) release ranging from 5% to 15%, based on the % amount released per 14 days from day 1 to day 112, when measured at 37° C. in PBS at a pH of 7.2 to 7.4 under sink-conditions and the hydrogel dissolves within 6 to 8 months.

In another specific aspect, the present invention is directed to a method treating intraocular pressure in a human subject with ocular hypertension or glaucoma such as open angle glaucoma for a period of about 3 to about 6 months or about 3 to about 4 months with one single prostaglandin antagonist (e.g., travoprost) sustained release biodegradable intracameral implant per eye in need of such treatment, the method comprising per said eye:

Step 1: providing one prostaglandin antagonist (e.g., travoprost) sustained release biodegradable intracameral implant, as defined above, containing 11 to 20 µg prostaglandin antagonist (e.g., travoprost), wherein the implant is in the form of a fiber that has a length of about 1.0 mm to about 2.5 mm and a diameter of not more than 0.3 mm in its dried state, comprising a biodegradable hydrogel, as defined above, and prostaglandin antagonist (e.g., travoprost) particles, as defined above, dispersed therein, wherein the intracameral implant has an in vitro release with an average prostaglandin antagonist (e.g., travoprost) release ranging from of about 65% to about 85% with a mean absolute deviation of at most 5%, or a prostaglandin antagonist (e.g., travoprost) release ranging from 65% to 85%, based on the %-amount released per 70 days from day 1 to day 84, when measured at 37° C. in PBS at a pH of 7.2 to 7.4 under sink-conditions and the hydrogel dissolves/fully biodegrades within 2 to 4 months or within 3 to 5 months; and Step 2: inserting the one sustained release biodegradable intracameral implant of step 1 into the anterior segment of said eye to place it within the iridocorneal angle of said eye.

In another specific aspect, the present invention is directed to a method treating intraocular pressure in a human subject with ocular hypertension or glaucoma such as open angle glaucoma for a period of about 3 to about 6 months or about 3 to about 4 months with one single prostaglandin antagonist (e.g., travoprost) sustained release biodegradable intracameral implant per eye in need of such treatment, the method comprising per said eye inserting the one sustained release biodegradable intracameral implant into the anterior segment of said eye to place it within the iridocorneal angle of said eye, wherein the insert is as defined above, containing 11 to 20 µg prostaglandin antagonist (e.g., travoprost), wherein the implant is in the form of a fiber that has a length of about 1.0 mm to about 2.5 mm and a diameter of not more than 0.3 mm in its dried state, comprising a biodegradable hydrogel, as defined above, and prostaglandin antagonist (e.g., travoprost) particles, as defined above, dispersed therein, wherein the intracameral implant has an in vitro release with an average prostaglandin antagonist (e.g., travoprost) release ranging from of about 65% to about 85% with a mean absolute deviation of at most 5%, or a prostaglandin antagonist (e.g., travoprost) release ranging from 65% to 85%, based on the %-amount released per 70 days from day 1 to day 84, when measured at 37° C. in PBS at a pH of 7.2 to 7.4 under sink-conditions and the hydrogel dissolves/fully biodegrades within 2 to 4 months or within 3 to 5 months.

In another specific aspect, the present invention is directed to a method of treating intraocular pressure in a human subject with ocular hypertension or glaucoma such as open angle glaucoma for a period of about 3 to about 6 months or about 3 to about 4 months with one single prostaglandin antagonist (e.g., travoprost) sustained release biodegradable intracameral implant per eye in need of such treatment, the method comprising per said eye:

Step 1: providing one prostaglandin antagonist (e.g., travoprost) sustained release biodegradable intracameral implant, as defined above, containing 2 to 10 µg prostaglandin antagonist (e.g., travoprost), wherein the implant is in the form of a fiber that has a length of about 1.0 mm to about 2.5 mm and a diameter of not more than 0.3 mm in its dried state, comprising a biodegradable hydrogel, as defined above, and prostaglandin antagonist (e.g., travoprost) particles, as defined above dispersed therein, wherein the intracameral implant has an in vitro release with an average prostaglandin antagonist (e.g., travoprost) release ranging from of about 60% to about 80% with a mean absolute deviation of at most 5%, or a prostaglandin antagonist (e.g., travoprost) release ranging from 60% to 80%, based on the %-amount released per 70 days from day 1 to day 98, when measured at 37° C. in PBS at a pH of 7.2 to 7.4 under sink-conditions and the hydrogel dissolves within 2 to 4 months; and Step 2: inserting the one sustained release biodegradable intracameral implant of step 1 into the anterior segment of said eye to place it within the iridocorneal angle of said eye.

In another specific aspect, the present invention is directed to a method of treating intraocular pressure in a human subject with ocular hypertension or glaucoma such as open angle glaucoma for a period of about 3 to about 6 months or about 3 to about 4 months with one single prostaglandin antagonist (e.g., travoprost) sustained release biodegradable intracameral implant per eye in need of such treatment, the method comprising per said eye inserting the one sustained release biodegradable intracameral implant into the anterior segment of said eye to place it within the iridocorneal angle of said eye, wherein the implant is as defined above, containing 2 to 10 µg prostaglandin antagonist (e.g., travoprost), wherein the implant is in the form of a fiber that has a length of about 1.0 mm to about 2.5 mm and a diameter of not more than 0.3 mm in its dried state, comprising a biodegradable hydrogel, as defined above, and prostaglandin antagonist (e.g., travoprost) particles, as defined above dispersed therein, wherein the intracameral implant has an in vitro release with an average prostaglandin antagonist (e.g., travoprost) release ranging from of about 60% to about 80% with a mean absolute deviation of at most 5%, or a prostaglandin antagonist (e.g., travoprost) release ranging from 60% to 80%, based on the %-amount released per 70 days from day 1 to day 98, when measured at 37° C. in PBS at a pH of 7.2 to 7.4 under sink-conditions and the hydrogel dissolves within 2 to 4 months.

The implant of the present invention may be provided by the physician performing the procedure. In certain embodiments the implant will be in a device such as a syringe packaged in sterile packaging and the medical professional will unwrap the implant just prior to the procedure and provide the implant for the methods of implanting/inserting described herein.

The disclosed implants are useful in lowering ocular pressure. Thus, provided herein are methods of lowering ocular pressure in a subject in need thereof comprising administering a hydrogel implant described herein. Also disclosed in the use of a disclosed implant for lowering ocular pressure in a subject. Further provided is the use of a disclosed implant in the manufacture of a medicament for lowering ocular pressure.

Also provided are methods of treating ocular hypertension in a subject in need thereof comprising administering a hydrogel implant described herein. Also disclosed in the use of a disclosed implant for treating ocular hypertension in a subject. Further provided is the use of a disclosed implant in the manufacture of a medicament for treating ocular hypertension.

Also provided are methods for treating glaucoma (open angle glaucoma) in a subject in need thereof comprising administering a hydrogel implant described herein. Also disclosed in the use of a disclosed implant for treating glaucoma (open angle glaucoma) in a subject. Further provided is the use of a disclosed implant in the manufacture of a medicament for treating glaucoma (open angle glaucoma).

As part of a further embodiment, the travoprost is delivered to the eye in a sustained manner for a period ranging from about 1 month to about 1 year, wherein the remaining features of the implants are described herein. Alternatively, as part of further embodiment, the travoprost is delivered to the eye in a sustained manner for a period ranging from about 1 month to about 11 months, wherein the remaining features of the implants are described herein. In another alternative, as part of an this embodiment, the travoprost is delivered to the eye in a sustained manner for a period ranging from about 1 month to about 10 months, wherein the remaining features of the implants are described herein. In another alternative, as part of this embodiment, the travoprost is delivered to the eye in a sustained manner for a period ranging from about 1 month to about 9 months, wherein the remaining features of the implants are described herein. In another alternative, as part of an this embodiment, the travoprost is delivered to the eye in a sustained manner for a period ranging from about 1 month to about 8 months, wherein the remaining features of the implants are described herein. In another alternative, as part of an this embodiment, the travoprost is delivered to the eye in a sustained manner for a period ranging from about 2 month to about 8 months, wherein the remaining features of the implants are described herein. In another alternative, as part of this embodiment, the travoprost is delivered to the eye in a sustained manner for a period ranging from about 3 month to about 7 months, wherein the remaining features of the implants are described herein. In another alternative, as part of this embodiment, the travoprost is delivered to the eye in a sustained manner for a period ranging from about 4 month to about 6 months, wherein the remaining features of the implants are described herein. In another alternative, as part of this embodiment, the travoprost is delivered to the eye in a sustained manner for a period of about 1 month, wherein the remaining features of the implants are described herein. In another alternative, as part of this embodiment, the travoprost is delivered to the eye in a sustained manner for a period of about 2 months, wherein the remaining features of the implants are described herein. In another alternative, as part of an this embodiment, the travoprost is delivered to the eye in a sustained manner for a period of about 3 months, wherein the remaining features of the implants are described herein. In another alternative, as part of this embodiment, the travoprost is delivered to the eye in a sustained manner for a period of about 4 months, wherein the remaining features of the implants are described herein. In another alternative, as part of this embodiment, the travoprost is delivered to the eye in a sustained manner for a period of about 5 months, wherein the remaining features of the implants are described herein e. In another alternative, as part of an this embodiment, the travoprost is delivered to the eye in a sustained manner for a period of about 6 months, wherein the remaining features of the implants are described herein.

As part of a further embodiment, sustained release of the travoprost occurs in the aqueous humor, wherein the remaining features of the implants are described herein.

As part of a further embodiment, the polymer network of the disclosed hydrogel implants is conjugated to fluorescein, wherein the remaining features of the implants are described herein.

As part of a further embodiment, the disclosed implants are designed for implantation near the corneal endothelial cells, wherein the remaining features of the implants are described herein.

As part of a further embodiment, the disclosed implants are designed for implantation in the inferior iridocorneal angle, wherein the remaining features of the implants are described herein.

As part of a further embodiment, the disclosed implants comprise 5 µg, 15 µg or 26 µg of travoprost, wherein the remaining features of the implants are described herein e.g., as in the first through fifteenth embodiments. Alternatively, as part of a the disclosed implants comprise 5 µg, 15 µg or 26 µg of travoprost; and comprises a polymer networks formed by reacting a plurality of polyethylene glycol (PEG) units comprising groups which are susceptible to nucleophilic attack with one or more PEG or Lysine based-amine groups selected from 4a20K PEG NH2, 8a20K PEG NH2, and trilysine, wherein the remaining features of the hydrogel are described herein.

As part of a further embodiment, the disclosed implants are fully degraded following complete release of travoprost, wherein the remaining features of the implants are described herein. Alternatively, the hydrogel implant is fully degraded after about 12 months, after about 11 months, after about 10 months, after about 9 months, after about 8 months, after about 6 months, after about 5 months, after about 4 months, after about 3 months, after about 2 months, after about 1 month (i.e., after about 30 days) following complete release of travoprost, wherein the remaining features of the implants are described herein. Alternatively, the hydrogel implant is fully degraded following at least 90% (e.g., at least 91%, at least 92%, at least 93%, at least 94%, at least 95%, at least 96%, at least 97%, at least 98%, or at least 99%) release of travoprost, wherein the remaining features of the implants are described herein.

In one aspect, the present invention is directed to a method disclosed herein, wherein the intraocular pressure is decreased by about 5 to about 7 mmHg, or about 7 to about 9 mmHg from baseline intraocular pressure during the treatment period such as about 2 to about 12 months or about 3 to about 9 months, such as about 6 months or during continued treatment with repeated administration.

Method of Treating Ocular Disease in a Human Subject

In one aspect, the present invention is directed to a method of treating ocular disease in a human subject for a period ranging from about 1 to about 24 months or from about 2 to about 12 moths or from about 3 to about 9 months with one single API containing sustained release biodegradable intracameral implant per eye in need of such treatment, the method comprising per said eye:
Step 1: providing one API containing sustained release biodegradable intracameral implant providing treatment for a period ranging from about 1 to about 24 months or from about 2 to about 12 moths or from about 3 to about 9 months comprising:
a biodegradable hydrogel as defined above and API particles,
the API particles being dispersed within the hydrogel; and
Step 2: inserting the one sustained release biodegradable intracameral implant of step 1 into the anterior segment of said eye to place it within the iridocorneal angle of said eye.

In one aspect, the present invention is directed to a method of treating ocular disease in a human subject for a period ranging from about 1 to about 24 months or from about 2 to about 12 moths or from about 3 to about 9 months with one single API containing sustained release biodegradable intracameral implant per eye in need of such treatment, the method comprising per said eye inserting the one sustained release biodegradable intracameral implant into the anterior segment of said eye to place it within the iridocorneal angle of said eye, wherein the implant is one API containing sustained release biodegradable intracameral implant providing treatment for a period ranging from about 1 to about 24 months or from about 2 to about 12 moths or from about 3 to about 9 months comprising:
a biodegradable hydrogel as defined above and API particles,
the API particles being dispersed within the hydrogel.

In another aspect, the present invention is directed to a method of treating ocular disease in a human subject for a period within 3 to 9 months with one single API containing implant in need of such treatment.

In a further aspect, the present invention is directed to an implant for use in method of treating ocular disease in a human subject for a period within 3 to 9 months with one single API containing implant in need of such treatment.

In one embodiment, said one API is a Prostaglandin antagonist. Specifically said one single API is selected from the group consisting of travoprost, bimatoprost and latanoprost.

Therapeutic agents also include, for example, agents for treating conditions that may result from inflammatory or abnormal vascular conditions, retinal vein occlusion, geographic atrophy, retinitis pigmentosa, retinoblastoma, etc. For cancer, agents may be, e.g., anti-cancer drugs, anti-VEGFs, or drugs known for use in cancer treatment.

Therapeutic agents may be those that are, e.g., anti-VEGF, blocks VEGFR1, blocks VEGFR2, blocks VEGFR3, anti-PDGF, anti-angiogenesis, Sunitinib, E7080, Takeda-6d, Tivozanib, Regorafenib, Sorafenib, Pazopanib, Axitinib, Nintedanib, Cediranib, Vatalanib, Motesanib, macrolides, sirolimus, everolimus, tyrosine kinase inhibitors (TKIs), Imatinib (GLEEVAC) gefinitib (IRESSA), toceranib (PALLADIA), Erlotinib (TARCEVA), Lapatinib (TYKERB) Nilotinib, Bosutinib Neratinib, lapatinib, Vatalanib, dasatinib, erlotinib, gefitinib, imatinib, lapatinib, lestaurtinib, nilotinib, semaxanib, toceranib, vandetanib.

The therapeutic agent may comprise a macromolecule, for example an antibody or antibody fragment. The therapeutic macromolecule may comprise a VEGF inhibitor, for example ranibizumab, the active ingredient in the commercially available Lucentis™. The VEGF (Vascular Endothelial Growth Factor) inhibitor can cause regression of the abnormal blood vessels and improvement of vision when released into the vitreous humor of the eye. Examples of VEGF inhibitors include Lucentis™ (ranibizumab), Eylea™ (VEGF Trap), Avastin™ (bevacizumab), Macugen™ (pegaptanib). Platelet derived growth factor (PDGF) inhibitors may also be delivered, e.g. Fovista™, an anti-PGDF aptamer.

The therapeutic agent may comprise small molecules such as of a steroid or corticosteroid and analogues thereof. For example, the therapeutic corticosteroid may comprise one or more of trimacinalone, trimacinalone acetonide, dexamethasone, dexamethasone acetate, fluocinolone, fluocinolone acetate, loteprednol etabonate, or analogues thereof. Alternatively or in combination, the small molecules of therapeutic agent may comprise a tyrosine kinase inhibitor.

The therapeutic agent may comprise an anti-VEGF therapeutic agent. Anti-VEGF therapies and agents can be used in the treatment of certain cancers and in age-related macular degeneration. Examples of anti-VEGF therapeutic agents suitable for use in accordance with the embodiments described herein include one or more of monoclonal antibodies such as bevacizumab (Avastin™) or antibody derivatives such as ranibizumab (Lucentis™), or small molecules that inhibit the tyrosine kinases stimulated by VEGF such as lapatinib (Tykerb™), sunitinib (Sutent™) sorafenib (Nexavar™), axitinib, or pazopanib.

The therapeutic agent may comprise a therapeutic agent suitable for treatment of dry AMD such as one or more of Sirolimus™ (Rapamycin), Copaxone™ (Glatiramer Acetate), Othera™ Complement C5aR blocker, Ciliary Neurotrophic Factor, Fenretinide or Rheopheresis.

The therapeutic agent may comprise a therapeutic agent suitable for treatment of wet AMD such as one or more of REDD14NP (Quark), Sirolimus™ (Rapamycin), ATG003; EYELEA (VEGF Trap) or complement inhibitor (POT-4).

The therapeutic agent may comprise a kinase inhibitor such as one or more of BIBW 2992 (small molecule targeting EGFR/Erb2), imatinib (small molecule), gefitinib (small molecule), ranibizumab (monoclonal antibody), pegaptanib (small molecule), sorafenib (small molecule), dasatinib (small molecule), sunitinib (small molecule), erlotinib (small molecule), nilotinib (small molecule), lapatinib (small molecule), panitumumab (monoclonal antibody), vandetanib (small molecule) or E7080 (targeting VEGFR2/VEGFR2, small molecule commercially available from Esai, Co.). The therapeutic agent may comprises antibody drugs, e.g. bevacizumab, trastuzumab, cetuximab, and panitumumab.

Therapeutic agents may include various classes of drugs. Drugs include, for instance, steroids, non-steroidal anti-inflammatory drugs (NSAIDS), anti-cancer drugs, antibiotics, an anti-inflammatory (e.g., Diclofenac), a pain reliever (e.g., Bupivacaine), a Calcium channel blocker (e.g., Nifedipine), an Antibiotic (e.g., Ciprofloxacin), a Cell cycle inhibitor (e.g., Simvastatin), a protein (e.g., Insulin). Therapeutic agents include classes of drugs including steroids, NSAIDS, antioxidants, antibiotics, pain relievers, inhibitors of vascular endothelial growth factor (VEGF), chemotherapeutics, anti-viral drugs, for instance. Examples of NSAIDS are Ibuprofen, Meclofenamate sodium, mefanamic acid, salsalate, sulindac, tolmetin sodium, ketoprofen, diflunisal, piroxicam, naproxen, etodolac, flurbiprofen, fenoprofen calcium, Indomethacin, celoxib, ketrolac, and nepafenac. The drugs themselves may be small molecules, proteins, RNA fragments, proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides, or other configurations.

Therapeutic agents may include a protein or other water soluble biologics. These include peptides of various molecular weights. Peptides include therapeutic proteins and peptides, antibodies, antibody fragments, short chain variable fragments (scFv), growth factors, angiogenic factors, and insulin. Other water soluble biologics are carbohydrates, polysaccharides, nucleic acids, antisense nucleic acids, RNA, DNA, small interfering RNA (siRNA), and aptamers.

The therapeutic agents may be used as part of a method of treating the indicated condition or making a composition for treating the indicated condition. For example, AZOPT (a brinzolamide opthalmic suspension) may be used for treatment of elevated intraocular pressure in patients with ocular hypertension or open-angle glaucoma. BETADINE in a Povidone-iodine ophthalmic solution may be used for prepping of the periocular region and irrigation of the ocular surface. BETOPTIC (betaxolol HCl) may be used to lower intraocular pressure, or for chronic open-angle glaucoma and/or ocular hypertension. CILOXAN (Ciprofloxacin HCl opthalmic solution) may be used to treat infections caused by susceptible strains of microorganisms. NATACYN (Natamycin opthalmic suspension) may be used for treatment of fungal blepharitis, conjunctivitis, and keratitis. NEVANAC (Nepanfenac opthalmic suspension) may be used for treatment of pain and inflammation associated with cataract surgery. TRAVATAN (Travoprost ophthalmic solution) may be used for reduction of elevated intraocular pressure-open-angle glaucoma or ocular hypertension. FML FORTE (Fluorometholone ophthalmic suspension) may be used for treatment of corticosteroid-responsive inflammation of the palperbral and bulbar conjunctiva, cornea and anterior segment of the globe. LUMIGAN (Bimatoprost ophthalmic solution) may be used for reduction of elevated intraocular pressure-open-angle glaucoma or ocular hypertension. PRED FORTE (Prednisolone acetate) may be used for treatment of steroid-responsive inflammation of the palpebral and bulbar conjunctiva, cornea and anterior segment of the globe. PROPINE (Dipivefrin hydrochloride) may be used for control of intraocular pressure in chronic open-angle glaucoma. RESTASIS (Cyclosporine ophthalmic emulsion) may be used to increases tear production in patients, e.g., those with ocular inflammation associated with keratoconjunctivitis sicca. ALREX (Loteprednol etabonate ophthalmic suspension) may be used for temporary relief of seasonal allergic conjunctivitis. LOTEMAX (Loteprednol etabonate ophthalmic suspension) may be used for treatment of steroid-responsive inflammation of the palpebral and bulbar conjunctiva, cornea and anterior segment of the globe. MACUGEN (Pegaptanib sodium injection) may be used for Treatment of neovascular (wet) age-related macular degeneration. OPTIVAR (Azelastine hydrochloride) may be used for treatment of itching of the eye associated with allergic conjunctivitis. XALATAN (Latanoprost ophthalmic solution) may be used to reduce elevated intraocular pressure in patients, e.g., with open-angle glaucoma or ocular hypertension. BETIMOL (Timolol opthalmic solution) may be used for treatment of elevated intraocular pressure in patients with ocular hypertension or open-angle glaucoma. Latanoprost is the pro-drug of the free acid form, which is a prostanoid selective FP receptor agonist. Latanoprost reduces intraocular pressure in glaucoma patients with few side effects. Latanoprost has a relatively low solubility in aqueous solutions, but is readily soluble in organic solvents typically employed for fabrication of microspheres using solvent evaporation.

Further embodiments of therapeutic agents for delivery include those that specifically bind a target peptide in vivo to prevent the interaction of the target peptide with its natural receptor or other ligands. AVASTIN, for instance, is an antibody that binds VEGF. An IL-1 trap that makes use of the extracellular domains of IL-1 receptors is also known; the trap blocks IL-1 from binding and activating receptors on the surface of cells. Embodiments of agents for delivery include nucleic acids, e.g., aptamers. Pegaptanib (MACUGEN), for example, is a pegylated anti-VEGF aptamer. An advantage of the particle-and-hydrogel delivery process is that the aptamers are protected from the in vivo environment until they are released. Further embodiments of agents for delivery include macromolecular drugs, a term that refers to drugs that are significantly larger than classical small molecule drugs, i.e., drugs such as oligonucleotides (aptamers, antisense, RNAi), ribozymes, gene therapy nucleic acids, recombinant peptides, and antibodies.

One embodiment comprises extended release of a medication for allergic conjunctivitis. For instance, ketotifen, an antihistamine and mast cell stabilizer, may be provided in particles and released to the eye as described herein in effective amounts to treat allergic conjunctivitis. Seasonal Allergic Conjunctivitis (SAC) and Perennial Allergic Conjunctivitis (PAC) are allergic conjunctival disorders. Symptoms include itching and pink to reddish eyes. These two eye conditions are mediated by mast cells. Non-specific measures to ameliorate symptoms conventionally include: cold compresses, eyewashes with tear substitutes, and avoidance of allergens. Treatment conventionally consists of antihistamine mast cell stabilizers, dual mechanism anti-allergen agents, or topical antihistamines. Corticosteroids might be effective but, because of side effects, are reserved for more severe forms of allergic conjunctivitis such as vernal keratoconjunctivitis (VKC) and atopic keratoconjunctivitis (AKC).

Moxifloxacin is the active ingredient in VIGAMOX, which is a fluoroquinolone approved for use to treat or prevent ophthalmic bacterial infections. VKC and AKC are chronic allergic diseases where eosinophils, conjunctival fibroblasts, epithelial cells, mast cells, and/or TH2 lymphocytes aggravate the biochemistry and histology of the conjunctiva. VKC and AKC can be treated by medications used to combat allergic conjunctivitis. Permeation agents are agents and may also be included in a gel, hydrogel, organogel, xerogel, and biomaterials as described herein. These are agents that assist in permeation of a drug into an intended tissue. Permeation agents may be chosen as needed for the tissue, e.g., permeation agents for skin, permeation agents for an eardrum, permeation agents for an eye.

The agent may be treatment of a back of the eye disease, e.g., wherein the back of the eye disease is age-related macular degeneration (AMD) cystoid macular edema (CME), diabetic macular edema (DME), posterior uveitis, and diabetic retinopathy, or glaucoma.

The agents may be, e.g., an agent comprises anti-VEGF, blocks VEGFR1, blocks VEGFR2, blocks VEGFR3, anti-PDGF, anti-PDGF-R blocks PDGFRP, an anti-angiogenic agent, Sunitinib, E7080, Takeda-6d, Tivozanib, Regorafenib, Sorafenib, Pazopanib, Axitinib, Nintedanib, Cediranib, Vatalanib, Motesanib, macrolides, sirolimus, everolimus, tyrosine kinase inhibitors (TKIs), Imatinibn gefinitib, toceranib, Erlotinib, Lapatinib, Nilotinib, Bosutinib Neratinib, lapatinib, Vatalanib, comprises low-soluble prostaglandin analogues for glaucoma, nepafenac, macrolides, rapamycin, sirolimus, tacrolimus, or serves to block mTOR receptors for AMD (also known as choroidal neovascularization (CNV). mTOR refers to mammalian target of rapamycin. Agents may be, e.g, moxifloxacin, dexamethasone, travoprost, steroids, fluoroquinolones, prostaglandin analogs, prostamides.

Ocular diseases include ocular pathologies, with hyphema, ocular hypertension, and glaucoma being conditions for treatment with an anterior chamber depot. Many agents are suitable for ocular delivery, e.g., NSAIDs, steroids, anti-glaucoma drugs, antivirals, antibiotics, mydriatics, and antifungals administered via intracameral injections.

Some of the disease states are back-of-the-eye diseases. The term back-of-the eye disease is recognized by artisans in these fields of endeavor and generally refers to any ocular disease of the posterior segment that affects the vasculature and integrity of the retina, macula or choroid leading to visual acuity disturbances, loss of sight or blindness. Disease states of the posterior segment may result from age, trauma, surgical interventions, and hereditary factors. Some back-of-the-eye disease are; age-related macular degeneration (AMD) cystoid macular edema (CME), diabetic macular edema (DME), posterior uveitis, and diabetic retinopathy. Some back-of-the-eye diseases result from unwanted angiogenesis or vascular proliferation, such as macular degeneration or diabetic retinopathy. Drug treatment options for these and other ocular conditions may be provided by delivery of agents from an implant.

EXAMPLES

The following Examples are included to demonstrate certain aspects and embodiments of the invention as described in the claims. It should be appreciated by those of skill in the art, however, that the following description is illustrative only and should not be taken in any way as a restriction of the invention.

Example 1: Manufacture of Travoprost Implants

Travoprost implants or "OTX-TIC travoprost Implants" having chemical composition and weight of formulations 1a, 1b, 2 and 3, respectively, (see Tables 1 and 2a) for use in the clinical phase 1 study, set forth in Example 3, were prepared. For the types of components as well as the masses and contents of the components used for the manufacturing of formulation 1a, 1b, 2 or 3, respectively, general reference is made to Table 1 displaying the chemical composition and contents. Said masses and contents of Table 1 will neither be repeated in detail nor be converted into the initial masses in the description of the corresponding manufacturing process of formulations 1a, 1b, 2 and 3 below.

TABLE 1

Chemical compositions and weight of OTX-TIC (travoprost) Implants based on formulations 1a, 1b, 2 and 3

| Ingredient | OTX-TIC (travoprost) Implant, 15 μg dose (Formulation 1a) | | OTX-TIC (travoprost) Implant, 26 μg dose (Formulation 1b) | | OTX-TIC (travoprost) Implant, 15 μg dose (Formulation 2) | | OTX-TIC (travoprost) Implant, 5 μg dose (Formulation 3) | | Function |
|---|---|---|---|---|---|---|---|---|---|
| | As Formulated (% dry basis) | Nominal Composition (μg, dry basis) | As Formulated (% dry basis) | Nominal Composition (μg, dry basis) | As Formulated (% dry basis) | Nominal Composition (μg, dry basis) | As Formulated (% dry basis) | Nominal Composition (μg, dry basis) | |
| Active Pharmaceutical Ingredient (Encapsulated in Microparticles) | | | | | | | | | |
| Travoprost | 19.1% | 14.8 | 25.9% | 25.8 | 19.4% | 14.9 | 11.6% | 5.4 | API |
| PLA Microparticles (Sustained Delivery of Travoprost) | | | | | | | | | |
| Poly (DL-lactide) | 24.8% | 19.2 | 33.6% | 33.5 | 25.2% | 19.3 | 15.1% | 7.0 | |
| 100 DL 4A | 5.0% | 3.8 | 6.7% | 6.7 | 6.3% | 4.8 | 7.1% | 3.3 | Biodegradable Polymers |
| 100 DL 7A | 5.0% | 3.8 | 6.7% | 6.7 | 10.1% | 7.7 | 8.0% | 3.7 | |
| 100 DL 9A | 2.5% | 1.9 | 3.4% | 3.4 | 8.8% | 6.8 | N/A | N/A | |
| 100 DL 5.5E | 12.4% | 9.6 | 16.8% | 16.8 | N/A | N/A | N/A | N/A | |
| Hydrogel (Inactive Delivery Platform) | | | | | | | | | |
| 8-arm 15K PEG SAZ | 49.3% | 38.3 | 35.7% | 35.6 | N/A | N/A | N/A | N/A | Biodegradable Polymers |
| 8-arm 15K PEG SG | N/A | N/A | N/A | N/A | 50.1% | 38.4 | 66.8% | 31.2 | |
| Trilysine Acetate | 3.2% | 2.5 | 2.3% | 2.3 | 3.2% | 2.5 | 4.3% | 2.0 | Cross-linking Agent |
| Sodium Phosphate Dibasic | 1.8% | 1.4 | 1.3% | 1.3 | 2.1% | 1.6 | 2.2% | 1.0 | Buffer |
| Sodium Phosphate Monobasic | 1.5% | 1.1 | 1.1% | 1.1 | N/A | N/A | N/A | N/A | Buffer |
| NHS-Fluorescein | 0.3% | 0.3 | 0.2% | 0.2 | N/A | N/A | N/A | N/A | Visualization Agent |
| Nominal OTX-TIC Implant Weight | N/A | 77 μg | N/A | 100 μg | N/A | 77 μg | N/A | 47 μg | |

Preparation of Biodegradable Travoprost Particles

In order to prepare travoprost implants according to any of formulations 1a, 1b, 2 or 3, travoprost particles in which travoprost is intermixed with a polylactide (PLA) were prepared first by an oil-in-water emulsification solvent evaporation/extraction technique. Polylactide and travoprost were dissolved in dichloromethane (DCM) to prepare a single-phase solution described as dispersed phase (DP) in the process (see Table 2a). The different molecular weight polymers are described as 4A, 7A, 9A and 5.5E PLA where the numerical value designates the target inherent viscosity (IV) of the polymer in chloroform which correlates to the PLA molecular weight and the letter suffix designates acid (A) or ester (E) end group. When measured in 0.5% w/v chloroform at 30° C., 4A PLA has an inherent viscosity specification of 0.35 to 0.45 dl/g; 7A PLA has an inherent viscosity specification of 0.60 to 0.80 or less dl/g and 9A PLA has an inherent viscosity specification of 0.80 to 1.0 dl/g. Details on measuring the inherent viscosity of polylactides are set forth in Table 2b below. When measured in 0.1% w/v chloroform at 25° C., 5.5E PLA has an inherent viscosity specification of 0.55 to 0.75 dl/g. The DP was injected via a syringe pump into a flowing stream of an aqueous solution of about 1% (w/w) polyvinyl alcohol (PVA) known as the continuous phase (CP) where PVA acts as an emulsifier. The injection occurred immediately prior to passing through an in-line homogenizer to disperse the DP into nascent microparticles. The addition of the dispersed phase to the continuous aqueous phase at this introduction stage allowed time to disperse the droplets before hardening to create the primary emulsion. These nascent microparticles in the CP stream then flowed into the stirring CP (quench medium) in a jacketed reactor maintained at a controlled temperature. This emulsion was stirred overnight in the quench medium to extract and evaporate DCM and harden the microparticles. The resultant microparticles were washed and sieved to the appropriate size fraction using a vibratory sieve agitator. These microparticles (travoprost-loaded 4A PLA, 7A PLA, 9A PLA, or 5.5 E PLA) were then collected in glass vials and lyophilized to yield the dry microparticles for the fabrication of the OTX-TIC (travoprost) Implant. The travoprost-loaded microparticles have a diameter ranging from 20 to 53 μm measured by sieving. The average microparticle diameter measured by laser diffraction is 35 μm.

TABLE 2a

Dispersed phase composition used to fabricate travoprost loaded microparticles for the different formulations, different mass ratios of microparticles for producing formulations 1a, 1b, 2 and 3, and actually measured average drug loading of the microparticles.

| PLA Type | 4A | 7A | 9A | 5.5E |
|---|---|---|---|---|
| Travoprost (g) in DCM | 5.51 | 5.12 | 4.54 | 2.42 |
| PLA (g) in DCM | 6.215 | 5.12 | 5.12 | 2.73 |
| Formulation 1a microparticle blend (wt.-%) composition | 20 | 20 | 10 | 50 |
| Formulation 1b microparticle blend (wt.-%) composition | 20 | 20 | 10 | 50 |
| Formulation 2 microparticle blend (wt.-%) composition | 25 | 40 | 35 | N/A |
| Formulation 3 microparticle blend (wt.-%) composition | 47 | 53 | N/A | N/A |
| Average drug load measured (wt.-%), dry basis of final microparticles | 44.4 | 45.9 | 42.3 | 42.5 |

TABLE 2b

Experimental parameters for measuring the inherent viscosity of the polylactides

| Variable | Experimental setup for 4A, 7A and 9A PLA & acid-terminated polymers | Experimental setup for 5.5E PLA & ester-terminated polymers |
|---|---|---|
| Concentration | 0.5% w/v | 0.1% w/v |
| Temperature | 30° C. | 25° C. |
| Ubbelohde Viscometer Size | 0 B | 0 B |
| Approximate Viscometer Constant (C) | 0.005 mm$^2$/s$^2$ | 0.005 mm$^2$/s$^2$ |
| Capillary Working Length (L) | 40 mm | 40 mm |
| Bulb Volume (V) | 3.0 ml | 3.0 ml |
| Capillary Inside Diameter (d) | 0.46 mm | 0.46 mm |
| Approximate flow time of solvent (CHCl$_3$) | 78 s | 78 s |

Preparation of the Travoprost Implant

General Procedure

The freeze-dried microparticles (4A, 7A, 9A and 5.5E, depending on the formulation a set forth in Table 1) were blended and weighed in a syringe in predetermined ratios (see Table 2a above) and suspended in water for injection (WFI). A blend of 4A (20%), 7A (20%), 9A (10%) and 5.5E (50%) PLA microparticles for the 15 μg and 26 μg, formulations 1a, 1b OTX-TIC implants, a blend of 4A (25%), 7A (40%), 9A (35%) PLA microparticles for the 15 μg, formulation 2 OTX-TIC implants, and a blend of 4A (47%), 7A (53%) PLA microparticles for the 5 μg, formulation 3 OTX-TIC implants were formulated. The multi-arm PEG precursor solution was separately dissolved in sodium phosphate monobasic or WFI in a syringe. The trilysine acetate or trilysine acetate/NHS-fluorescein buffered solution was transferred into a syringe. All syringes were placed under vacuum. The microparticles and PEG precursor syringes were first mixed and then combined with the TLA or TLA/FL buffered solution, which initiates hydrogel formation. The resulting suspension was injected in to a small ID tubing. Table 3 highlights the differences between each formulation.

TABLE 3

Differences between each formulation for preparing the travoprost implant

| Phase 1 Cohort (formulation used) | Travoprost-loaded PLA Microparticle Blend | Fluorescein | Solvent for PEG Solution | Tubing ID |
|---|---|---|---|---|
| 1 (formulation 1a) | 4A, 7A, 9A, 5.5E | Present | Sodium Phosphate in WFI | 0.5 mm |
| 2 (formulation 1b) | 4A, 7A, 9A, 5.5E | Present | Sodium Phosphate in WFI | 0.5 mm |

TABLE 3-continued

Differences between each formulation for preparing the travoprost implant

| Phase 1 Cohort (formulation used) | Travoprost-loaded PLA Microparticle Blend | Fluorescein Present | Solvent for PEG Solution | Tubing ID |
|---|---|---|---|---|
| 3 (formulation 2) | 4A, 7A, 9A | Not Present | Sodium Phosphate in WFI | 0.5 mm |
| 4 (formulation 3) | 4A, 7A | Not Present | Sodium Phosphate in WFI | 0.4 mm |

Preparation of Trilysine Acetate/NHS Fluorescein (TLA/FL) Solution and Syringes for 15 µg and 26 µg Doses; Formulations 1a and 1b The amount of Trilysine Acetate (TLA) was calculated based on a one-to-one molar ratio of amines to reactive PEG end groups which form the PEG hydrogel network when mixed in a buffered aqueous solution.

The TLA solution was prepared in Sodium Phosphate Dibasic buffer. The pH of the solution was adjusted to 8.40±0.05 by adding 1N NaOH to provide optimal reaction environment for TLA and NHS-Fluorescein (FL). After adjustment, NHS-Fluorescein was added to the vial of TLA solution. The vial was capped and vortexed to dissolve NHS-Fluorescein. The TLA/FL solution was left in the vial covered in aluminum foil to react for 1 to 24 hours at room temperature.

At the end of the reaction time, the pH of the solution was measured and predefined volume of TLA/FL solution is pipetted into four separate syringes. The syringes were placed upright into a beaker and transferred to a vacuum chamber for degassing of the solution.

Preparation of Trilysine Acetate (TLA) Solution and Syringes for 15 µg Dose; Formulation 2 and 5 µg Dose; Formulation 3

The amount of Trilysine Acetate (TLA) was calculated based on a one-to-one molar ratio of amines to reactive PEG end groups which form the PEG hydrogel network when mixed in a buffered aqueous solution. The TLA solution was prepared in Sodium Phosphate Dibasic buffer. At the end of mixing, the pH of the solution was measured and predefined volume of TLA solution is pipetted into four separate syringes. The syringes were placed upright into a beaker and transferred to a vacuum chamber for degassing of the solution.

Preparation of Microparticle Syringes

For 15 µg and 26 µg doses (Formulations 1a and 1b), each microparticle syringe contained predefined ratios of 4A PLA, 7A PLA, 9A PLA and 5.5E PLA microparticles (see "General Procedure" above). For the 15 µg Formulation 2 dose, each microparticle syringe contained predefined ratios of 4A PLA, 7A PLA, and 9A PLA microparticles (see "General Procedure" above). For the 5 µg Formulation 3 dose, each microparticle syringe contained predefined ratios of 4A PLA, and 7A PLA microparticles (see "General Procedure" above). After the microparticles were weighed, WFI was added into each of the total four syringes to suspend microparticles. The syringes were placed upright into a beaker and transferred to a vacuum chamber for degassing of the suspension.

Preparation of PEG Syringes

A predefined amount of 8a15k PEG was weighed and transferred to four different syringes. For 15 µg and 26 µg doses (Formulations 1a and 1b), Sodium Phosphate Monobasic solution was pipetted into each syringe to dissolve 8a15k PEG-SAZ. For 15 µg Formulation 2 and 5 µg Formulation 3, WFI was pipetted into each syringe to dissolve 8a15k PEG-SG. The PEG solution was used within 60 minutes after preparation. The syringes were placed upright into a beaker and transferred to a vacuum chamber for degassing of the solution.

Casting

For each run a microparticle syringe and PEG syringe were connected by a female to female luer connector. Slow even pressure was used to pass the contents of each syringe back (1 pass) and forth (1 pass) for total 25-50 times to mix the contents of the syringes together. The suspension was pulled into a single syringe and then connected to the TLA/FL (15 µg and 26 µg doses Formulations 1a and 1b) or TLA (15 µg dose Formulation 2 and 5 µg Formulation 3 doses) syringe. When the content of the syringes was first mixed, a calibrated stopwatch was started to measure the time for the suspension to gel. Slow even pressure was used to pass the contents of each syringe back (1 pass) and forth (1 pass) for total 25-50 times to create the PEG/microparticle/TLA/FL (15 µg and 26 µg doses Formulation 1) or PEG/microparticle/TLA (15 µg dose Formulation 2 and 5 µg Formulation 3 doses) suspension. The suspension was drawn into one syringe and primed to remove any excess air.

While the suspension was still in liquid form, the syringe is connected to tubing and the suspension was injected into the tubing. Once the tubing was full, it is capped on the bottom end, detached from the syringe and capped at the casting end. The remaining 11 pieces of tubing were filled in the same manner until the gel sets.

Once all the tubing per a syringe set had been capped, a small amount of the remaining suspension was placed on a glass slide to monitor gel formation. The suspension was gently tapped with a pipette tip until the suspension begins to strand (i.e., remains connected to the pipette tip during a complete tapping cycle). This was repeated for each syringe set (total four runs or syringe sets).

Drying

The tubing was placed on the drying fixture which held the hydrogel strands taut during drying. Each drying fixture could hold up to six strands at a time. The drying fixtures were placed horizontally within an incubator set to 33° C. with a nitrogen flow (10 L/min). The hydrogel strands remained in the incubator for 48 to 72 hours for drying.

Cutting and Implant Inspection

The dry strands were removed from the tubing and any strands that were damaged during the removal process were discarded. The strands were fed into a cutter that cut the strand into approximately 2.0 mm long implants. During the cutting process, each syringe run was collected in sterile clear vials designated with batch number, part number and associated run number and labeled as 'Not Inspected'. If the vials of drug implants were not inspected immediately, they were sealed under a blanket of dry nitrogen in the glovebox and refrigerated.

The final chemical compositions and weight of the formulations 1a, 1b, 2 and 3 travoprost implants are shown in Table 1. The physical characteristics of formulations 1a, 1b, 2 and 3 travoprost implants are shown in Table 4.

TABLE 4

Physical characteristics, such as measured dimensions of the implants, and duration of therapy for formulations 1a, 1b, 2 and 3.

| | OTX-TIC (travoprost) Implant For Intracameral Use Duration of the Therapy | | | |
|---|---|---|---|---|
| | 6-9 months | 6-9 months | 3-6 months | 3-6 months |
| | | Dose | | |
| | 15 µg (formulation 1a)[a] | 26 µg (formulation 1b)[a] | 15 µg (formulation 2)[b] | 5 µg (formulation 3)[c] |
| Dry Dimensions [d] (upon administration) | Diameter: 0.21 ± 0.01 mm Length: 1.99 ± 0.02 mm | Diameter: 0.25 ± 0.01 mm Length: 2.00 ± 0.02 mm | Diameter: 0.21 ± 0.01 mm Length: 1.99 ± 0.02 mm | Diameter: 0.17 ± 0.01 mm Length: 1.99 ± 0.03 mm |
| Hydrated Dimensions [e] | Diameter: 0.47 ± 0.01 mm Length: 2.25 ± 0.06 mm | Diameter: 0.48 ± 0.01 mm Length: 2.30 ± 0.03 mm | Diameter: 0.52 ± 0.01 mm Length: 2.44 ± 0.05 mm | Diameter: 0.41 ± 0.01 mm Length: 2.36 ± 0.04 mm |
| Visibility | OTX-TIC fluoresces when illuminated with a blue light, | OTX-TIC fluoresces when illuminated with a blue light. | Contains no fluorescein | Contains no fluorescein |
| Hydrogel persistence | 5-8 months | 5-8 months | 2-4 months | 2-4 months |

The in vitro release in physiological (pH 7.4) dissolution media under sink conditions at 37° C. is the approximate following durations for each formulation:
[a]denotes releases for 120 days
[b]denotes releases for 90 days
[c]denotes releases for 60 days
[d] Dry dimensions means that the implant has a water content of <1% tested using a Karl Fischer coulometric method.
[e] Dimensions are measured after 24 hours of hydration in vitro in phosphate-buffered saline (PBS) at a pH of 7.4 at 37° C. in 5 ml PBS.

Each individual OTX-TIC drug product was visually inspected by rotating the drug implant 360° and evaluating for cylindrical shape with no visual voids or foreign particulates using a vision system or a microscope. The implants passing visual inspection were dimensionally inspected to the required specifications per dose and strength (see Table 5).

TABLE 5

OTX-TIC In Process Controls (IPC) for Dimensional Aspects

| | Length | Diameter |
|---|---|---|
| 15 µg Formulation 1 | 2.00 ± 0.08 mm | 0.22 ± 0.02 mm |
| 26 µg Formulation 1 | | 0.26 ± 0.02 mm |
| 15 µg Formulation 2 | | 0.21 ± 0.02 mm |
| 5 µg Formulation 3 | | 0.17 ± 0.02 mm |

OTX-TIC implants that did not meet the in-process visual, length, or diameter requirements were placed in separate vials clearly labeled as 'Fail Inspection'.

OTX-TIC implants that had met visual and dimensional inspection were sealed under a blanket of dry nitrogen in the glovebox and refrigerated.

Packaging of OTX-TIC (Travoprost) Implant

The OTX-TIC implants that met all the in-process specifications were prepared for packaging. A single OTX-TIC implant was packaged in a syringe (a 27G (5 µg and 15 µg dose formulations) or 26G (26 µg dose) ½" ultra-thin wall sterile needle) assembly and sealed in a peelable foil-LDPE laminate pouch.

Example 2: Characterizations

Example 2a: In Vitro Release Measurements

Travoprost in vitro release from OTX-TIC is performed under simulated physiological sink conditions using 10 OTX-TIC implants in 50 mL of 1×PBS, 0.5% castor oil, 0.01% sodium fluoride buffer at pH 7.2-7.4 at 37° C. in a 60 mL polypropylene bottle in a water bath. Sampling is performed at pre-determined time points for subsequent sample analysis on a C18 reversed-phase column using ultra high-performance liquid chromatography with UV detection at 220 nm.

In vitro release of travoprost from OTX-TIC Test at 37° C. results are shown in FIG. 1a the travoprost release duration is dependent upon the travoprost loaded PLA microparticles blend as listed in Table 3.

The data points corresponding to FIG. 1a for the in vitro releases (expressed in terms of percentages) of the implants constituted by formulations 1a, 1b, 2 and 3 are shown in Table 6 below. The in vitro release values (in nanogram) per 7 days are shown in Table 7 below.

TABLE 6

In vitro travoprost release data points measured for OTX-TIC for formulations 1a, 1b, 2 and 3, respectively.

| Formulation 1a | | | Formulation 1b | | | Formulation 2 | | | Formulation 3 | | |
|---|---|---|---|---|---|---|---|---|---|---|---|
| Time (days) | Travoprost release[a] | Slope (based on 14 day intervals)[b] | Time (days) | Travoprost release[a] | Slope (based on 14 day intervals)[b] | Time (days) | Travoprost release[a] | Slope (per 70 day intervals)[c] | Time (days) | Travoprost release[a] | Slope (based on 70 days)[c] |
| 1 | 13% | | 1 | 13% | | 1 | 11% | | 1 | 11% | |
| 7 | 19% | | 7 | 18% | | 7 | 15% | | 8 | 18% | |
| 14 | 24% | 11% | 14 | 23% | 11% | 13 | 19% | | 15 | 24% | |
| 21 | 28% | 10% | 21 | 27% | 9% | 21 | 25% | | 21 | 31% | |
| 28 | 34% | 11% | 28 | 33% | 9% | 28 | 29% | | 28 | 40% | |
| 35 | 40% | 11% | 35 | 38% | 11% | 35 | 36% | | 35 | 50% | |
| 42 | 46% | 11% | 42 | 42% | 9% | 42 | 42% | | 42 | 56% | |

TABLE 6-continued

In vitro travoprost release data points measured for OTX-TIC for formulations 1a, 1b, 2 and 3, respectively.

| Formulation 1a | | | Formulation 1b | | | Formulation 2 | | | Formulation 3 | | |
|---|---|---|---|---|---|---|---|---|---|---|---|
| Time (days) | Travoprost release[a] | Slope (based on 14 day intervals)[b] | Time (days) | Travoprost release[a] | Slope (based on 14 day intervals)[b] | Time (days) | Travoprost release[a] | Slope (per 70 day intervals)[c] | Time (days) | Travoprost release[a] | Slope (based on 70 days)[c] |
| 49 | 50% | 10% | 49 | 45% | 7% | 49 | 46% | | 49 | 61% | |
| 56 | 53% | 8% | 56 | 49% | 7% | 57 | 53% | | 56 | 68% | |
| 63 | 58% | 8% | 63 | 54% | 8% | 63 | 62% | | 63 | 79% | |
| 70 | 64% | 11% | 70 | 60% | 11% | 70 | 76% | 65% | 70 | 89% | 65% |
| 77 | 71% | 14% | 77 | 66% | 13% | 77 | 88% | 73% | 77 | 94% | 73% |
| 84 | 77% | 13% | 84 | 72% | 12% | 84 | 96% | 77% | 84 | 95% | 77% |
| 91 | 82% | 11% | 91 | 76% | 9% | 91 | 99% | 74% | | | |
| 98 | 87% | 10% | 98 | 80% | 8% | 98 | 100% | 71% | | | |
| 105 | 93% | 10% | 105 | 84% | 8% | 105 | | | | | |
| 112 | 99% | 12% | 112 | 91% | 11% | 112 | | | | | |
| | | | 119 | 97% | 13% | 119 | | | | | |

| Average of Slopes based on 14 days | Average of Slopes based on 14 days | Average of Slopes based on 70 days | Average of Slopes based on 70 days |
|---|---|---|---|
| 11% | 10% | 72% | 75% |

| Mean average deviation of Average of Slopes | Mean average deviation of Average of Slopes | Mean average deviation of Average of Slopes | Mean average deviation of Average of Slopes |
|---|---|---|---|
| 1% | 1% | 3% | 3% |

[a]Travoprost release percentage is calculated based on the maximum measured release.
[b]Slopes are increases of the released travoprost amount per 14 days and the slopes were calculated by subtracting the release on day 14 minus the release on day 1, and by subtracting the release on day 21 minus the release on day 7 etc.
[c]Slopes are increases of the released travoprost amount per 70 days and the slopes were calculated by subtracting the release on day 70 minus the release on day 1, and by subtracting the release on day 77 minus the release on day 7 etc.

Figure 1B:
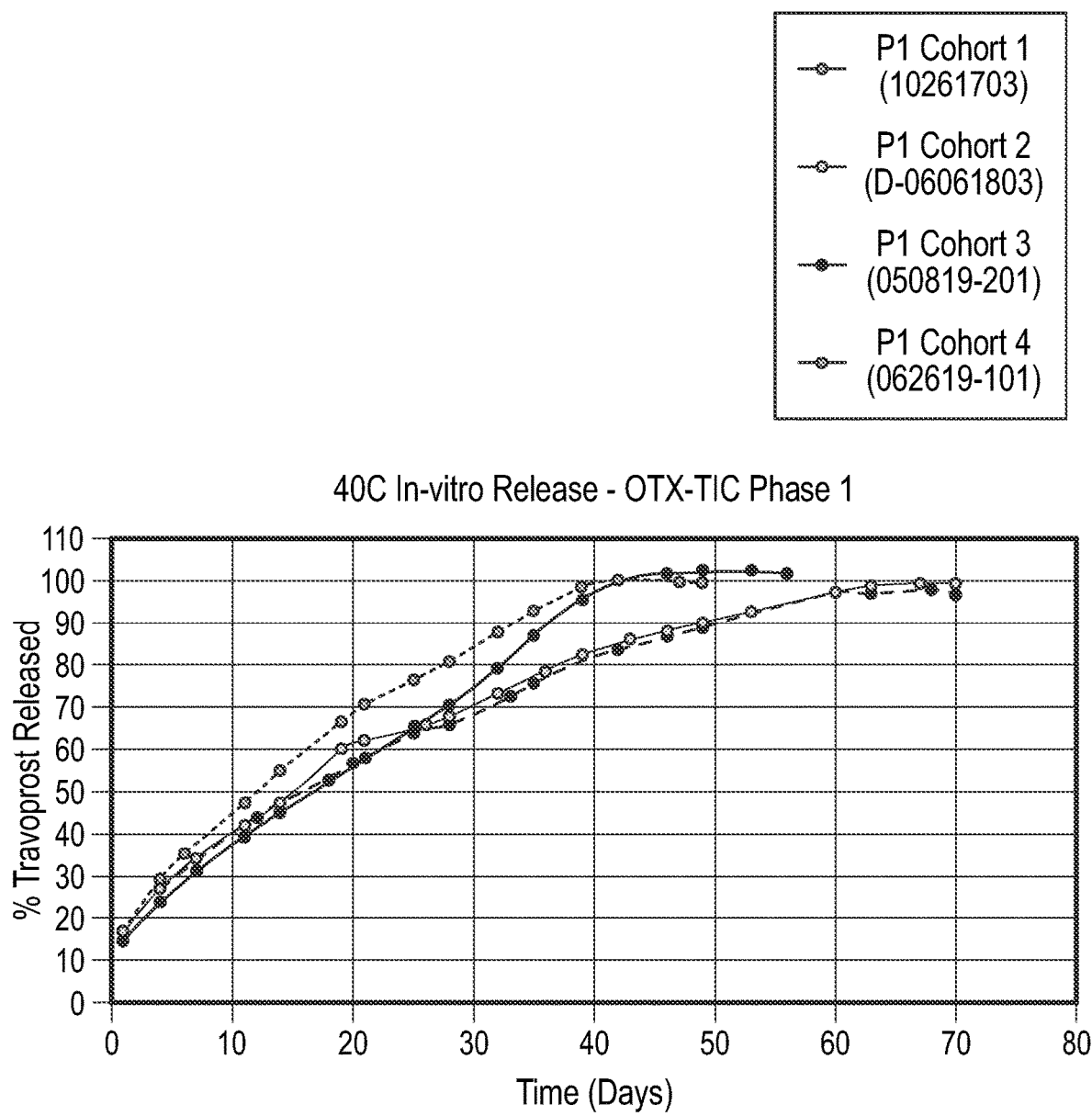
FIG. 1b An in vitro release of formulations 1a, 1b, 2 and 3 measured at 40° C.

Travoprost in vitro release for formulations 1a, 1b, 2 and 3 measured under the same conditions as set forth above, with the exception that the release is measured at 40° C., is shown in FIG. 1b.

TABLE 7

Releases per 7 days measured for the 37° C. release experiments

| Formulation 1a | | Formulation 1b | | Formulation 2 | | Formulation 3 | |
|---|---|---|---|---|---|---|---|
| Time (days) | Travoprost Release (ng/week)* | Time (days) | Travoprost Release (ng/week) | Time (days) | Travoprost Release (ng/week) | Time (days) | Travoprost Release (ng/week) |
| 1 | 1871 | 1 | 3259 | 1 | 1656 | 1 | 646 |
| 7 | 1021 | 7 | 1358 | 7 | 602 | 8 | 352 |
| 14 | 680 | 14 | 1358 | 13 | 602 | 15 | 352 |
| 21 | 680 | 21 | 1086 | 21 | 903 | 21 | 411 |
| 28 | 851 | 28 | 1358 | 28 | 602 | 28 | 470 |
| 35 | 851 | 35 | 1358 | 35 | 903 | 35 | 587 |
| 42 | 851 | 42 | 1086 | 42 | 903 | 42 | 352 |
| 49 | 510 | 49 | 815 | 49 | 753 | 49 | 293 |
| 56 | 680 | 56 | 1086 | 57 | 1054 | 56 | 411 |
| 63 | 680 | 63 | 1086 | 63 | 1355 | 63 | 587 |
| 70 | 851 | 70 | 1629 | 70 | 1957 | 70 | 646 |
| 77 | 1021 | 77 | 1629 | 77 | 1806 | 77 | 235 |
| 84 | 1021 | 84 | 1358 | 84 | 1204 | 84 | 59 |
| 91 | 680 | 91 | 1086 | 91 | 452 | — | — |
| 98 | 680 | 98 | 1086 | 98 | 151 | — | — |
| 105 | 851 | 105 | 1086 | — | — | — | — |
| 112 | 851 | 112 | 1629 | — | — | — | — |
| 119 | 170 | 119 | 1629 | — | — | — | — |
| — | — | 126 | 543 | — | — | — | — |
| — | — | 133 | 272 | — | — | — | — |

TABLE 7-continued

Releases per 7 days measured for the 37° C. release experiments

| Formulation 1a | | Formulation 1b | | Formulation 2 | | Formulation 3 | |
|---|---|---|---|---|---|---|---|
| Time (days) | Travoprost Release (ng/week)* | Time (days) | Travoprost Release (ng/week) | Time (days) | Travoprost Release (ng/week) | Time (days) | Travoprost Release (ng/week) |
| Travoprost Released per Week Post Day 1 Burst | | | | | | | |
| Average | 761 (days 7 to day 119) | — | 1278 (days 7 to day 119) | — | 946 (days 7 to day 98) | — | 396 (days 7 to day 84) |
| Median | 851 | — | 1358 | — | 903 | — | 382 |
| Std Dev | 210 | — | 250 | — | 502 | — | 164 |

*Travoprost release per week post day 1 burst (rounded release percent between sampling timepoints × dose)

Example 2b: Integrity/Softness of the Implant

Figure 1C:
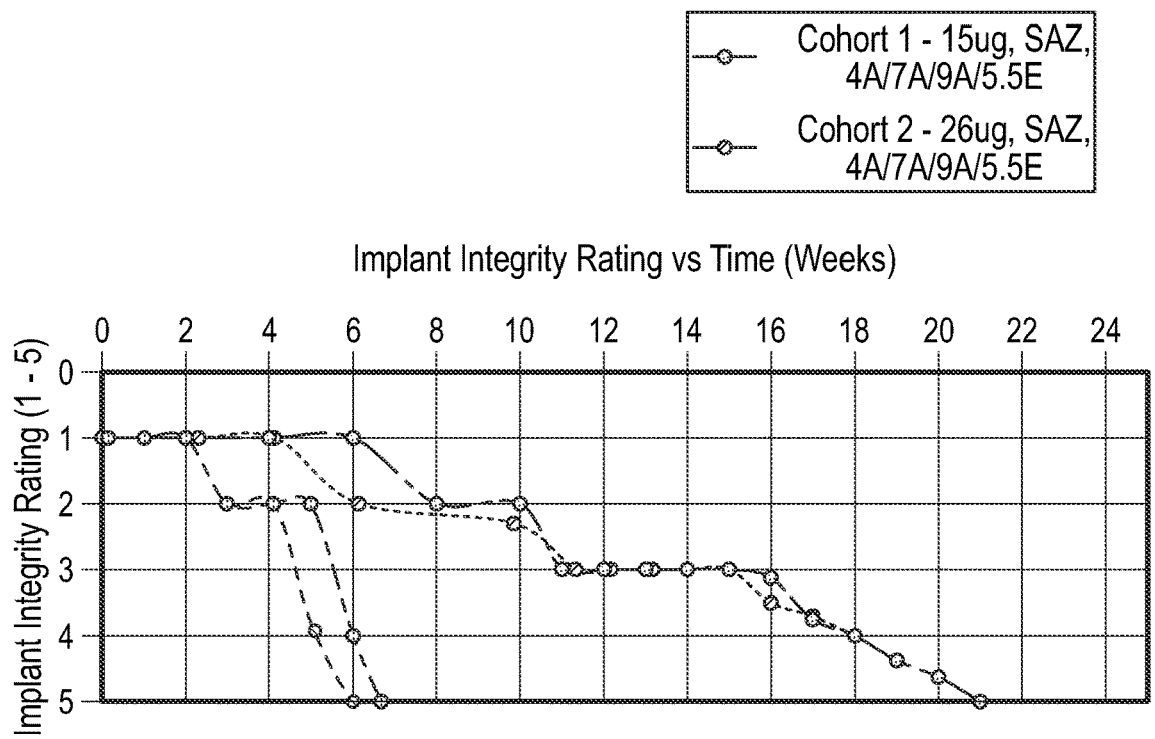
FIG. 1c Implant Integrity Rating vs Time (Weeks)

The implant integrity can be deemed as a qualitative parameter for the softness of the implant with respect to the tissue of the anterior chamber of the eye (in particular the iridocorneal angle). The implant integrity was determined based on the criteria shown in the box below. The corresponding results for formulations 1a, 1b, 2 and 3 for cohorts 1 to 4 are shown in FIG. 1c.

| Scale | Description |
|---|---|
| 1 | Firm implant, no damage as a result of handling (similar to initial dosing) |
| 2 | Softer implant, no damage as a result of handling (initiation of degradation observable) |
| 3 | Soft implant, prone to damage from handling (significant degradation) |
| 4 | Implant not able to be handled/measured, does not maintain cylindrical shape when handled, disintegrates/breaks |
| 5 | Complete liquefaction of hydrogel |

Example 2c: Water Content of the Dry Implant

A protocol for determining the water content of the intracameral implant of the present invention in its dried state is described in this example.

1.0 Purpose

To describe the procedure used to determine the water content of Travoprost intracanalicular inserts (OTX-TP) using a Karl Fischer coulometric method.

2.0 Scope

This procedure applies to OTX-TP Travoprost intracanalicular inserts requiring water content determination.

Note: This test method was validated per TP-1332/TR-1297 Method Validation for

Optimized Water Content Determination of Travoprost Intracanalicular Depots

Protocol/Report 3.0 Referenced Documents

Document Number Title
   SOP-10050 Balances
   SOP-10053 Gloveboxes
   SOP-10080 Metrohm Karl Fischer Coulometer with 874 Oven Sample Processor using Tiamo software.
   TP-1332 Method Validation for Optimized Water Content Determination of Travoprost Intracanalicular Depots Protocol
   TR-1297 Method Validation for Optimized Water Content Determination of Travoprost Intracanalicular Depots Report 4.0 Reagents, Materials, and Equipment Hydranal Water Standard—KF Oven 140-160° C.
   4.1.1 Reference Standard. The exact water % is specified on the Certificate of Analysis (CoA) for each lot.

Reagents
   4.2.1 Hydranal Coulomat AG Oven Anolyte

Materials
   4.3.1 Molecular Sieves, 0.3 nm (VWR P/N: EM-MX1583D-1 or equivalent)
   4.3.2 Magnetic stir bar
   4.3.3 Crimpers
   4.3.4 20 mm vials Karl Fischer Vials with septa crimp caps Equipment
   4.4.1 Analytical balance
   4.4.2 Portable glove box with regulated nitrogen gas supply
   4.4.3 Flow meter, in line between regulated nitrogen supply and glove box.
   4.4.4 Karl Fischer Coulometric Titrator equipped with an oven sample processor (autosampler) and Dosino bottle top dispenser.
   4.4.5 Karl Fischer Coulometric Titrator with Tiamo software 5.0 Equipment Set-Up Set up the portable glovebox per SOP-10053 Gloveboxes. Ensure flow meter is sitting vertically and securely. Open the valve on the flow meter fully by rotating dial counter-clockwise until a soft stop is achieved. Open the valve on regulated nitrogen supply and adjust the regulators, if necessary, to achieve a nitrogen flow with at least ~2-3 psi. This is "full flow" nitrogen. Purge the glovebox at full flow for at least 30 minutes.

Refer to SOP-10080 Karl Fischer Coulometer with 874 Oven Sample Processor using Tiamo Software for instrument set up and analysis procedure.

6.0 Blank Preparation

Benchtop Blank preparation—perform in triplicate (n=3)—System Suitability Blanks
   6.1.1 Equilibrate an empty vial on benchtop conditions for at least 30 minutes.
   6.1.2 Crimp seal the empty vial prior to standard preparation.
   6.1.3 Place vial in the autosampler.
   6.1.4 Analyze blanks for water content according to Section 9.0.

Glovebox Blank preparation—perform in triplicate (n=3)—Sample Blanks
   6.2.1 Equilibrate an empty vial under full flow nitrogen for at least 30 minutes.
   6.2.2 Crimp seal the empty vial prior to sample preparation.
   6.2.3 Place vial in the autosampler.
   6.2.4 Analyze blanks for water content according to Section 9.0.

7.0 Standard Preparation

Water standard preparation—perform in triplicate (n=3)
   7.1.1 Equilibrate an empty vial on benchtop conditions for at least 30 minutes.
   7.1.2 Weigh 50.0 t 5.0 mg of Hydranal water standard with an analytical balance per SOP-10050 Balances, directly into a vial that has been equilibrated at benchtop conditions for at least 30 minutes.
   7.1.3 Record the exact weight and water content (from CoA) of the standard in the Tiamo software on the appropriate lines.
   7.1.4 Crimp seal the vial and place it in the autosampler.
   7.1.5 Analyze standards for water content according to Section 9.0.

Bracket standard preparation
   7.2.2 Equilibrate an empty vial on benchtop conditions for at least 30 minutes.
   7.2.2 Weigh 50.0 t 5.0 mg of Hydranal water standard with an analytical balance per SOP-10050, directly into a vial that has been equilibrated at benchtop conditions for at least 30 minutes.
   7.2.3 Record the exact weight and water content (from CoA) of the standard in the Tiamo software on the appropriate lines.
   7.2.4 Crimp seal the vial and place it in the autosampler.
   7.2.5 Analyze standards for water content according to Section 9.0.

8.0 Sample Preparations

OTX-TP intracanalicular insert sample preparation—Perform in triplicate (n=3)
   8.1.1 Equilibrate sample vials and caps under full flow nitrogen for at least 30 minutes.
   8.1.3 Place cap loosely on vial and remove from glove box.

8.1.3 Obtain the weight of the empty vial and cap for each sample, ensuring that the vial and cap are kept matched together for duration of sample preparation. Record exact weight.

8.1.4 Replace vial and cap in glove box. Allow glove box to re-equilibrate under full flow nitrogen for a minimum of 5 minutes.

8.1.5 Just prior to sample preparation, adjust the dial on the flow meter until 4 t 1 L/min is reached. This is achieved by first rotating the dial clockwise until the flow is below 4 L/min, then rotating the dial counter clockwise back up to 4 L/min. The flow rate is read at the center of the float.

8.1.6 For each sample, remove cap and place 30 OTX-TP intracanalicular inserts into one vial.

8.1.7 Crimp seal cap onto vial.

8.1.8 Remove sealed vial from glove box and obtain weight of vial with inserts. Record exact weight.

8.1.9 Calculate sample weight: Sample Weight (mg) =Weight of vial with inserts (mg)−Weight of empty vial (mg)

8.1.10 Record the exact weight of the sample in the Tiamo software under the appropriate sample line.

8.1.11 Place sample in the autosampler.

8.1.12 Analyze samples for water content according to Section 9.0.

8.1.13 Samples are stable for four hours after preparation under ambient conditions of the instrument.

9.0 Analysis Procedure

Figure 1D:
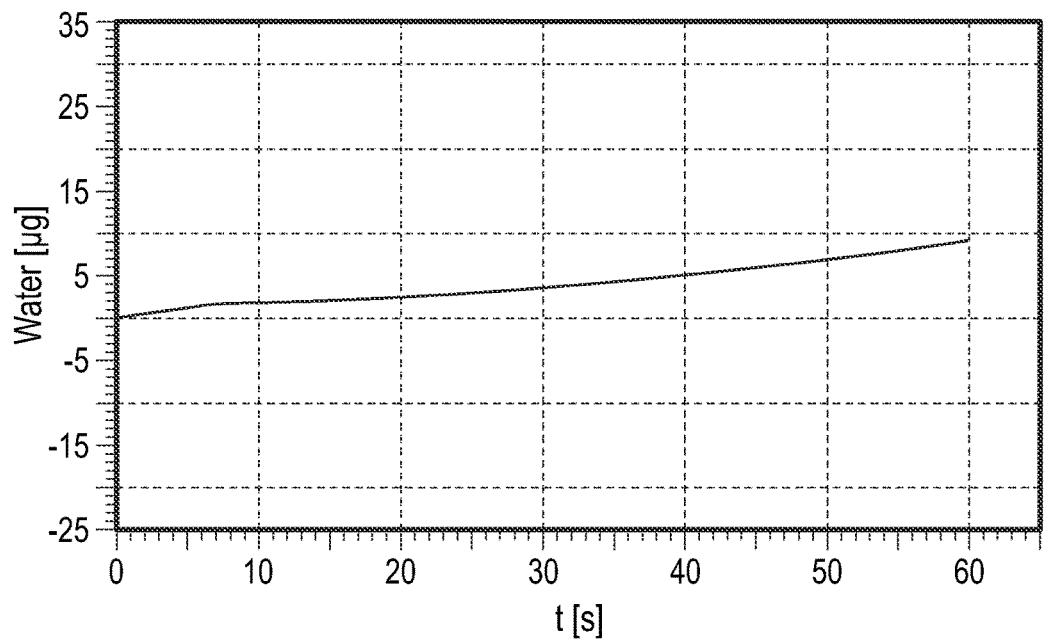
FIG. 1d typical Karl Fischer plot of the blank obtained using the method disclosed herein.

Procedural References 9.1.1 See FIG. 1d for a typical Karl Fischer plot of the blank obtained using this procedure.

Figure 1E:
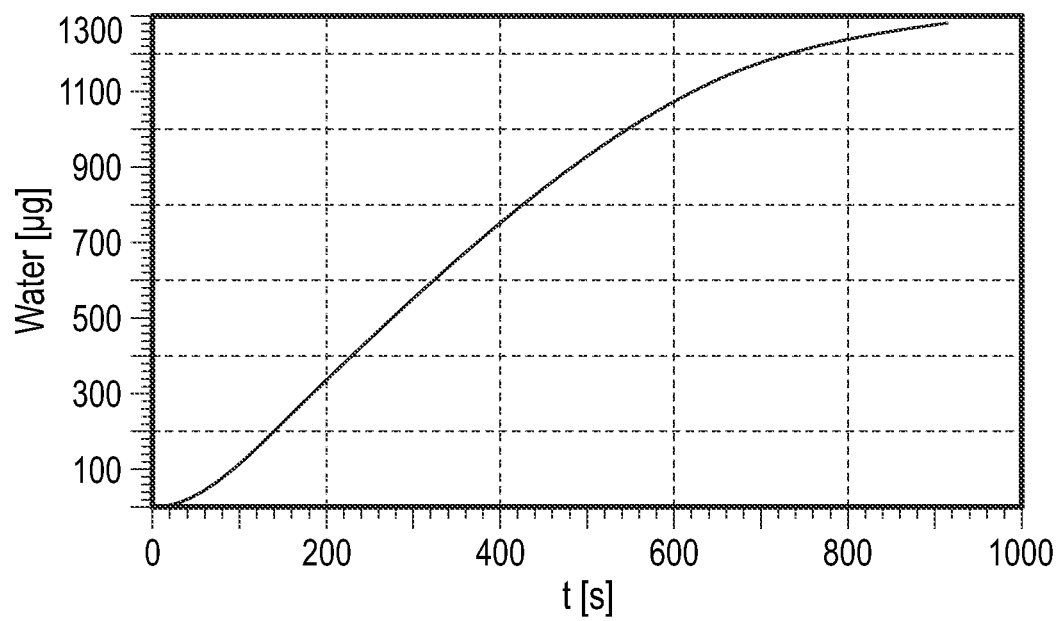
FIG. 1e typical Karl Fischer plot of the water standard obtained using the method disclosed herein.

9.1.2 See FIG. 1e for a typical Karl Fischer plot of the water standard obtained using this procedure.

Figure 1F:
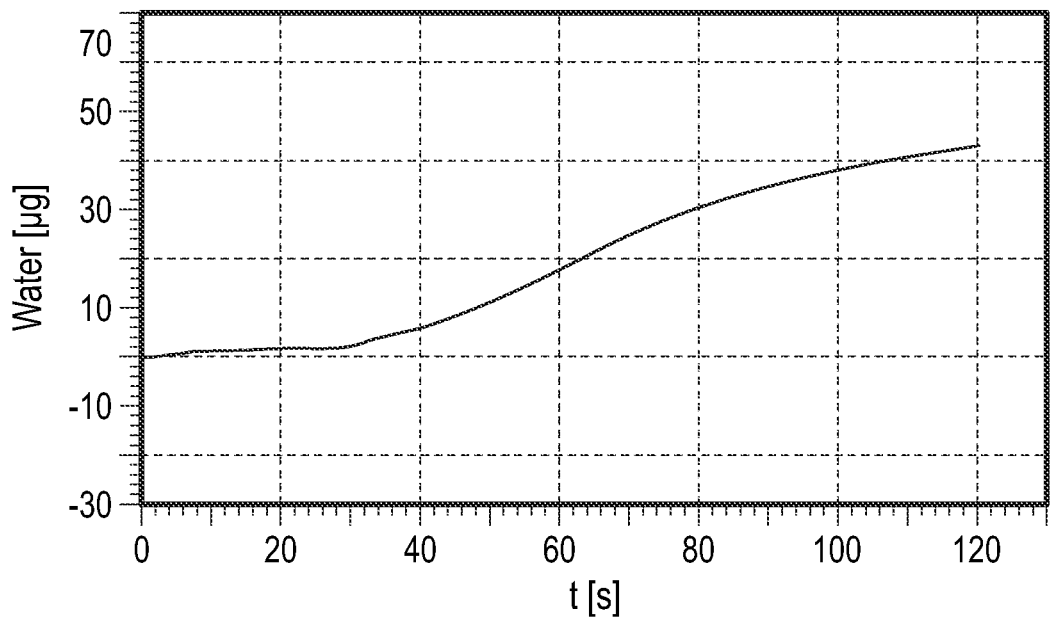
FIG. 1f typical Karl Fischer plot of an OTX-TP sample obtained using the method disclosed herein.

9.1.3 See FIG. 1f for a typical Karl Fischer plot of an OTX-TP sample obtained using this procedure.

9.2 Ensure that the Karl Fischer Titrator with oven sample processor system is set to the following parameters:

| Gas Flow | 75 mL/min |
| --- | --- |
| Oven Temperature | 104° C. |
| Stir Speed | 10 |
| Extraction Time | 120 seconds* |
| Start Drift | 20 µg/min |
| Stop Drift | 10 µg/min |
| Minimum Titration Rate | 15 µg/min |

*Note:
The KF Blank and System Suitability Blank methods use an extraction time of 60 seconds Common Variables 9.3.1 Two common variables are required in the Tiamo software to ensure that the proper blank values are applied to the standard and sample injections. Standards prepared under ambient conditions are corrected for ambient moisture by preparing blanks under ambient conditions. Samples prepared in the glovebox under nitrogen are corrected for glovebox moisture by preparing blanks under glovebox conditions.

9.3.1.1 Common Variable #1—System Suitability Blank: This common variable features the average blank value for the three "system suitability blank" injections. This common variable value is used to determine the water content values of the "system suitability standard" and "bracket standard" injections.

9.3.1.2 Common Variable #2—Sample Blank: This common variable features the average blank value for the three "sample blank" injections. This common variable value is used to determine the water content values of the sample injections.

Note: For a summary of the common variables used, see the table below:

| Blank Injections Performed | Prepared Conditions | Common Variable Name | Injections the Common Variable is Applied to for Blank Subtraction |
| --- | --- | --- | --- |
| System Suitability Blanks (1-3) | Ambient (Benchtop) | "System Suitability Blank" | System Suitability Standards, Bracket Standard |
| Sample Blanks (1-3) | Glovebox | "Sample Blank" | Samples |

Karl Fischer Analysis 9.4.1 Load one previously injected blank vial into the autosampler at position 1 and another into the "condition" position. These are for system preparation (equilibration). If previously injected blank vials are not available, use freshly crimped empty vials. Run system preparation at the start of every run using the "KF System Prep" method in Tiamo.

Note: If freshly crimped empty vials 9.4.2 Make one injection of each system suitability blank vial (n=3) using the "System Suitability Blank" method in Tiamo.

9.4.3 Make one injection of each water standard vial (n=3) using the "KF Benchtop Standard" method in Tiamo.

9.4.4 Make one injection of each glovebox sample blank vial (n=3) using the "Sample Blank" method in Tiamo.

9.4.5 Make one injection of each glovebox sample vial using the "KF Glovebox Sample" method in Tiamo.

9.4.6 As a system check, make an injection of a bracket standard vial after every 15 samples and at the end of the analysis using the "KF Benchtop Standard" method in Tiamo.

9.5 Example Injection Sequence:

| Vial # | Injection Name/Description | Tiamo Method |
| --- | --- | --- |
| 1 | System Prep Vial | KF System Prep |
| 2-4 | System Suitability Blank 1-3 | System Suitability Blank |
| 5-7 | System Suitability Standard 1-3 | KF Benchtop Standard |
| 8-10 | Sample Blank 1-3 | Sample Blank |
| 11-25 | Samples 1-15 | KF Glovebox Sample |
| 26 | Bracket Standard | KF Benchtop Standard |

System Suitability Criteria 9.6.1 Calculate the percent relative standard deviation (% RSD) for the water % for the 3 consecutive injections of the water standards. The RSD of the water % must be less than or equal to 2.0%

9.6.2 The Tiamo Software will calculate the percent recovery of the water content for the standard injections against the water content of the CoA.

9.6.2.1 The total average water content percent recovery listed on the third standard must fall in the range of 95.0-105.0%.

9.6.3 Calculate the recovery of water % for the bracket standard against the total average water content percent for the three system suitability standards as follows:

$$\% \text{ Recovery} = \frac{\text{Water\% for bracket standard}}{\text{Average Water\% for three system suitability standards}} \times 100$$

9.6.3.1 The bracket standard percent recovery must fall in the range of 95.0-105.0%.

10.0 Sample Calculations

The Tiamo software will automatically calculate the water % for each sample.

10.1.1 Each sample with a water % value that is less than (<) 1.0%, report as "<1.0%"

10.1.2 Each sample with a water % value that is greater than or equal to (≥) 1.0%, report the value to two decimals. Calculate the mean water % for the 3 samples.

10.2.1 If the water % of all 3 samples are less than 1.0%, report mean water % result as "<1.0%".

10.2.2 If the water % of any sample is greater than or equal to 1.0%, calculate the mean water % using the values that are ≥1.0%. Any values<1.0% will not be included in the mean water % calculation.

10.2.2.1 Report the mean water % to one decimal.

Example 3: Clinical Phase 1 Study

A prospective, multi-center, open-label phase 1 study to evaluate the safety, tolerability and efficacy of OTX-TIC (travoprost) intracameral implant in subjects with primary open-angle glaucoma (OAG) or ocular hypertension (OHT) was conducted.

Study Objective

The primary study objective was to assess the safety, tolerability and efficacy of a single dose of the OTX-TIC (travoprost) intracameral implant in subjects with primary OAG or OHT.

Study Outcome Measures

Safety Outcome Measures

The Investigator graded the ease of the injection procedure. The safety outcome measures were assessed immediately (within 1 hour) following injection of the implant and continued throughout the study.
Safety evaluations included:
  Adverse event reporting (Adverse events were assessed to determine if they are procedure related)
  Subject ocular comfort assessment
  Investigator global tolerance score
  BCVA
  Slit lamp biomicroscopy
  Gonioscopy
  Fundus exam
  Endothelial cell count with specular microscopy
  Pachymetry
  Anterior segment (AS)-OCT
  Automatic Visual Field
  OCT Optic nerve NFL
  Posterior segment OCT Efficacy Outcome Measures The efficacy outcome measures were:
  Diurnal IOP (8 a.m., 10 a.m., 4 p.m.) were checked at baseline, Day 14 (Visit 5), Day 42 (Visit 7), Day 85 (Visit 8), Month 4 (Visit 9) and Month 6 (Visit 11).
  In addition, intraocular pressure at 8 a.m. on the day of injection; Days 3, 7, and 28; and Month 5 (Visit 10) were checked.

Exploratory Measures

In order to determine if there is sufficient space in the iridocorneal angle so that the implant may be safely injected, the Investigator determined the iridocorneal angle size using gonioscopy. A comparison of the determination of the angle utilizing AS-OCT read by a masked reading center served as an exploratory endpoint.

Study Design

This was a multicenter, open label, Phase 1 clinical study. This study treated 19 subjects in one of four cohorts:
  Cohort 1 (15 µg, formulation 1a, as described in Example 1) consisted of 5 subjects each to receive a single implant to one eye
  Cohort 2 (26 µg, formulation 1b, as described in Example 1) consisted of 4 subjects each to receive a single implant to one eye.
  Cohort 3 (15 µg, formulation 2, as described in Example 1) consisted of 5 subjects each to receive a single implant to one eye
  Cohort 4 (5 µg, formulation 3, as described in Example 1) consisted of 5 subjects each to receive a single implant to one eye The subjects were intended to be followed for approximately 7 months (one month washout and 6 months follow-up after injection of the OTX-TIC implant). However, several were followed much longer.

If biological activity was noted or the implant was present at the 6 month visit, subjects were followed monthly until their IOP is within 10% of their baseline measurement or until the Investigator believes the subject is clinically stable.

Subject Selection

Study Population

The subjects enrolled in this study had stable primary OAG or OHT in the study eye and were managed topical medications or were treatment naïve. The current IOP lowering medication was stopped at the start of the screening visit (Visit 1), if applicable. Prior to randomization on Day 1, eligible subjects completed the washout period of 4 to 6 weeks. Subjects were considered stable if the Investigator had not recommended additional IOP lowering therapy to the subject over the past 8 weeks prior to the screening visit and had shown no evidence of functionally significant central visual field loss or documented significant progressive field loss within the last year in either eye based upon the assessment by the Investigator. Following the washout period, eligible subjects had to have a baseline IOP as described in the inclusion criteria below. If both eyes qualified (i.e., all inclusion and none of the exclusion criteria are met) then the eye with the highest baseline IOP following the washout period was the study eye. If both eyes qualified AND both eyes had the same baseline IOP following the washout period, the right eye was selected as the study eye.

Inclusion Criteria

Individuals of either gender were eligible for study participation if they:
1. Were 18 years of age or older at the time of screening
2. Had a documented diagnosis of OHT, or primary OAG in the study eye
3. Had IOP that was currently controlled (as assessed by the Investigator)
4. Had a mean baseline IOP following a 4 to 6 weeks washout period of current therapy (if needed) in the study eye of:
5. ≥24 mmHg and ≤36 mmHg at hour 0 (T0) at Baseline Visit 2 (Day 0) after the washout period, and
6. ≥22 mmHg at ($T_0$+2 h)
7. Had open, normal appearing anterior chamber angles in the study eye (as determined by gonioscopy) sufficient to fit an implant without corneal endothelial cell touch, i.e., an angle of approach 20° or larger according to the Shaffer-Etienne classification of Grade 3 (20°-35°, scleral spur visible) or Grade 4 (35°-45°, ciliary body is visible)
8. Were able to comply with all study requirements
9. Had provided a written signed informed consent Exclusion Criteria Individuals were not eligible for study participation if they:
1. Had closed angle glaucoma, narrow angle glaucoma, pseudoexfoliation syndrome, pseudoexfoliation glaucoma, pigment dispersion or pigmentary glaucoma, glaucoma diagnosis prior to 15 years of age, inflammatory, neovascular or other secondary glaucoma in the study eye
2. Prior history of intracameral implant in the anterior chamber in the study eye
3. Were unwilling to discontinue use of contact lenses prior to pachymetry (3 days) and throughout the entire study
4. Had a known or suspected allergy and/or hypersensitivity to a prostaglandin (i.e., travoprost), fluorescein or to any component of the study products
5. Had any corneal or other ocular or adnexal abnormality preventing reliable applanation tonometry of either eye
6. Had a central corneal thickness <480 μm or >620 μm in either eye (or difference between eyes >70 μm)
7. Had a cup to disc ratio >0.8 (horizontal or vertical measurement) in the study eye as assessed by the Investigator
8. Had a functionally significant central visual field loss or documented significant progressive field loss within the last year in the study eye based upon the assessment by the Investigator
9. Had active lid or eye disease (i.e., moderate or severe blepharitis, meibomitis, dry eye disease, ocular infections (viral or fungal, or recurrent bacterial), scleritis, uveitis, or corneal edema, within the previous 3 months in either eye
10. Had an endothelial cell count<1,800 cells/mm$^2$ and/or had other endothelial abnormalities in the study eye (based on specular microscopy and confirmed by Central Reading Center)
11. Had an endothelial cell count<1,800 cells/mm$^2$ and/or had other endothelial abnormalities in the non-study eye (based on specular microscopy and confirmed by Central Reading Center)
12. Had a history of significant ocular trauma within the past six months in the study eye
13. Had a history of peripheral iridotomy/iridectomy in the inferior 180° of the iris in the study eye
14. Had any history of bleeding disorder of use of medications which in the Investigator's opinion places at the subjects at high risk during insertion of the implant
15. Had any ophthalmic surgical procedures (e.g., glaucoma laser, minimally invasive glaucoma surgery, refractive surgery) in the study eye within the last 6 months or will require ophthalmic surgery during the study period. Subjects at enrolment or planning to be treated during the study with a CyPass implant were excluded.
16. Had a history of penetrating keratoplasty in the study eye
17. Had proliferative diabetic retinopathy, or have a history of macular edema in either eye
18. Had an uncontrolled systemic disease or a debilitating disease (e.g., cardiovascular, hypertension, uncontrolled diabetes, or cystic fibrosis)
19. Had participated in any study involving an investigational drug either in the U.S. or outside the U.S. within the past 30 days
20. Were an employee of the site that is directly involved in the management, administration, or support of the study, or were an immediate family member of the same
21. Were pregnant at enrollment or breast-feeding or of childbearing potential without the use of adequate contraceptive methods during the length of the study Study Data Collection The study time and event schedule is presented in Table 8

TABLE 8

Time and event schedule of the clinical phase 1 study.

| | Visit Type | | | | | | | |
|---|---|---|---|---|---|---|---|---|
| | Screening[a] up to −4 to −6 weeks | Baseline Visit[a] Day 0 (−4 days) | Insertion Day 1 | Post-Insert Follow up Day 3 (−1 day) | Follow-up Day 7 (±1 day) | Follow-up Day 14 (±1 day) | Follow-up Day 28 (±2 days) | Follow-up Day 42 (±2 days) |
| Visit Number | Visit 1 | Visit 2 | Visit 3 | Visit 4 | Visit 4.1 | Visit 5 | Visit 6 | Visit 7 |
| Informed Consent | X | | | | | | | |
| Demographic Information | X | | | | | | | |

TABLE 8-continued

Time and event schedule of the clinical phase 1 study.

| | | | | | | | | |
|---|---|---|---|---|---|---|---|---|
| Medical and Ophthalmic History[b] | X | | | | | | | |
| Inclusion and Exclusion Criteria | X | X | | | | | | |
| Concomitant Medication | X | X | X | X | X | X | X | X |
| Adverse event assessment | X | X | X[g] | X | X | X | X | X |
| Vital Signs (heart rate, blood pressure) | X | | X | | | | | |
| Subject Ocular Comfort Score | | | X[g] | X | X | X | X | X |
| Investigator Global Tolerance Score | | | X[g] | X | X | X | X | X |
| BCVA (ETDRS) | X | X | X | X | X | X | X | X |
| Slit Lamp Biomicroscopy including External Eye Exam | X | X | X | X | X | X | X | X |
| Product Visualization description (via slit lamp) | | | X | X | X | X | X | X |
| IOP Measurement by applanation (Goldmann) | X | X[d] | X | X | X | X[d] | X | X[d] |
| Gonioscopy | X | | | | | | | |
| Fundus Exam | X[e] | X | | | | | | |
| Visual Field | X | | | | | | | |
| Pachymetry | X | | | | | | | X |
| Anterior Segment OCT | | X | | | | | | |
| Posterior Segment OCT | X | | | | | | | |
| OCT Optic Nerve NFL | X | | | | | | | |
| Endothelial Cell Count (specular microscopy) | X | | | | | | | |
| Intracameral Injection of OTX-TIC | | | X | | | | | |
| Urine Pregnancy Test | X | | | | | | | |

| | Visit Type | | | | | | | |
|---|---|---|---|---|---|---|---|---|
| | Follow-up Day 85 (±2 days) | Follow-up Month 4 (±3 days) | Follow-up Month 5 (±3 days) | Final Study Visit Month 6 (±3 days) | Follow-up Month 7[f] (±3 days) | Follow-up Month 8[f] (±3 days) | Follow-up Month 9[f] (±3 days) | Unscheduled Visit[c] |
| Visit Number | Visit 8 | Visit 9 | Visit 10 | Visit 11 | Visit 12 | Visit 13 | Visit 14 | |
| Informed Consent | | | | | | | | |
| Demographic Information | | | | | | | | |
| Medical and Ophthalmic History | | | | | | | | |
| Inclusion and Exclusion Criteria | | | | | | | | |
| Concomitant Medication | X | X | X | X | X | X | X | X |
| Adverse event assessment | X | X | X | X | X | X | X | X |
| Vital Signs (heart rate, blood pressure) | | | | X | | | | X |
| Subject Ocular Comfort Score | X | X | X | X | X | X | X | X |
| Investigator Global Tolerance Score | X | X | X | X | X | X | X | X |
| BCVA (ETDRS) | X | X | X | X | X | X | X | X |
| Slit Lamp Biomicroscopy including External Eye Exam | X | X | X | X | X | X | X | X |
| Product Visualization and Description (via slit lamp) | X | X | X | X | X | X | X | X |
| IOP Measurement by applanation (Goldmann) | X[d] | X[d] | X | X[d] | X | X | X[d] | X |
| Gonioscopy | X | | | X | | | X | X |
| Fundus Exam | X | | | X[e] | | | X | X |
| Visual Field | | | | X | | | | X |
| Pachymetry | X | | | X | | | X | X |
| Anterior Segment OCT | X | | | X | | | X | X |

TABLE 8-continued

Time and event schedule of the clinical phase 1 study.

| | | | | |
|---|---|---|---|---|
| Posterior Segment OCT | X | X | X | X |
| OCT Optic Nerve NFL | X | X | X | X |
| Endothelial cell count (specular microscopy) | X | X | X | X |
| Intracameral Injection of OTX-TIC | | | | |
| Urine Pregnancy Test | | X | | |

[a] Screening Visit (Visit 1) and Baseline Visit (Day 0) could be combined into one visit for naïve treatment subjects.
[b] Medical and Ophthalmic History.
[c] Unscheduled Visits: The Investigator had to determine which assessments need to be performed based on the reason for the unscheduled visit; not all assessment needed to be performed
[d] IOP measurement at 8 a.m. (±1 hour), 10 a.m. (±1 hour) and 4 p.m. (±1 hour) at Baseline Visit, Day 14 (Visit 5), Day 42 (Visit 7), Day 85 (Visit 8), Month 4 (Visit 9), and Month 6 (Visit 11), Month 9 (Visit 14, if necessary), and the Final Visit post-Month 9 (if necessary).
[e] Fundus exam at Screening (Visit 1) and 6 month Visit (11) were required to be dilated.
[f] Only to be completed for subjects who still had evidence of biological activity or residual implant. These subjects were followed monthly until their IOP is within 10% of their baseline measurement or until the Investigator believed the subject is clinically stable. If remnant microspheres are observed at Month 12, then subjects were followed at the discretion of the Investigator. For all visits beyond month 9, the same schedule of assessments was to be followed as that delineated for Month 7 visit. The Final Study Visit followed the Visit 11 assessments.
[g] Assessment was completed prior and post implant placement on Day 1 visit Study Observations and Procedures Subject Screening and Informed Consent Prior to enrollment in the study, subjects were evaluated to determine potential eligibility. The Investigator and study staff determined the subject's willingness and ability to meet the follow-up requirements. If the subject desired to participate in the study, written informed consent was obtained prior to performance of any study-specific examinations. Following completion of the screening and baseline evaluations, a determination was made by the Investigator and study staff as to whether or not the subject has met all the eligibility criteria. If the subject met the eligibility criteria and agrees to participate, the subject was enrolled.

A subject was considered enrolled in the study at the time the subject signed the informed consent. Once a subject qualifies for the study and is randomized, they had to be followed whether or not the subject received the study assigned treatment.

If the injection of the OTX-TIC implant was unsuccessful, record the reason for injection failure on the eCRF as an injection failure and not as an AE; and the subjects were followed as long as medically appropriate.

Screen Failures

Subjects who were enrolled, i.e., have signed the Informed Consent Form, but were determined to be ineligible during the screening assessments or at the Baseline visit but prior to treatment with OTX-TIC, were considered screen failures, were to be withdrawn from the study, and were not required additional study follow-up visits. The reason(s) for the screening failure were recorded in the eCRF.

If subjects who failed eligibility criteria experience an AE during the Screening or Baseline visits, they were followed until the AE is resolved or stabilized.

Subject Withdrawal

All subjects treated in the study were required to adhere to the follow-up schedule as described in this protocol.

Subjects could withdraw from the clinical study at any time for any reason without jeopardy or prejudice and without compromising their clinical care by the Investigator. The Investigator also had the right to withdraw subjects from the trial in the event of an intercurrent illness, AE, protocol violation and/or administrative reason.

For any subject who withdrew their consent following treatment, to the extent possible, the reason(s) for withdrawal were documented on the End of Study eCRF. Subjects were encouraged, but not required, to return for removal of the intracameral implant (if it has been placed) prior to withdrawing from the study.

If the withdrawal from the study is a result of an AE, or death, an AE Form was also completed. If a subject was withdrawn from the study as a result of an AE, every attempt would have been made by the Investigator to follow the subject until the AE has resolved or stabilized.

Every attempt was made to contact subjects who are non-compliant or lost to follow-up and such attempts were documented in the subject's study record.

Subjects who withdrew from the study after receiving the OTX-TIC (travoprost) intracameral implant were not replaced.

Product Malfunctions

All malfunctions of the OTX-TIC (travoprost) intracameral implant injector were be documented on the appropriate eCRF and reported to Ocular Therapeutix within 24 hours. Ocular Therapeutix advised how the intracameral implant was returned for analysis. The incidence of malfunctions will be included in the final analysis.

Point of Treatment

Once a subject has been determined to be eligible for participation in the study and has completed all screening assessments, including the washout period, the Investigator confirmed eligibility prior to treatment.

This study treated 19 subjects (~5 subjects per cohort) at one of four possible cohorts: 15 µg (formulation 1a as described in Example 1), 26 µg (formulation 1b as described in Example 1), 15 µg (formulation 2 as described in Example 1), and 5 µg (formulation 3 as described in Example 1).

Subjects could have only 1 eye treated with OTX-TIC as part of this study; that eye was designated as the study eye SE. If both eyes qualify for study entry, the SE was selected on the basis of the eye with the highest IOP after the protocol described washout period. If both eyes had the same IOP after the washout period, the right eye was chosen as the SE.

The Data Safety Monitoring Committee (DSMC) reviewed safety data from Cohort 1 prior to enrollment of any subject into Cohort 2.

Cohort 1 was fully enrolled, and all safety and tolerability data of OTX-TIC for each subject in Cohort 1 (minimum follow up data for two weeks) was assessed prior to any subject entering Cohort 2. Dose escalation to Cohort 2 were based on the recommendation of the DSMC and determined by the medical monitor (MM) or the Sponsor.

Cohorts 3 and 4 were initiated in parallel as cohort 4 is a lower dose and the implant lasts for a shorter duration than the doses studied in Cohorts 1, 2 and 3.

In the event that one dose limiting toxicity (DLT) was identified in the Cohort 2 dose group, enrollment continued; however, if another DLT were identified, the previous (lower-Cohort 1) dose was declared as the MTD. However, there were no MTDs.

The contralateral eye, designated as the non-study eye (NSE), if needed, was treated with Travatan Z (if not contraindicated). The treatment of the NSE remained consistent for the duration of the study. All ocular assessments were done on both eyes at all visits.

Concomitant Medications

The use of any concurrent ophthalmic medications and systemic medications, prescription or over-the-counter, from up to 3 years prior to the Screening Visit, had to be recorded on the subject's medical records and corresponding eCRF along with the reason the medication was taken, starting at the Screening Visit through the end of the study. The use of any herbal or vitamin supplements and any dilation and other standard of care drops used for the ophthalmic assessments including IOP measurement and the insertion procedure (i.e., betadine or topical anesthetic) were not recorded, except for the antibiotics, NSAIDs or steroids.

The following restrictions related to medications and treatments applied:
  Topical or systemic ocular hypotensive medications were not to be used for the duration of the study with the exception of the study treatment. The washout period for medications between the Screening and Baseline Visit (Visit 2, Day 0) for subjects currently taking prostaglandin analogues for OAG/OHT, was approximately 4 to 6 weeks.
  Note: A subject's current ocular hypertensive medication could be substituted with one requiring a shorter washout period to minimize the potential risk to the subject due to IOP elevation during the washout period. (For example, a subject currently taking a prostaglandin requiring a 4 to 6 weeks of washout could instead, be placed on a carbonic anhydrase inhibitor for 3 weeks, then allow the wash out of the carbonic anhydrase inhibitor for one week before inclusion into the study at Visit 2 (Day 0).
  Systemic beta blockers were allowed, but any initiation of or alterations in systemic regimen of beta-blocker containing medications from 8 weeks prior to screening through the final study visit was excluded.
  Use of short-term inhaled (using mouthpiece), local injection, nasal, and topical dermal steroids were allowed and were to be recorded in the eCRF if used.
  Any medication or substance administered by any route and used on a chronic basis that has not been on a stable dose for 8 weeks prior to Screening.
  Non-diagnostic topical ophthalmic solutions (other than the study treatment) could not be used from Baseline Visit through the duration of the study. Note: Use of artificial tears or ocular lubricants were to be avoided but if necessary, intermittent use could be allowed.
  Contact lenses were not to be used at any point during the study after the Screening Visit. In addition, contact lens wear had to be discontinued prior to pachymetry a minimum of 3 days.

Rescue Therapy

If at any point in the study, the Investigator determined that the IOP was not adequately controlled, IOP-lowering drops were provided as rescue therapy at the Investigator's discretion to ensure the subject's safety. The IOP lowering medication was recorded on the appropriate eCRF.

Study Assessments

Screening Evaluations: Up to 4 to 6 Weeks Prior to Baseline Visit

At the screening visit, the subject's eligibility for study participation was determined by checking all inclusion and exclusion criteria as specified above, respectively. If a subject failed one of the inclusion or exclusion criteria the subject was a screening failure and no further assessments were done.

Details of the procedures for these assessments can be found in below and both eyes were evaluated at every visit. The following assessment was performed as per the reading center study manual: AS-OCT, OCT optic nerve NFL, posterior segment OCT, endothelial cell count.

The following procedures and assessments were completed within a maximum of 4 to 6 weeks prior to baseline Visit 2 (Day 0). Pupil dilation was to be conducted after the completion of the last IOP measurement of the day.
  Screening Visit (Visit 1, up to 4 to 6 weeks)
  Obtain written informed consent
  Demographic information to include age, gender, race, ethnicity
  Medical and ophthalmic history including interventions
  Inclusion and exclusion criteria
  Prior and concomitant medications and procedures
  Vital signs (blood pressure, and heart rate)
  BCVA
  Slit Lamp biomicroscopy (including external eye exam)
  IOP measurement by applanation (Goldmann) tonometry
  Gonioscopy
  Dilated fundus exam
  Visual field
  Pachymetry (contact lens wear must be discontinued 3 days prior to pachymetry)
  Posterior segment OCT
  OCT optic nerve NFL
  Endothelial cell count (specular microscopy confirmed by Central Reading Center)
  Urine pregnancy test: if female of childbearing potential, subject had to utilize reliable contraceptive methods for the duration of the study as judged by the Investigator, and had to have a negative urine pregnancy test
  At the end of the screening Visit 1 potentially eligible subjects were instructed to start washout from current IOP lowering medications Note: For subjects with stable primary OAG or OHT not previously on IOP lowering medication prior to enrollment, screening visit and baseline visit could be combined into one single visit.

For screening failures due to reasons that are expected to be temporary, the sponsor was to be contacted, and one re-screening visit potentially could be conducted. Subjects who are re-screened were given a new subject number and needed to have all screening procedures repeated (including signing of a new Informed Consent Form).

For eligible subjects, all information has to be recorded in the subject's eCRF. For subjects who did not meet the eligibility criteria, the minimum information to be recorded in the eCRF were the following: date of screening, subject number and reason for screening failure.

Baseline Visit (Visit 2, Day 0, −4 Days)

The following assessments were performed on both eyes. IOP measurements taken on Day 0 were the baseline IOP measurements.
At 8 a.m. ($T_0$)
Inclusion and exclusion criteria confirmation
Concomitant medications
Adverse event assessment
BCVA
Slit lamp biomicroscopy, including external eye exam
IOP
Fundus exam
Anterior segment OCT
At 10 a.m. ($T_0$+2 hrs) and 4 p.m. ($T_0$+8 hrs)
IOP measurement by applanation (Goldmann) Tonometry
NOTE: All IOP measurements had to be conducted within ±60 minutes of the required time and had to be conducted at approximately the same time at each of the follow-up visits. IOP were measured using a 2-person masked reading method.

Intracameral Injection Day, Visit 3 (Day 1)

Assessments Performed Prior To Procedure

The following procedures and assessments were performed prior to treatment:
Review of concomitant medications and procedures
Adverse events (prior to injection)
Vital signs (heart rate and blood pressure)
Subject Ocular Comfort Score
Investigator Global Tolerance Score
BCVA
Slit Lamp biomicroscopy, including external eye exam
IOP by applanation (Goldmann) tonometry at 8 a.m. only.
  IOP measurement had to be conducted within t 60 min of the required time.

Treatment with OTX-TIC Intracameral Implant

After all evaluations were completed, the study drug treatment (OTX-TIC implant) assigned to the subject was administered by the Investigator and study staff according to the procedure recommended in the Study Manual. The Investigator recorded the ease of injection procedure.

If both eyes were eligible (i.e., all inclusion and none of the exclusion criteria were met) the study eye had to be selected as described above. The contralateral eye, designated as the non-study eye (NSE), if needed, was treated with Travatan Z (if not contraindicated). The treatment of the NSE had to remain consistent for the duration of the study.

At approximately 1 hour post-injection and prior to discharge from the visit the Investigator and study staff were responsible for the following:
The Investigator confirmed the proper placement of the OTX-TIC (travoprost) intracameral implant.
Whenever possible, the Investigator documented the presence of the intracameral implant with a slit lamp photograph
Adverse events (post-injection)
Subject Ocular Comfort Assessment
Investigator Global Tolerance Assessment Discharge Instructions Subjects were instructed to refrain from rubbing their eyes and to contact the Investigator in the event that they experience excessive pain, excessive discomfort, eye redness, change in vision, or loss of vision.

Standard post-ocular injection treatment included topical broad spectrum antibiotic drops and topical steroids up to four times a day for a week, at the Investigator's discretion.

Follow-up Assessments

Visit 4 (Day 3, ±1 Day)

The following were performed on both eyes of each subject by the Investigator and study staff, at 8 a.m. only:
Concomitant medications and procedures
Adverse events
Subject Ocular Comfort Assessment
Investigator Global Tolerance Score
BCVA
Slit lamp biomicroscopy, including external eye exam
Product visualization and description (via slit lamp)
IOP measurement Visit 4.1 (Day 7, ±1 Day)

The following were performed on both eyes of each subject by the Investigator and study staff, at 8 a.m. only:
Concomitant medications and procedures
Adverse events
Subject ocular comfort
Investigator Global Tolerance Score
BCVA
Slit lamp biomicroscopy, including external eye exam
Product visualization and description (via slit lamp)
IOP measurement Visit 5 (Day 14, ±1 Day)

The following were performed in both eyes:
At 8 a.m. ($T_0$)
Concomitant medications
Adverse events
Subject ocular comfort
Investigator Global Tolerance Score
BCVA
Slit lamp biomicroscopy, including external eye exam
Product visualization and description (via slit lamp)
IOP measurement
At 10 a.m. ($T_0$+2 h) and 4 p.m. ($T_0$+8 h)
IOP measurement.

Visit 6 (Day 28, ±2 Days)

The following were performed on both eyes of each subject by the Investigator and study staff, at 8 a.m. only:
Concomitant medications and procedures
Adverse events
Subject ocular comfort Investigator Global Tolerance Score
BCVA
Slit lamp biomicroscopy, including external eye exam
Product visualization and description (via slit lamp)
IOP measurement Visit 7 (Day 42, ±2 Days)

The following were performed in both eyes:
At 8 a.m. (To)
Concomitant medications
Adverse events
Subject ocular comfort
Investigator Global Tolerance Score
BCVA
Slit lamp biomicroscopy, including external eye exam
Product visualization and description (via slit lamp)
IOP measurement
Pachymetry
At 10 a.m. ($T_0$+2 h) and 4 p.m. ($T_0$+8 h)
IOP measurement.

Visit 8 (Day 85, ±2 Days)

The following were performed in both eyes during the study visit, at 8 a.m. ($T_0$):
  Concomitant medications
  Adverse events
  Subject ocular comfort
  Investigator Global Tolerance Score
  BCVA
  Slit lamp biomicroscopy, including external eye exam
  Product visualization and description (via slit lamp)
  IOP measurement
  Gonioscopy
  Fundus exam
  Pachymetry
  Anterior Segment OCT
  Posterior Segment OCT
  OCT Optic Nerve NFL
  Endothelial Cell Count (specular microscopy confirmed by Central Reading Center)
  At 10 a.m. ($T_0$+2 h) and 4 p.m. ($T_0$+8 h)
  IOP measurement.

Visit 8 (Day 85, ±2 Days)

The following were performed in both eyes during the study visit, at 8 a.m. ($T_0$):
  Concomitant medications
  Adverse events
  Subject ocular comfort
  Investigator Global Tolerance Score
  BCVA
  Slit lamp biomicroscopy, including external eye exam
  Product visualization and description (via slit lamp)
  IOP measurement
  Gonioscopy
  Fundus exam
  Pachymetry
  Anterior Segment OCT
  Posterior Segment OCT
  OCT Optic Nerve NFL
  Endothelial Cell Count (specular microscopy confirmed by Central Reading Center)
  At 10 a.m. ($T_0$+2 h) and 4 p.m. ($T_0$+8 h)
  IOP measurement Visit 9 (Month 4, ±3 Days)

The following were performed in both eyes:
At 8 a.m. ($T_0$)
Concomitant medications
Adverse events
Subject ocular comfort
Investigator Global Tolerance Score
BCVA
Slit lamp biomicroscopy, including external eye exam
Product visualization and description (via slit lamp)
IOP measurement
At 10 a.m. ($T_0$+2 h) and 4 p.m. ($T_0$+8 h)
IOP measurement.

Visit 10 (Month 5, ±3 Days)

The following were performed on both eyes of each subject by the Investigator and study staff, at 8 a.m. only:
  Concomitant medications and procedures
  Adverse events
  Subject ocular comfort
  Investigator Global Tolerance Score
  BCVA
  Slit lamp biomicroscopy, including external eye exam
  Product visualization and description (via slit lamp)
  IOP measurement Final Study Visit: Visit 11 (Month 6, ±3 Days)

The following were performed on both eyes:
At 8 a.m. ($T_0$)
Concomitant medications
Adverse events
Vital signs (heart rate and blood pressure)
Subject ocular comfort
Investigator Global Tolerance Score
BCVA
Slit lamp biomicroscopy, including external eye exam
Product visualization and description (via slit lamp)
IOP measurement
Gonioscopy
Dilated Fundus exam
Visual Field
Pachymetry
Anterior Segment OCT
Posterior Segment OCT
OCT Optic Nerve NFL
Endothelial Cell Count (specular microscopy confirmed by Central Reading Center)
Urine pregnancy test (if applicable)
At 10 a.m. ($T_0$+2 h) and 4 p.m. ($T_0$+8 h)
IOP measurement If biological activity is noted or the implant is present at the 6 month visit, subjects were followed monthly until their IOP is within 10% of their baseline measurement or until the Investigator believed the subject is clinically stable (see below). For all visits beyond Month 9, the same schedule of assessments had to be followed as that delineated for Month 7 (see below). If remnant microspheres are observed at Month 12, then subjects were followed at the discretion of the Investigator. The Final Study Visit should follow the Visit 11 assessments.

Follow-Up Visit 12, Month 7(±3 Days) and Visit 13 Month 8 (±3 Days)

If necessary, the following were performed on both eyes of each subject by the Investigator and study staff, at 8 a.m. only.
Concomitant medications and procedures
Adverse events
Subject ocular comfort
Investigator Global Tolerance Score
BCVA
Slit lamp biomicroscopy, including external eye exam
Product visualization and description (via slit lamp)
IOP measurement Follow-Up Visit 14 Month 9 (±3 Days)

If necessary, the following were performed during the study visit:
Concomitant medications
Adverse events
Subject ocular comfort
Investigator Global Tolerance Score
BCVA
Slit lamp biomicroscopy, including external eye exam
Product visualization and description (via slit lamp)
IOP measurement
Gonioscopy
Fundus exam
Pachymetry
Anterior Segment OCT
Posterior Segment OCT
OCT Optic Nerve NFL
Endothelial Cell Count (specular microscopy confirmed by Central Reading Center)
At 10 a.m. ($T_0$+2 h) and 4 p.m. ($T_0$+8 h)
IOP measurement Unscheduled Visit An unscheduled visit could occur at any time that the Investigator decides it was necessary to see the subject outside of the study visit windows. As many of these visits as necessary could be scheduled. The examinations and assessments were at the Investigator's discretion based on the reason for the visit. For example, if there was evidence of clinical corneal edema then the assessments had to include an AS-OCT.

Any unscheduled visits were recorded on the "unscheduled" visit electronic Case Report Form with the reason for the visit.

Adverse Events

Throughout the course of the study, all efforts were made to remain alert to possible AEs or untoward findings. If an AE occurs, the first concern was the safety and welfare of the subject. Appropriate medical intervention was undertaken. Any AEs observed by the Investigator or study staff or reported by the subject, whether or not ascribed to the study treatment, were recorded on the subject's Adverse Event eCRF.

Documentation regarding the AE had to be made as to the nature, date of onset, end date, severity and relationship to the study drug, action(s) taken, seriousness, and outcome of any sign or symptom observed by the physician or reported by the subject.

NOTE: Subjects were queried for the presence or absence of the following ocular complaints: excessive tearing, foreign body sensation, stinging/burning, and itching. Positive responses to these standardized ocular complaint inquiries were to be reported as ocular complaints and not as AEs unless the complaint: (1) meets the criteria of a specific event as listed, (2) is outside of normal limits, or (3) is associated with clinical sequelae (e.g., adverse slit lamp findings).

Definition of an Adverse Event

An AE is any untoward medical occurrence in a subject or clinical investigation subject administered a pharmaceutical product and which does not necessarily have a causal relationship with the treatment.

An AE can therefore be any unfavorable and unintended sign (including a clinically significant abnormal laboratory finding), symptom or disease temporally associated with the use of a medicinal (investigational) product, whether or not related to the medicinal (investigational) product. Lack of efficacy of an investigational agent does not constitute an adverse event.

Definition of a Serious Adverse Event (SAE)

An SAE is any untoward medical occurrence that at any dose:
Results in death
Is life-threatening
The term "life-threatening" refers to an event in which the subject was at risk of death at the time of the event; it does not refer to an event which hypothetically might have caused death if it were more severe.
Requires in-patient hospitalization or prolongation of existing hospitalization. Hospitalizations for elective surgeries do not constitute an SAE.
Results in persistent or significant disability/incapacity
Is a congenital abnormality/birth defect
Medical and scientific judgment had to be exercised in deciding whether other situations had to be considered SAEs, such as important medical events that might not be immediately life-threatening or result in death or hospitalization but might jeopardize the subject or might require intervention to prevent one of the other outcomes listed above.
Examples of such events are intensive treatment in an emergency room or at home for allergic bronchospasm, blood dyscrasias, neoplasms or convulsion that to not result in hospitalization.
An AE that is assessed as 'severe' should not be confused with a SAE. The term "severe" is often used to describe the intensity (i.e., severity) of a specific event (as in mild, moderate, or severe myocardial infarction); the event itself, however, may be of relatively minor medical significance (such as a severe headache). This is not the same as "serious", which is based on the outcome or action criteria usually associated with events that pose a threat to life or functioning. Seriousness (not severity) and causality serve as a guide for defining regulatory reporting obligations.

Severity

Severity of an AE is defined as a qualitative assessment of the degree of intensity of the AE as determined by the Investigator or reported to the Investigator by the subject. The assessment of severity is made irrespective of relationship to the study drug or seriousness of the event and should be evaluated according to the following scale:

Mild Event is noticeable to the subject, but is easily tolerated and does not interfere with the subject's daily activities Moderate Event is bothersome, possibly requiring additional therapy, and may interfere with the subject's daily activities Severe Event is intolerable, necessitates additional therapy or alteration of therapy, and interferes with the subject's daily activities For AEs that change in intensity, the start and stop date of each intensity were to be recorded.

Relationship to Intracameral Implant, or Procedure

For each (S)AE, the treating Investigator had to determine whether the event was related to the injection procedure or the intracameral implant. In order to do so, the Investigator had to determine whether, in his/her medical judgment, there was a reasonable possibility that the event may have been caused by the intracameral implant, or the injection procedure.

The following is a guideline which had to be used by the Investigator when assessing the causal relationship of an (S)AE. The attribution of causality to the injection procedure or the intracameral implant was identified in the CRF.

No RELATIONSHIP SUSPECTED This category applies to those (S)AEs which, after careful consideration, are clearly and incontrovertibly due to extraneous causes (disease, environment, etc.); there is no reasonable probability that the (S)AE may have been caused by the injection procedure or the intracameral implant. If the Investigator determined that the AE is unlikely to be related to the study drug, then this would have been the appropriate category.

RELATIONSHIP SUSPECTED The following criteria had to be applied in considering inclusion of an (S)AE in this category:

1) It bears a reasonable temporal relationship to the injection procedure or the presence of the intracameral implant.
2) It could not be reasonably explained by the known characteristics of the subject's clinical state, environmental or toxic factors or other factors (e.g., disease under study, concurrent disease(s) and concomitant medications) and modes of therapy administered to the subject.
3) It disappears or decreases on removal of the intracameral implant.
4) It follows a known pattern of response to the injection procedure or the intracameral implant.

A suspected AE is any event for which there is a reasonable possibility that the study drug caused the AE. "Reasonable possibility" means there is evidence to suggest a causal relationship between the study drug and the AE. Types of evidence that would suggest a causal relationship between the study drug and the AE include: a single occurrence of an event that is uncommon and known to be strongly associated with drug exposure; one or more occurrences of an event that is not commonly associated with drug exposure, but is otherwise uncommon in the population exposed to the drug (e.g., tendon rupture); an aggregate analysis of specific events observed in a clinical trial (such as known consequences of the underlying disease or condition under investigation or other events that commonly occur in the study population independent of drug therapy) that indicates those events occur more frequently in the drug treatment group than in a concurrent or historical control group.

Expectedness

The expectedness of an (S)AE had to be determined based upon existing safety information about the study drug using these guidelines:

UNEXPECTED An AE or that is not listed in the study protocol, Investigators' Brochure, or prescribing information for the registered formulation of travoprost (Travatan®) or is not listed at the specificity or severity that has been observed EXPECTED An AE that is listed in the study protocol, Investigators' Brochure, or prescribing information for travoprost at the specificity and severity that has been observed AEs that are mentioned in the Investigators' Brochure as occurring with a class of drugs or as anticipated from the pharmacological properties of the drug but are not specifically mentioned as occurring with the particular drug under investigation are to be considered as expected.

The Investigator should initially classify the expectedness of an AE, but the final classification is subject to the Medical Monitor's determination.

Clarifications

Diagnosis

To the extent possible, the event to be recorded and reported is the event diagnosis as opposed to the event signs or symptoms.

Hospitalization

Hospitalization for the elective treatment of a pre-existing condition (i.e., a condition present prior to the subject's signature of the Informed Consent Form) that did not worsen during the study is not considered an SAE. Complications that occur during hospitalization are AEs. If a complication prolongs hospitalization, or meets any of the other SAE criteria, the complication is an SAE.

Pre-Existing Conditions, Including Glaucoma

Anticipated day-to-day fluctuations of pre-existing condition(s) that do not worsen with respect to baseline are not (S)AEs.

Worsening or progression of glaucoma is considered to be a "lack of efficacy" or "failure of expected pharmacological action" per protocol and is already recorded as part of the efficacy assessment and therefore did not need to be recorded as an (S)AE.

Medical or Surgical Procedures

In the case of elective medical or surgical procedures, or pre-study planned medical or surgical procedures for pre-existing conditions (i.e., a condition present prior to the subject's signature of the Informed Consent Form) that did not worsen during the study the condition that leads to the procedure does not need to be reported as an (S)AE.

Death

Death is not an SAE; the condition that leads to the death is an SAE.

Abnormal Laboratory Values

Abnormal laboratory values that were judged by the Investigator to be clinically significant must be recorded as an (S)AE. Clinically significant abnormal laboratory findings that were present at baseline and significantly worsen following the start of the study were also reported as an (S)AE. Investigators were expected to review, sign, date, and make a determination of clinical significance within 24 to 48 hours after receiving them.

Timing of AEs

All AEs observed during the course of this study from the time the subject signs the Informed Consent Form, regardless of severity or relationship to the injection or intracameral implant were recorded on the appropriate eCRF(s).

Procedures for Reporting Adverse Events

All AEs that were "Suspected" and "Unexpected" were to be reported to Ocular Therapeutix and the IRB as required by the IRB/IEC, local regulations and the governing Health Authorities. Unanticipated events were to be reported to Salus IRB within 10 business days of identification of the event. Serious Unexpected Suspected Adverse events were reported to the Food and Drug Administration within 7 days for death and life-threatening events; all others within 15 days.

Any Serious Adverse Event or any severe AE, whether ascribed to the study treatment or not, were communicated within 24 hours, by fax or phone to Ocular Therapeutix. The Investigator had to obtain and maintain in his/her files all pertinent medical records, information, and medical judgments from colleagues who assisted in the treatment and follow-up of the subject; provide Ocular Therapeutix with a complete case history, which includes a statement as to whether the event was or was not suspected to be related to the use of the study drug; and inform the IRB/IEC of the AE within the IRB/IEC guidelines for reporting SAEs. A written report detailing the event, signed by the Investigator, had to be submitted to the Sponsor within 5 working days. All subjects who experienced an SAE must be followed until resolution or stabilization of the event and the outcome ware reported in the CRF.

Type and Duration of the Follow-Up of Adverse Events

AEs were followed until:
Resolution of the event, i.e., return to the baseline value or status or to 'normal'
AEs could be determined to have resolved completely or resolved with sequelae
The Principal Investigator determined, for events that did not end (e.g., metastasis), the condition to be chronic; the event could be determined to be resolved or resolved with sequelae
The event had stabilized, i.e., no worsening expected by the Investigator All AEs were documented in the CRFs. For subjects that reach the final scheduled visit (i.e., Visit 11 [Month 6]), an unscheduled visit could be conducted thereafter to follow-up on any AEs that the Investigator has not deemed to be resolved or stabilized.

Study Oversight

Data Safety Monitoring Committee (DSMC)

A DSMC was appointed by the Sponsor to monitor the safety of the study subjects during the course of the trial. The DSMC was comprised of a panel of independent glaucoma physician experts from the ophthalmology field. In the safety monitoring role, the DSMC established a charter including a mission statement, operating procedures, and proposed monitoring criteria for the study, including any supplementary proposed study stopping rules in addition to the criteria listed in the next section. The DSMC reviewed safety data from Cohort 1 prior to enrollment of any subject into Cohort 2; this prior review could not be conducted for Cohorts 3 and 4 as the doses for these Cohorts are less than Cohort 2 and for a shorter duration of therapy then those studied for Cohorts 1 and 2.

Written minutes of all meetings had to be developed after each DSMC meeting and major conclusions (i.e., the assessment for study continuation vs. recommendation to stop the study) had to be documented.

Statistical Analysis

Statistical and Analytical Plans

This study is not designed to show statistical significance, therefore, there are no statistical analyses completed. There is a general Statistical Plan that will briefly summarize how the data will be presented, i.e., descriptive statistics, etc.

Determination of Sample Size

For this Phase 1 study, no formal sample size calculations have been performed. A sample size of 5 subjects is considered sufficient to inform on safety of the product.

Analysis Datasets

The safety population consisted of all subjects receiving the OTX-TIC implant. All safety and efficacy analyses were performed on the safety population.

Demographics and Baseline Data

Subject disposition were presented, including the number of subjects screened, enrolled and treated. The number of subjects who completed the study and reasons for discontinuation were summarized.

Demographic and baseline characteristics (including disease and medical history) were summarized.

Safety Analyses

Safety was assessed by adverse events, subject ocular comfort assessment, Investigator global tolerance score and other ocular-related outcomes.

Adverse events were coded using Medical Dictionary for Regulatory Activities (MedDRA) by system organ class and preferred term. Separate summaries were made for adverse events that are related to the injection procedure and the intracameral implant. In addition, serious adverse events were summarized.

Summaries of other safety related outcomes were provided.

Efficacy Analyses

Efficacy was assessed on diurnal IOP. Measures taken (8 a.m., 10 a.m., 4 p.m.) at baseline, Day 14 (Visit 5), Day 42 (Visit 7), Day 85 (Visit 8), Month 4 (Visit 9), and Month 6 (Visit 11) was summarized. IOP was continued to be measured if biological activity is noted at Month 6 (see below). In addition, intraocular pressure at 8 a.m. on the day of insertion, Days 3, 7 and 28, and Month 5 (Visit 10) was summarized.

Exploratory Analyses

Angle size was assessed by two methods. The Investigator determined the angle size using gonioscopy. In addition, angle size utilizing AS-OCT read by a masked reading center was done. Angle size by method obtained was summarized.

General Information

Study Termination

Ocular Therapeutix reserved the right to discontinue the study at any stage, with suitable written notice to the Investigator and the IRB/IEC and other regulatory authorities as appropriate. Similarly, the Investigator could withdraw from participation in the study subject to providing written notification to Ocular Therapeutix within 30 days of their intent to withdraw. However, Ocular Therapeutix and the Investigator were bound by their obligation to complete the follow-up of subjects already treated in the clinical study. The subjects had to be followed according to the clinical protocol and information obtained during subject follow-up had to be reported on CRFs.

All serious AEs were evaluated and if the Sponsor determines that unreasonable risk to the subject is possible, the study was terminated, and all regulating authorities and the participating Investigator(s) were notified. Termination occurred not later than 5 working days after the Sponsor makes this determination and not later than 15 working days after the Sponsor first received notice of the effect.

A terminated investigation could not be resumed without the local research ethics committee or regulatory authority approval, as required.

Monitoring

The Investigator and the investigating center permit authorized clinical research personnel and clinical study monitors assigned by Ocular Therapeutix to review completed CRFs, IRB/IEC decisions, and Investigator and clinical site records at regular intervals throughout the study. Additionally, subject charts and clinical records were requested and reviewed so that protocol adherence and source documentation could be verified. In instances where data protection regulations and/or hospital policies prohibit the direct examination of hospital records by the study Sponsor or designee(s), the Investigator cooperated in a system of source data verification with the Sponsor. Further details of the study monitoring procedures are outlined in a Monitoring Plan.

If the Monitor discovers that the Investigator is not complying with the signed Investigator Agreement, the investigation plan, or other applicable regulations, or any conditions of approval imposed by the reviewing IRB/IEC, the Monitor would have reported to the Sponsor and take such steps necessary to promptly secure compliance. If compliance cannot be secured, investigational product shipments to the Investigator could have been be discontinued and the Investigator's participation in the clinical study was terminated. The Monitor also had to require such an Investigator to dispose of or return the unused product, unless this action would jeopardize the rights, safety or welfare of a subject.

Retention of Documentation

The Investigator maintains all study related documentation including all correspondence, records of financial interest, individual subject records, informed consent forms, all drug product accountability records, the protocol with any/all amendments, all correspondence with and approval from the IRB/IEC, the budget agreement, the Investigator agreement, and copies of CRFs for 2 years after the latter of the following dates:
1. The date a marketing application is approved for the drug for the indication for which it is being studied, or
2. The date that the records are no longer required for purposes of supporting an application to a regulatory agency.

The files may be discarded only upon notification from Ocular Therapeutix. To avoid error, the Investigator should contact Ocular Therapeutix before the destruction of any records and reports pertaining to the study to ensure they no longer need to be retained.

Slit Lamp Photographs

The Investigator captured the proper placement of the OTX-TIC (travoprost) intracameral implant on Day 1 and at any subsequent visits after it is injection with a slit lamp photograph. The photographs had to be identified using the subject number and subject initials and should not contain any identifiers such as the subject's name or birth date. The photographs document the continued correct placement of the implant. The photographs may also be used for training, advertising or in scientific conferences, journals or magazines.

Compliance with Good Clinical Practices, Ethical Considerations and Administrative Issues The study was conducted in compliance with the protocol, International Conference on Harmonization (ICH) Good Clinical Practices (GCP) Guidelines, and consistent with the 1996 version of the Declaration of Helsinki.

Procedures for Study Examinations

Best Corrected Visual Acuity

Visual Acuity had to be evaluated at the beginning of each study visit prior to performing other tests such as Goldmann tonometry and gonioscopy and prior to pupil dilation (i.e., prior to slit-lamp examination). Every effort had to be made to have the same BCVA assessor throughout the study period. Visual acuity testing had to be done starting with most recent correction.

BCVA had to be measured using a backlit ETDRS chart such as Precision Vision's or equivalent. It was recommended that the site use a backlit, wall-mounted or caster stand ETDRS distance eye chart with a luminance of 85 cd/m2 set at 4 meters from the subject. A trial lens frame, or phoropter, set at 12.0 mm vertex distance had to be used to obtain manifest refraction measurements. If possible, final refinement of sphere had to be done at 4 meters with a trial lens set.

Eye Charts

All distance visual acuity measurement had to be made using an illuminator box (or equivalent) set at 4 meters from the subject. Any subject unable to read at least 20 or more letters on the ETDRS chart at 4 meters had to be tested at 1 meter according to the instructions provided for 1 meter testing. The fluorescent tubes in the light box had to be checked periodically for proper functioning.

A maximum effort had to be made to identify each letter on the chart. When the subject said he or she could not read a letter, he or she had to be encouraged to guess. If the subject identifies a letter as one of two letters, he or she had to be asked to choose one letter and, if necessary, to guess. When it became evident that no further meaningful readings can be made, despite encouragement to read or guess, the examiner had to stop the test for that eye. However, all letters on the last line had to be attempted as letter difficulties vary and the last could be the only one read correctly. The number of letters missed or read incorrectly had to be noted.

Log MAR Visual Acuity Calculations

The last line in which a letter is read correctly is taken as the base log MAR reading. To this value was added the number "N×0.02" where 'N' represents the total number of letters missed up to and included in the last line read. This total sum represents the log MAR visual acuity for that eye. For Example: Subject correctly reads 4 of 5 letters on the 0.2 line, and 2 of 5 letters on the 0.1 line.

| | |
|---|---|
| Base logMAR | =0.1 |
| N (total number of letters incorrect on line 0.2 as well as 0.1) | =4 |
| N × T (T = 0.02) | =0.08 |
| Base logMAR + (N × T) | =0.1 + 0.08 |
| logMAR VA | =0.18 |

BCVA examination had to begin with the right eye (OD). The procedure had to be repeated for the left eye (OS).

1-Meter Testing

The subject had to sit for the 1-meter test. The avoidance of any head movement forward or backward was particularly important during this test.

B. Slit Lamp Biomicroscopy Examination

The slit beam observations had to be assessed in a dark room using the highest lamp voltage, an aperture of 0.3 mm, an illumination angle of 30 degrees and a magnification of 16×.

The clinician used a slit lamp to assess the following as normal, abnormal clinically significant or abnormal not clinically significant:
- External adnexa—Presence or absence of lid erythema, edema or other abnormalities, evaluation of lashes for scurf or other abnormalities
- Conjunctiva—presence or absence of edema, erythema or other abnormalities
- Iris—presence or absence of stromal or other abnormalities
- Cornea—clarity, presence or absence of superficial punctate keratopathy or other abnormalities asses with fluorescein stain
- Anterior chamber—adequacy of formation depth, cell score and flare count
- Lens Explanation/comments had to be provided on the case report form for any abnormal observations. If a corneal edema was observed, a notation on whether it is general or local should be added.

Anterior Chamber Cells and Flare

Assessment of anterior chamber cells had to be performed as follows:
Low ambient lighting
1×1 mm slit beam
Highest slit lamp voltage
Illumination angle of 45 degrees
High magnification The anterior chamber was examined for the presence of signs of ocular inflammation. Anterior chamber cell count and flare were graded using the SUN* Working Group grading scheme: Although an anterior chamber cell grade of "0" is reported as "<1 cell" in the SUN Working Group grading scheme, it was characterized as 0 cells in the field for this study.

The anterior chamber cell count was assessed as the actual number of cells counted within the slit beam of 1.0 mm height and 1.0 mm width described above, if fewer than 16 cells are seen. Only white blood cells were counted. (Red blood cells and pigment cells were not to be counted). The number of cells counted and the corresponding grade per the below scale were both recorded in the CRF.

| Anterior Chamber Cells | | Flare | |
|---|---|---|---|
| Grade | Number of Cells in Field | Grade | Description |
| 0 | 0 (rare cells, i.e., one cell in a minority of fields) | 0 | None |
| 0.5+ | 1-5 (trace) | 1+ | Faint |
| 1+ | 6-15 (cells) | 2+ | Moderate iris and lens details clear |
| 2+ | 16-25 (cells) | 3+ | Marked iris a nd lens details hazy |
| 3+ | 26-50 (cells) | 4+ | Intense fibrin or plastic aqueous |
| 4+ | >50 (cells) | | |

*Standardization of the Uveitis Nomenclature (SUN)

If hypopyon is present this had to be noted in the source documents and eCRF.

Pachymetry

The following procedure was recommended for conducting pachymetry:

Central corneal thickness measurements of each eye were made at the screening visit using an ultrasonic pachymeter. Measurements were made after IOP is taken. For ultrasound probes, the Probe Quality Factor had to be greater than or equal to 85% (if applicable). With the subject seated and visualizing a consistent fixation target, position the probe tip on the cornea, perpendicular to the corneal surface, on the visual axis (i.e., centered on the pupil). Once the probe tip was positioned properly, a measurement was taken. A total of 3 acceptable measurements, as described above, had to be made for each eye, and the 3 measurements were recorded in microns. The average of the 3 measurements were calculated to determine subject eligibility.

IOP Measurement

Goldmann tonometry as the international gold standard for tonometry is quite accurate and reproducible if proper technique is used. When performing Goldmann tonometry the following procedures had to be followed:
1. Pre-tonometry procedures: Set tonometer in the correct position and make sure the prism is in the horizontal position on the slit lamp. Set the tension at 1 mmHg. Use Cobalt filter with slit beam open maximally with the angle between the illumination and the microscope at approximately 60 degrees.
2. Instill one drop of a topical anesthetic and a moistened fluorescein strip may be lightly touched against the tarsal conjunctiva of the lower lid of each eye, taking care not to flood the ocular surface with fluorescein dye. Alternatively, a drop of topical anesthetic-fluorescein (e.g., Fluress) solution may be instilled into the lower conjunctival fornix of each eye, taking care not to flood the ocular surface with fluorescein dye. Ask subject to blink a few times just prior to tonometry.
3. Place subject in adjustable chair so chin can fit comfortably on the slit lamp chin rest and the forehead can be snug against the forehead bar.
4. Apply tonometer to the subject's eye while subject looks straight ahead and increase the force of applanation until the observer sees the inner portion of the two half fluorescein circles are touching. Record pressure on the case report form.

IOP measurement was masked based on the following procedure:

Measurements was taken by two qualified independent study site personnel using a Goldmann applanation tonometer affixed to a slit lamp with the subject seated. One person adjusted the dial in masked fashion and a second person read and recorded the value. The subject and slit lamp had to be adjusted so that the subject's head was firmly positioned on the chin rest and against the forehead rest without leaning forward or straining. Both eyes were tested, with the right eye preceding the left eye. Each IOP measurement was to be recorded.

One person ("the measurer") looked through the binocular viewer of the slit lamp at low power. The tension knob was pre-set at a low pressure value (4 to 6 mmHg). The measurer followed the image of the fluorescein-stained semicircles while he/she slowly rotated the tension knob until the inner borders of the fluorescein rings touched each other at the midpoint of their pulsation in response to the cardiac cycle. When this image was reached, the measurer took his/her fingers off the tension knob and the second person ("the reader") read and recorded the IOP reading along with the date and time of day in the source document, thus maintaining a masked IOP reading. Two measurements had to be performed, and if the IOP is within 1 mm Hg, the average of the first two measurements had to be recorded. If the IOP from the first two readings showed a greater than 1 mm Hg difference, a third reading had to be taken and the average of all three readings recorded. As much as possible, the same person had to do the IOP measurement for a subject at every visit.

Dilated Fundus Exam

Assessments should be conducted using indirect ophthalmoscopy. It is acceptable to perform the dilated fundus examination without scleral depression. Each of the following was evaluated and documented as normal, abnormal clinically significant or abnormal not clinically significant:
Macula
Peripheral retina
Choroid
Vitreous
Optic nerve.

The cup to disc (C/D) ratio was also measured. Explanation/comment should be provided on the case report form for any abnormal pathology.

The following scale was used to define the extent of vitreous haze:
Absent Clear view of optic disc, retinal vessels and nerve fiber layer
Trace Slight blurring of optic disc margin and of normal striations and reflex of nerve fiber layer cannot be visualize
1+ Mild blurring of optic disc margin and slight loss of retinal vessel definition
2+ Moderate blurring of optic disc margin and loss of retinal vessel definition
3+ Optic nerve head and large vessels visible but borders quite (very) blurry
4+ Optic nerve head obscured Gonioscopy The following procedure was recommended for conducting gonioscopy:

Clean and sterilize the front (curved) surface of the goniolens. Apply lubricating fluid to the front surface. Anaesthetize the subject's cornea with topical anesthetic. Prepare the slit lamp for viewing through the goniolens. Gently move the subject's eyelids away from the cornea. Slowly apply the goniolens to the ocular surface, forming suction. Fine-tune the slit lamp to optimize the view. The angle can now be viewed by rotating the lens gently through 360 degrees. Grade the angle based on the Shaffer System as follows. Subjects with a Grade 2 or lower should be excluded for angle closure glaucoma.
Grade 4—45° to 35° angle wide open
Grade 3—35° to 20° angle wide open
Grade 2—20° angle narrow
Grade 1—≤10° angle Extremely narrow
Slit—0° angle Narrowed to slit Automated Perimetry The following procedure was recommended for conducting automated perimetry.

If the brow is heavy or the upper lid is drooping, tape accordingly. Visual field results must be reliable (i.e., 33% fixation losses, false positive or false negative errors) or the field should be repeated within two weeks. Visual field examinations were performed, preferably using a Humphrey automated perimetry test (full threshold 24-2 program or SITA standard or FAST assessment). Preferred equipment is the Humphrey 700 HFA-2 series machines (e.g., 740 or 750). Visual fields were reported as normal or abnormal and the mean deviation will also be recorded in decibels (dB).

Begin by testing the right eye. Adjust the chin rest and the table height as needed to achieve proper alignment as well as to maintain the subject in a comfortable seated position throughout the test. It is permissible to encourage the subject occasionally if the subject seems to be fatigued or losing concentration, and to allow the subject to pause and rest if necessary. The subject should also be informed that a good time to blink is when the response button is pushed so as not to affect the results of the test. Repeat for the left eye.

Subject Ocular Discomfort

Subjects were be asked to grade their comfort level by asking them the following question:

"On a scale of 0 to 10, 0 being very comfortable and 10 being very uncomfortable, how comfortable does your eye feel at this time?"

The examiner recorded the number selected by the subject on the appropriate Case Report Form.

Investigator Global Assessment

The Investigator assessed if the implant is well tolerated by the subject judging the global tolerance scale, as follows:
0=very satisfactory, 1=satisfactory, 2=not very satisfactory, 3=unsatisfactory The examiner recorded the number selected by the subject on the appropriate Case Report Form.

Investigator Injection Rating

The Investigator will grade the level of ease of injection of the intracameral implant as "easy" (1), "moderate" (2) or "difficult" (3).

The Investigator recorded ease of injection procedure on the appropriate Case Report Form.

Study Results

All 4 cohorts were fully enrolled: cohort 1 (5 subjects, 15 µg), cohort 2 (4 subjects, 26 µg), and cohort 3 (5 subjects, 15 µg formulation 2), cohort 4 (5 subjects, 5 µg formulation 3).

Subjects were followed for 7 months to 22 months (cohorts 1 and 2), cohort 3 were followed for 6 months to 9 months, cohort 4 were followed for Day 14 to Month 6 (3 subjects still in follow up).

Figure 2:
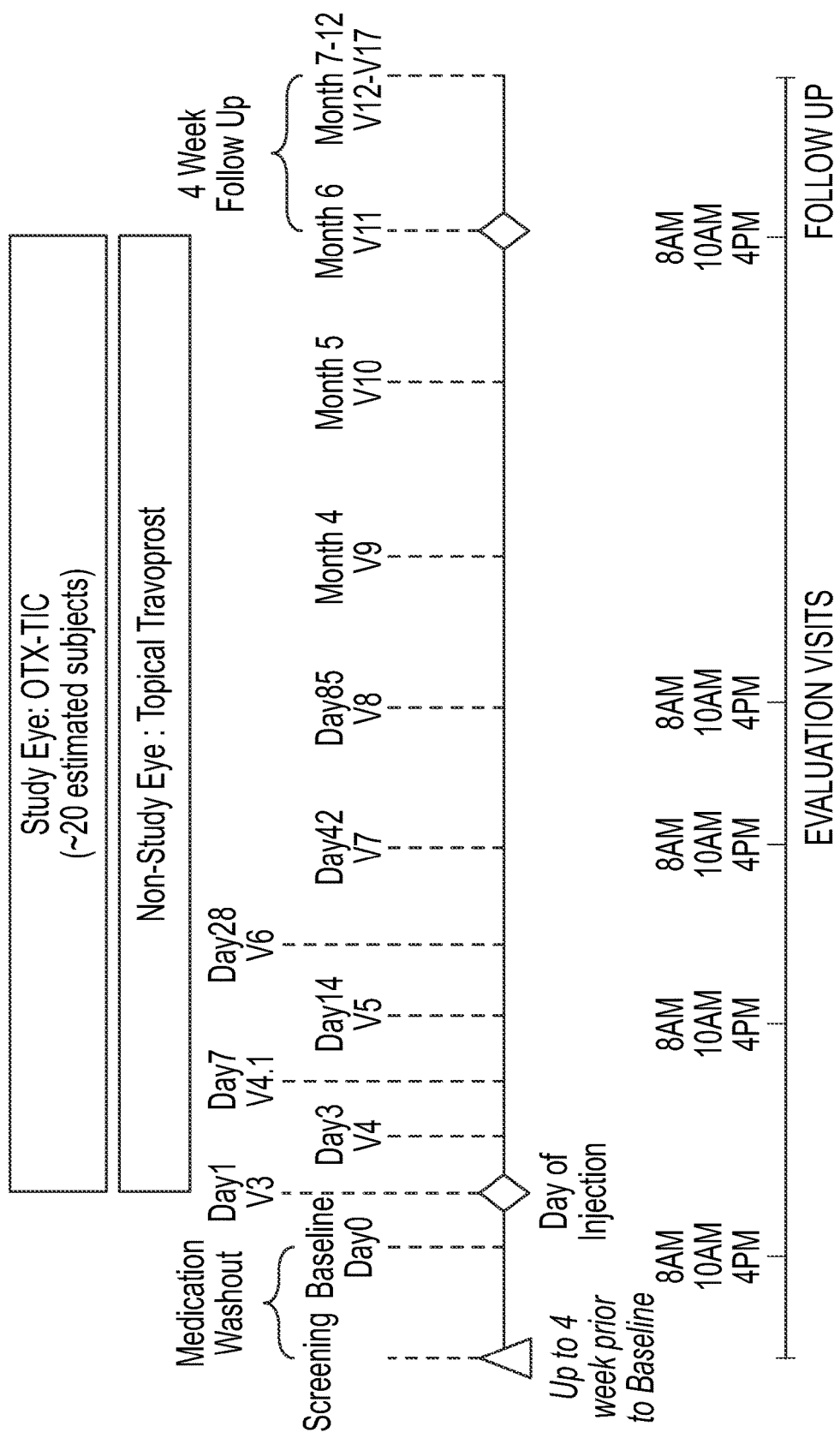
FIG. 2 An illustration of the clinical phase 1 study design.
Figure 5A:
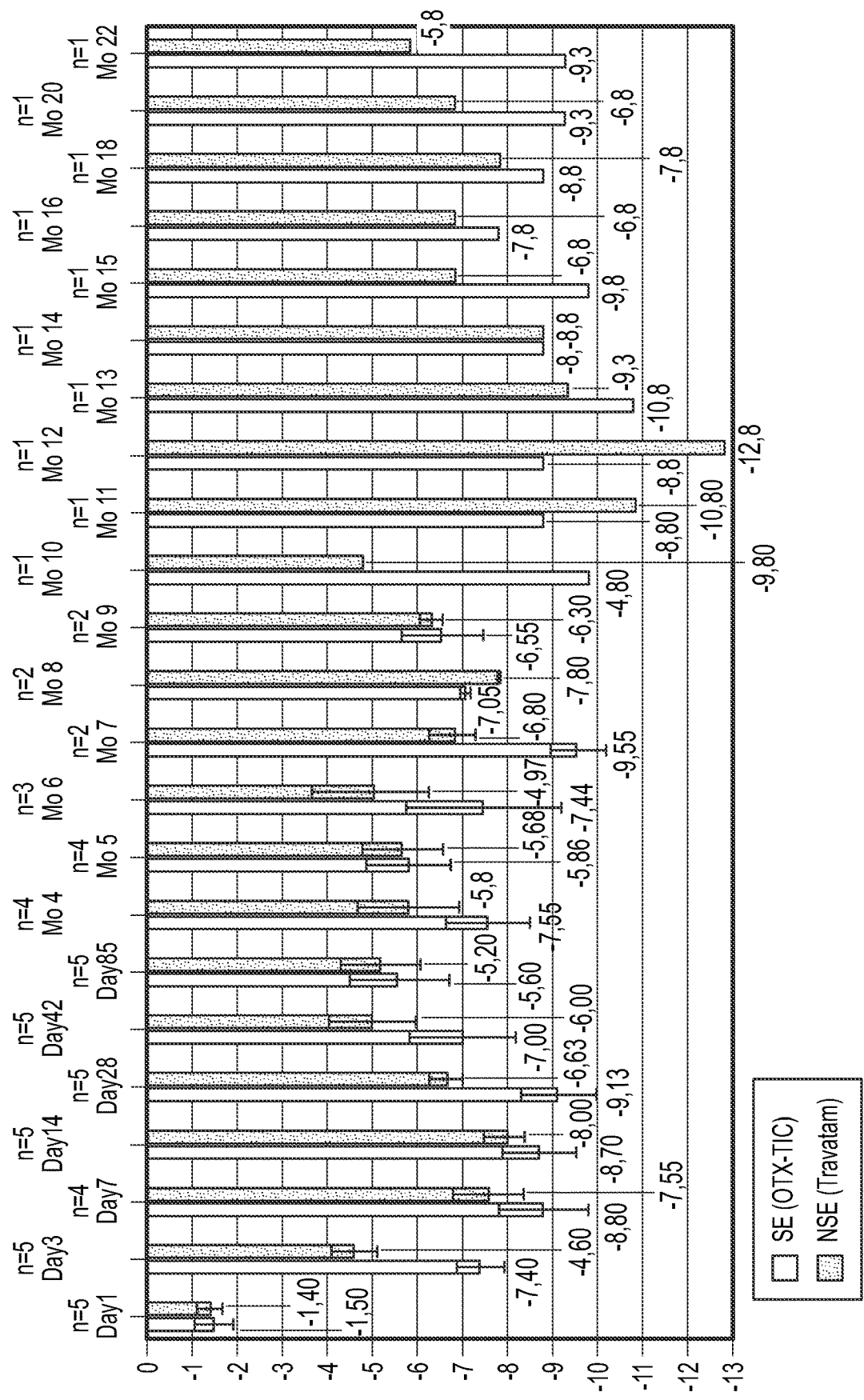
FIG. 5a Mean IOP change from baseline in cohort 1 of the clinical phase 1 study.
Figure 5B:
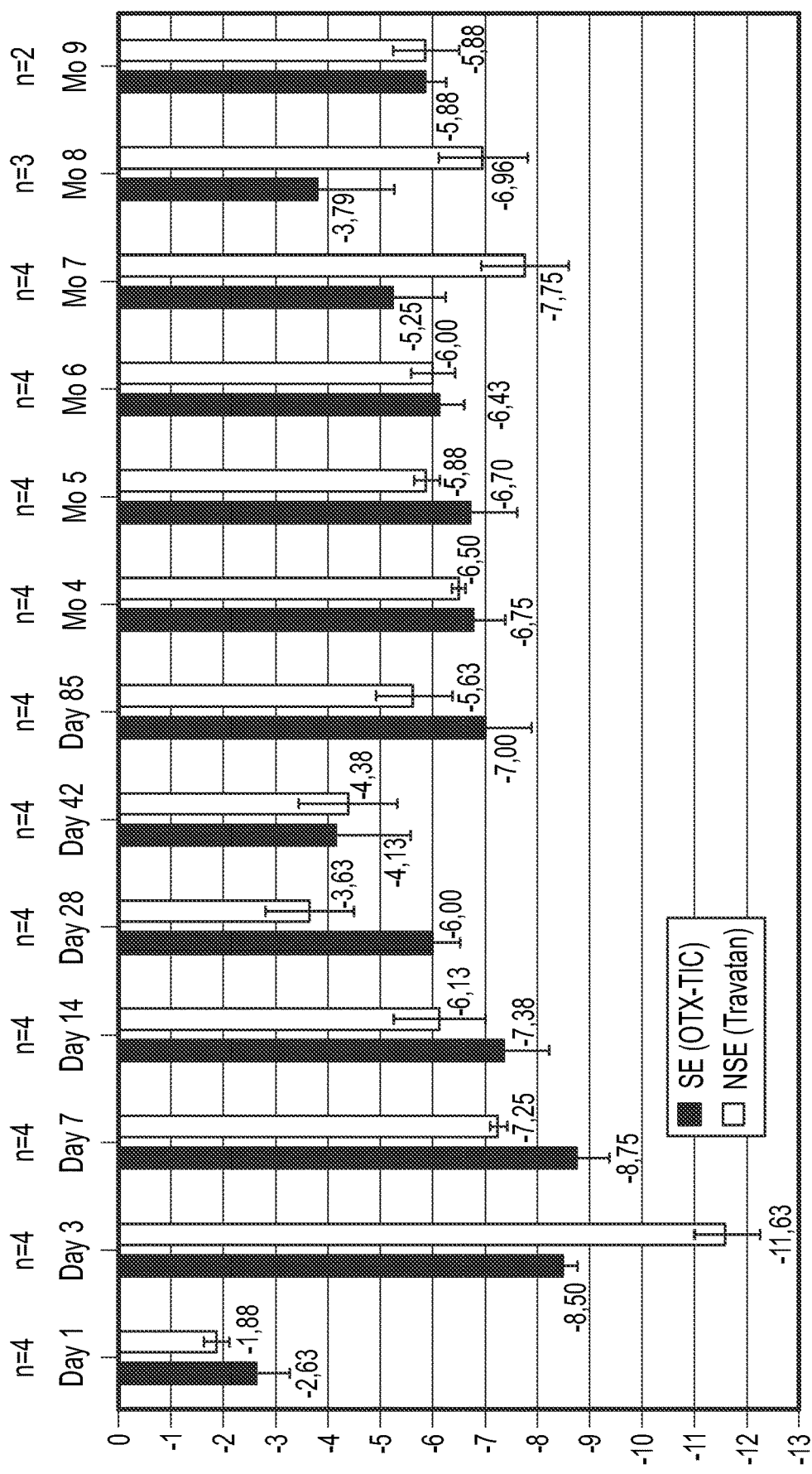
FIG. 5b Mean IOP change from baseline in cohort 2 of the clinical phase 1 study.
Figure 5C:
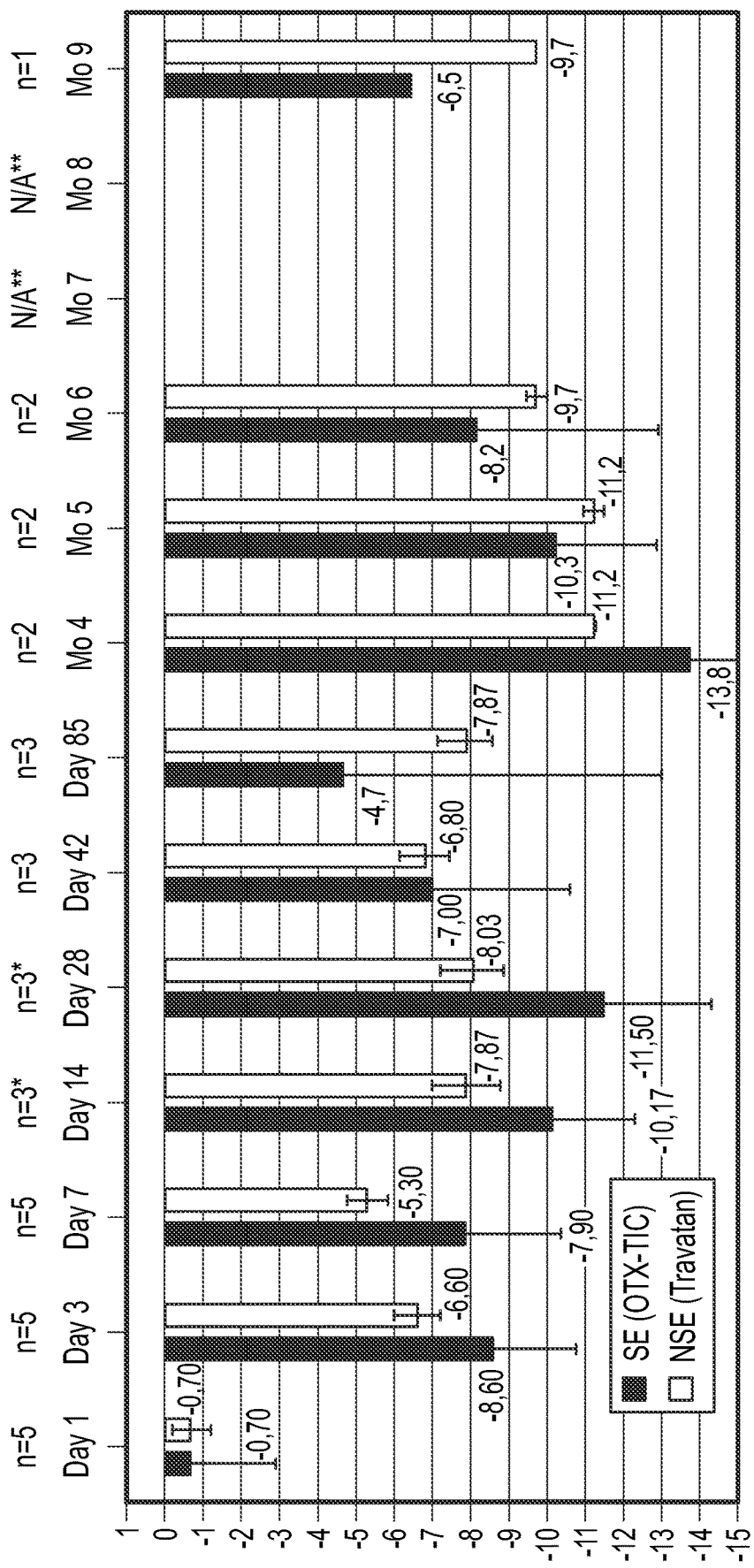
FIG. 5c Mean IOP change from baseline in cohort 3 of the clinical phase 1 study.
Figure 5D:
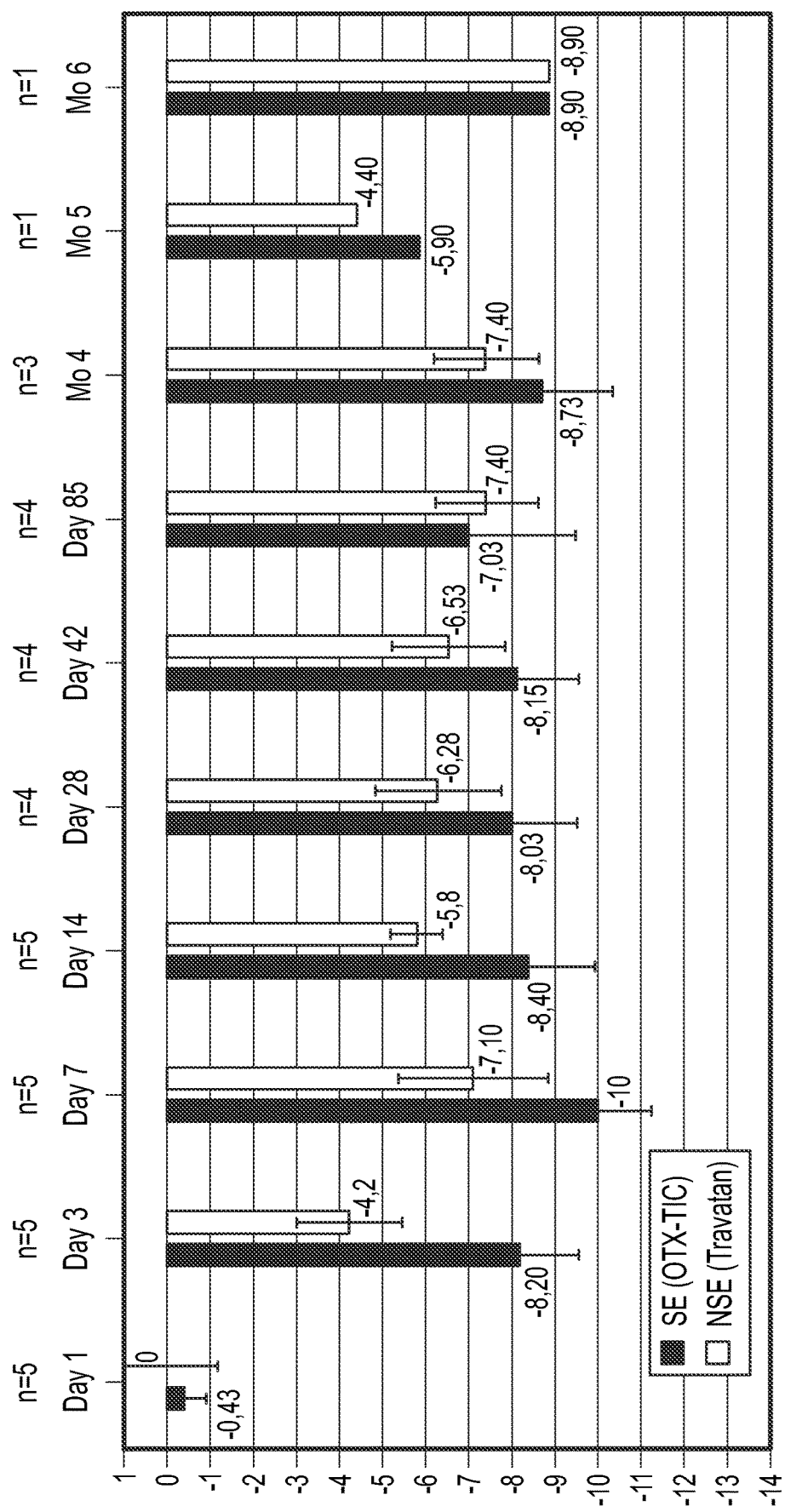
FIG. 5d Mean IOP change from baseline of the clinical phase 1 study.

FIG. 2 depicts the administration schedule (which has also been described above) for the study eye and the non-study eye. The treatment of the non-study eye was continued after Month 6 V11, if applicable.

Safety

FIGS. 3a to 3d show average pachymetry values of the subjects of cohorts 1 to 4, respectively.

FIGS. 4a to 4c show average EEC of the subjects of cohorts 1 to 4, respectively.

No serious adverse events were reported to date. Table 9 below depicts the ocular adverse events reported during the study to date.

TABLE 9

Ocular adverse events in the study eye (unmonitored data)

| | Cohort 1 (15 µg, F1) N = 5 | Cohort 2 (26 µg, F1) N = 4 | Cohort 3 (15 µg, F2) N = 5 | Cohort 4 (5 µg, F3) N = 5 | OTX-TIC N = 19 |
|---|---|---|---|---|---|
| Number of subjects with ocular AEs: | | | | | |
| Iritis | 2 | 2 | 1 | 1 | 6 |
| Peripheral anterior synechiae | 3 | — | — | — | 3 |
| Corneal Edema | — | 1 | — | — | 1 |
| Subconjuctival Hemorrhage | — | — | 1 | — | 1 |
| Elevated IOP | — | — | 2 | — | 2 |
| Total AEs per cohort | 5 | 5 | 4 | 1 | 13 |

Efficacy

A lowering of intraocular pressure (IOP) could be demonstrated for each subject in each cohort. FIGS. 5a to 5d each depict the developments of the mean IOP change from baseline in the study eye and in the non-study eye for cohorts 1 to 4, respectively.

Figure 6:
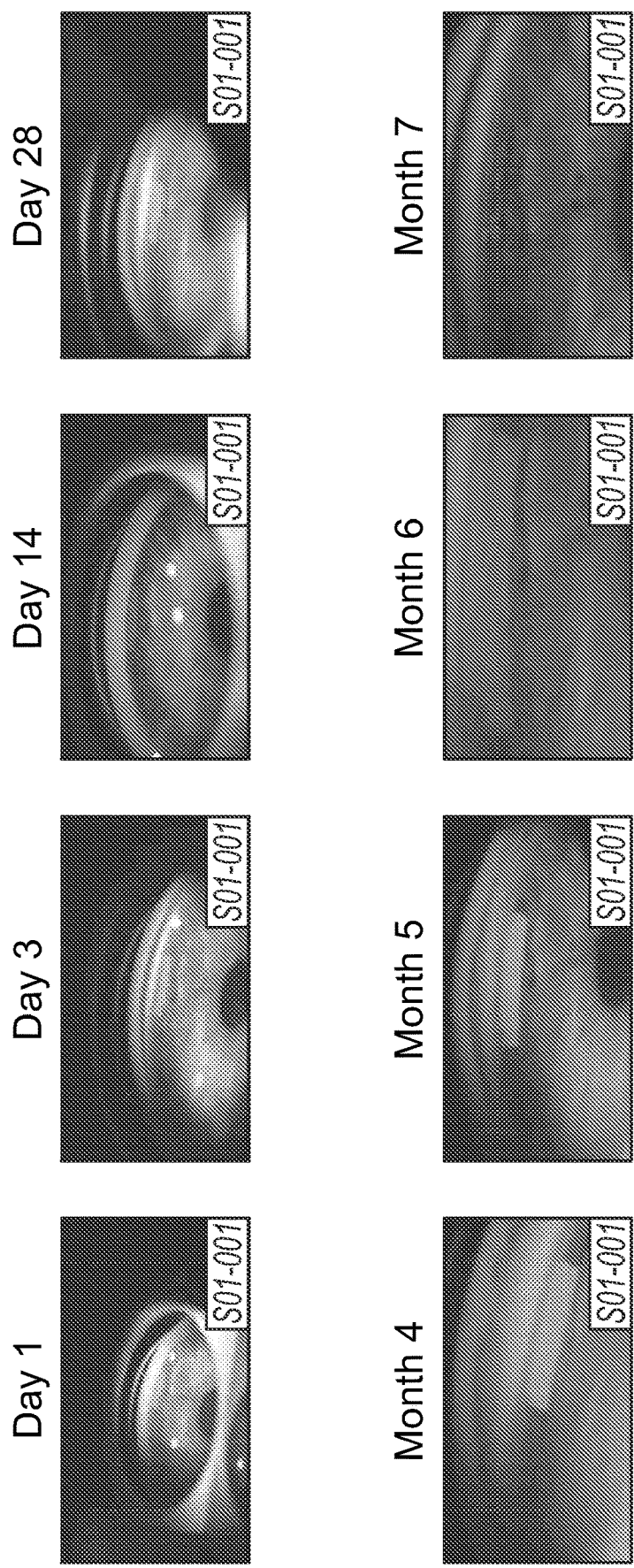
FIG. 6 Photographs of the inserted implant of one human subject between day 1 and month 7.

FIG. 6 shows photographs of the inserted implant in a subject of cohort 1 from day 1 to month 7.

Abbreviations

TABLE 10

Abbreviations used in the above description of the clinical study

| Abbreviation | Meaning |
|---|---|
| AE | Adverse Event |
| API | Active pharmaceutical ingredient |
| AS-OCT | Anterior segment Optical coherence tomography |
| BCVA | Best corrected visual acuity |
| CRC | Central Reading Center |
| CRF | Case report form |
| DSMC | Data Safety Monitoring Committee |
| EDTRS | Early Treatment Diabetic Retinopathy Study |
| FDA | Food and Drug Administration |
| GCP | Good Clinical Practices |
| IRB | Institutional Review Board |
| IEC | Institutional Ethics Committee |
| IOP | Intraocular Pressure |
| NFL | Nerve Fiber Layer |
| OAG | Open-angle glaucoma |
| OCT | Optical coherence tomography |
| OHT | Ocular hypertension |
| OTX-TIC | OTX-TIC (travoprost) Intracameral Implant |
| OTX-TP | OTX-TP (travoprost) Intracanalicular Insert |
| PAS | Peripheral anterior synechia |
| PEG | Polyethylene glycol |
| PLA | Polylactide |
| POAG | Primary Open Angle Glaucoma |
| PV | Placebo vehicle |
| SE | Study eye |
| NSE | Non-study eye |

Example 4: Syringe Used for Injecting the Implant

Figure 7:
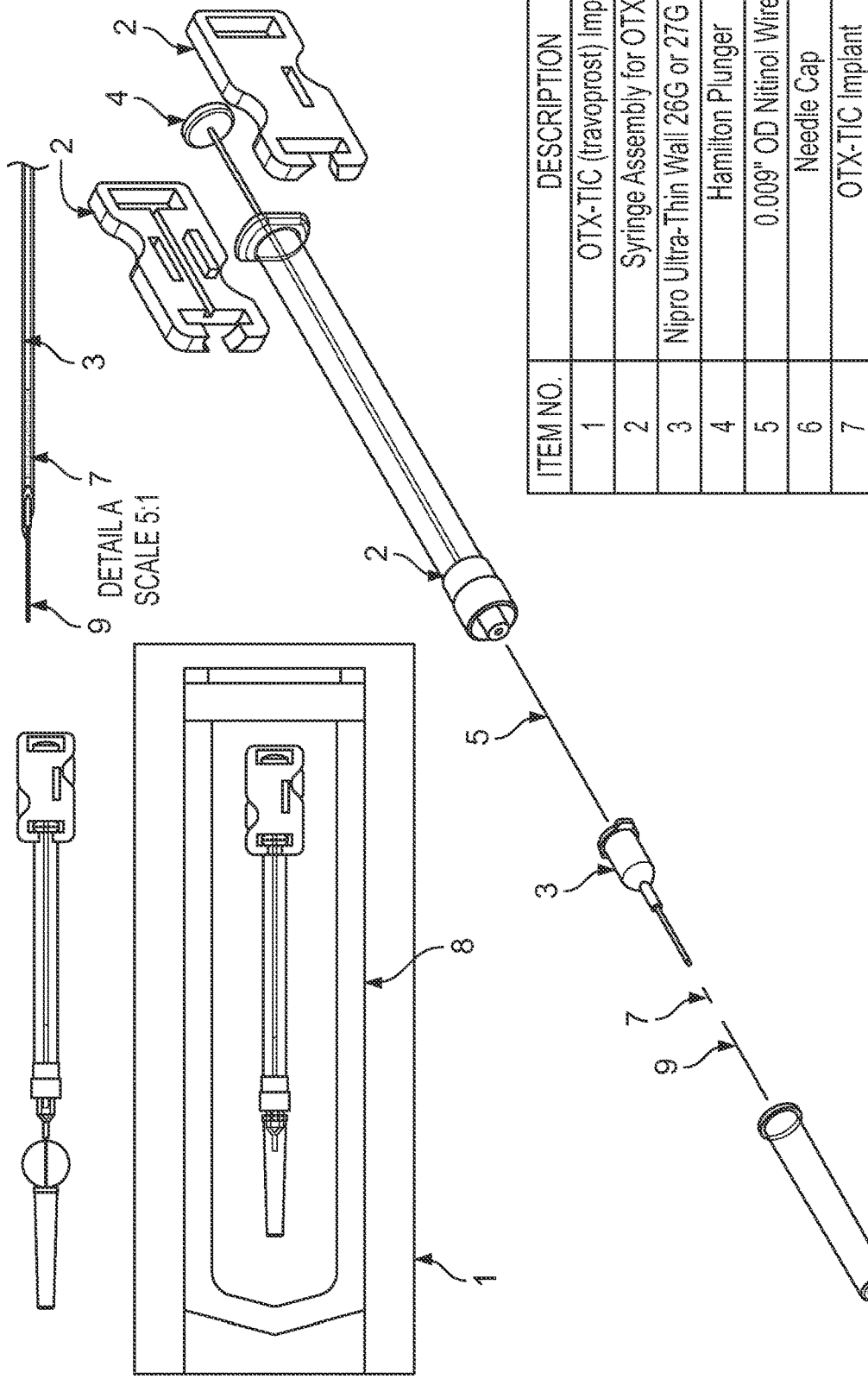
FIG. 7 A syringe assembly for administering a OTX-TIC travoprost implant.

A single dose OTX-TIC (travoprost) Implant is loaded in a 26G (26 µg dose) or 27G (5 µg and 15 µg doses) needle attached to a sterile syringe assembly as shown in FIG. 7. A wire is inserted in the tip of the needle to retain the implant in the needle during shipping and handling. The syringe assembly containing the drug product is sealed within a low vapor-transmission peelable foil-LDPE pouch in a nitrogen environment. The terminal sterilization of the preassembled syringe assembly and final packaged drug product is performed by gamma irradiation at a validated irradiation dose in accordance with ISO 11137-2:2013 Sterilization of Health Care Products-Radiation. The foil pouch provides protection from moisture, oxygen and light, and serves as a sterile barrier for the OTX-TIC implant.

Container integrity and strength are ensured through two primary tests, bubble emission and seal strength testing. A minimum seal strength of 1.0 lbf is required for the foil pouch during in-process and stability testing. Additionally, per whole package integrity testing of the foil pouch during shelf life evaluation, it must withstand bubble emission while pressurized at 10±2 inches $H_2O$. Use of the bubble emission test to support the continued capability of container closures to maintain sterility is permitted by FDA Guidance for Industry: Container and Closure System Integrity Testing in Lieu of Sterility Testing as a Component of the Stability Protocol for Sterile Products, February 2008. Drug product packaging and container-closure will be confirmed by stability testing at refrigerated (2° C.-8° C.) storage conditions.

The component information is provided in Table 11.

| Component | Manufacturer | Description/Material |
|---|---|---|
| 50 µL Hamilton Syringe | Hamilton Company | Model 1705TLL Gastight Syringe with PTFE Luer-Lock |
| Hamilton Syringe Lock Clip | Proto Labs Inc. | Makrolon RX2530-451118 (Blue Tint PC) |
| Ultra-Thin Wall 26 G or 27 G ½" Needles | Nipro Medical | Stainless Steel Hypodermic Needle |
| 0.009" OD Nitinol Wire, 1.77" in Length | Wytech Industries, Inc. | Ni-Ti Shape Memory Alloy, (Nitinol 55) |
| 0.009" OD Nitinol Wire, 2.00 cm Length | Wytech Industries, Inc. | |
| Peelable Foil Pouch (2.5" × 9.581") | Mangar Industries, Inc. | 48 GA PET/.001 WLDPE/.0007 ALUM F/.0007 LDPE/.002 Peelable Film (MRMPLK235) |

First List of Items

1. A sustained release biodegradable intracameral hydrogel implant comprising travoprost and a polymer network.
2. The hydrogel implant of item 1, wherein the polymer network comprises a plurality of polyethylene glycol (PEG) units.
3. The hydrogel implant of item 1 or 2, wherein the polymer network comprises a plurality of multi-arm PEG units having from 2 to 10 arms.
4. The hydrogel implant of any one of items 1 to 3, wherein the polymer network comprises a plurality of multi-arm PEG units having from 4 to 10 arms.
5. The hydrogel implant of any one of items 1 to 4, wherein the polymer network comprises a plurality of multi-arm PEG units having from 4 to 8 arms.
6. The hydrogel implant of any one of items 1 to 5, wherein the polymer network comprises a plurality of multi-arm PEG units having 8 arms.
7. The hydrogel implant of any one of items 1 to 6, wherein the polymer network comprises a plurality of multi-arm PEG units having 4 arms.
8. The hydrogel implant of any one of items 1 to 5, wherein the polymer network comprises a plurality of multi-arm PEG units having the formula:

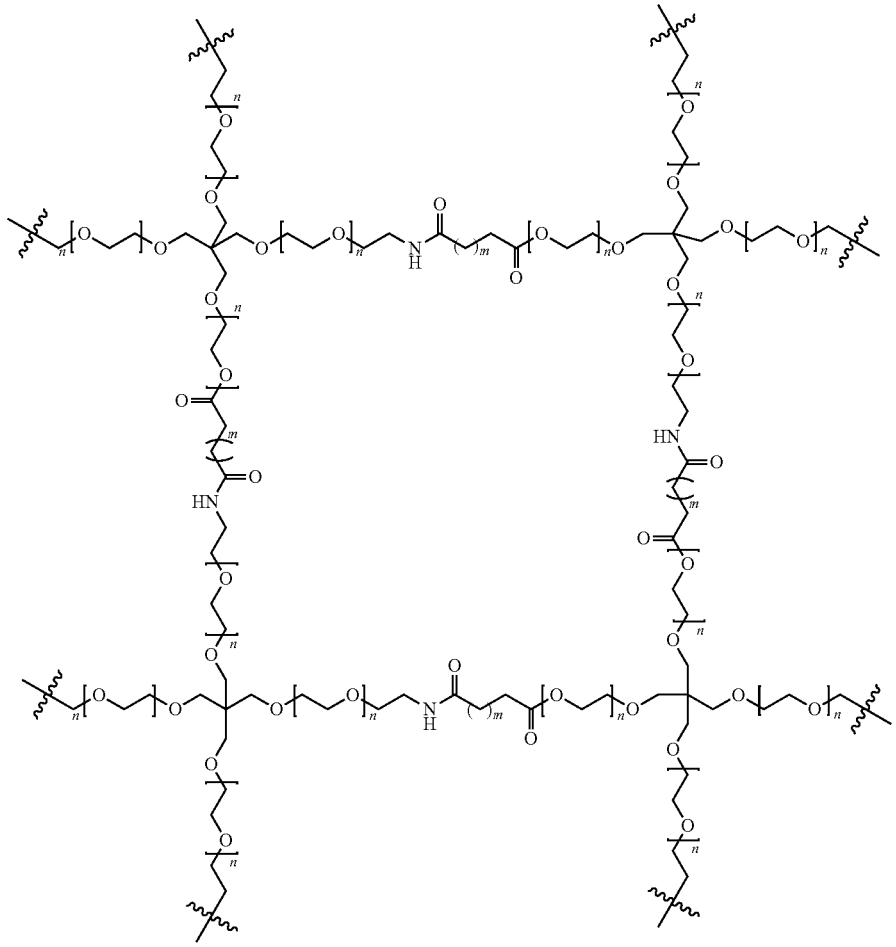

wherein n represents an ethylene oxide repeating unit and the wavy lines represent the points of repeating units of the polymer network.
9. The hydrogel implant of any one of items 1 to 8, wherein the polymer network is formed by reacting a plurality of polyethylene glycol (PEG) units selected from 4a20K PEG SAZ, 4a20K PEG SAP, 4a20K PEG SG, 4a20K PEG SS, 8a20K PEG SAZ, 8a20K PEG SAP, 8a20K PEG SG, 8a20K PEG SS with one or more PEG or Lysine based-amine groups selected from 4a20K PEG NH2, 8a20K PEG NH2, and trilysine, or a salt thereof.
10. The hydrogel implant of any one of items 1 to 9, wherein the polymer network is formed by reacting 8a15K PEG-SAZ with trilysine or a salt thereof.
11. The hydrogel implant of any one of items 1 to 10, wherein the polymer network is amorphous.
12. The hydrogel implant of any one of items 1 to 11, wherein the polymer network is semi-crystalline.
13. The hydrogel implant of any one of items 1 to 12, wherein the travoprost is homogenously dispersed within the polymer network.
14. The hydrogel implant of any one of items 1 to 13, wherein the travoprost is delivered to the eye in a sustained manner for a period ranging from about 2 to about 8 months.
15. The hydrogel implant of any one of items 1 to 14, wherein the travoprost is delivered to the eye in a sustained manner for a period ranging from about 3 to about 7 months.
16. The hydrogel implant of any one of items 1 to 15, wherein the travoprost is delivered to the eye in a sustained manner for a period ranging from about 4 to about 6 months.
17. The hydrogel implant of any one of items 1 to 16, wherein sustained release occurs in the aqueous humor.
18. The hydrogel implant of any one of items 1 to 17, wherein the travoprost is microencapsulated.
19. The hydrogel implant of any one of items 1 to 18, wherein the travoprost is microencapsulated with poly(lactic-co-glycolic acid) (PLGA) or poly(lactic acid) (PLA), or a combination thereof.
20. The hydrogel implant of any one of items 1 to 19, wherein the travoprost is microencapsulated with PLA.
21. The hydrogel implant of any one of items 1 to 20, wherein the polymer networks is conjugated to fluorescein.
22. The hydrogel implant of any one of items 1 to 21, wherein the implant is designed for implantation near the corneal endothelial cells.
23. The hydrogel implant of any one of items 1 to 21, wherein the implant is designed for implantation in the inferior iridocorneal angle.
24. A method of lowering ocular pressure in a subject in need thereof comprising administering the hydrogel implant of any one of items 1 to 23 to the eye of a subject.
25. A method of treating ocular hypertension in a subject in need thereof comprising administering the hydrogel implant of any one of items 1 to 23 to the eye of a subject.
26. A method of treating glaucoma in a subject in need thereof comprising administering the hydrogel implant of any one of items 1 to 23 to the eye of a subject.
27. The method of item 23, wherein the glaucoma is open angle glaucoma.
28. The method of any one of items 24 to 27, wherein essentially no endothelial damage occurs following administration of a disclosed implant.

Second List of Items

1. A method of treating intraocular pressure in a human subject with ocular hypertension and/or glaucoma for a period ranging from about 1 to about 24 months such as from about 3 to about 9 months with one single travoprost sustained release biodegradable intracameral implant per eye in need of treating, the method comprising per said eye:
   Step 1: providing one travoprost sustained release biodegradable intracameral implant providing treatment for a period ranging from about 1 to about 24 month or from about 3 to about 9 months comprising:
   a biodegradable hydrogel and travoprost particles,
   the travoprost particles being in the form of travoprost intermixed with a biodegradable polymer, and
   the travoprost particles being dispersed within the hydrogel; and
   Step 2: inserting the one sustained release biodegradable intracameral implant of step 1 into the anterior segment of said eye to place it within the iridocorneal angle of said eye.
2. The method according to item 1, wherein the travoprost particles are uniformly dispersed within the hydrogel.
3. The method according to item 1 or 2, wherein the travoprost particles have a diameter ranging from 1 to 150 μm determined by sieving or have an average diameter ranging from 1 to 150 μm determined by laser diffraction.
4. The method according to item 3, wherein the travoprost particles have a diameter ranging from 1 to 100 μm, 20 to 75 μm, 20 to 106 μm, or 20 to 55 μm determined by sieving or have an average diameter ranging from 1 to 100 μm, 20 to 75 μm, 20 to 106 μm, or 20 to 55 μm determined by laser diffraction.
5. The method according to any one of the preceding items, wherein the biodegradable polymer comprises a polylactide.
6. The method according to item 5, wherein the polylactide has an acid end group or an ester end group.
7. The method according to any one of the preceding items, wherein the travoprost particles are a blend of different types of particles, such as particles in the form of travoprost intermixed with a first polylactide and particles in the form of travoprost intermixed with a second polylactide.
8. The method of item 7, wherein the first and the second polylactide each have an acid end group.
9. The method of item 8, wherein the first polylactide has an inherent viscosity specification ranging from about 0.05 to about less than about 0.5 dl/g, or ranging from about 0.35 to about 0.45 dl/g.
10. The method of item 8 or 9, wherein the second polylactide has an inherent viscosity specification ranging from about 0.5 to about 1.7 dl/g, or ranging from about 0.6 to about 0.8 dl/g.
11. The method of any one of items 7 to 10, wherein the travoprost particles consist of a blend of two types of particles, the first type of particle being in the form of travoprost intermixed with the biodegradable polymer consisting of the first polylactide and the second type of particle being in the form of travoprost intermixed with the biodegradable polymer consisting of the second polylactide.

12. The method according to any one of items 7 to 11, wherein the intracameral implant does not include a further polylactide.

13. The method according to any one of items 1 to 12, wherein the intracameral implant has an in vitro release with an average travoprost release ranging from of about 65% to about 85% with a mean absolute deviation of at most 5%, or a travoprost release ranging from 65% to 85%, based on the % amount released per 70 days from day 1 to day 84, when measured at 37° C. in PBS at a pH of 7.2 to 7.4 under sink-conditions.

14. The method according to any one of the preceding items, wherein the implant has an in vitro release with an average travoprost release ranging from about 300 to about 500 ng/week with a standard deviation ranging from 100 to 200 ng/week, wherein the average travoprost release is based on the weekly travoprost release values between days 7 to 84 excluding post dose day 1 burst when measured at 37° C. in PBS at a pH of 7.2 to 7.4 under sink-conditions; or wherein the weekly travoprost release ranges from about 10 to about 700 ng, when measured in a time interval between days 7 to 84 excluding post dose day 1 burst when measured at 37° C. in PBS at a pH of 7.2 to 7.4 under sink-conditions.

15. The method of any one of items 7 to 14, wherein the first and the second polylactide have a mass ratio in the particle blend of about 1.5:1 to about 1:1.5, or about 1:1.

16. The method of any one of items 1 to 10, wherein the travoprost particles are a blend of different types of particles including particles in the form of travoprost intermixed with a first polylactide, particles in the form of travoprost intermixed a second polylactide and particles in the form of travoprost intermixed with a third polylactide, wherein each of the polylactides have an acid end group.

17. The method of item 16, wherein the first polylactide has an inherent viscosity specification ranging from about 0.05 to less than about 0.5 dl/g, or ranging from about 0.35 to about 0.45 dl/g, the second polylactide has an inherent viscosity specification ranging from about 0.5 to less than about 0.80 dl/g, or ranging from about 0.6 to less than about 0.8 dl/g, and the third polylactide has an inherent viscosity specification ranging from about 0.8 to about 1.7 dl/g, or ranging from about 0.8 to about 1.0 dl/g.

18. The method according to item 17, wherein the biodegradable polymer consists of a blend of three types of particles, the first type of particle being in the form of travoprost intermixed with the biodegradable polymer consisting of the first polylactide, and the second type of particles being in the form of travoprost intermixed with the biodegradable polymer consisting of the second polylactide and the third type of particles in the form of travoprost intermixed with the biodegradable polymer consisting of the third polylactide.

19. The method according to item 18, wherein the intracameral implant does not include a further polylactide.

20. The method according to a one of items 14 to 19, wherein a mass ratio of the first and the second polylactide in the particle blend is about 2:1 to about 1:2 or about 1:1.6.

21. The method according to any one of items 14 to 20, wherein a mass ratio of the first and the third polylactide in the particle blend is about 2:1 to about 1:2, or about 1:1.4.

22. The method according to any one of items 1 to 21, wherein the intracameral implant has an in vitro release with an average travoprost release ranging from of about 60% to about 80% with a mean absolute deviation of at most 5%, or a travoprost release ranging from 60% to 80%, based on the %-amount released per 70 days from day 1 to day 98, when measured at 37° C. in PBS at a pH of 7.2 to 7.4 under sink-conditions.

23. The method according to any one of the preceding items, wherein the implant has an in vitro release with an average travoprost release ranging from about 800 to about 1100 ng/week with a standard deviation ranging from 450 to 550 ng/week, wherein the average is based on the weekly travoprost release values between days 7 to 98 excluding post dose day 1 burst when measured at 37° C. in PBS at a pH of 7.2 to 7.4 under sink-conditions st; or wherein the weekly travoprost release ranges from about 100 to about 2300 ng, when measured in a time interval between days 7 to 98 excluding post dose day 1 burst when measured at 37° C. in PBS at a pH of 7.2 to 7.4 under sink-conditions.

24. The method according to any one of items 1 to 10 or 15 to 17, wherein the travoprost particles are a blend of different types of particles including particles in the form of travoprost intermixed with a first polylactide, particles in the form of travoprost intermixed a second polylactide, particles in the form of travoprost intermixed with a third polylactide and particles in the form of travoprost intermixed with a fourth polylactide.

25. The method according to item 24, wherein the first polylactide has an inherent viscosity specification ranging from about 0.05 to less than about 0.5 dl/g, or ranging from about 0.35 to about 0.45 dl/g and has an acid end group, the second polylactide has an inherent viscosity specification ranging from about 0.5 to less than about 0.80 dl/g, or ranging from about 0.6 to less than about 0.8 dl/g and has an acid end group, the third polylactide has an inherent viscosity specification ranging from about 0.8 to about 1.7 dl/g, or ranging from about 0.8 to about 1.0 dl/g and has an acid end group, and the fourth polylactide has an inherent viscosity ranging from about 0.05 to about 1.7 dl/g, such as ranging from about 0.55 to about 0.75 dl/g, and has an ester end group.

26. The method according to any one of items 24 or 25, wherein the travoprost particles consist of a blend of four type of particles, the first type of particle being in the form of travoprost intermixed with the biodegradable polymer consisting of the first polylactide, the second type of particles being in the form of travoprost intermixed with the biodegradable polymer consisting of the second polylactide, the third type of particles being in the form of travoprost intermixed with the biodegradable polymer consisting of the third polylactide and the fourth type of particles being in the form of travoprost intermixed with the biodegradable polymer consisting of the fourth polylactide.

27. The method according to item 27, wherein the intracameral implant does not include a further polylactide.

28. The method according to any one of items 24 to 27, wherein a mass ratio of the first and the second polylactide in the particle blend is about 1.25:1 to about 1:1.25 or about 1:1.

29. The method according to any one of items 24 to 28, wherein a mass ratio of the first and the third polylactide in the particle blend is about 3:1 to about 1:1, or about 2:1.
30. The method according to any one of items 24 to 28, wherein a mass ratio of the first and the fourth polylactide in the particle blend is about 1:1 to about 1:3, or about 1:2.5, or about 1:2.6.
31. The method according to any one of items 1 to 30, wherein the intracameral implant has an in vitro release with an average travoprost release ranging from of about 5% to about 15% with a mean absolute deviation of at most 3%, or a travoprost release ranging from 5% to 15%, based on the % amount released per 14 days from day 1 to day 112, when measured at 37° C. in PBS at a pH of 7.2 to 7.4 under sink-conditions.
32. The method according to any one of the preceding items, wherein the implant has an in vitro release with an average travoprost release ranging from about 1000 to about 1500 ng/week with a standard deviation ranging from 100 to 400 ng/week, wherein the average is based on the weekly travoprost release values between days 7 to 119 excluding post dose day 1 burst when measured at 37° C. in PBS at a pH of 7.2 to 7.4 under sink-conditions; or wherein the weekly travoprost release ranges from about 100 to about 2000 ng, when measured in a time interval between days 7 to 119 excluding post dose day 1 burst when measured at 37° C. in PBS at a pH of 7.2 to 7.4 under sink-conditions.
33. The method according to any one of the preceding items, wherein the implant has an in vitro release with an average travoprost release ranging from about 500 to about 900 ng/week with a standard deviation ranging from 150 to 250 ng/week, wherein the average is based on the weekly travoprost release values between days 7 to 119 excluding post dose day 1 burst when measured at 37° C. in PBS at a pH of 7.2 to 7.4 under sink conditions; or wherein the weekly travoprost release ranges from about 100 to about 1500 ng, when measured in a time interval between days 7 to 119 excluding post dose day 1 burst; when measured at 37° C. in PBS at a pH of 7.2 to 7.2 under sink conditions.
34. The method according to any one of the preceding items, wherein the mass ratio between travoprost and the total amount of the biodegradable polymer in the travoprost particles is about 2:1 to 1:2 or about 0.77:1.
35. The method according to any one of the preceding items, wherein the content of the biodegradable polymer with respect to the total weight of the travoprost sustained release biodegradable intracameral implant is about 10 wt.-% to about 35 wt.-%, or about 23 to about 27 wt.-%, or about 12 to about 17 wt.-%, or about 30 to about 35 wt.-%, or about 25 wt.-%, or about 15 wt.-%, or about 34 wt.-%.
36. The method according to any one of the preceding items, wherein the travoprost particles consist of travoprost and the biodegradable polymer and other pharmaceutically acceptable residual amounts of manufacturing components.
37. The method according to any one of the preceding items, wherein the travoprost particles are spherical particles.
38. The method according to any one of the preceding items, wherein the hydrogel comprises a polymer network comprising one or more units of polyethylene glycol.
39. The method according to item 38, wherein the polyethylene glycol units are 4- to 10-arm polyethylene glycol units, or 8-arm polyethylene glycol units.
40. The method according to item 38 or 39, wherein the polymer network is formed by reacting an electrophilic group-containing multi-arm-polymer precursor with a nucleophilic group-containing cross-linking agent.
41. The method according to item 40, wherein the multi-arm-polymer precursor is a 4- to 10-arm polyethylene glycol precursor, or an 8-arm polyethylene glycol precursor.
42. The method according to item 40 or 41, wherein the electrophilic group is selected from the group consisting of a succinimidylglutarate (SG) group and a succinimidylazelate (SAZ) group.
43. The method according to any one of items 40 to 42, wherein the multi-arm polymer precursor is selected from the group consisting of 8-arm-15K-SG polyethylene glycol or 8-arm-15K-SAZ polyethylene glycol.
44. The method according to any one of items 40 to 43, wherein the multi-arm-polymer precursor has a mass average molecular weight in the range from about 10,000 to about 20,000 Daltons.
45. The method according to items, wherein the multi-arm-polymer precursor has a mass average molecular weight of 15,000±10% Daltons.
46. The method according to any one of items 38 to 45, wherein the content of the biodegradable hydrogel with respect to the total weight of the one sustained release biodegradable intracameral implant is about 30 to about 70 wt.-%, or about 32 to about 37 wt.-%, or about 45 to about 55 wt.-%, or about 60 to about 70 wt.-%, or about 49.3 wt.-% or about 37.5 wt.-% or about 50.1 wt.-% or about 66.8 wt.-%.
47. The method according to any one of items 40 to 46, wherein the nucleophilic group-containing crosslinking agent is an amine.
48. The method according to any one of items 40 to 47, wherein the nucleophilic group-containing crosslinking agent is a small molecule amine with a molecular weight below 1,000 Da, comprising two or more primary aliphatic amine groups.
49. The method according to any of items 40 to 49, wherein the nucleophilic group-containing crosslinking agent is a small molecule amine selected from the group consisting of dilysine, trilysine, tetralysine, ethylenediamine, 1,3-diaminopropane, 1,3-diaminopropane, diethylenetriamine, and trimethylhexamethylenediamine.
50. The method according to any one of items 40 to 49, wherein the nucleophilic group-containing crosslinking agent is a trilysine.
51. The method according to item 50, wherein the nucleophilic group-containing crosslinking agent is trilysine acetate.
52. The method according to any one of items 40 to 51, wherein the content of the nucleophilic group-containing crosslinking agent with respect to the total weight of the one sustained release biodegradable intracameral implant is about 1 to about 5 wt.-% or 1 to about 3 wt.-%, or 2 to about 4 wt.-% or 4 to about 5 wt.-%, or about 3.2 wt.-%, or about 2.3 wt.-%, or about 4.3 wt.-%.
53. The method according to any one of items 49 to 50, wherein the trilysine is labeled with a visualization agent selected from the group consisting of a fluorophore such as fluorescein, rhodamine, coumarin, and cyanine.

54. The method according to item 53, wherein the nucleophilic group-containing crosslinking agent is fluorescein-conjugated trilysine.

55. The method according to item 54, wherein the fluorescein-conjugated trilysine is obtained by reacting trilysine acetate with N-hydroxysuccinimide (NHS)-fluorescein.

56. The method according to item 54 or 55, wherein the trilysine is labeled by partial conjugation with the visualization agent.

57. The method according to any one of items 53 to 56, wherein the content of the visualization agent with respect to the total weight of the one sustained release biodegradable intracameral implant is about 0.1 to about 0.5 wt.-%, or 0.2 wt.-%, or 0.3 wt.-%.

58. The method according to any one of the preceding items, wherein the implant is in a dried state prior to insertion and becomes hydrated once inserted into the eye.

59. The method according to any one of the preceding items, wherein the implant contains a dose of about 2 µg to about 30 µg of travoprost.

60. The method according to any one of items 1 to 56, wherein the implant contains a dose of about 5 µg of travoprost.

61. The method according to any one of items 1 to 56, wherein the implant contains a dose of about 15 µg of travoprost.

62. The method according to any one of items 1 to 56, wherein the implant contains a dose of about 26 µg of travoprost.

63. The method of any one of the preceding items, wherein the implant is in the form of a fiber.

64. The method of any one of the preceding items, wherein the implant is in the form of a fiber that has a length of about 1.0 mm to about 2.5 mm and a diameter of not more than 0.3 mm in its dried state.

65. The method of any one of items 1 to 59, wherein the implant is in the form of a fiber that has an diameter of 0.6 mm or less and a length of 3.0 mm or less in equilibrium state after 24 hours of hydration in vitro in phosphate-buffered saline at a pH of 7.4 at 37° C.

66. The method of any one of the preceding items, wherein the implant has a total weight of about 20 to about 150 µg, or about 70 µg to about 80 µg, or about 40 µg to about 50 µg, or about 90 µg to 110 µg.

67. The method according to any one of the preceding items, wherein the treatment period is about 6 to about 9 months and the travoprost sustained release biodegradable intracameral implant provides treatment for about 6 to 9 months.

68. The method according to any one of items 1 to 66, wherein the treatment period is 4 to 7 months and the travoprost sustained release biodegradable intracameral implant provides treatment for about 4 to about 7 months.

69. The method according to any one of items 1 to 66, wherein the treatment period is about 3 to about 6 months or is about 3 to 4 months and the travoprost sustained release biodegradable intracameral implant provides treatment about 3 to about 6 months or for 3 to 4 months.

70. The method according to any one of the preceding items, wherein the treatment period is about 7 to about 8 months, or about 7 to about 9 months, or about 4 months, or about 5 months, or about 6 months, or about 7 months, or about 8 months, or about 9 months and the travoprost sustained release biodegradable intracameral implant provides treatment for about 7 to about 8 months, or about 7 to about 9 months, or about 4 months, or about 5 months, or about 6 months, or about 7 months, or about 8 months, or about 9 months, respectively 71. The method according to any one of items 1 to 70, wherein the treatment is continued after said treatment period ranging from about 2 to about 12 months or from about 3 to about 9 months by repeating step 1 and step 2.

72. The method according to item 71, wherein the treatment is continued by repeating steps 1 and 2 until no further treatment is required.

73. The method according to item 72, wherein the treatment includes a repetition of steps 1 and 2 once a year, two times a year, 3 times a year or four times a year in about equal time distances with a travoprost sustained release biodegradable intracameral implant providing treatment for about 12 months for once a year, for about 6 to about 9 months for 2 times a year and with a travoprost sustained release biodegradable intracameral implant providing treatment for about 3 to about 4 months for 3 times a year or 4 times a year.

74. The method according to any one of preceding items 71 to 73, wherein the first treatment period is about 3 to about 4 months and the travoprost sustained release biodegradable intracameral implant providing treatment for about 3 to about 4 months, and the treatment continues with a treatment period of about 6 to about 12 months with a travoprost sustained release biodegradable intracameral implant providing treatment for about 6 to about 12 months.

75. The method according to any one of the preceding items, wherein the treatment is against mild, moderate or severe open angle glaucoma.

76. The method according to any one of the preceding items, wherein the intraocular pressure is decreased by at least 4 mmHg, or at least 5 mmHg from base line intraocular pressure during the treatment period such as about 2 to about 12 months or about 3 to about 9 months, such as about 6 months.

77. The method according to any one of the preceding items, wherein no change of endothelial cell count occurs in the treated eye during the treatment period and/or entire treatment.

78. The method according to any one of the preceding items, wherein no change of the thickness of the cornea occurs in the treated eye or during the treatment period and/or entire treatment.

79. A method of treating intraocular pressure in a human subject with ocular hypertension and/or glaucoma for a period ranging from about 6 to about 12 months such as from about 6 to about 9 months with one single travoprost sustained release biodegradable intracameral implant per eye in need of treating, the method comprising per said eye:
Step 1: providing one travoprost sustained release biodegradable intracameral implant containing 21 to 30 µg travoprost, wherein the implant is in the form of a fiber that has a length of about 1.0 mm to about 2.5 mm and a diameter of not more than 0.3 mm in its dried state, comprising:

a biodegradable hydrogel and travoprost particles, the travoprost particles being in the form of travoprost intermixed with a biodegradable polymer, wherein the travoprost particles contain a blend of four types of particles, the first type of particles being in the form of travoprost intermixed with the biodegradable polymer consisting of a first polylactide having an inherent viscosity specification ranging from about 0.35 to about 0.45 dl/g and having an acid end group; and the second type of particles being in the form of travoprost intermixed with the biodegradable polymer consisting of a second polylactide having an inherent viscosity specification ranging from about 0.6 to less than about 0.8 dl/g and having an acid end group; and the third type of particles being in the form of travoprost intermixed with the biodegradable polymer consisting of a third polylactide having an inherent viscosity specification ranging from about 0.8 to about 1.0 dl/g and having an acid end group; and the fourth type of particles being in the form of travoprost intermixed with the biodegradable polymer consisting of a fourth polylactide having an inherent viscosity specification ranging from about 0.55 to 0.75 dl/g and having an ester end group; and the travoprost particles being dispersed within the hydrogel, wherein the hydrogel comprises a polymer network being formed by reacting a 8-arm-15K-SAZ polyethylene glycol with a mass average molecular weight of 15,000±10% Daltons with trilysine acetate; and Step 2: inserting the one sustained release biodegradable intracameral implant of step 1 into the anterior segment of said eye to place it within the iridocorneal angle of said eye.

80. A method of treating intraocular pressure in a human subject with ocular hypertension and/or glaucoma for a period ranging from about 6 to about 12 months such as from about 6 to about 9 months with one single travoprost sustained release biodegradable intracameral implant per eye in need of treating, the method comprising per said eye:

Step 1: providing one travoprost sustained release biodegradable intracameral implant containing 11 to 20 μg travoprost, wherein the implant is in the form of a fiber that has a length of about 1.0 mm to about 2.5 mm and a diameter of not more than 0.3 mm in its dried state, comprising:

a biodegradable hydrogel and travoprost particles, the travoprost particles being in the form of travoprost intermixed with a biodegradable polymer, wherein the travoprost particle contain a blend of four types of particles, the first type of particles being in the form of travoprost intermixed with the biodegradable polymer consisting of a first polylactide having an inherent viscosity specification ranging from about 0.35 to about 0.45 dl/g and having an acid end group; and the second type of particles being in the form of travoprost intermixed with the biodegradable polymer consisting of a second polylactide having an inherent viscosity specification ranging from about 0.6 to less than about 0.8 dl/g and having an acid end group; and the third type of particles being in the form of travoprost intermixed with the biodegradable polymer consisting of a third polylactide having an inherent viscosity specification ranging from about 0.8 to about 1.0 dl/g and having an acid end group; and the fourth type of particles being in the form of travoprost intermixed with the biodegradable polymer consisting of a fourth polylactide having an inherent viscosity specification ranging from about 0.55 to 0.75 dl/g and having an ester end group, and the travoprost particles being dispersed within the hydrogel, wherein the hydrogel comprises a polymer network being formed by reacting a 8-arm-15K-SAZ polyethylene glycol with a mass average molecular weight of 15,000±10% Daltons with trilysine acetate; and Step 2: inserting the one sustained release biodegradable intracameral implant of step 1 into the anterior segment of said eye to place it within the iridocorneal angle of said eye.

81. A method of treating intraocular pressure in a human subject with ocular hypertension and/or glaucoma for a period ranging from about 3 to about 6 months such as from about 3 to about 4 months with one single travoprost sustained release biodegradable intracameral implant per eye in need of treating, the method comprising per said eye:

Step 1: providing one travoprost sustained release biodegradable intracameral implant containing 11 to 20 μg travoprost, wherein the implant is in the form of a fiber that has a length of about 1.0 mm to about 2.5 mm and a diameter of not more than 0.3 mm in its dried state, comprising:

a biodegradable hydrogel and travoprost particles, the travoprost particles being in the form of travoprost intermixed with a biodegradable polymer, wherein the travoprost particles contain a blend of three types of particles, the first type of particles being in the form of travoprost intermixed with the biodegradable polymer consisting of a first polylactide having an inherent viscosity specification ranging from about 0.35 to about 0.45 dl/g and having an acid end group; and the second type of particles being in the form of travoprost intermixed with the biodegradable polymer consisting of a second polylactide having an inherent viscosity specification ranging from about 0.6 to less than about 0.8 dl/g and having an acid end group; and the third type of particles being in the form of travoprost intermixed with the biodegradable polymer consisting of a third polylactide having an inherent viscosity specification ranging from about 0.8 to about 1.0 dl/g and having an acid end group; and the travoprost particles being dispersed within the hydrogel, wherein the hydrogel comprises a polymer network being formed by reacting a 8-arm-15K-SG polyethylene glycol with a mass average molecular weight of 15,000±10% Daltons with trilysine acetate; and Step 2: inserting the one sustained release biodegradable intracameral implant of step 1 into the anterior segment of said eye to place it within the iridocorneal angle of said eye.

82. A method of treating intraocular pressure in a human subject with ocular hypertension and/or glaucoma for a period ranging from about 3 to about 6 months such as from about 3 to about 4 months with one single travoprost sustained release biodegradable intracameral implant per eye in need of treating, the method comprising per said eye:
- Step 1: providing one travoprost sustained release biodegradable intracameral implant containing 2 to 10 μg travoprost, wherein the implant is in the form of a fiber that has a length of about 1.0 mm to about 2.5 mm and a diameter of not more than 0.3 mm in its dried state, comprising:
- a biodegradable hydrogel and travoprost particles,
- the travoprost particles being in the form of travoprost intermixed with a biodegradable polymer, wherein the travoprost particles contain a blend of two types of particles, the first type of particle being in the form of travoprost intermixed with the biodegradable polymer consisting of a first polylactide having an inherent viscosity specification ranging from about 0.35 to about 0.45 dl/g and having an acid end group; and the second type of particles being in the form of travoprost intermixed with the biodegradable polymer consisting of a second polylactide having an inherent viscosity specification ranging from about 0.6 to about 0.8 dl/g and having an acid end group; and
- the travoprost particles being dispersed within the hydrogel, wherein the hydrogel comprises a polymer network being formed by reacting a 8arm-15K-SG polyethylene glycol with a mass average molecular weight of 15,000110% Daltons with trilysine acetate; and
- Step 2: inserting the one sustained release biodegradable intracameral implant of step 1 into the anterior segment of said eye to place it within the iridocorneal angle of said eye.

83. A method of treating intraocular pressure in a human subject with ocular hypertension and/or glaucoma for a period ranging from about 6 to about 12 months such as from about 6 to about 9 months with one single travoprost sustained release biodegradable intracameral implant per eye in need of treating, the method comprising per said eye:
- Step 1: providing one travoprost sustained release biodegradable intracameral implant containing 21 to 30 μg travoprost, wherein the implant is in the form of a fiber that has a length of about 1.0 mm to about 2.5 mm and a diameter of not more than 0.3 mm in its dried state, comprising a biodegradable hydrogel and travoprost particles dispersed therein, wherein the intracameral implant has an in vitro release with an average travoprost release ranging from of about 5% to about 15% with a mean absolute deviation of at most 3%, or a travoprost release ranging from 5% to 15%, based on the % amount released per 14 days from day 1 to day 112, when measured at 37° C. in PBS at a pH of 7.2 to 7.4 under sink-conditions and the hydrogel dissolves within 6 to 8 months; and
- Step 2: inserting the one sustained release biodegradable intracameral implant of step 1 into the anterior segment of said eye to place it within the iridocorneal angle of said eye.

84. A method of treating intraocular pressure in a human subject with ocular hypertension and/or glaucoma for a period ranging from about 3 to about 6 months such as from about 3 to about 4 months with one single travoprost sustained release biodegradable intracameral implant per eye in need of treating, the method comprising per said eye:
- Step 1: providing one travoprost sustained release biodegradable intracameral implant containing 11 to 20 μg travoprost, wherein the implant is in the form of a fiber that has a length of about 1.0 mm to about 2.5 mm and a diameter of not more than 0.3 mm in its dried state, comprising a biodegradable hydrogel and travoprost particles dispersed therein, wherein the intracameral implant has an in vitro release with an average travoprost release ranging from of about 65% to about 85% with a mean absolute deviation of at most 5%, or a travoprost release ranging from 65% to 85%, based on the %-amount released per 70 days from day 1 to day 84, when measured at 37° C. in PBS at a pH of 7.2 to 7.4 under sink-conditions and the hydrogel dissolves within 2 to 4 months; and
- Step 2: inserting the one sustained release biodegradable intracameral implant of step 1 into the anterior segment of said eye to place it within the iridocorneal angle of said eye.

85. A method of treating intraocular pressure in a human subject with ocular hypertension and/or glaucoma for a period ranging from about 3 to about 6 months such as from about 3 to about 6 months with one single travoprost sustained release biodegradable intracameral implant per eye in need of treating, the method comprising per said eye:
- Step 1: providing one travoprost sustained release biodegradable intracameral implant containing 2 to 10 μg travoprost, wherein the implant is in the form of a fiber that has a length of about 1.0 mm to about 2.5 mm and a diameter of not more than 0.3 mm in its dried state, comprising a biodegradable hydrogel and travoprost particles dispersed therein, wherein the intracameral implant has an in vitro release with an average travoprost release ranging from of about 60% to about 80% with a mean absolute deviation of at most 5%, or a travoprost release ranging from 60% to 80%, based on the %-amount released per 70 days from day 1 to day 98, when measured at 37° C. in PBS at a pH of 7.2 to 7.4 under sink-conditions and the hydrogel dissolves within 2 to 4 months; and
- Step 2: inserting the one sustained release biodegradable intracameral implant of step 1 into the anterior segment of said eye to place it within the iridocorneal angle of said eye.

86. Travoprost particles made of a mixture of:
Travoprost and
a biodegradable polymer consisting of a polylactides having an acid end group and an inherent viscosity specification ranging from about 0.05 to less than about 0.5 dl/g, such as from about 0.35 to about 0.45 dl/g,
wherein the mixture contains from about 40 wt.-% to about 50 wt.-%, such as from about 43 wt.-% to about 45 wt.-% travoprost based on the total mass of the mixture.

87. Travoprost particles made of a mixture of:
Travoprost and
a biodegradable polymer consisting of a polylactides having an acid end group and an inherent viscosity specification ranging from about 0.5 to less than about 0.80 dl/g, such as ranging from about 0.6 to less than about 0.80 dl/g,
wherein the mixture contains from about 40 wt.-% to about 50 wt.-%, such as more than from about 45 wt.-% to about 47 wt.-% travoprost based on the total mass of the mixture.

88. Travoprost particles made of a mixture of:
Travoprost and
a biodegradable polymer consisting of a polylactides having an acid end group and an inherent viscosity specification ranging from about 0.8 to about 1.7 dl/g, such as ranging from about 0.8 to about 1.0 dl/g,
wherein the mixture contains from about 40 wt.-% to about 50 wt.-%, such as from about 41 wt.-% to about 43 wt.-% travoprost based on the total mass of the mixture.

89. Travoprost particles made of a mixture of:
Travoprost and
a biodegradable polymer consisting of a polylactides having an ester end group and an inherent viscosity specification ranging from about 0.05 to about 1.7 dl/g, such as ranging from about 0.55 to about 0.75 dl/g,
wherein the mixture contains from about 40 wt.-% to about 50 wt.-%, such as from about 41 wt.-% to about 43 wt.-% travoprost based on the total mass of the mixture.

90. A multiplicity of travoprost particles being formed from a blend of particles of items 86 to 89, such as based on the total amount of particles about 15 to about 25 wt.-% particles of item 86 and about 15 to about 25 wt.-% particles of item 87 and about 5 to about 15% of particles of item 88 and about 40 to about 60 wt.-% of particles of item 89; or wherein about 15 wt.-% to about 25 wt.-% of the total amount of travoprost is present in the form of particles of item 86 and about 15 wt.-% to about 25 wt.-% of the total amount of travoprost is present in the form of particles of item 87 and about 5 wt.-% to about 15 wt.-% of the total amount of travoprost is present in the form of particles of item 88 and about 40 wt.-% to about 60 wt.-% of the total amount of travoprost is present in the form of particles of item 89.

91. A multiplicity of travoprost particles being formed from a blend of particles of items 86 to 88, such based on the total amount of particles as about 20 to about 35 wt.-% particles of item 86 and about 30 to about 50 wt.-% particles of item 87 and about 25 to about 45 wt.-% of particles of item 88; or wherein about 20 wt.-% to about 35 wt.-% of the total amount of travoprost is present in the form of particles of item 86 and about 5' 30 wt.-% to about 50 wt.-% of the total amount of travoprost is present in the form of particles of item 87, and about 25 wt.-% to about 45 wt.-% of the total amount of travoprost is present in the form of particles of item 88.

92. A multiplicity of travoprost particles being formed from a blend of particles of items 86 and 87 such as based on the total amount of particles about 35 to about 55 wt.-% particles of item 86 and about 35 to about 55 wt.-% particles of item 87 or wherein about 35 wt.-% to about 55 wt.-% of the total amount of travoprost is present in the form of particles of item 86 and about 35 wt.-% to about 55 wt.-% of the total amount of travoprost is present in the form of particles of item 87.

93. A multiplicity of travoprost particles being formed from a blend of particles, the particles consisting of a mixture of:
travoprost;
a biodegradable polymer consisting of polylactides having an acid end group, and
optionally other pharmaceutically acceptable residual amounts of manufacturing components 94. The multiplicity of travoprost particles according to item 93, wherein the blend of particles is composed of three types of particles, wherein the three types of particles distinguish from each other by including polylactide components having different inherent viscosities.

95. The multiplicity of travoprost particle according to item 94, wherein the three polylactides have an inherent viscosity specification ranging from about 0.05 to less than about 0.5 dl/g, such as about 0.35 to about 0.45 dl/g; ranging from about 0.5 to less than about 0.80 dl/g, such as about 0.6 to less than about 0.8 dl/g; and ranging from about 0.8 to about 1.7, such as about 0.8 to about 1.0 dl/g, respectively.

96. The multiplicity of travoprost particles according to item 95, wherein the blend of particles is composed of two types of particles, wherein the two types of particles distinguish from each other by including polylactide components having different inherent viscosities.

97. The multiplicity of travoprost particle according to item 96, wherein the two polylactides have an inherent viscosity specification ranging from about 0.05 to less than about 0.5 dl/g, such as about 0.35 to about 0.45 dl/g; and ranging from about 0.5 dl/g to about 1.7 dl/g, such as about 0.6 to about 0.8 dl/g, respectively.

98. The multiplicity of travoprost particle according to any one of items 93 to 97, wherein the particles have a number-/weight-average diameter of 1 to 100 µm, 20 to 75 µm, 20 to 106 µm, and/or 20 to 55 µm.

99. A travoprost sustained release sustained release biodegradable intracameral implant including
a multiplicity of travoprost particles according to any one of items 90 to 98; and
a biodegradable hydrogel,
wherein the multiplicity of travoprost particles are dispersed within the hydrogel.

100. A travoprost sustained release sustained release biodegradable intracameral implant including
a biodegradable hydrogel and travoprost particles,
the travoprost particles being in the form of travoprost intermixed with a polylactide.
the travoprost particles being dispersed within the hydrogel, wherein the hydrogel comprises a polymer network being formed by reacting a 8-arm-15K-SG or 8-arm-15K-SAZ polyethylene glycol each having a mass average molecular weight of 15,000±10% Daltons with trilysine acetate.

101. A method of manufacturing a travoprost sustained release sustained release biodegradable intracameral implant, the method comprising the steps of:
a) preparing travoprost particles being in the form of travoprost intermixed with a biodegradable polymer,
b) preparing a precursor mixture containing hydrogel precursors and the travoprost particles,
c) cross-linking the precursor mixture using a cross-linker to form a polymer network and to obtain a hydrogel mixture comprising the polymer network, and
d) drying the hydrogel mixture to provide the implant.

102. A sustained release biodegradable intracameral implant obtainable by the method according to item 101.

103. A syringe for intracameral injection including the sustained release biodegradable intracameral implant according to any one of items 99, 100 and 102.

104. A method of treating ocular disease in a human subject for a period within 3 to 9 months with one single API containing sustained release biodegradable intracameral implant per eye in need of such treatment, the method comprising per said eye:
Step 1: providing one API containing sustained release biodegradable intracameral implant providing treatment for a period within 3 to 9 months comprising:
a biodegradable hydrogel and API particles,
the API particles being dispersed within the hydrogel; and
Step 2: inserting the one sustained release biodegradable intracameral implant of step 1 into the anterior segment of said eye to place it within the iridocorneal angle of said eye.

105. A method according to any item or method disclosed herein, wherein the intraocular pressure is decreased by about 5 to about 7 mmHg, or about 7 to about 9 mmHg from baseline intraocular pressure during the treatment period such as about 2 to about 12 months or about 3 to about 9 months, such as about 6 months or during continued treatment with repeated administration.

Third List of Items

1. A travoprost sustained release biodegradable intracameral implant comprising:
a biodegradable hydrogel and travoprost particles,
the travoprost particles being in the form of travoprost intermixed with a biodegradable polymer, wherein the biodegradable polymer comprises a polylactide and
the travoprost particles being dispersed within the hydrogel, wherein
the hydrogel comprises a polymer network comprising one or more units of polyethylene glycol, the polymer network is formed by reacting an electrophilic group-containing multi-arm-polymer precursor with a nucleophilic group-containing cross-linking agent, the electrophilic group is a succinimidylazelate (SAZ) group, and the multi-arm polymer precursor is an 8-arm-15K-SAZ polyethylene glycol; and the nucleophilic group-containing cross-linking agent is a trilysine or a salt thereof.

2. The travoprost sustained release biodegradable intracameral implant according to claim 1, wherein the travoprost particles contain PLA 4A, PLA 7A, PLA 9A and PLA 5.5.

3. The travoprost sustained release biodegradable intracameral implant according to claim 1, wherein the implant contains a dose of about 15 µg of travoprost.

4. The travoprost sustained release biodegradable intracameral implant according to claim 1, wherein the implant contains a dose of about 26 µg of travoprost.

5. A travoprost sustained release biodegradable intracameral implant comprising:
a biodegradable hydrogel and travoprost particles,
the travoprost particles being in the form of travoprost intermixed with a biodegradable polymer, wherein the biodegradable polymer comprises a polylactide and
the travoprost particles being dispersed within the hydrogel, wherein
the hydrogel comprises a polymer network comprising one or more units of polyethylene glycol, the polymer network is formed by reacting an electrophilic group-containing multi-arm-polymer precursor with a nucleophilic group-containing cross-linking agent, the electrophilic group is a succinimidylglutarate (SG) group, and the multi-arm polymer precursor is an 8-arm-15K-SG polyethylene glycol; and the nucleophilic group-containing cross-linking agent is a trilysine or a salt thereof.

6. The travoprost sustained release biodegradable intracameral implant according to claim 5, wherein the travoprost particles contain PLA 4A, PLA 7A, and PLA 9A 7. The travoprost sustained release biodegradable intracameral implant according to claim 5, wherein the travoprost particles contain PLA 4A and PLA 7A.

8. The travoprost sustained release biodegradable intracameral implant according to claim 5, wherein the implant contains a dose of about 15 µg of travoprost.

9. The travoprost sustained release biodegradable intracameral implant according to claim 5, wherein the implant contains a dose of about 5 µg of travoprost.

10. A method of treating intraocular pressure in a human subject with ocular hypertension and/or glaucoma for a period ranging from about 3 to about 9 months by administering a travoprost sustained release biodegradable intracameral implant comprising:
a biodegradable hydrogel and travoprost particles,
the travoprost particles being in the form of travoprost intermixed with a biodegradable polymer, wherein the biodegradable polymer comprises a polylactide and the travoprost particles being dispersed within the hydrogel,
wherein the hydrogel comprises a polymer network comprising one or more units of polyethylene glycol, the polymer network is formed by reacting an electrophilic group-containing multi-arm-polymer precursor with a nucleophilic group-containing cross-linking agent, the electrophilic group is a succinimidylazelate (SAZ) group, and the multi-arm polymer precursor is an 8-arm-15K-SAZ polyethylene glycol; and the nucleophilic group-containing cross-linking agent is a trilysine or a salt thereof.

11. The travoprost sustained release biodegradable intracameral implant according to claim 10, wherein the travoprost particles contain PLA 4A, PLA 7A, PLA 9A and PLA 5.5.

12. The travoprost sustained release biodegradable intracameral implant according to claim 10, wherein the implant contains a dose of about 26 µg of travoprost.

13. The method according to claim 10, wherein the glaucoma is open-angle glaucoma.

14. The method according to claim 10, wherein essentially no endothelial damage occurs following administration of the implant.

15. The method according to claim 10, wherein the implant is designed for implantation in the iridocorneal angle.

16. The method according to claim 10, wherein the hydrogel is fully degraded after 5 months or 6 months or 8 months.

17. The method according to claim 10, wherein the ocular pressure is lowered during the period of treatment.

18. The method according to claim 10, wherein the ocular pressure is lowered by 5 to 11 mmHg.

19. The method according to claim 10, wherein essentially no change in pachymetry occurs following administration.

20. A method of treating intraocular pressure in a human subject with ocular hypertension and/or glaucoma for a period ranging from about 3 to about 7 months by administering a travoprost sustained release biodegradable intracameral implant comprising:

a biodegradable hydrogel and travoprost particles, the travoprost particles being in the form of travoprost intermixed with a biodegradable polymer, wherein the biodegradable polymer comprises a polylactide and the travoprost particles being dispersed within the hydrogel, wherein the hydrogel comprises a polymer network comprising one or more units of polyethylene glycol, the polymer network is formed by reacting an electrophilic group-containing multi-arm-polymer precursor with a nucleophilic group-containing cross-linking agent, the electrophilic group is a succinimidylglutarate (SG) group, and the multi-arm polymer precursor is an 8-arm-15K-SG polyethylene glycol; and the nucleophilic group-containing crosslinking agent is a trilysine or a salt thereof.

21. The travoprost sustained release biodegradable intracameral implant according to claim 20, wherein the implant contains a dose of about 5 μg of travoprost.

22. The travoprost sustained release biodegradable intracameral implant according to claim 20, wherein the travoprost particles contain PLA 4A, PLA 7A, and PLA 9A; or PLA 4A and PLA 7A.

23. The method according to claim 20, wherein the treatment period is about 3 months, about 4 months, about 5 months, about 6 months, or about 7 months.

24. The method according to claim 20, wherein the glaucoma is open-angle glaucoma.

25. The method according to claim 20, wherein essentially no endothelial damage occurs following administration of the implant.

26. The method according to claim 20, wherein essentially no change in pachymetry occurs following administration.

27. The method according to claim 20, wherein the implant is designed for implantation in the iridocorneal angle.

28. The method according to claim 20, wherein the hydrogel is fully degraded after 2 months or 3 months or 4 months.

29. The method according to claim 20, wherein the ocular pressure is lowered during the period of treatment.

30. The method according to claim 20, wherein the ocular pressure is lowered by 5 to 11 mmHg.

Fourth List of Items

1. A travoprost sustained release biodegradable intracameral implant comprising:

a biodegradable hydrogel, wherein the hydrogel comprises a polymer network comprising one or more units of polyalkylene glycol, and travoprost particles, the travoprost particles being in the form of travoprost intermixed with a biodegradable polymer, and the travoprost particles being dispersed within the hydrogel, wherein the implant has a length of about 1.00 mm to about 2.50 mm and a diameter of not more than 0.30 mm in its dried state.

2. The travoprost sustained release biodegradable intracameral implant according to item 1, wherein the implant has a diameter of less than 0.50 mm after 24 hours of hydration in vitro in phosphate-buffered saline at a pH of 7.4 at 37° C.

3. The travoprost sustained release biodegradable intracameral implant according to item 2, wherein the implant has a diameter ranging from about 0.30 mm to 0.49 mm, or from about 0.40 mm to about 0.49 mm, after 24 hours of hydration in vitro in phosphate-buffered saline at a pH of 7.4 at 37° C.

4. The travoprost sustained release biodegradable intracameral implant according to any one of items 1 to 3, wherein a ratio of the diameter of the implant after 24 hours of hydration in vitro in phosphate-buffered saline at a pH of 7.4 at 37° C. to the diameter of the implant in its dried state is less than 2.5.

5. The travoprost sustained release biodegradable intracameral implant according to any one of the preceding items, wherein the implant contains a dose of about 2 μg to about 30 μg of travoprost 6. The travoprost sustained release biodegradable intracameral implant according to any one of the preceding items, wherein the biodegradable polymer comprises a polylactide.

7. The travoprost sustained release biodegradable intracameral implant according to any one of the preceding items, wherein the hydrogel comprises a polymer network comprising one or more units of polyethylene glycol.

8. The travoprost sustained release biodegradable intracameral implant according to any one of the preceding items, wherein the implant is in the form of a fiber.

9. The travoprost sustained release biodegradable intracameral implant according to any one of the preceding items, wherein the implant has a total weight of about 20 μg to about 110 μg, or of about 30 μg to about 105 μg in its dried state.

10. The travoprost sustained release biodegradable intracameral implant according to any one of the preceding items, wherein the implant shows a burst of less than 15%, based on the total weight of travoprost in the implant, on day 1 measured in vitro under simulated physiological sink conditions in 50 mL of 1×PBS, 0.5% castor oil, 0.01% sodium fluoride buffer at pH 7.2-7.4 at 37° C.

11. The travoprost sustained release biodegradable intracameral implant according to any one of the preceding items, wherein the total mass of the biodegradable polymer in the implant is less than 34 μg, less than 30 μg, less than 20 μg, or less than 10 μg.

12. The travoprost sustained release biodegradable intracameral implant according to any one of the preceding items, wherein the travoprost in the implant is less than 25 μg, or less than 20 μg, or less than 10 μg.

13. The travoprost sustained release biodegradable intracameral implant according to any one of the preceding items, wherein the total mass of the implant in its dried state is less than 103 μg, less than 80 μg or less than 50 μg.

14. The travoprost sustained release biodegradable intracameral implant according to any one of the preceding items, wherein the travoprost particles have a diameter ranging from 1 to 100 μm, 20 to 75 μm, 20 to 106 μm, or 20 to 55 μm determined by sieving or have an average diameter ranging from 1 to 100 μm, 20 to 75 μm, 20 to 106 μm, or 20 to 55 μm determined by laser diffraction.

15. The travoprost sustained release biodegradable intracameral implant according to any one of the preceding items, wherein the polymer network is formed by reacting an electrophilic group-containing multi-arm-polymer precursor with a nucleophilic group-containing cross-linking agent, the electrophilic group is selected from the group consisting of a succinimidylglutarate (SG) group and a succinimidylazelate (SAZ) group, and the multi-arm polymer precursor is selected from the group consisting of 8-arm-15K-SG polyethylene glycol or 8-arm-15K-SAZ polyethylene glycol; and the nucleophilic group-containing cross-linking agent is a trilysine, or the polymer network comprises 8-arm-polyethylene glycols being cross-linked including a group represented by the following formula

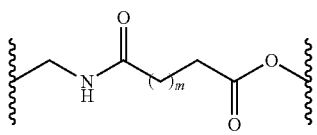

wherein m is 2 or 6.

16. The travoprost sustained release biodegradable intracameral implant according to any one of the preceding items, wherein the travoprost particles are a blend of at least two types of travoprost particles selected from the group consisting of
  1) a first type of travoprost particles made of a mixture of:
     travoprost and
     a biodegradable polymer consisting of a polylactide or polylactides having an acid end group and an inherent viscosity specification ranging from about 0.05 to less than about 0.5 dl/g, such as from about 0.35 to about 0.45 dl/g,
     such as wherein the first type of particles contains from about 40 wt.-% to about 50 wt.-%, such as from about 43 wt.-% to about 45 wt.-% travoprost, based on the total mass of the first type of particles;
  2) a second type of travoprost particles made of a mixture of:
     travoprost and
     a biodegradable polymer consisting of a polylactide or polylactides having an acid end group and an inherent viscosity specification ranging from about 0.5 to less than about 0.80 dl/g, such as ranging from about 0.6 to less than about 0.80 dl/g,
     such as wherein the second type of particles contains from about 40 wt.-% to about 50 wt.-%, such as from more than about 45 wt.-% to about 47 wt.-% travoprost, based on the total mass of the second type of particles;
  3) a third type of travoprost particles made of a mixture of:
     travoprost and
     a biodegradable polymer consisting of a polylactide or polylactides having an acid end group and an inherent viscosity specification ranging from about 0.8 to about 1.7 dl/g, such as ranging from about 0.8 to about 1.0 dl/g,
     such as wherein the third type of particles contains from about 40 wt.-% to about 50 wt.-%, such as from about 41 wt.-% to about 43 wt.-% travoprost based on the total mass of third type of particles;
  4) a fourth type of travoprost particles made of a mixture of:
     travoprost and
     a biodegradable polymer consisting of a polylactide or polylactides having an ester end group and an inherent viscosity specification ranging from about 0.05 to about 1.7 dl/g, such as ranging from about 0.55 to about 0.75 dl/g,
     such as wherein the fourth type of particles contains from about 40 wt.-% to about 50 wt.-%, such as from about 41 wt.-% to about 43 wt.-% travoprost based on the total mass of the fourth type of particles.

17. The travoprost sustained release biodegradable intracameral implant according to any one of preceding items, wherein the travoprost particles a blend of particles made of
  1) a first type of travoprost particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles; and
  2) a second type of travoprost particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particles contains from about 40 wt.-% to about 50 wt.-%, such as more than from about 45 wt.-% to about 47 wt.-% travoprost, based on the total mass of the second type of particles,
  such as wherein the blend contains, based on the total amount of the blend, about 35 wt.-% to about 55 wt.-% particles of the first type of particles and about 35 wt.-% to about 55 wt.-% particles of the second type of particles; or
  such as wherein about 35 wt.-% to about 55 wt.-% of the total amount of travoprost in the implant is present in the form of particles of the first type of particles and about 35 wt.-% to about 55 wt.-% of the total amount of travoprost in the implant is present in the form of particles of the second type of particles, wherein optionally the polymer network is formed by reacting an electrophilic group-containing multi-arm-polymer precursor with a nucleophilic group-containing cross-linking agent, the electrophilic group is a succinimidylglutarate (SG) group and the multi-arm polymer precursor an 8-arm-15K-SG polyethylene glycol; and the nucleophilic group-containing cross-linking agent is a trilysine, or the polymer network comprises 8-arm-polyethylene glycols being cross-linked including a group represented by the following formula

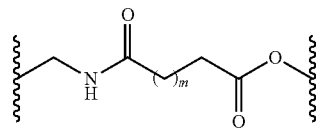

wherein m is 2.

18. The travoprost sustained release biodegradable intracameral implant according to any one of the preceding items, wherein the travoprost particles are a blend of particles made of
  1) a first type of particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles,
  2) a second type of travoprost particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particle contains from about 40 wt.-% to about 50 wt.-%, such as more than from about 45 wt.-% to about 47 wt.-% travoprost, based on the total mass of the second type of particles, and
  3) a third type of travoprost particles made of a mixture of travoprost and the biodegradable polymer consisting of a polylactide or polylactides having an acid end group and an inherent viscosity specification ranging from about 0.8 to about 1.7 dl/g, such as ranging from about 0.8 to about 1.0 dl/g, wherein the third type of particles contains from about 40 wt.-% to about 50 wt.-%, such as from about 41 wt.-% to about 43 wt.-% travoprost, based on the total mass of the third type of particles,
  such as wherein the blend contains, based on the total amount of blend, about 20 wt.-% to about 35 wt.-% particles of the first type of particles and about 30 wt.-% to about 50 wt.-% particles of the second type of particles and about 25 wt.-% to about 45 wt.-% of particles of the third type of particles; or
  such as wherein about 20 wt.-% to about 35 wt.-% of the total amount of travoprost in the implant is present in the form of particles of the first type of particles and about 30 wt.-% to about 50 wt.-% of the total amount of travoprost in the implant is present in the form of particles of the second type of particles, and about 25 wt.-% to about 45 wt.-% of the total amount of travoprost in the implant is present in the form of particles of the third type of particles,
  wherein optionally the polymer network is formed by reacting an electrophilic group-containing multi-arm-polymer precursor with a nucleophilic group-containing cross-linking agent, the electrophilic group is a succinimidylglutarate (SG) group and the multi-arm polymer precursor an 8-arm-15K-SG polyethylene glycol; and the nucleophilic group-containing cross-linking agent is a trilysine or the polymer network comprises 8-arm-polyethylene glycols being cross-linked including a group represented by the following formula

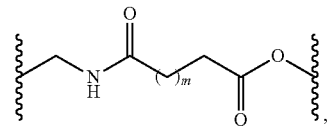

wherein m is 2.
19. The travoprost sustained release biodegradable intracameral implant according to any one of the preceding items, wherein the travoprost particles are a blend of particles made of
  1) a first type of particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles,
  2) a second type of particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particles contains from about 40 wt.-% to about 50 wt.-%, such as more than from about 45 wt.-% to about 47 wt.-% travoprost, based on the total mass of the second type of particles,
  3) a third type of particles made of travoprost and the biodegradable polymer consisting of a polylactide or polylactides having an acid end group and an inherent viscosity specification ranging from about 0.8 to about 1.7 dl/g, such as ranging from about 0.8 to about 1.0 dl/g, wherein the third type of particles contain from about 40 wt.-% to about 50 wt.-%, such as from about 41 wt.-% to about 43 wt.-% travoprost, based on the total mass of the third type of particles, and
  4) a fourth type of particles made of travoprost and the biodegradable polymer consisting of a polylactide or polylactides having an ester end group and an inherent viscosity specification ranging from about 0.05 to about 1.7 dl/g, such as ranging from about 0.55 to about 0.75 dl/g, wherein the fourth type of particles contains from about 40 wt.-% to about 50 wt.-%, based on the total mass of the fourth type of particles.
  such as wherein the blend contains, based on the total amount of blend, about 15 wt.-% to about 25 wt.-% particles of the first type of particles and about 15 wt.-% to about 25 wt.-% particles of the second type of particles and about 5 wt.-% to about 15% of particles of the third type of particles and about 40 wt.-% to about 60 wt.-% of particles of the fourth type of particles; or
  such as wherein about 15 wt.-% to about 25 wt.-% of the total amount of travoprost in the implant is present in the form of particles of the first type of particles and about 15 wt.-% to about 25 wt.-% of the total amount of travoprost in the implant is present in the form of particles of the second type of particles and about 5 wt.-% to about 15 wt.-% of the total amount of travoprost in the implant is present in the form of particles of the third type of particles and about 40 wt.-% to about 60 wt.-% of the total amount of travoprost in the implant is present in the form of particles of the fourth type of particles,
wherein optionally the polymer network is formed by reacting an electrophilic group-containing multi-arm-polymer precursor with a nucleophilic group-containing cross-linking agent, the electrophilic group is a succinimidylazelate (SAZ) group, and the multi-arm polymer precursor is a 8-arm-15K-SAZ polyethylene glycol; and the nucleophilic group-containing cross-linking agent is a trilysine, or the polymer network comprises 8-arm-polyethylene glycols being cross-linked including a group represented by the following formula

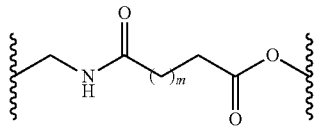

wherein m is 6.

20. A travoprost sustained release biodegradable intracameral implant according to any one of items 1 to 19 for use in a method of treating intraocular pressure in a human subject with ocular hypertension and/or glaucoma for a period ranging from about 1 to about 24 months such as from about 3 to about 9 months with one single travoprost sustained release biodegradable implant per eye in need of treating.

21. The travoprost sustained release biodegradable intracameral implant for use according to item 20, wherein the treatment period is about 7 to about 8 months, or about 7 to about 9 months, or about 4 months, or about 5 months, or about 6 months, or about 7 months, or about 8 months, or about 9 months and the travoprost sustained release biodegradable implant provides treatment for about 7 to about 8 months, or about 7 to about 9 months, or about 4 months, or about 5 months, or about 6 months, or about 7 months, or about 8 months, or about 9 months, respectively.

22. The travoprost sustained release biodegradable intracameral implant for use according to item 20 or 21, wherein
the implant has an in vitro release with an average travoprost release ranging from of about 65% to about 85% with a mean absolute deviation of at most 5%, based on the % amount released per 70 days, from day 1 to day 84, when measured at 37° C. in PBS at a pH of 7.2 to 7.4 under sink-conditions wherein the treatment period is about 3 to about 6 months or is about 3 to 4 months; or
wherein the implant has an in vitro release with an average travoprost release ranging from of about 60% to about 80% with a mean absolute deviation of at most 5%, based on the %-amount released per 70 days, from day 1 to day 98, when measured at 37° C. in PBS at a pH of 7.2 to 7.4 under sink-conditions wherein the treatment period is about 3 to about 7 months or is about 4 to 7 months; or
wherein the implant has an in vitro release with an average travoprost release ranging from of about 5% to about 15% with a mean absolute deviation of at most 3%, based on the % amount released per 14 days, from day 1 to day 112, when measured at 37° C. in PBS at a pH of 7.2 to 7.4 under sink-conditions, wherein the treatment period is about 6 to about 9 months or about 6 to about 12 months.

23. The travoprost sustained release biodegradable intracameral implant for use according to any one of items 20 to 22, wherein the treatment period is about 3 to about 7 months or is about 4 to 7 months or is about 3 to about 6 months or is about 3 to 4 months and the travoprost sustained release biodegradable implant provides treatment for about 3 to about 7 months or for about 4 to 7 months or for about 3 to about 6 months or for 3 to 4 months, wherein the polymer network is formed by reacting an electrophilic group-containing multi-arm-polymer precursor with a nucleophilic group-containing cross-linking agent, the electrophilic group is a succinimidylglutarate (SG) group and the multi-arm polymer precursor an 8-arm-15K-SG polyethylene glycol; and the nucleophilic group-containing cross-linking agent is a trilysine and the hydrogel dissolves within 2 to 4 months.

24. The travoprost sustained release biodegradable intracameral implant for use according to any one of items 20 to 23, wherein the treatment period is about 6 to about 9 months or about 6 to about 12 months and the travoprost sustained release biodegradable implant provides treatment for about 6 to 9 months or for about 6 to about 12 months, wherein the polymer network is formed by reacting an electrophilic group-containing multi-arm-polymer precursor with a nucleophilic group-containing cross-linking agent, the electrophilic group is a succinimidylazelate (SAZ) group, and the multi-arm polymer precursor is a 8-arm-15K-SAZ polyethylene glycol; and the nucleophilic group-containing cross-linking agent is a trilysine and the hydrogel dissolves within 6 to 8 months.

25. The travoprost sustained release biodegradable intracameral implant for use according to any one of items 20 to 24, wherein the treatment period is about 3 to about 6 months or is about 3 to 4 months and the travoprost sustained release biodegradable implant provides treatment about 3 to about 6 months or for 3 to 4 months, wherein the travoprost particles are a blend of particles made of
1) a first type of travoprost particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles; and
2) a second type of travoprost particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particles contains from about 40 wt.-% to about 50 wt.-%, such as more than from about 45 wt.-% to about 47 wt.-% travoprost, based on the total mass of the second type of particles, wherein the blend contains, based on the total amount of particles, about 35 wt.-% to about 55 wt.-% particles of the first type of particles and about 35 wt.-% to about 55 wt.-% particles of the second type of particles; or wherein about 35 wt.-% to about 55 wt.-% of the total amount of travoprost in the implant is present in the form of particles of the first type of particles and about 35 wt.-% to about 55 wt.-% of the total amount of travoprost in the implant is present in the form of particles of the second type of particles.

26. The travoprost sustained release biodegradable intracameral implant for use according to any one of items 20 to 25 wherein the treatment period is 4 to 7 months and the travoprost sustained release biodegradable implant provides treatment for about 4 to about 7 months, wherein the travoprost particles are a blend of particles made of
1) a first type of particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles,
2) a second type of particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particle contains from about 40 wt.-% to about 50 wt.-%, such as more than from about 45 wt.-% to about 47 wt.-% travoprost, based on the total mass of the second type of particles, and
3) a third type of particles made of a mixture of travoprost and the biodegradable polymer consisting of a polylactide or polylactides having an acid end group and an inherent viscosity specification ranging from about 0.8 to about 1.7 dl/g, such as ranging from about 0.8 to about 1.0 dl/g, wherein the third type of particles contains from about 40 wt.-% to about 50 wt.-%, such as from about 41 wt.-% to about 43 wt.-% travoprost based on the total mass of the third type of particles,
wherein the blend contains, based on the total amount of particles, about 20 wt.-% to about 35 wt.-% particles of the first type of particles and about 30 wt.-% to about 50 wt.-% particles of the second type of particles and about 25 wt.-% to about 45 wt.-% of particles of the third type of particles; or wherein about 20 wt.-% to about 35 wt.-% of the total amount of travoprost in the implant is present in the form of particles of the first type of particles and about 30 wt.-% to about 50 wt.-% of the total amount of travoprost in the implant is present in the form of particles of the second type of particles, and about 25 wt.-% to about 45 wt.-% of the total amount of travoprost in the implant is present in the form of particles of the third type of particles.

27. The travoprost sustained release biodegradable intracameral implant for use according to any one of items 20 to 22 or 24, wherein the treatment period is about 6 to about 12 months about 6 to about 9 months and the travoprost sustained release biodegradable implant provides treatment for about 6 to 12 months or for about 6 to 9 months, wherein the travoprost particles are a blend of particles made of
1) a first type of particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles,
2) a second type of particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particles contains from about 40 wt.-% to about 50 wt.-%, such as more than from about 45 wt.-% to about 47 wt.-% travoprost, based on the total mass of the second type of particles,
3) a third type of particles made of travoprost and the biodegradable polymer consisting of a polylactide or polylactides having an acid end group and an inherent viscosity specification ranging from about 0.8 to about 1.7 dl/g, such as ranging from about 0.8 to about 1.0 dl/g, wherein the third type of particles contain from about 40 wt.-% to about 50 wt.-%, such as from about 41 wt.-% to about 43 wt.-% travoprost, based on the total mass of the third type of particles, and
4) a fourth type of particles made of travoprost and the biodegradable polymer consisting of a polylactide or polylactides having an ester end group and an inherent viscosity specification ranging from about 0.05 to about 1.7 dl/g, such as ranging from about 0.55 to about 0.75 dl/g, wherein the fourth type of particles contains from about 40 wt.-% to about 50 wt.-%, such as from about 41 wt.-% to about 43 wt.-% travoprost, based on the total mass of the fourth type of particles,
wherein the blend contains, based on the total amount of particles, about 15 wt.-% to about 25 wt.-% particles of the first type of particles and about 15 wt.-% to about 25 wt.-% particles of the second type of particles and about 5 wt.-% to about 15% of particles of the third type of particles and about 40 wt.-% to about 60 wt.-% of particles of the fourth type of particles; or wherein about 15 wt.-% to about 25 wt.-% of the total amount of travoprost in the implant is present in the form of particles of the first type of particles and about 15 wt.-% to about 25 wt.-% of the total amount of travoprost in the implant is present in the form of particles of the second type of particles and about 5 wt.-% to about 15 wt.-% of the total amount of travoprost in the implant is present in the form of particles of the third type of particles and about 40 wt.-% to about 60 wt.-% of the total amount of travoprost in the implant is present in the form of particles of the fourth type of particles.

28. The travoprost sustained release biodegradable intracameral implant for use according to any of items 20 to 23, wherein the treatment period is about 3 to about 6 months or is about 3 to 4 months, the implant contains a dose of about 5 µg of travoprost, and wherein the implant has an in vitro release with an average travoprost release ranging from about 300 to about 500 ng/week with a standard deviation ranging from 100 to 200 ng/week, wherein the average travoprost release is based on the weekly travoprost release values between days 7 to 84 excluding post dose day 1 burst when measured at 37° C. in PBS at a pH of 7.2 to 7.4 under sink-conditions; or wherein the weekly travoprost release ranges from about 10 to about 700 ng, when measured in a time interval between days 7 to 84 excluding post dose day 1 burst when measured at 37° C. in PBS at a pH of 7.2 to 7.4 under sink-conditions.

29. The travoprost sustained release biodegradable intracameral implant for use according to any of items 20 to 23, wherein the treatment period is about 3 to about 7 months or is about 4 to 7 months, the implant contains a dose of about 15 µg of travoprost, and the implant has an in vitro release with an average travoprost release ranging from about 800 to about 1100 ng/week with a standard deviation ranging from 450 to 550 ng/week, wherein the average is based on the weekly travoprost release values between days 7 to 98 excluding post dose day 1 burst when measured at 37° C. in PBS at a pH of 7.2 to 7.4 under sink-conditions st; or wherein the weekly travoprost release ranges from about 100 to about 2300 ng, when measured in a time interval between days 7 to 98 excluding post dose day 1 burst when measured at 37° C. in PBS at a pH of 7.2 to 7.4 under sink-conditions.

30. The travoprost sustained release biodegradable intracameral implant for use according to any of items 20 to 22 or 24, wherein the treatment period is about 6 to about 9 months or about 6 to about 12 months, the implant contains a dose of about 15 µg of travoprost, and wherein the implant has an in vitro release with an average travoprost release ranging from about 500 to about 900 ng/week with a standard deviation ranging from 150 to 250 ng/week, wherein the average is based on the weekly travoprost release values between days 7 to 119 excluding post dose day 1 burst when measured at 37° C. in PBS at a pH of 7.2 to 7.4 under sink conditions; or wherein the weekly travoprost release ranges from about 100 to about 1500 ng, when measured in a time interval between days 7 to 119 excluding post dose day 1 burst; when measured at 37° C. in PBS at a pH of 7.2 to 7.2 under sink conditions.

31. The travoprost sustained release biodegradable intracameral implant for use according to any of items 20 to 22 or 24, wherein the treatment period is about 6 to about 9 months or about 6 to about 12 months, the implant contains a dose of about 26 µg of travoprost, and wherein the implant has an in vitro release with an average travoprost release ranging from about 1000 to about 1500 ng/week with a standard deviation ranging from 100 to 400 ng/week, wherein the average is based on the weekly travoprost release values between days 7 to 119 excluding post dose day 1 burst when measured at 37° C. in PBS at a pH of 7.2 to 7.4 under sink-conditions; or wherein the weekly travoprost release ranges from about 100 to about 2000 ng, when measured in a time interval between days 7 to 119 excluding post dose day 1 burst when measured at 37° C. in PBS at a pH of 7.2 to 7.4 under sink-conditions.

32. The travoprost sustained release biodegradable intracameral implant for use according to any of items 20 to 31, wherein the treatment is continued after said treatment period ranging from about 1 to about 12 months or from about 3 to about 9 months by repeating said treatment.

33. The travoprost sustained release biodegradable intracameral implant for use according to item 32, wherein the first treatment period is about 3 to about 4 months with a travoprost sustained release biodegradable implant providing treatment for about 3 to about 4 months, and the treatment continues with a treatment period of about 6 to about 12 months with a travoprost sustained release biodegradable implant providing treatment for about 6 to about 12 months.

The invention claimed is:
1. An intracameral implant comprising:
a biodegradable hydrogel, wherein the hydrogel comprises a polymer network comprising one or more units of polyalkylene glycol, and travoprost particles,
the travoprost particles being in the form of travoprost intermixed with a biodegradable polymer, and
the travoprost particles being dispersed within the hydrogel;
the intracameral implant having a length of about 1.00 mm to about 2.50 mm.
2. The intracameral implant according to claim 1, wherein the implant has a diameter of not more than 0.30 mm in its dried state.
3. The intracameral implant according to claim 1, wherein the implant has a diameter of less than 0.50 mm after 24 hours of hydration in vitro in phosphate-buffered saline at a pH of 7.4 at 37° C.
4. The intracameral implant according to claim 3, wherein the implant has a diameter ranging from about 0.30 mm to 0.49 mm, after 24 hours of hydration in vitro in phosphate-buffered saline at a pH of 7.4 at 37° C.
5. The intracameral implant according to claim 1, wherein a ratio of the diameter of the implant after 24 hours of hydration in vitro in phosphate-buffered saline at a pH of 7.4 at 37° C. to the diameter of the implant in its dried state is less than 2.5.
6. The intracameral implant according to claim 1, wherein the implant contains a dose of about 2 µg to about 30 µg of travoprost.
7. The intracameral implant according to claim 1, wherein the biodegradable polymer comprises a polylactide.
8. The intracameral implant according to claim 1, wherein the hydrogel comprises a polymer network comprising one or more units of polyethylene glycol.
9. The intracameral implant according claim 1, wherein the implant provides a therapeutic effect for a period ranging from about 3 to about 9 months.
10. The intracameral implant according to claim 1, wherein the implant has a total weight of about 20 µg to about 110 µg in its dried state.
11. The intracameral implant according to claim 1, wherein the implant shows a burst of less than 15%, based on the total weight of travoprost in the implant, on day 1 measured in vitro under simulated physiological sink conditions in 50 mL of 1×PBS, 0.5% castor oil, 0.01% sodium fluoride buffer at pH 7.2-7.4 at 37° C.
12. The intracameral implant according to claim 1, wherein the total mass of the biodegradable polymer in the implant is less than 34 µg.
13. The intracameral implant according to claim 1, wherein the travoprost in the implant is less than 25 µg.

14. The intracameral implant according to claim 1, wherein the total mass of the implant is less than 103 µg in its dried state.

15. The intracameral implant according to claim 1, wherein the travoprost particles have a diameter ranging from 1 to 100 µm determined by sieving or have an average diameter ranging from 1 to 100 µm determined by laser diffraction.

16. The intracameral implant according to claim 1, wherein the polymer network is formed by reacting an electrophilic group-containing multi-arm-polymer precursor with a nucleophilic group-containing cross-linking agent, the electrophilic group is selected from the group consisting of a succinimidylglutarate (SG) group and a succinimidylazelate (SAZ) group, and the multi-arm polymer precursor is selected from the group consisting of 8-arm-15K-SG polyethylene glycol or 8-arm-15K-SAZ polyethylene glycol; and the nucleophilic group-containing cross-linking agent is a trilysine, or the polymer network comprises an 8-arm-polyethylene glycols being cross-linked including a group represented by the following formula

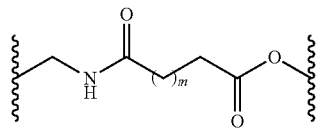

wherein m is 2 or 6.

17. The intracameral implant according to claim 1, wherein the travoprost particles comprise a blend of at least two types of travoprost particles selected from the group consisting of
1. A first type of travoprost particles made of a mixture of:
    travoprost and
    a biodegradable polymer consisting of a polylactide or polylactides having an acid end group and an inherent viscosity specification ranging from about 0.05 to less than about 0.5 dl/g, such as from about 0.35 to about 0.45 dl/g,
   such as wherein the first type of particles contains from about 40 wt.-% to about 50 wt.-%, such as from about 43 wt.-% to about 45 wt.-% travoprost, based on the total mass of the first type of particles;
2) A second type of travoprost particles made of a mixture of:
    travoprost and
    a biodegradable polymer consisting of a polylactide or polylactides having an acid end group and an inherent viscosity specification ranging from about 0.5 to less than about 0.80 dl/g, such as ranging from about 0.6 to less than about 0.80 dl/g,
   such as wherein the second type of particles contains from about 40 wt.-% to about 50 wt.-%, such as from more than about 45 wt.-% to about 47 wt.-% travoprost, based on the total mass of the second type of particles;
3) A third type of travoprost particles made of a mixture of:
    travoprost and
    a biodegradable polymer consisting of a polylactide or polylactides having an acid end group and an inherent viscosity specification ranging from about 0.8 to about 1.7 dl/g, such as ranging from about 0.8 to about 1.0 dl/g,
   such as wherein the third type of particles contains from about 40 wt.-% to about 50 wt.-%, such as from about 41 wt.-% to about 43 wt.-% travoprost based on the total mass of third type of particles;
4) A fourth type of travoprost particles made of a mixture of:
    travoprost and
    a biodegradable polymer consisting of a polylactide or polylactides having an ester end group and an inherent viscosity specification ranging from about 0.05 to about 1.7 dl/g, such as ranging from about 0.55 to about 0.75 dl/g,
   such as wherein the fourth type of particles contains from about 40 wt.-% to about 50 wt.-%, such as from about 41 wt.-% to about 43 wt.-% travoprost based on the total mass of the fourth type of particles.

18. The intracameral implant according to claim 1, wherein the travoprost particles comprise a blend of particles made of
a first type of travoprost particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles; and
a second type of travoprost particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particles contains from about 40 wt.-% to about 50 wt.-%, such as more than from about 45 wt.-% to about 47 wt.-% travoprost, based on the total mass of the second type of particles,
such as wherein the blend contains, based on the total amount of the blend, about 35 wt.-% to about 55 wt.-% particles of the first type of particles and about 35 wt.-% to about 55 wt.-% particles of the second type of particles; or
such as wherein about 35 wt.-% to about 55 wt.-% of the total amount of travoprost in the implant is present in the form of particles of the first type of particles and about 35 wt.-% to about 55 wt.-% of the total amount of travoprost in the implant is present in the form of particles of the second type of particles,
wherein optionally the polymer network is formed by reacting an electrophilic group-containing multi-arm-polymer precursor with a nucleophilic group-containing cross-linking agent, the electrophilic group is a succinimidylglutarate (SG) group and the multi-arm polymer precursor an 8-arm-15K-SG polyethylene glycol; and the nucleophilic group-containing cross-linking agent is a trilysine, or the polymer network comprises an 8-arm-polyethylene glycols being cross-linked including a group represented by the following formula

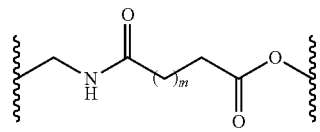

wherein m is 2.

19. The intracameral implant according to claim 1, wherein the travoprost particles comprise a blend of particles made of
- a first type of particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles,
- a second type of travoprost particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particle contains from about 40 wt.-% to about 50 wt.-%, such as more than from about 45 wt.-% to about 47 wt.-% travoprost, based on the total mass of the second type of particles, and
- a third type of travoprost particles made of a mixture of travoprost and the biodegradable polymer consisting of a polylactide or polylactides having an acid end group and an inherent viscosity specification ranging from about 0.8 to about 1.7 dl/g, such as ranging from about 0.8 to about 1.0 dl/g, wherein the third type of particles contains from about 40 wt.-% to about 50 wt.-%, such as from about 41 wt.-% to about 43 wt.-% travoprost, based on the total mass of the third type of particles,
- such as wherein the blend contains, based on the total amount of blend, about 20 wt.-% to about 35 wt.-% particles of the first type of particles and about 30 wt.-% to about 50 wt.-% particles of the second type of particles and about 25 wt.-% to about 45 wt.-% of particles of the third type of particles; or
- such as wherein about 20 wt.-% to about 35 wt.-% of the total amount of travoprost in the implant is present in the form of particles of the first type of particles and about 30 wt.-% to about 50 wt.-% of the total amount of travoprost in the implant is present in the form of particles of the second type of particles, and about 25 wt.-% to about 45 wt.-% of the total amount of travoprost in the implant is present in the form of particles of the third type of particles,
- wherein optionally the polymer network is formed by reacting an electrophilic group-containing multi-arm-polymer precursor with a nucleophilic group-containing cross-linking agent, the electrophilic group is a succinimidylglutarate (SG) group and the multi-arm polymer precursor an 8-arm-15K-SG polyethylene glycol; and the nucleophilic group-containing cross-linking agent is a trilysine or the polymer network comprises an 8-arm-polyethylene glycols being cross-linked including a group represented by the following formula

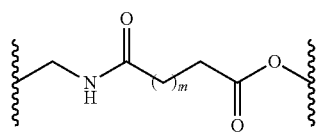

wherein m is 2.

20. The intracameral implant according to claim 1, wherein the travoprost particles comprise a blend of particles made of
- a first type of particles made of a mixture of travoprost and the biodegradable polymer consisting of a polylactide or polylactides having an acid end group and an inherent viscosity specification ranging from about 0.05 to less than about 0.5 dl/g, such as from about 0.35 to about 0.45 dl/g, wherein the first type of particles contains from about 40 wt.-% to about 50 wt.-%, such as from about 43 wt.-% to about 45 wt.-% travoprost, based on the total mass of the first type of particles,
- a second type of particles made of a mixture of travoprost and the biodegradable polymer consisting of a polylactide or polylactides having an acid end group and an inherent viscosity specification ranging from about 0.5 to less than about 0.80 dl/g, such as ranging from about 0.6 to less than about 0.80 dl/g, wherein the second type of particles contains from about 40 wt.-% to about 50 wt.-%, such as more than from about 45 wt.-% to about 47 wt.-% travoprost, based on the total mass of the second type of particles,
- a third type of particles made of travoprost and the biodegradable polymer consisting of a polylactide or polylactides having an acid end group and an inherent viscosity specification ranging from about 0.8 to about 1.7 dl/g, such as ranging from about 0.8 to about 1.0 dl/g, wherein the third type of particles contain from about 40 wt.-% to about 50 wt.-%, such as from about 41 wt.-% to about 43 wt.-% travoprost, based on the total mass of the third type of particles, and
- a fourth type of particles made of travoprost and the biodegradable polymer consisting of a polylactide or polylactides having an ester end group and an inherent viscosity specification ranging from about 0.05 to about 1.7 dl/g, such as ranging from about 0.55 to about 0.75 dl/g, wherein the fourth type of particles contains from about 40 wt.-% to about 50 wt.-% travoprost, based on the total mass of the fourth types of particles, such as wherein the blend contains, based on the total amount of blend, about 15 wt.-% to about 25 wt.-% particles of the first type of particles and about 15 wt.-% to about 25 wt.-% particles of the second type of particles and about 5 wt.-% to about 15% of particles of the third type of particles and about 40 wt.-% to about 60 wt.-% of particles of the fourth type of particles; or
- such as wherein about 15 wt.-% to about 25 wt.-% of the total amount of travoprost in the implant is present in the form of particles of the first type of particles and about 15 wt.-% to about 25 wt.-% of the total amount of travoprost in the implant is present in the form of particles of the second type of particles and about 5 wt.-% to about 15 wt.-% of the total amount of travoprost in the implant is present in the form of particles of the third type of particles and about 40 wt.-% to about 60 wt.-% of the total amount of travoprost in the implant is present in the form of particles of the fourth type of particles, wherein optionally the polymer network is formed by reacting an electrophilic group-containing multi-arm-polymer precursor with a nucleophilic group-containing cross-linking agent, the electrophilic group is a succinimidylazelate (SAZ) group, and the multi-arm polymer precursor is a 8-arm-15K-SAZ polyethylene glycol; and the nucleophilic group-containing cross-linking agent is a trilysine, or the polymer network comprises an 8-arm-polyethylene glycols being cross-linked including a group represented by the following formula
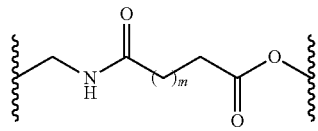
wherein m is 6.